US009040263B2

(12) United States Patent
Anton et al.

(10) Patent No.: US 9,040,263 B2
(45) **Date of Patent: *May 26, 2015**

(54) PRODUCTION OF ALCOHOL ESTERS AND IN SITU PRODUCT REMOVAL DURING ALCOHOL FERMENTATION

(75) Inventors: Douglas Robert Anton, Wilmington, DE (US); Stephane Francois Bazzana, Wilmington, DE (US); Keith H. Burlew, Middletown, DE (US); Jelena Cirakovic, Towson, MD (US); Robert Dicosimo, Chadds Ford, PA (US); Bruce A. Diner, Chadds Ford, PA (US); Michael Charles Grady, Oaklyn, NJ (US); Brian Michael Roesch, Middletown, DE (US); Francis J. Woerner, Bear, DE (US)

(73) Assignee: BUTAMAX ADVANCED BIOFUELS LLCDE (US)

( * ) Notice: Subject to any disclaimer, the term of this patent is extended or adjusted under 35 U.S.C. 154(b) by 328 days.

This patent is subject to a terminal disclaimer.

(21) Appl. No.: 13/193,147

(22) Filed: Jul. 28, 2011

(65) Prior Publication Data

US 2012/0208246 A1 Aug. 16, 2012

Related U.S. Application Data

(60) Provisional application No. 61/368,451, filed on Jul. 28, 2010, provisional application No. 61/368,436, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.

| | |
|---|---|
| ***C12P 7/64*** | (2006.01) |
| ***A23K 1/00*** | (2006.01) |
| ***A23K 1/06*** | (2006.01) |
| ***C12P 7/16*** | (2006.01) |
| ***C12P 7/62*** | (2006.01) |

(52) U.S. Cl.

CPC . *A23K 1/007* (2013.01); *A23K 1/06* (2013.01); *C12P 7/16* (2013.01); *C12P 7/62* (2013.01); *Y02E 50/10* (2013.01); *C12P 2203/00* (2013.01); *C12P 7/649* (2013.01); *Y02E 50/13* (2013.01)

(58) Field of Classification Search

None

See application file for complete search history.

(56) References Cited

U.S. PATENT DOCUMENTS

| | | | | |
|---|---|---|---|---|
| 5,036,005 | A | 7/1991 | Tedder | |
| 5,071,754 | A | 12/1991 | Walkup et al. | |
| 5,514,583 | A | 5/1996 | Picataggio et al. | |
| 5,710,030 | A | 1/1998 | Anderson | |
| 5,712,133 | A | 1/1998 | Picataggio et al. | |
| 5,723,639 | A | 3/1998 | Datta et al. | |
| 5,780,275 | A | 7/1998 | Oda | |
| 6,242,015 | B1 | 6/2001 | Egi et al. | |
| 6,291,708 | B1 | 9/2001 | Cockrem | |
| 6,398,707 | B1 | 6/2002 | Wu et al. | |
| 6,509,051 | B1 | 1/2003 | Wills | |
| 6,613,551 | B2 | 9/2003 | Davies et al. | |
| 6,646,146 | B1 | 11/2003 | Sinnema et al. | |
| 6,664,413 | B1 | 12/2003 | Cockrem | |
| 6,703,227 | B2 | 3/2004 | Jakel et al. | |
| 6,732,454 | B2 | 5/2004 | Anderson et al. | |
| 6,766,595 | B2 | 7/2004 | Anderson | |
| 6,996,917 | B2 | 2/2006 | Anderson | |
| 7,083,954 | B2 | 8/2006 | Jakel et al. | |
| 7,223,575 | B2 | 5/2007 | Zhang et al. | |
| 7,378,549 | B2 | 5/2008 | Ayoub | |
| 7,501,062 | B2 | 3/2009 | Den Boestert et al. | |
| 7,507,562 | B2 | 3/2009 | Verser et al. | |
| 7,612,221 | B2 | 11/2009 | Haas et al. | |
| 7,666,282 | B2 | 2/2010 | Sylvester et al. | |
| 7,741,119 | B2 | 6/2010 | Viitanen et al. | |
| 7,799,544 | B2 | 9/2010 | Schorken et al. | |
| 8,076,110 | B2 | 12/2011 | Chou | |
| 8,476,047 | B2 * | 7/2013 | Burlew et al. | 435/155 |
| 8,697,404 | B2 * | 4/2014 | Anton et al. | 435/134 |
| 2001/0004462 | A1 | 6/2001 | Sugiura et al. | |
| 2004/0063184 | A1 | 4/2004 | Grichko | |
| 2006/0024801 | A1 | 2/2006 | Holtzapple et al. | |
| 2007/0031918 | A1 | 2/2007 | Dunson et al. | |

(Continued)

FOREIGN PATENT DOCUMENTS

| | | | |
|---|---|---|---|
| CN | 1248617 | A | 3/2000 |
| CN | 101058740 | A | 10/2007 |

(Continued)

OTHER PUBLICATIONS 9.9.7 Corn Wet Milling—US Environmental Protection Agency < http://www.epa.gov/ttnchie1/ap42/ch09/final/c9s09-7.pdf > Feb. 1, 2001; pp. 9.9.7-1-9.9.7-9.*

(Continued)

*Primary Examiner* — Suzanne M Noakes

(57) ABSTRACT

An alcohol fermentation process and composition that includes production of alcohol esters by esterification of product alcohol in a fermentation medium with a carboxylic acid (e.g., fatty acid) and a catalyst (e.g., lipase) capable of esterifying the product alcohol, such as butanol, with the carboxylic acid to form the alcohol esters. The alcohol esters can be extracted from the fermentation medium, and the product alcohol recovered from the alcohol esters. The carboxylic acid can also serve as an extractant for removal of the alcohol esters from the fermentation medium.

26 Claims, 8 Drawing Sheets

(56) References Cited

U.S. PATENT DOCUMENTS

| | | | |
|---|---|---|---|
| 2007/0077635 | A1 | 4/2007 | Brunner et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0051592 | A1 | 2/2008 | McNeff et al. |
| 2008/0113419 | A1 | 5/2008 | Abo et al. |
| 2008/0153143 | A1 | 6/2008 | Schorken et al. |
| 2008/0182308 | A1 | 7/2008 | Donaldson et al. |
| 2008/0199924 | A1 | 8/2008 | Holm et al. |
| 2008/0261230 | A1 | 10/2008 | Liao et al. |
| 2008/0271364 | A1 | 11/2008 | Wiesman et al. |
| 2008/0289248 | A1 | 11/2008 | Gao |
| 2008/0293109 | A1 | 11/2008 | Berka et al. |
| 2009/0056201 | A1 | 3/2009 | Morgan |
| 2009/0133322 | A1 | 5/2009 | Basheer et al. |
| 2009/0163376 | A1 | 6/2009 | Li et al. |
| 2009/0171129 | A1 | 7/2009 | Evanko et al. |
| 2009/0203098 | A1 | 8/2009 | Verser |
| 2009/0203099 | A1 | 8/2009 | Caimi et al. |
| 2009/0246846 | A1 | 10/2009 | Viitanen et al. |
| 2009/0269823 | A1 | 10/2009 | Bramucci et al. |
| 2009/0305363 | A1 | 12/2009 | Anthony et al. |
| 2009/0305370 | A1 | 12/2009 | Grady et al. |
| 2010/0043281 | A1 | 2/2010 | De Angelis |
| 2010/0071259 | A1 | 3/2010 | Hu et al. |
| 2010/0081154 | A1 | 4/2010 | Flint et al. |
| 2010/0092603 | A1 | 4/2010 | Bruinsma et al. |
| 2010/0124773 | A1 | 5/2010 | Yang |
| 2010/0146843 | A1 | 6/2010 | Dumenil |
| 2010/0146844 | A1 | 6/2010 | Dumenil |
| 2010/0147771 | A1 | 6/2010 | McNeff et al. |
| 2010/0159538 | A1 | 6/2010 | Both et al. |
| 2010/0197519 | A1 | 8/2010 | Li et al. |
| 2010/0199548 | A1 | 8/2010 | Delcardayre et al. |
| 2010/0209968 | A1 | 8/2010 | Akers |
| 2010/0221802 | A1 | 9/2010 | Grady et al. |
| 2010/0234458 | A1 | 9/2010 | Dubreucq et al. |
| 2011/0124060 | A1 | 5/2011 | Anthony et al. |
| 2011/0244536 | A1 | 10/2011 | Nagarajan |
| 2011/0312053 | A1 | 12/2011 | Burlew |

FOREIGN PATENT DOCUMENTS

| | | | |
|---|---|---|---|
| CN | 101285078 | A | 10/2008 |
| CN | 101412989 | A | 4/2009 |
| CN | 101532038 | A | 9/2009 |
| DE | 10231029 | A1 | 1/2003 |
| DE | 60317699 | T2 | 10/2008 |
| EP | 0216221 | B1 | 4/1987 |
| EP | 0305901 | A2 | 6/1988 |
| EP | 0614983 | A2 | 9/1994 |
| EP | 0789079 | A2 | 8/1997 |
| EP | 1775344 | A2 | 4/2007 |
| EP | 1556475 | B1 | 11/2007 |
| EP | 1905821 | A1 | 4/2008 |
| EP | 2189535 | A1 | 5/2010 |
| FR | 2831886 | A1 | 5/2003 |
| GB | 2146638 | A | 4/1985 |
| IN | 201474 | A1 | 2/2007 |
| IT | 1337648 | B1 | 1/2007 |
| JP | 1986192291 | | 8/1986 |
| JP | 1997071594 | | 3/1997 |
| JP | 2009106274 | | 5/2009 |
| KR | 20100097543 | A | 9/2010 |
| WO | 9528476 | A1 | 10/1995 |
| WO | 9911752 | A1 | 3/1999 |
| WO | 0005395 | A1 | 2/2000 |
| WO | 2004092392 | A2 | 10/2004 |
| WO | 2005014765 | A1 | 2/2005 |
| WO | 2005077485 | A1 | 8/2005 |
| WO | 2007050671 | A2 | 5/2007 |
| WO | 2007130521 | A2 | 11/2007 |
| WO | 2008092207 | A1 | 8/2008 |
| WO | 2008111941 | A2 | 9/2008 |
| WO | 2008125574 | A1 | 10/2008 |
| WO | 2009009320 | A1 | 1/2009 |
| WO | 2009009322 | A1 | 1/2009 |
| WO | 2009009323 | A1 | 1/2009 |
| WO | 2009009391 | A9 | 1/2009 |
| WO | WO 2009/009391 | * | 1/2009 |
| WO | 2009029344 | A1 | 3/2009 |
| WO | 2009042950 | A1 | 4/2009 |
| WO | 2009063296 | A2 | 5/2009 |
| WO | 2009079213 | A2 | 6/2009 |
| WO | 2009100434 | A1 | 8/2009 |
| WO | 2009149270 | A2 | 12/2009 |
| WO | 2010005391 | A8 | 1/2010 |
| WO | 2010021711 | A1 | 2/2010 |
| WO | 2010022090 | A1 | 2/2010 |
| WO | 2010043013 | A2 | 4/2010 |
| WO | 2010049491 | A1 | 5/2010 |
| WO | 2010057996 | A3 | 5/2010 |
| WO | 2010075241 | A1 | 7/2010 |
| WO | 2010063402 | | 5/2011 |

OTHER PUBLICATIONS

Google Search Results for 9.9.7 Corn Wet Milling—US Environmental Protection Agency—Feb. 1, 2001.*

Christianson et al., Multifunctional yeast high-copy-No. shuttle vectors, Gene, 110, 1992, 119-122.

Ma et al., Plasmid construction by homologous recombination in yeast, Gene, 58, 1987, 201-216.

Akada et al., "PCR-mediated seamless gene deletion and marker recycling in *Saccharomyces cerevisiae*", Yeast (2006) 23, pp. 399-405.

Bellion et al., Microb. Growth C1 Compd., [Int. Symp.], 7th (1993), 415 32, Editor(s): Murrell, J. Collin; Kelly, Don P. Publisher: Intercept, Andover, UK.

Bligh et al., A Rapid Method of Total Lipid Extraction and Purification, Canadian Journal of Biochemistry and Physiology, 1959, 911-917, 37.

Barros et al., Integration of Enzyme Catalysis in an Extraction Fermentation Process, Studies in Organic Chemistry 29, 1986.

Chen et al., Regeneration of Immobilized *Candida antarctica* Lipase for Transesterification, Journal of Bioscience and Bioengineering, 2003, 466-469, 95 (5).

Deng et al., Enzymatic Production of Alkyl Esters Through Alcoholysis: A Critical Evaluation of Lipases and Alcohols, 2005, 341, 82 (5).

Elias et al., Role of Hydrodynamic Shear on Activity and Structure of Proteins, Advances in Biochemical Engineering/Biotechnology, 1998, 59.

Enfors et al., Physiological Responses to Mixing in Large Scale Bioreactors, Journal of Biotechnology, 2001, 175-187, 85.

Feldmann et al., Pentose Metalbolism in *Zymomonas mobilis* Wild-type and Recombinant Strains, Applied Microbiology and Biotechnology, 1992, 354-361, 38.

Ghadge et al, Enzyme deactiviation in a Bubble Column, a Stirred Vessel and an Inclined Plane, Chemical Engineering Science, 2003, 58, 5125-5134.

Hahnai et al., Engineered Synthetic Pathway for Isopropanol Production in *Escherichia coli*, Applied and Environmental Microbiology, 2007, 7814-7818, 73(24).

Horton et al., Engineering Hybrid Genes without the use of Restriction Enzymes: Gene Splicing by Overlap Extension, Gene, 1989, 61-68, 77.

Iso et al., Production of Biodiesel Fuel from Triglycerides and Alcohol Using Immobolized Lipase, Journal of Molecular Catalysis B: Enzymatic, 2001, 53-58, 16.

Kalscheuer et al., Microdiesel: *Escherichia coli* Engineered for Fuel Production, Microbiology, 2006, 2529-2536, 152.

Kim et al., Extractive Recovery of Products from Fermentation Broths, Biotechnology and Bioprocess Engineering, 1999, 1-11, 4.

Lara et al., Potential Application of Waste Activated Bleaching Earth on the Production of Fatty Acid Alkyl Esters using *Candida cylindracea* Lipase in organic Solvent System, Enzyme and Microbial Technology, 34 (2004) 270-277.

(56) References Cited

OTHER PUBLICATIONS

Lee et al., The Kinetics and Mechanism of Shear Inactivation of Lipase from *Candida cylindracea*, Biotechnology and Bioengineering, 1989, 183-190, 33.
Leung et al, A Review on Biodiesel Production using Catalyzed Transesterification, Applied Energy, 2010, 1083-1095, 87.
Lynd et al., Microbial Cellulose Utilization: Fundamentals and Biotechnology, Microbiology and Molecular Biology Reviews, 2002, 506-577, 66(3).
Malinowski, Two-phase Bioreactors in Fermentation Technology, Biotechnology Advances, 2001, 525-538, 19.
Ohta et al., Genetic Improvement of *Escherichia coli* for Ethanol Production: Chromosomal Integration of *Zymomonas mobilis* Genes Encoding Pyruvate Decarboxylase and Alcohol Dehydrogenase II, Applied and Environmental Microbiology, 1991, 893-900, 57(4).
Oliveira et al., Production and Extractive Biocatalysis of Ethanol Using Microencapsulated Yeast Cells and Lipase System, Journal of Chemical Technology and Biotechnology, 1991, 219-225, 52.
Oliveira et al., Immobilization of *Saccharomyces cerevisiae* Cells and *Rhizomucor miehi* Lipase for the Production and Extractive Biocatalysis of Ethanol, Bioprocess Engineering, 1997, 349-353, 16.
Oliveira et al., Improvement f Alcoholic Fermentations by Simultaneous Extraction and Enzymatic Esterification of Ethanol, Journal of Molecular Catalysis B: Enzymatic, 1998, 29-33, 5.
Oliveira et al., Effect of extraction and Enzymatic Esterification of Ethanol on glucose Consumption by Two *Saccharomyces cerevisiae* Strains: A comparative study, Journal of Chemical Technology and Biotechnology, 2001, 285-290, 76.
Ognajanovic et al, Lipases as Biocatalysts for Biodiesel Production, Hemijska Industria, 2010, 1-8, 64(1) (Abstract Only).
Rothstein, Targeting, Disruption, Replacement, and Allele Rescue: Integrative DNA Transformation in Yeast, Methods in Enzymology, 1991, 281-301, 194.
Rodrigues et al., Enzymatic Synthesis of Biodiesel from Transesterification Reactions of Vegetable Oils and Short Chain Alcohols, Journal of the American Oil Chemists Society, 2008, 925-930, 85(10).
Ross et al., Organic Solvent Functional Group Effect on Enzyme Inactivation by the Interfacial Mechanism, Journal of Molecular Catalysis B: Enzymatic, 2000, 183-192, 8.
Roffler, Extractive fermentation—Lactic Acid and Acetone/Butanol Production, University of California dissertation 1986.
Saravanan et al., An Experimental Comparison of Transesterification Process with Different Alcohols using Acid Catalysts, Biomass and Bioenergy, 2010, 999-1005, 34.
Shen et al., Metabolic Engineering of *Escherichia coli* for 1-butanol and 1-propanol Production via the keto-acid Pathways, Metabolic Engineering, 2008, 312-320, 10.
Schugerl, Integrated Processing of Biotechnology Products, Biotechnology Advances, 2000, 581-599, 18.
Singh et al., American Society of Agricultural Engineers, 1998, 1775-1777, 41(6).
Stahmann et al., Regulation and Properties of a Fungal Lipase Showing Interfacial Inactivation by Gas Bubbles, or Droplets of Lipid or Fatty Acid, European Journal of Biochemistry, 1997, 220-225, 244.
Sulter et al., Proliferation and Metabolic Significance of Peroxisomes in *Candida boidinii* during growth on D-alanine or oleic acid as the Sole Carbon Source, Archives of Microbiology, 1990, 485-489, 153.
Talukder et al., Two-step Lipase Catalysis for Production of Biodiesel, Biochemical Engineering Journal, 2010, 207-212, 49.
Van Dijken et al., An Interlaboratory Comparison of Physiological and Genetic Properties of Four *Saccharomyces cerevisiae* Strains, Enzyme and Microbial Technology, 2000, 706-714, 26.
Van Hoek et al., Fermentative Capacity in High-Cell-Density Fed-Batch Cultures of Baker's Yeast, Biotechnology and Bioengineering, 2000, 517-523, 68(5).
Underwood et al., Flux through Citrate synthase Limits the Growth of Ethanlogenic *Escherichia coli* KO11 during Xylose Fermentation, Applied and Environmental Microbiology, 2002, 1071-1081, 68(3).
Zhang et al., Metabolic Engineering of a Pentose Metabolism Pathway in Ethanologenic *Zymomonas mobilis*, Science, 1995, 24, 267.
Narasimharao et al., Catalysts in Production of Biodiesel: A Review, Journal of Biobased Materials and Bioenergy, 2007, 19-30, 1(1).
Methods in Yeast Genetics, 2005, Cold Spring Harbor Laboratory Press, Cold Spring Harbor, NY, pp. 201-202.
Patil et al., Lipase Deactivation at Gas-Liquid Interface and Its Subsequent Reactivation, AIChE Journal, 2000, 1280-1283, 46.
Barros et al., Production of ethanol by immobilized *Saccharomyces bayanus* in an extractive fermentation system, Biotechnology and Bioengineering, vol. XXIX, pp. 1097-1104 (1987).
International Search Report and Written Opinion of copending PCT/US2011/040856 mailed Dec. 29, 2011.
U.S. Appl. No. 13/163,243, filed Jun. 17, 2011.
U.S. Appl. No. 13/227,016, filed Sep. 7, 2011.
U.S. Appl. No. 13/161,168, filed Jun. 15, 2011.

* cited by examiner

PRODUCTION OF ALCOHOL ESTERS AND IN SITU PRODUCT REMOVAL DURING ALCOHOL FERMENTATION

This application claims the benefit of U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates to the fermentative production of alcohols including ethanol and butanol, and all related co-products, and processes for improving alcohol fermentation employing in situ product removal methods.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical and drop-in fuel component with a variety of applications including use as a renewable fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds. Thus, there is a continuing need to develop efficient methods and systems for producing butanol in high yields despite low butanol toxicity thresholds of the butanol-producing microorganisms in the fermentation medium.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In general, with regard to butanol fermentation, the fermentation medium which includes the microorganism is contacted with an organic extractant at a time before the butanol concentration reaches a toxic level. The organic extractant and the fermentation medium form a biphasic mixture. The butanol partitions into the organic extractant phase decreasing the concentration of butanol in the aqueous phase containing the microorganism, thereby limiting the exposure of the microorganism to the inhibitory butanol. In order to be technically and economically viable, liquid-liquid extraction requires contact between the extractant and the fermentation broth for efficient mass transfer of the product alcohol into the extractant; phase separation of the extractant from the fermentation broth (during an/or after fermentation); efficient recovery and recycle of the extractant; and minimal decrease of the partition coefficient of the extractant over a long-term operation.

The extractant can become contaminated over time with each recycle, for example, by the build-up of lipids present in the biomass that is fed to the fermentation vessel as feedstock of hydrolyzable starch. As an example, during the conversion of glucose to butanol, a liquified corn mash loaded to a fermentation vessel at 30 wt % dry corn solids can result in a fermentation broth that contains about 1.2 wt % corn oil generated by simultaneous saccharification and fermentation (with saccharification of the liquified mash occurring during fermentation by the addition of glucoamylase to produce glucose). The dissolution of the corn oil lipids into oleyl alcohol (OA) serving as an extractant during ISPR can result in build-up of lipid concentration with each OA recycle decreasing the partition coefficient for the product alcohol in OA as the lipid concentration in OA increases with each recycle of OA.

In addition, the presence of the undissolved solids during extractive fermentation can negatively affect the efficiency of the alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the partition coefficient of the extractant used in extractive fermentation have included wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ, which contains a majority of the lipids present in ground whole corn resulting in a fractionated corn that has a higher starch (endosperm) content. Dry fractionation does not separate the germ from fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in co-pending, commonly owned U.S. Provisional Application Ser. No. 61/356,290, filed Jun. 18, 2010. However, it would be advantageous if the degradation of the partition coefficient of the extractant caused by contamination by lipid can be reduced even without fractionation or removal of substantially all undissolved solids. Converting the lipids present in a liquefied mash into an extractant that can be used in ISPR is another method of decreasing the amount of lipids that are fed to the fermentation vessel as described, for example, in co-pending, commonly owned U.S. Provisional Application Ser. No. 61/368,436 and U.S. Provisional Application Ser. No. 61/368,444, both filed on Jul. 28, 2010.

There is a continuing need for alternative extractive fermentation methods which do not necessitate the partitioning of the product alcohol between the fermentation medium and the ISPR extractant as a means to reduce the toxic effect of the product alcohol such as butanol on the microorganism, and which can also reduce the degradation of the partition coefficient of a fermentation product extractant.

BRIEF SUMMARY OF THE INVENTION

Conversion of alcohol such as butanol produced from a microorganism in a fermentation medium into a substance less toxic to the microorganism can allow increased production of alcohol such as butanol for a given fermentation vessel volume. Alcohol esters can be formed by contacting the alcohol in a fermentation medium with a carboxylic acid (e.g., fatty acids) and a catalyst capable of esterifying the alcohol with the carboxylic acid. Moreover, the carboxylic acid can serve as an ISPR extractant into which the alcohol esters partition. The carboxylic acid can be supplied to the fermentation vessel and/or derived from the biomass supplying fermentable carbon feed to the fermentation vessel. Lipids present in the feedstock can be catalytically hydrolyzed to carboxylic acid and the same catalyst (e.g., enzymes) can esterify the carboxylic acid with the alcohol (e.g., butanol); lipids can also be directly transesterified by the catalyst to produce alcohol esters. The catalyst can be supplied to the feedstock prior to fermentation or can be supplied to the fermentation vessel before or contemporaneously with the supplying of the feedstock. When the catalyst is supplied to the fermentation vessel, alcohol esters can be obtained by hydrolysis of the lipids into carboxylic acid and concurrent esterification of carboxylic acid with butanol present in the fermentation vessel; lipids can also be directly transesterified with butanol by the catalyst to produce alcohol esters. Carboxylic acid and/or native oil not derived from the feedstock can also be fed to the fermentation vessel, with the native oil being hydrolyzed into carboxylic acid. Carboxylic acid and/or native oil not derived from the feedstock can be fed into the fermentation vessel in an amount sufficient such that a two-phase mixture comprising an organic phase and an aqueous phase is formed. As such, in some embodiments, any carboxylic acid not esterified with the alcohol can serve as the ISPR extractant or as a part thereof. The extractant containing alcohol esters can be separated from the fermentation medium, and the alcohol can be recovered from the extractant. The extractant can be recycled to the fermentation vessel. Thus, in the case of butanol production, for example, the conversion of butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to carboxylic acid, thereby decreasing the rate of build-up of lipids in the ISPR extractant.

The present invention is directed to a method for producing butyl esters comprising contacting butanol produced in a fermentation process with at least one carboxylic acid and at least one catalyst capable of esterifying the carboxylic acid with the butanol to form butyl esters of the carboxylic acid; wherein the carboxylic acid in the fermentation process is present at a concentration sufficient to produce a two-phase mixture. In one embodiment, the production of butanol and the production of butyl esters occur simultaneously or sequentially. In one embodiment, a feedstock in the fermentation process comprises one or more fermentable sugars. In another embodiment, the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In one embodiment, the method further comprises providing a native oil and converting at least a portion of the native oil into carboxylic acid by contacting the oil with one or more enzymes. In one embodiment, the carboxylic acid comprises fatty acids. In another embodiment, the carboxylic acid comprises 12 to 22 carbons. In one embodiment, the carboxylic acid is a mixture of carboxylic acids. In another embodiment, the butyl esters of the carboxylic acid are butyl esters of fatty acids. In one embodiment, the catalyst is an enzyme capable of esterifying the carboxylic acid with the butanol to form butyl esters of the carboxylic acid. In another embodiment, the enzyme is an esterase, lipase, phospholipase, or lysophospholipase.

The present invention is also directed to a method for producing butanol and butyl esters from a feedstock comprising: (a) providing a feedstock; (b) liquefying the feedstock to create a liquefied biomass comprising oligosaccharides; (c) separating the feedstock slurry to produce a product comprising an aqueous stream comprising oligosaccharides, an oil stream, and solids; (d) adding the aqueous stream to a fermentation vessel containing a fermentation broth; (e) saccharifying the oligosaccharides of the aqueous stream; (f) fermenting the products of the oligosaccharide saccharification present in the aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; and optionally steps (e) and (f) occur concurrently. In one embodiment, the method further comprises obtaining an oil from the oil stream and converting at least a portion of the oil into carboxylic acid. In one embodiment, the feedstock slurry is separated by decanter bowl centrifugation, tricanter centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof. In another embodiment, the carboxylic acid comprises fatty acids. In one embodiment, the carboxylic acid comprises 12 to 22 carbons. In one embodiment, the method further comprises adding the oil to the fermentation vessel prior to the step of converting at least a portion of the oil into carboxylic acid. In one embodiment, the method further comprises adding additional carboxylic acid to the fermentation vessel. In one embodiment, the oil is converted to carboxylic acid after the step of adding the additional carboxylic acid. In another embodiment, the carboxylic acid is corn oil fatty acid, soya oil fatty acid, or a mixture of corn oil fatty acid and soya oil fatty acid. In one embodiment, the oil obtained from the oil stream comprises glycerides and the one or more catalysts hydrolyze the glycerides into fatty acids. In another embodiment, the butyl esters of carboxylic acid are butyl esters of fatty acids. In one embodiment, the catalyst is an enzyme capable of esterifying the carboxylic acid with the butanol to form butyl esters of the carboxylic acid. In one embodiment, the enzyme is an esterase, lipase, phospholipase, or lysophospholipase. In one embodiment, the method further comprises the step of washing the solids with a solvent. In one embodiment, the solvent is select from hexane, isobutanol, isohexane, ethanol, petroleum distillates such as petroleum ether, or mixtures thereof. In another embodiment, the solids are processed to form an animal feed product. In one embodiment, the solids are processed to form an animal feed product. In one embodiment, the animal feed product comprises one or more crude protein, crude fat, triglycerides, fatty acid, fatty acid isobutyl ester, lysine, neutral detergent fiber (NDF), and acid detergent fiber (ADF). In another embodiment, the animal feed product further comprises one or more vitamins, minerals, flavoring, or coloring. In one embodiment, the animal feed product comprises 20-35 wt % crude protein, 1-20 wt % crude fat, 0-5 wt % triglycerides, 4-10 wt % fatty acids, and 2-6 wt % fatty acid isobutyl esters. In one embodiment, the step of separating the solids from the feedstock slurry increases the efficiency of the butanol production by increasing a liquid-liquid mass transfer coefficient of the butanol from the fermentation broth to the extractant; increases the efficiency of the butanol production by increasing an extraction efficiency of the butanol with an extractant; increases the efficiency of the butanol production by increasing a rate of phase separation between the fermentation broth and an extractant; increases the efficiency of the butanol production by increasing recovery and recycling of an extractant; or increases the efficiency of the butanol production by decreasing a flow rate of an extractant.

The present invention is also directed to a method for producing butanol and butyl esters from a feedstock comprising: (a) providing a feedstock; (b) liquefying the feedstock to create a liquefied biomass comprising oligosaccharides; (c) separating the feedstock slurry to produce a stream comprising oligosaccharides and oil, and solids; (d) adding the stream to a fermentation vessel containing a fermentation broth; (e) saccharifying the oligosaccharides of the stream; (f) fermenting the products of the oligosaccharide saccharification present in the stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; and optionally steps (e) and (f) occur concurrently. In one embodiment, the method further comprising converting at least a portion of the oil into carboxylic acid. In one embodiment, the feedstock slurry is separated by decanter bowl centrifugation, tricanter centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof. In another embodiment, the carboxylic acid comprises fatty acids. In one embodiment, the carboxylic acid comprises 12 to 22 carbons. In one embodiment, the method further comprises adding oil to the fermentation vessel. In one embodiment, the method further comprising adding additional carboxylic acid to the fermentation vessel. In one embodiment, the oil is converted to carboxylic acid after the step of adding the additional carboxylic acid. In one embodiment, the carboxylic acid is corn oil fatty acid, soya oil fatty acid, or a mixture of corn oil fatty acid and soya oil fatty acid. In one embodiment, the oil comprises glycerides and the one or more catalysts hydrolyze the glycerides into fatty acids. In one embodiment, the butyl esters of carboxylic acid are butyl esters of fatty acids. In one embodiment, the catalyst is an enzyme capable of esterifying the carboxylic acid with the butanol to form butyl esters of the carboxylic acid. In one embodiment, the enzyme is an esterase, lipase, phospholipase, or lysophospholipase. In one embodiment, the method further comprises the step of washing the solids with a solvent. In one embodiment, the solvent is select from hexane, isobutanol, isohexane, ethanol, petroleum distillates such as petroleum ether, or mixtures thereof. In one embodiment, the solids are processed to form an animal feed product. In one embodiment, the solids are processed to form an animal feed product. In some embodiments, the animal feed product comprises one or more crude protein, crude fat, triglycerides, fatty acid, fatty acid isobutyl ester, lysine, neutral detergent fiber (NDF), and acid detergent fiber (ADF). In some embodiments, the animal feed product further comprises one or more vitamins, minerals, flavoring, or coloring. In some embodiments, the animal feed product comprises 20-35 wt % crude protein, 1-20 wt % crude fat, 0-5 wt % triglycerides, 4-10 wt % fatty acids, and 2-6 wt % fatty acid isobutyl esters. In some embodiments, the step of separating the solids from the feedstock slurry increases the efficiency of the butanol production by increasing a liquid-liquid mass transfer coefficient of the butanol from the fermentation broth to the extractant; increases the efficiency of the butanol production by increasing an extraction efficiency of the butanol with an extractant; increases the efficiency of the butanol production by increasing a rate of phase separation between the fermentation broth and an extractant; increases the efficiency of the butanol production by increasing recovery and recycling of an extractant; or increases the efficiency of the butanol production by decreasing a flow rate of an extractant.

The present invention is also directed to a method for producing butanol comprising (a) contacting butanol produced in a fermentation process with at least one carboxylic acid and at least one catalyst capable of esterifying the carboxylic acid with the butanol to form butyl esters of the carboxylic acid; wherein the carboxylic acid in the fermentation process is present at a concentration sufficient to produce a two-phase mixture comprising an aqueous phase and a butyl ester-containing organic phase; (b) separating the butyl ester-containing organic phase from the aqueous phase; and (c) recovering butanol from the butyl esters. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the butyl esters are hydrolyzed in the presence of water and wherein the hydrolysis catalyst comprises an acid catalyst, an organic acid, an inorganic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, enzyme reaction conditions favor enzymatic hydrolysis over esterification. In some embodiments, the enzyme reaction conditions comprise a cosolvent. In some embodiments, fatty acid butyl esters, fatty acids, isobutanol, and water are soluble in the cosolvent, and wherein free fatty acids do not react with the cosolvent. In some embodiments, the cosolvent is selected from acetone, tert-butanol, 2-Me-2-butanol, 2-Me-2-pentanol, and 3-Me-3-pentanol. In some embodiments, the enzyme reaction conditions comprise end-product removal. In some embodiments, the end-product is isobutanol or fatty acids. In some embodiments, isobutanol is removed by vacuum distillation, pervaporartion, permselective filtration, gas sparging, or membrane separation. In some embodiments, the fatty acids are removed by precipitation, permselective filtration, or electrophorectically. In some embodiments, the hydrolysis reaction occurs in a reaction vessel. In some embodiments, recovering butanol from the butyl esters comprises transesterifying the butyl esters into butanol and fatty acid alkyl esters or acyl glycerides. In some embodiments, the fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the butyl esters to form butanol. In some embodiments, the enzyme is an esterase, lipase, phospholipase, or lysophospholipase. In some embodiments, the carboxylic acid comprises fatty acids. In some embodiments, the carboxylic acid has carbon chain lengths ranging from 12 to 22 carbons. In some embodiments, at least about 10% of butanol is recovered from the butyl esters. In some embodiments, at least about 50% of butanol is recovered from the butyl esters. In some embodiments, at least about 90% of butanol is recovered from the butyl esters. In some embodiments, carboxylic acid is recovered from the butyl esters. In some embodiments, the method further comprising the steps of removing butanol from the fermentor as extractant stream; and adding the extractant stream to two or more distillation columns. In some embodiments, the distillation column is a super-atmospheric distillation column with a steam heated reboiler. In some embodiments, the method further comprises the steps of recovering water and solvent from the distillation columns; and recycling the water and solvent. In some embodiments, the method further comprises the steps of recovering heat from the distillation process; and recycling the heat to evaporate water.

The present invention is also directed to a method for producing butanol from a feedstock comprising (a) providing a feedstock; (b) liquefying the feedstock to create a feedstock slurry; (c) separating the feedstock slurry to produce a product comprising an aqueous stream, an oil stream, and solids; (d) adding the aqueous stream to a fermentation vessel containing a fermentation broth; (e) saccharifying the aqueous stream; (f) fermenting the saccharified aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; (g) separating the butyl ester-containing organic phase from the aqueous phase; and (h) recovering butanol from the butyl esters; and optionally steps (e) and (f) occur concurrently. In some embodiments, the method further comprises obtaining an oil from the oil stream and converting at least a portion of the oil into carboxylic acid. In some embodiments, the feedstock slurry is separated by centrifugation, filtration, or decantation. In some embodiments, the carboxylic acid comprises fatty acids. In some embodiments, the carboxylic acid has carbon chain lengths ranging from 12 to 22 carbons. In some embodiments, the method further comprises adding the oil to the fermentation vessel prior to the step of converting at least a portion of the oil into carboxylic acid. In some embodiments, the method further comprises adding additional carboxylic acid to the fermentation vessel. In some embodiments, the oil is converted to carboxylic acid after the step of adding the additional carboxylic acid. In some embodiments, the carboxylic acid is corn oil fatty acid, soya oil fatty acid, or a mixture of corn oil fatty acid and soya oil fatty acid. In some embodiments, the oil obtained from the oil stream comprises glycerides and the one or more catalysts hydrolyze the glycerides into fatty acids. In some embodiments, the butyl esters of carboxylic acid are butyl esters of fatty acids. In some embodiments, the catalyst is an enzyme capable of esterifying the carboxylic acid with the butanol to form butyl esters of the carboxylic acid. In some embodiments, the enzyme is an esterase, lipase, phospholipase, or lysophospholipase. In some embodiments, the solids are processed to form to an animal feed product. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the butyl esters are hydrolyzed in the presence of water and wherein the hydrolysis catalyst comprises an acid catalyst, an organic acid, an inorganic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, the hydrolysis reaction occurs in a reaction vessel. In some embodiments, recovering butanol from the butyl esters comprises transesterifying the butyl esters into butanol and fatty acid alkyl esters or acyl glycerides. In some embodiments, the fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the butyl esters to form butanol. In some embodiments, the enzyme is an esterase, lipase, phospholipase, or lysophospholipase.

The present invention is also directed to a method for producing butanol and butyl esters from a feedstock comprising (a) providing a feedstock; (b) liquefying the feedstock to create a liquefied biomass comprising oligosaccharides; (c) separating the feedstock slurry to produce an aqueous stream comprising oligosaccharides and oil, and solids; (d) adding the aqueous stream to a fermentation vessel containing a fermentation broth; (e) saccharifying the oligosaccharides of the aqueous stream; (f) fermenting the products of the oligosaccharide saccharification present in the aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; (g) separating the butyl ester-containing organic phase from the aqueous phase; and (h) recovering butanol from the butyl esters; and optionally steps (e) and (f) occur concurrently. In some embodiments, the method further comprises converting at least a portion of the oil into carboxylic acid. In some embodiments, the feedstock slurry is separated by centrifugation, filtration, or decantation. In some embodiments, the carboxylic acid comprises fatty acids. In some embodiments, the carboxylic acid comprises 12 to 22 carbons. In some embodiments, the method further comprises adding oil to the fermentation vessel. In some embodiments, the method further comprises adding additional carboxylic acid to the fermentation vessel. In some embodiments, the oil is converted to carboxylic acid after the step of adding the additional carboxylic acid. In some embodiments, the carboxylic acid is corn oil fatty acid or soya oil fatty acid. In some embodiments, the carboxylic acid is a mixture of corn oil fatty acid and soya oil fatty acid. In some embodiments, the oil comprises glycerides and the one or more catalysts hydrolyze the glycerides into fatty acids. In some embodiments, the butyl esters of carboxylic acid are butyl esters of fatty acids. In some embodiments, the catalyst is an enzyme capable of esterifying the carboxylic acid with the butanol to form butyl esters of the carboxylic acid. In some embodiments, the enzyme is an esterase, lipase, phospholipase, or lysophospholipase. In some embodiments, the solids are processed to form to an animal feed product. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the butyl esters are hydrolyzed in the presence of water and wherein the hydrolysis catalyst comprises an acid catalyst, an organic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, the hydrolysis reaction occurs in a reaction vessel. In some embodiments, recovering butanol from the butyl esters comprises transesterifying the butyl esters into butanol and other fatty acid alkyl esters or acyl glycerides. In some embodiments, the other fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the butyl esters to form butanol. In some embodiments, the enzyme is an esterase, lipase, phospholipase, or lysophospholipase.

The present invention is also directed to a method for producing alcohol esters comprising contacting an alcohol produced in a fermentation process with at least one carboxylic acid and at least one catalyst capable of esterifying the carboxylic acid with the alcohol to form alcohol esters of the carboxylic acid; wherein the carboxylic acid in the fermentation process is present at a concentration sufficient to produce a two-phase mixture. In some embodiments, the production of the alcohol and the production of alcohol esters occur simultaneously or sequentially. In some embodiments, a feedstock in the fermentation process comprises one or more fermentable sugars. In some embodiments, the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In some embodiments, the method further comprises providing a native oil and converting at least a portion of the native oil into carboxylic acid by contacting the oil with one or more enzymes. In some embodiments, the carboxylic acid comprises fatty acids. In some embodiments, the carboxylic acid has carbon chain lengths ranging from 12 to 22 carbons. In some embodiments, the alcohol esters of the carboxylic acid are alcohol esters of fatty acids. In some embodiments, the catalyst is an enzyme capable of esterifying the carboxylic acid with the butanol to form butyl esters of the carboxylic acid. In some embodiments, the enzyme is an esterase, lipase, phospholipase, or lysophospholipase. In some embodiments, the alcohol is a $C_2$ to $C_8$ alkyl alcohol. In some embodiments, the $C_2$ to $C_8$ alkyl alcohol is ethanol, propanol, butanol, pentanol, or 2-methyl-1 butanol.

The present invention is also directed to a method for producing an alcohol comprising (a) contacting an alcohol produced in a fermentation process with at least one carboxylic acid and at least one catalyst capable of esterifying the carboxylic acid with the alcohol to form alcohol esters of the carboxylic acid; wherein the carboxylic acid in the fermentation process is present at a concentration sufficient to produce a two-phase mixture comprising an aqueous phase and a alcohol ester-containing organic phase; (b) separating the alcohol ester-containing organic phase from the aqueous phase; and (c) recovering alcohol from the alcohol esters. In some embodiments, recovering alcohol from the alcohol esters comprises hydrolyzing the esters into carboxylic acid and alcohol. In some embodiments, the alcohol esters are hydrolyzed in the presence of a hydrolysis catalyst. In some embodiments, the alcohol esters are hydrolyzed in the presence of water and wherein the hydrolysis catalyst comprises an acid catalyst, an organic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, the hydrolysis reaction occurs in a reaction vessel. In some embodiments, recovering the alcohol from the alcohol esters comprises transesterifying the alcohol esters into alcohol and fatty acid alkyl esters or acyl glycerides. In some embodiments, the fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the alcohol esters to form alcohol. In some embodiments, the enzyme is an esterase, lipase, phospholipase, or lysophospholipase. In some embodiments, the carboxylic acid comprises fatty acids. In some embodiments, the carboxylic acid has carbon chain lengths ranging from 12 to 22 carbons. In some embodiments, the alcohol is a $C_2$ to $C_8$ alkyl alcohol. In some embodiments, the $C_2$ to $C_8$ alkyl alcohol is ethanol, propanol, butanol, pentanol, or 2-methyl-1 butanol. In some embodiments, carboxylic acid is recovered from the butyl esters.

The present invention is directed to a method for producing butanol and butyl esters from a feedstock comprising (a) providing a feedstock; (b) liquefying the feedstock to create a liquefied biomass comprising oligosaccharides; (c) separating the feedstock slurry to produce an aqueous stream comprising oligosaccharides and oil, and solids; (d) adding the aqueous stream to a fermentation vessel containing a fermentation broth; (e) saccharifying the oligosaccharides of the aqueous stream; (f) fermenting the products of the oligosaccharide saccharification present in the aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; (g) separating the butyl ester-containing organic phase from the aqueous phase; and (h) recovering butanol from the butyl esters; and optionally steps (e) and (f) occur concurrently. In some embodiments, the feedstock in the fermentation process comprises one or more fermentable sugars. In some embodiments, the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In some embodiments, the method further comprises converting at least a portion of the oil into carboxylic acid. In some embodiments, the feedstock slurry is separated by decanter bowl centrifugation, tricanter centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof. In some embodiments, the carboxylic acid comprises fatty acids. In some embodiments, the carboxylic acid comprises 12 to 22 carbons. In some embodiments, the method further comprises adding additional carboxylic acid to the fermentation vessel. In some embodiments, the oil is converted to carboxylic acid after the step of adding the additional carboxylic acid. In some embodiments, the carboxylic acid is corn oil fatty acid, soya oil fatty acid, or a mixture of corn oil fatty acid and soya oil fatty acid. In some embodiments, the oil comprises glycerides and the one or more catalysts hydrolyze the glycerides into fatty acids. In some embodiments, the catalyst is an enzyme capable of esterifying the carboxylic acid with the butanol to form butyl esters of the carboxylic acid. In some embodiments, the enzyme is an esterase, lipase, phospholipase, or lysophospholipase. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the hydrolysis catalyst comprises an acid catalyst, an organic acid, a water soluble acid, water insoluble acid, or base. In some embodiments, the butyl esters are hydrolyzed in the presence of water. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, recovering butanol from the butyl esters comprises transesterifying the butyl esters into butanol and other fatty acid alkyl esters or acyl glycerides. In some embodiments, the other fatty acid alkyl esters comprise fatty acid methyl esters, fatty acid ethyl esters, or fatty acid propyl esters. In some embodiments, the solids are processed to form to an animal feed product.

The present invention is directed to a fermentation broth comprising (a) a recombinant microorganism capable of producing a product alcohol; (b) a fermentable carbon substrate; (c) a catalyst capable of extracellularly esterifying fatty acids with said product alcohol into fatty acid alcohol esters; and (d) fatty acid alcohol esters, wherein the fatty acid alcohol esters are produced during the fermentation. In some embodiments, the fermentation broth further comprises one or more of the following acyl glycerides, fatty acids, product alcohol, or oleic acid. In some embodiments, the fermentation broth further comprises a catalyst wherein said catalyst esterifies fatty acids with alcohol into fatty acid alcohol esters and hydrolyzes triglycerides into free fatty acids. In some embodiments, the catalyst is one or more lipase enzymes. In some embodiments, the fermentation broth further comprises a saccharification enzyme capable of converting oligosaccharides into fermentable sugar. In some embodiments, the saccharification enzyme comprises glucoamylase. In some embodiments, the fermentable sugar comprises monomeric glucose. In some embodiments, the recombinant microorganism is capable of producing butanol. In some embodiments, the fatty acid alcohol esters are fatty acid butyl esters. In some embodiments, the fermentation broth further comprises isobutanol.

The present invention is also directed to a recombinant yeast cell capable of producing isobutanol, the yeast cell comprising an isobutanol biosynthetic pathway wherein said isobutanol biosynthetic pathway comprises at least one enzyme that catalyzes each of the following substrate to product conversions: i) pyruvate to acetolactate; ii) acetolactate to 2,3-dihydroxyisovalerate; iii) 2,3-dihydroxyisovalerate to α-ketoisovalerate; iv) α-ketoisovalerate to isobutyraldehyde; and v) isobutyraldehyde to isobutanol; and wherein at least one of the enzyme of iii) or the enzyme of v) are encoded by heterologous polynucleotides integrated into the chromosome. In some embodiments, the yeast cell is substantially free of pyruvate decarboxylase activity. In some embodiments, the recombinant yeast cell comprises deletions of pdc1, pdc5, and pdc6 genes. In some embodiments, the yeast cell is substantially free of an enzyme having NAD-dependent glycerol-3-phosphate dehydrogenase activity. In some embodiments, the recombinant yeast cell comprises a deletion of gpd2. In some embodiments, both the enzyme of iii) and the enzyme of iv) are encoded by heterologous polynucleotides integrated into the chromosome. In some embodiments, the isobutanol biosynthetic pathway comprises at least one heterologous polynucleotide encoding an enzyme for each of the substrate to product conversions. In some embodiments, the recombinant yeast cell further comprises a plasmid having at least 80% identity to each of the coding regions of pYZ090 or a plasmid having at least 80% identity to each of the coding regions of pLH468. In some embodiments, the recombinant yeast cell comprises a plasmid of SEQ ID NO: 1 or a plasmid of SEQ ID NO: 2 or both.

The present invention is directed to a fermentation composition comprising (a) a fermentable carbon substrate; (b) a catalyst capable of esterifying free fatty acids with an alcohol into fatty acid alkyl esters and optionally capable of hydrolyzing glycerides into free fatty acids; (c) alcohol; (d) free fatty acids; and (e) fatty acid alcohol esters formed in situ from esterification of the free fatty acids with the alcohol using the catalyst. In some embodiments, the composition further comprises oil, wherein the oil comprises glycerides. In some embodiments, the oil, the free fatty acids, and the fermentable carbon substrate are derived from a biomass. In some embodiments, the oil and the fermentable carbon substrate are derived from the same biomass source or from different biomass sources. In some embodiments, the biomass source of the oil is soya or corn oil, and wherein biomass source of the fermentable carbon substrate is corn. In some embodiments, the free fatty acids are corn oil fatty acids. In some embodiments, the free fatty acids are formed from hydrolysis of at least a portion of the glycerides in the oil using the catalyst. In some embodiments, the composition further comprises at least one of diglycerides and monoglycerides formed from the partial hydrolysis of a portion of the glycerides in the oil using the catalyst. In some embodiments, the composition further comprises glycerol. In some embodiments, the composition further comprises undissolved solids derived from the biomass source of the fermentable carbon substrate. In some embodiments, the composition contains less than about 25 wt % of the undissolved solids. In some embodiments, the composition further comprises a saccharification enzyme capable of converting starch into fermentable sugar and wherein the alcohol is butanol.

The present invention is directed to a composition comprising butanol produced by the methods described herein. In some embodiments, the composition is used as a fuel additive, feedstock chemical, reagent, solvent, antiseptic, or food-grade extractant. Butanol produced by the methods described herein as a fuel additive, feedstock chemical, reagent, solvent, antiseptic, or food-grade extractant.

In other embodiments, a fermentation method may include: providing an aqueous feedstream obtained from biomass where the aqueous feedstream includes water, fermentable carbon source derived from the biomass, and oil; contacting the aqueous feedstream with a catalyst whereby at least a portion of the oil is hydrolyzed into free fatty acids to form a catalyst-treated feedstream including the free fatty acids and the catalyst; contacting the catalyst-treated feedstream with a fermentation broth in a fermentation vessel; fermenting the fermentable carbon source in the fermentation vessel to produce a product alcohol; and contacting the product alcohol with the free fatty acids and the catalyst during fermentation so as to catalyze the esterification of the free fatty acids and the product alcohol in the fermentation vessel to produce alcohol esters of fatty acids. In some embodiments, the steps of contacting the feedstream with catalyst and fermentation broth and the steps of fermenting and contacting the product alcohol with the free fatty acids and the catalyst may occur simultaneously. In some embodiments, the product alcohol is butanol and the alcohol esters of fatty acids are butyl esters of fatty acids.

The present invention provides methods for removing alcohol from a fermentation medium during fermentation including: providing a fermentation medium including a microorganism that produces alcohol in the fermentation medium; and contacting the fermentation medium during fermentation with a carboxylic acid and a catalyst capable of esterifying the alcohol with the carboxylic acid to form an alcohol ester. In some embodiments, the alcohol that is produced by the microorganism is butanol, and the alcohol ester is butyl ester. In some embodiments, the fermentation medium is contacted with a carboxylic acid that is substantially insoluble in the fermentation medium and with a catalyst capable of esterifying the alcohol with the carboxylic acid to form an alcohol ester.

The present invention also provides methods for producing alcohol esters of fatty acids during a fermentation process including: providing a fermentation medium comprising alcohol, fermentable carbon source, and free fatty acids; and contacting the fermentation medium with one or more enzymes capable of esterifying the free fatty acids with the alcohol whereby the free fatty acids are esterified with the alcohol to form alcohol esters of fatty acids. In some embodiments, the fermentable carbon source is derived from biomass. In some embodiments, the microorganism of the fermentation medium is a recombinant microorganism. In some embodiments, the alcohol is butanol and the alcohol esters of fatty acids are butyl esters of fatty acids.

In another embodiment, a method for producing a product alcohol may include providing a biomass feedstock including water, fermentable carbon source, and oil where the oil includes acyl glycerides; liquefying the biomass feedstock to create a liquefied biomass comprising oligosaccharides; contacting the biomass feedstock or the liquefied biomass with a composition comprising one or more enzymes capable of converting at least a portion of the acyl glycerides into free fatty acids whereby the free fatty acids form an extractant, the one or more enzymes also being capable of esterifying free fatty acids with product alcohol into alcohol esters of fatty acids; contacting the liquefied biomass with a saccharification enzyme capable of converting oligosaccharides into fermentable sugar; contacting the liquefied biomass with a recombinant microorganism capable of converting the fermentable sugar to product alcohol whereby a fermentation product comprising product alcohol is produced; contacting the product alcohol with the free fatty acids and the one or more enzymes so as to catalyze the esterification of the free fatty acids and the product alcohol to produce alcohol esters of fatty acids; and contacting the fermentation product with extractant. In embodiments, the contacting with extractant results in the formation of a two-phase mixture including an aqueous phase and an extractant phase and the alcohol esters of fatty acids partition into the extractant phase to form an ester-containing extractant phase. In some embodiments, the product alcohol is butanol and the alcohol esters of fatty acids are butyl esters of fatty acids.

In another embodiment, a method for producing a product alcohol may include providing a biomass feedstock including water, fermentable carbon source, and oil where the oil includes acyl glycerides; liquefying the biomass feedstock to create a liquefied biomass comprising oligosaccharides; contacting the liquefied biomass with a composition comprising one or more enzymes capable of converting at least a portion of the acyl glycerides into free fatty acids, the one or more enzymes also being capable of esterifying free fatty acids with product alcohol into alcohol esters of fatty acids; contacting the liquefied biomass with a saccharification enzyme capable of converting oligosaccharides into fermentable sugar; contacting the saccharified biomass with a recombinant microorganism capable of converting the fermentable sugar to product alcohol during fermentation whereby a fermentation medium comprising product alcohol is produced; contacting the fermentation medium during fermentation with a carboxylic acid extractant, where the fermentation medium comprises one or more enzymes capable of esterifying free fatty acids with product alcohol to form alcohol esters of fatty acids. In additional embodiments of this method, the fermentation medium is contacted with a carboxylic acid that is substantially insoluble in the fermentation medium and with a catalyst capable of esterifying the alcohol with the carboxylic acid to form an alcohol ester. In other embodiments of this method, the alcohol that is produced by the microorganism is butanol and the alcohol ester is butyl ester.

The present invention also provides a process to produce a product alcohol from a feedstock including: liquefying starch or a fermentable carbon source in a feedstock to create a slurry having oligosaccharides; centrifuging the feedstock slurry to produce a centrifuge product comprising (i) an aqueous layer comprising oligosaccharides, (ii) an oil layer, and (iii) solids; feeding the aqueous layer to a fermentation vessel containing a fermentation broth; and fermenting the aqueous layer to produce the product alcohol. The product alcohol is then contacted with the carboxylic acid and the catalyst whereby the carboxylic acid is esterified with the product alcohol to form the alcohol esters. In some embodiments, the oil is plant-derived oil. In other embodiments, the product alcohol is butanol and the alcohol esters of carboxylic acids are butyl esters of fatty acids.

In some embodiments, a method for producing a product alcohol includes providing a fractionated biomass feedstock including water, starch, and/or a fermentable carbon source, and only residual amounts of oil remaining after fractionation of the biomass, the residual oil including acyl glycerides;

liquefying the fractionated biomass feedstock to create a liquefied fractionated biomass comprising oligosaccharides; contacting the liquefied fractionated biomass with a composition comprising one or more enzymes capable of converting at least a portion of the residual acyl glycerides into free fatty acids, the one or more enzymes also being capable of esterifying free fatty acids with product alcohol to form alcohol esters of fatty acids; contacting the liquefied fractionated biomass with a saccharification enzyme capable of converting oligosaccharides into fermentable sugar; contacting the saccharified biomass with a recombinant microorganism capable of converting the fermentable sugar to product alcohol during fermentation whereby a fermentation medium comprising product alcohol is produced; contacting the fermentation medium during fermentation with a carboxylic acid extractant, where the fermentation medium comprises one or more enzymes capable of esterifying free fatty acids with product alcohol to form alcohol esters of fatty acids. In additional embodiments of this method, the fermentation medium is contacted with a carboxylic acid in the fermentation medium and with a catalyst capable of esterifying the alcohol with the carboxylic acid to form an alcohol ester. In a further embodiment, the carboxylic acid may be substantially insoluble in the fermentation medium. In other embodiments of this method, the alcohol that is produced by the microorganism is butanol and the alcohol ester is butyl ester.

The present invention also provides a composition including: a mash formed from biomass and including water and fermentable sugar; a catalyst capable of esterifying free fatty acids with alcohol into fatty acid alkyl esters and optionally capable of hydrolyzing acyl glycerides into free fatty acids; alcohol; free fatty acids; and fatty acid alcohol esters formed in situ from esterification of the free fatty acids with the alcohol by the catalyst. In some embodiments, the alcohol is butanol and the fatty acid alcohol esters are fatty acid butyl esters.

The present invention also provides a fermentation broth including: a recombinant microorganism capable of producing alcohol; a fermentable carbon source; and fatty acid alcohol esters, wherein the fatty acid alcohol esters are produced during the fermentation. In some embodiments, the recombinant microorganism is capable of producing butanol. In some embodiments, the fatty acid alcohol esters are fatty acid butyl esters. In some embodiments, the fermentable carbon source comprises sugar. In some embodiments, the fermentable carbon source comprises methane, the recombinant microorganism is capable of producing methanol, and the fatty acid alcohol esters are fatty acid methyl esters.

Also provided herein are recombinant yeast cells useful for production of product alcohols. In embodiments, the recombinant host cells disclosed herein can be any bacteria, yeast or fungi host useful for genetic modification and recombinant gene expression. In other embodiments, a recombinant host cell can be a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia*, or *Saccharomyces*. In other embodiments, the host cell can be *Saccharomyces cerevisiae, Schizosaccharomyces pombe, Kluyveromyces lactis, Kluyveromyces thermotolerans, Kluyveromyces marxianus, Candida glabrata, Candida albicans, Pichia stipitis, Yarrowia lipolytica, E. coli*, or *L. plantarum*. In still other embodiments, the host cell is a yeast host cell. In some embodiments, the host cell is a member of the genera *Saccharomyces*. In some embodiments, the host cell is *Kluyveromyces lactis, Candida glabrata* or *Schizosaccharomyces pombe*. In some embodiments, the host cell is *Saccharomyces cerevisiae. S. cerevisiae* yeast are known in the art and are available from a variety of sources, including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Gert Strand Prestige Turbo yeast, Ferm Pro™ yeast, Bio-Ferm® XR yeast, Gert Strand Distillers Yeast, FerMax™ Green yeast, FerMax™ Gold yeast, Thermosacc® yeast, BG-1, PE-2, CAT-1, CBS7959, CBS7960, and CBS7961.

Also provided are methods of producing isobutanol including: providing a recombinant host cell comprising an isobutanol biosynthetic pathway wherein at least one of the enzyme that catalyzes the substrate to product conversion α-ketoisovalerate to isobutyraldehyde or the enzyme that catalyzes the substrate to product conversion isobutyraldehyde to isobutanol are encoded by heterologous polynucleotides integrated into the chromosome; and contacting the recombinant host cell with a fermentable carbon source to form a fermentation broth under conditions whereby isobutanol is produced. In some embodiments, the methods further include: adding an extractant to form a two-phase mixture. In other embodiments, the extractant comprises a carboxylic acid. In some embodiments, the extractant comprises fatty acids. In other embodiments, the methods further include: adding an esterification enzyme capable of catalyzing the esterification of isobutanol with the carboxylic acid.

Also provided herein are methods including: providing a fermentation medium comprising product alcohol, water, fermentable carbon source, and a microorganism that produces the product alcohol; contacting the fermentation medium during fermentation with an extractant to form a two-phase mixture comprising an aqueous phase and an organic phase; and contacting the fermentation medium with a carboxylic acid and an enzyme capable of esterifying the carboxylic acid with the product alcohol. In some embodiments, the extractant comprises the carboxylic acid. In some embodiments, the carboxylic acid is produced by hydrolysis of oil from a biomass feedstock. In some embodiments, the fermentable carbon and the carboxylic acid are derived from the same biomass feedstock source. In some embodiments, the carboxylic acid comprises saturated, mono-unsaturated, poly-unsaturated carboxylic acids having 12 to 22 carbons, and mixtures thereof. In some embodiments, contacting the fermentation medium with an extractant and a carboxylic acid and an enzyme occur contemporaneously. In some embodiments, the microorganism is a genetically modified microorganism (e.g., a recombinant microorganism or host cell such as recombinant yeast cells).

Also provided herein are compositions comprising: PNY1504, PNY2205, or a recombinant host cell; an extractant; and optionally an esterification enzyme. Also provided herein are compositions comprising PNY1504, PNY2205, or a recombinant host cell and butyl ester.

Further provided herein are uses of PNY1504, PNY2205, or other recombinant yeast cells, and compositions comprising recombinant yeast cells for the production of isobutanol.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a catalyst for alcohol esterification is supplied to a fermentation vessel along with carboxylic acid and/or native oil.

FIG. 2 schematically illustrates an exemplary method and system of the present invention, in which native oil is converted into carboxylic acid using a catalyst, and the carboxylic acid and the catalyst are supplied to a fermentation vessel.

FIG. 3 schematically illustrates an exemplary method and system of the present invention, in which a liquefied biomass is contacted with a catalyst for lipid hydrolysis before fermentation.

FIG. 4 schematically illustrates an exemplary method and system of the present invention, in which a liquefied and saccharified biomass is contacted with a catalyst for lipid hydrolysis before fermentation.

FIG. 5 schematically illustrates an exemplary method and system of the present invention, in which an amount of lipids and undissolved solids are removed from a liquefied biomass before fermentation, and in which the removed lipids are converted into carboxylic acid using a catalyst, and the carboxylic acid and the catalyst are supplied to the fermentation vessel.

FIG. 6 shows the aqueous and solvent phase concentrations of isobutanol produced by fermentation with sucrose as a carbon source. Aqueous phase titer (Panel A) is reported in g/L and the solvent phase species (isobutanol, Panel B and isobutanol as FABE, Panel C. Panel D is the total isobutanol in the solvent phase) in weight percent.

DETAILED DESCRIPTION OF THE INVENTION

Figure 1:
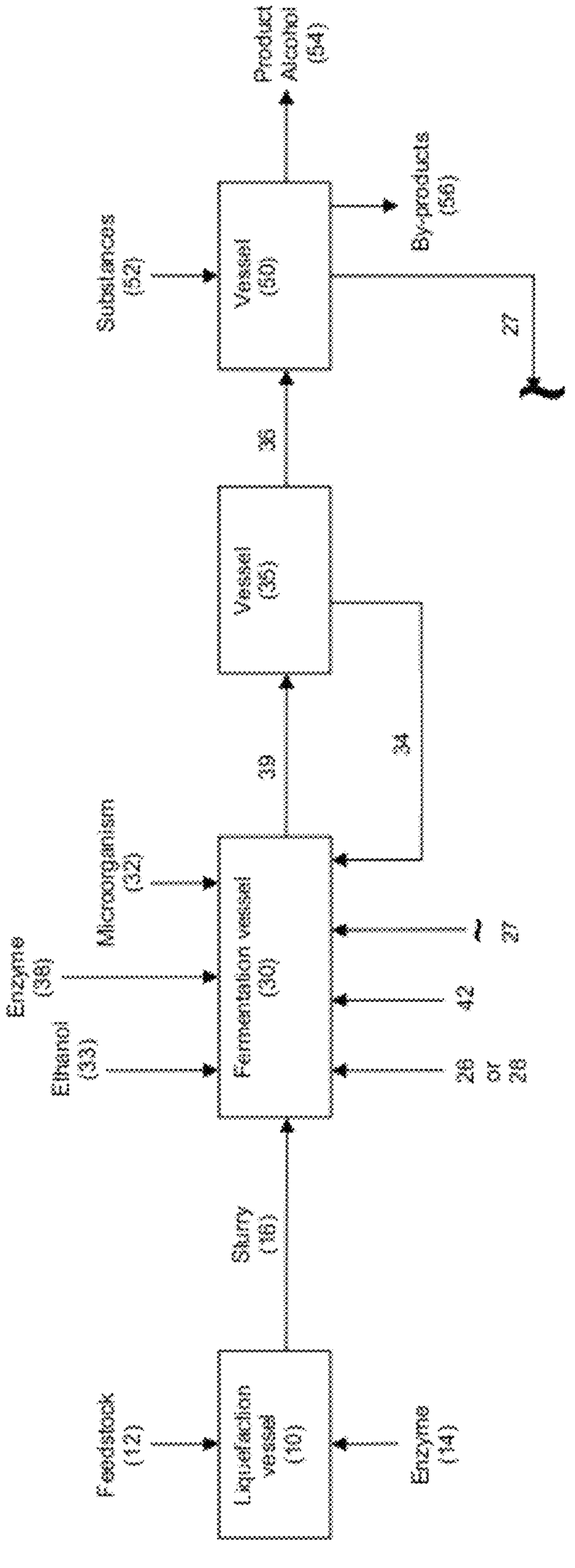

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

Unless otherwise specified, when the following abbreviations are used herein, they have the following meaning:

ADH alcohol dehydrogenase
ALS acetolactate synthase
AQ aqueous fraction
BuO-COFA butyl ester(s) of corn oil fatty acid(s)
CALB *Candida antarctica* lipase B
COFA corn oil fatty acid(s)
DDGS Dried Distillers' Grains with Solubles
DG diglyceride(s)
DHAD dihydroxyacid dehydratase
EOR end of run
EtOH ethanol
EtO-COFA ethyl ester(s) of corn oil fatty acid(s)
FABE fatty acid butyl ester(s)
FAEE fatty acid ethyl ester(s)
FAME fatty acid methyl ester(s)
FFA free fatty acid(s)
FOA fluoro-orotic acid
HADH horse liver alcohol dehydrogenase
IBA isobutanol
i-BuOH isobutanol
i-BuO-COFA isobutyl ester(s) of corn oil fatty acid(s)
i-BuO-oleate iso-butyl oleate
i-PrOH isopropanol
i-PrO-COFA isopropyl ester(s) of corn oil fatty acid(s)
ISPR in situ product removal
KARI ketol-acid reductoisomerase
KivD ketoisovalerate decarboxylase
MAG monoacylglyceride(s)
MeBOH 2-methyl-1-butanol
MeBO-COFA 2-methyl-1-butyl ester(s) of corn oil fatty acid(s)
MeOH methanol
MeO-COFA methyl ester(s) of corn oil fatty acid(s)
MG monoglyceride(s)
n-BuOH n-butanol
OA oleyl alcohol
ORG organic fraction
PenOH 1-pentanol
PenO-COFA 1-pentyl ester(s) of corn oil fatty acid(s)
PrOH 1-propanol
PrO-COFA 1-propyl ester(s) of corn oil fatty acid(s)
SOFA soya oil fatty acids
SSF simultaneous saccharification and fermentation
t-BuOH tert-butyl alcohol
TG triglyceride(s)
3M3P 3-Me-3-pentanol In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. Particularly useful is a low ammonia pretreatment as disclosed U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Biomass yield" as used herein refers to the grams of biomass produced (i.e., cell biomass production) per gram of carbon substrate produced.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Fermentation medium" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation broth" and "fermented mixture" can be used synonymously with "fermentation medium."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten. For example, the non-fermentable portions of feedstock include the portion of feedstock that remains as solids and can absorb liquid from the fermentation broth.

Dried Distillers' Grains with Solubles (DDGS) as used herein refers to a co-product or by-product from a fermentation of a feedstock or biomass (e.g., fermentation of grain or grain mixture that produces a product alcohol). In some embodiments, DDGS may also refer to an animal feed product produced from a process of making a product alcohol (e.g., butanol, isobutanol, etc.).

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (i-BuOH), 2-butanol (2-BuOH), tert-butanol (t-BuOH), and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butyl ester in either the organic or aqueous phase.

The term "effective rate" as used herein is the effective titer divided by the fermentation time.

The term "effective yield" as used herein is the total grams of product alcohol produced per gram of glucose consumed.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COOH in which a carbon atom is bonded to an oxygen atom by a double bond to make a carbonyl group (—C═O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated.

The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

The term "butanol biosynthetic pathway" as used herein refers to an enzyme pathway to produce 1-butanol, 2-butanol, or isobutanol.

The term "1-butanol biosynthetic pathway" as used herein refers to an enzyme pathway to produce 1-butanol from acetyl-coenzyme A (acetyl-CoA).

The term "2-butanol biosynthetic pathway" as used herein refers to an enzyme pathway to produce 2-butanol from pyruvate.

The term "isobutanol biosynthetic pathway" as used herein refers to an enzyme pathway to produce isobutanol from pyruvate.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene (i.e., it is modified from its native state or is from another source) comprising regulatory and coding sequences that are not found together in nature. Accordingly, a chimeric gene may comprise regulatory sequences and coding sequences that are derived from different sources or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found as a native gene in the host organism, but that is introduced into the host organism by gene transfer. Foreign genes can comprise native genes inserted into a non-native organism or chimeric genes.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site, and stem-loop structure.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Codon optimization is within the ordinary skill in the art.

The term "polynucleotide" is intended to encompass a singular nucleic acid as well as plural nucleic acids, and refers to a nucleic acid molecule or construct, for example, messenger RNA (mRNA) or plasmid DNA (pDNA). As used herein, a "gene" is a polynucleotide. A polynucleotide can contain the nucleotide sequence of the full-length cDNA sequence or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA (e.g., heterologous DNA). For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment having dihydroxyacid dehydratase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA, or synthetic DNA.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposes of the invention, as are native or recombinant polypeptides which have been separated, fractionated, or partially or substantially purified by any suitable technique.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention satisfies the need for alternative extractive fermentation methods which do not necessitate the partitioning of the product alcohol between the fermentation medium and the ISPR extractant as a means to reduce the toxic effect of the product alcohol (such as butanol) on the microorganism. It also satisfies the need to reduce the degradation of the partition coefficient of a fermentation product ISPR extractant by providing methods for producing alcohol such as butanol in which the product alcohol is converted into alcohol esters which can be less toxic to the microorganism and where there is realized a concomitant reduction in the degradation of the partition coefficient of a fermentation product extractant, resulting in improved production yields of alcohol (as a combination of free alcohol and alcohol esters that can be converted back to alcohol after separation from the fermentation medium). Moreover, the present invention offers solutions to disadvantages of alternative alcohol product removal processes such that the methods herein can be combined with existing processes (e.g., solids removal) to provide increased product removal at economic and environmental advantage. As such, the present invention provides further related advantages, as will be made apparent by the description of the embodiments that follow.

The present invention provides methods for removing alcohol from a fermentation medium by esterifying the alcohol with carboxylic acid and extracting the resulting alcohol ester from the fermentation medium, whereafter the alcohol can be recovered from the alcohol ester. The acid may be added to the fermentation medium directly as free fatty acid or may be derived from oil. The present invention also provides methods for removing or reducing oil from an alcohol fermentation process by hydrolyzing the oil derived from a feedstock into carboxylic acid which can be used for the esterification of alcohol and/or serve as an ISPR extractant or a component of the ISPR extractant for extracting the alcohol ester.

Decreasing the amount of water present in a reaction system, or employing a reaction system that uses only one or more non-aqueous solvents, has typically been necessary for esterification of alcohols by carboxylic acids when catalyzed by enzymes such as lipases. Described herein is the surprising finding that lipase enzymes can efficiently catalyze the esterification of a product alcohol with a carboxylic acid during fermentation of a fermentable carbon source to produce product alcohol. Also described herein is the surprising finding that esterification of a product alcohol with a carboxylic acid during a fermentation can provide improvements in the fermentation performance. For example, by capturing the product alcohol (e.g., butanol) as produced in ester form it effectively reduces the concentration of the product alcohol in the aqueous phase and thus, mitigates the toxic effects of the product alcohol on glucose consumption and product production.

The present invention will be described with reference to the Figures. FIG. 1 illustrates an exemplary process flow diagram for production of fermentative alcohol such as ethanol or butanol, according to an embodiment of the present invention. As shown, a feedstock 12 can be introduced to an inlet in a liquefaction vessel 10 and liquefied to produce a feedstock slurry 16. Feedstock 12 contains hydrolysable polysaccharides that supplies a fermentable carbon substrate (e.g., fermentable sugar such as glucose), and can be a biomass such as, but not limited to, rye, wheat, cane or corn, or can otherwise be derived from a biomass. In some embodiments, feedstock 12 can be one or more components of a fractionated biomass, and in other embodiments, feedstock 12 can be a milled, unfractionated biomass. In some embodiments, feedstock 12 can be corn, such as dry milled, unfractionated corn kernels, and the undissolved particles can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. Furthermore, as one skilled in the art can appreciate, maximizing feedstock content (e.g., corn content) can maximize sugar content as well as product titer. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides free fatty acids having a high oleic acid content for contacting with a fermentation broth.

The process of liquefying feedstock 12 involves hydrolysis of polysaccharides in feedstock 12 into sugars including, for example, dextrins and oligosaccharides, and is a conventional process. Any known liquefying processes as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to free fatty acids.

Feedstock slurry 16 produced from liquefying feedstock 12 comprises fermentable carbon substrate (e.g., sugar), oil, and undissolved solids derived from the feedstock. Feedstock slurry 16 can be discharged from an outlet of liquefaction vessel 10. In some embodiments, feedstock 12 is corn or corn kernels and therefore, feedstock slurry 16 is a corn mash slurry. In some embodiments, feedstock 12 is a lignocellulosic feedstock and therefore, feedstock slurry 16 may be a lignocellulosic hydrolysate. In some embodiments, feedstock 12 is sugar cane.

Feedstock slurry 16 is introduced into a fermentation vessel 30 along with a microorganism 32. Fermentation vessel 30 is configured to ferment slurry 16 to produce alcohol. In particular, microorganism 32 metabolizes the fermentable sugar in slurry 16 and excretes a product alcohol. Microorganism 32 is selected from the group of bacteria, cyanobacteria, filamentous fungi, and yeasts. In some embodiments, microorganism 32 can be a bacteria such as *E. coli*. In some embodiments, microorganism 32 can be a fermentative recombinant microorganism. The slurry can include sugar, for example, in the form of oligosaccharides, and water, and in some embodiments, can comprise less than about 20 g/L of monomeric glucose, less than about 10 g/L, or less than about 5 g/L of monomeric glucose. Suitable methodology to determine the amount of monomeric glucose is well known in the art. Such suitable methods known in the art include HPLC.

In some embodiments, slurry 16 is subjected to a saccharification process in order to break the complex sugars (e.g., oligosaccharides) in slurry 16 into monosaccharides that can be readily metabolized by microorganism 32. Any known saccharification process, normally utilized by the industry can be used including, but not limited to, the acid process, the acid-enzyme process, or the enzyme process. In some embodiments, simultaneous saccharification and fermentation (SSF) can occur inside fermentation vessel 30 as shown in FIG. 1. In some embodiments, an enzyme 38 such as glucoamylase, can be introduced to an inlet in fermentation vessel 30 in order to breakdown the starch or oligosaccharides to glucose capable of being metabolized by microorganism 32.

Carboxylic acid 28 and/or native oil 26 are introduced into fermentation vessel 30, along with a catalyst 42. Catalyst 42 can be introduced before, after, or contemporaneously with enzyme 38. Thus, in some embodiments, addition of enzyme 38 and catalyst 42 can be stepwise (e.g., catalyst 42, then enzyme 38, or vice versa) or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes). Catalyst 42 is capable of esterifying the product alcohol with carboxylic acid 28 to form an alcohol ester. For example, in the case of butanol production, catalyst 42 is capable of esterifying butanol with carboxylic acid 28 to form a butyl ester.

In the instance that native oil 26 is supplied to fermentation vessel 30, at least a portion of the acyl glycerides in oil 26 can be hydrolyzed to carboxylic acid 28 by contacting oil 26 with catalyst 42. The resulting acid/oil composition from hydrolyzing oil 26 is typically at least about 17 wt % carboxylic acid 28 (as free fatty acids). In some embodiments, the resulting acid/oil composition from hydrolyzing oil 26 is at least about 20 wt % carboxylic acid, at least about 25 wt % carboxylic acid, at least about 30 wt % carboxylic acid, at least about 35 wt % carboxylic acid, at least about 40 wt % carboxylic acid, at least about 45 wt % carboxylic acid, at least about 50 wt % carboxylic acid, at least about 55 wt % carboxylic acid, at least about 60 wt % carboxylic acid, at least about 65 wt % carboxylic acid, at least about 70 wt % carboxylic acid, at least about 75 wt % carboxylic acid, at least about 80 wt % carboxylic acid, at least about 85 wt % carboxylic acid, at least about 90 wt % carboxylic acid, at least about 95 wt % carboxylic acid, or at least about 99 wt % carboxylic acid. In some embodiments, the resulting acid/oil composition includes monoglycerides and/or diglycerides from the partial hydrolysis of the acyl glycerides in the oil. In some embodiments, the resulting acid/oil composition includes glycerol, a by-product of acyl glyceride hydrolysis. In some additional embodiments, the resulting acid/oil composition includes lysophospholipids from the partial hydrolysis of phospholipids in the oil.

In some embodiments, after hydrolysis of the acyl glycerides in oil 26, the remaining acyl glycerides from oil 26 are from about 0 wt % to at least about 2 wt % of the fermentation broth composition. In some additional embodiments, after hydrolysis of the acyl glycerides in oil 26, the remaining acyl glycerides from oil 26 are at least about 0.5 wt % of the fermentation broth composition. Thus, in some embodiments, the acyl glycerides from oil 26 can be catalytically hydrolyzed to carboxylic acid 28 using catalyst 42, and catalyst 42 can also esterify carboxylic acid 28 with the product alcohol. In some embodiments, a second catalyst (not shown) can be introduced to the fermentation vessel for hydrolysis of the acyl glycerides. In addition, the acyl glycerides in the oil derived from feedstock 12 and present in slurry 16 can also be hydrolyzed to carboxylic acid 28' (see, e.g., the embodiment of FIG. 3). In some embodiments, the concentration of the carboxylic acid (such as fatty acid) in the fermentation vessel exceeds the solubility limit in the aqueous phase and results in the production a two-phase fermentation mixture comprising an organic phase and an aqueous phase. In some embodiments, the concentration of carboxylic acids in the fermentation broth is typically not greater than about 0.8 g/L and is limited by the solubility of the carboxylic acid in the broth.

In some embodiments, catalyst 42 and the second catalyst, if used, can be one or more enzymes, for example, lipase enzymes. In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus coagulans, Bacillus pumilus, Bacillus strearothermophilus, Bacillus subtilis, Brochothrix thermosohata, Candida cylindracea* (*Candida rugosa*), *Candida paralipolytica, Candida antarctica* lipase A, *Candida antarctica* lipase B, *Candida emobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. *thermoidea, Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei*, and *Yarrowia lipolytica*. In a further preferred aspect, the lipase is selected from the group consisting of *Thermomcyces lanuginosus* lipase, *Aspergillus* sp. lipase, *Aspergillus niger* lipase, *Aspergillus tubingensis* lipase, *Candida antarctica* lipase B, *Pseudomonas* sp. lipase, *Penicillium roqueforti* lipase, *Penicillium camembertii* lipase, *Mucor javanicus* lipase, *Burkholderia cepacia* lipase, *Alcaligenes* sp. lipase, *Candida rugosa* lipase, *Candida parapsilosis* lipase, *Candida deformans* lipase, lipases A and B from *Geotrichum candidum, Neurospora crassa* lipase, *Nectria haematococca* lipase, *Fusarium heterosporum* lipase *Rhizopus delemar* lipase, *Rhizomucor miehei* lipase, *Rhizopus arrhizus* lipase, and *Rhizopus oryzae* lipase. Suitable commercial lipase preparations suitable as catalyst 42 include, but are not limited to, Lipolase® 100 L, Lipex® 100L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei*, hog pancreas, *Candida cylindracea, Candida rugosa, Rhizopus niveus, Candida antarctica, Rhizopus arrhizus* or *Aspergillus* available from SigmaAldrich. In one embodiment, the lipase may be thermostable and/or thermotolerant, and/or solvent tolerant.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term “phospholipase” encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase A1 or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof.

The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase AI (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and 1-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

An alcohol (e.g., butanol) that is produced by fermentation of one or more fermentable sugars may be converted to a carboxylic acid ester by an enzyme-catalyzed reaction where the carboxylic acid is esterified with the alcohol. Enzymes such as lipase, phospholipase, and lysophospholipase may catalyzed this reaction; however, these enzymes may be inactivated due to one or more factors including, but not limited to, hydrodynamic shear or inactivation at gas-liquid and liquid-liquid interfaces. In fermentations where oligosaccharides are additionally converted to one or more fermentable sugars, the enzyme that converts oligosaccharides to fermentable sugars (e.g., glucoamylase) may also be inactivated by one or more of these same factors.

Inactivation of enzymes at a gas-liquid interface (e.g., may occur at the interface of bubbles with the fermentation broth) that results from aeration of the fermentation broth and/or is produced by the evolution of gaseous carbon dioxide in the broth during fermentation of one or more fermentable sugars, is well-known in the art. Inactivation of Hen egg white lysozyme and *Thermomyces lanuginosus* lipase produced in *Aspergillus oryzae* (Novozymes Lipolase®) was observed at the gas-liquid interface in three different reactor configurations: bubble column, stirred vessel with baffles (with no aeration by gas sparging), and falling film (Ghadge, et al., Chem. Eng. Sci. 58:5125-5134, 2003). The mechanism of inactivation of *Thermomyces lanuginosus* lipase (produced in *Aspergillus oryzae*; Novozymes Lipolase 100L®) at the gas-liquid interface in a baffled stirred-tank reactor (with no aeration by gas sparging) has been reported (Patil, et al., AlChE J. 46:1280-1283, 2000).

Stahmann, et al. (Eur. J. Biochem. 244:220-225, 1997) have reported that *Ashbya gossypii* lipase was inactivated within minutes in stirred gas/water, trioleoylglycerol/water or oleic acid/water mixtures, due to interfacial inactivation at either a gas/liquid or liquid/liquid interface. Elias, et al. (Adv. Biochem. Engineering/Biotechnology 59:47-71, 1998) have reported that: (i) some enzymes are inactivated by hydrodynamic shear even in the absence of a gas-liquid interface; (ii) for enzymes that are inactivated by hydrodynamic shear, the rate of inactivation increases in the presence of gas-liquid interface; (iii) some enzymes are not inactivated in the absence of gas-liquid interface regardless of the applied hydrodynamic shear; and (iv) for enzymes that require a gas-liquid interface for inactivation, the rate of inactivation increases with an increase in hydrodynamic shear. Ross, et al. (J. Mol. Catal. B: Enzymatic 8:183-192, 2000) have described the interfacial inactivation of α-chymotrypsin, β-chymotrypsin, papain, and pig liver esterase in a variety of aqueous/organic solvent mixtures by passing solvent droplets up through an aqueous enzyme solution in a bubble column apparatus. The kinetics and mechanism of shear inactivation of *Candida cylindracea* lipase in a stirred tank reactor has also been reported, where the mechanism of inactivation was found to be due to a shear-induced gas-liquid interface effect (Lee, et al., Biotechnol. Bioeng. 33:183-190, 1989).

Under the fermentation conditions employed in some methods described herein, hydrodynamic shear and gas-liquid and liquid-liquid interfaces are each present over the course of the fermentation, and capable of causing enzyme inactivation. The potential effect of each of these factors on the stability and activity of one or more of the enzymes (e.g., glucoamylase, lipase, phospholipase, and lysophospholipase) present in the two-phase mixture (e.g., fermentation broth and carboxylic acid) during fermentation under the conditions described herein could not have been anticipated based on the prior art. Although each of these factors could have resulted in the inactivation of one or more enzymes in the fermentation mixture, sufficient enzyme activity to catalyze esterification of the product alcohol by carboxylic acid to produce carboxylic acid esters was maintained over the course of the fermentation. In reactions where glucoamylase was also present in the two-phase fermentation mixture of fermentation broth and carboxylic acid, sufficient enzyme activity (i.e., to convert oligosaccharide to fermentable sugars) was also maintained.

Carboxylic acid 28 can be any carboxylic acid capable of esterifying with a product alcohol such as butanol or ethanol, to produce an alcohol ester of the carboxylic acid. For example, in some embodiments, carboxylic acid 28 can be free fatty acid, and in some embodiments, the carboxylic acid or free fatty acid has 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, carboxylic acid 28 is one or more of the following fatty acids: azaleic, capric, caprylic, castor, coconut (i.e., as a naturally-occurring combination of fatty acids including lauric, myrisitic, palmitic, caprylic, capric, stearic, caproic, arachidic, oleic, and linoleic, for example), isostearic, lauric, linseed, myristic, oleic, palm oil, palmitic, palm kernel, pelargonic, ricinoleic, sebacic, soya, stearic acid, tall oil, tallow, and #12 hydroxy stearic. In some embodiments, carboxylic acid 28 is one or more of diacids.

In some embodiments, carboxylic acid 28 can be a mixture of two or more different fatty acids. In some embodiments, carboxylic acid 28 comprises free fatty acid derived from hydrolysis of acyl glycerides by any method known in the art including chemical or enzymatic hydrolysis. In some embodiments as noted above, carboxylic acid 28 can be derived from native oil 26 by enzymatic hydrolysis of the oil glycerides using an enzyme as catalyst 42. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations. In some embodiments, stabilizers may be utilized to mitigate the degradation of carboxylic acid(s).

In some embodiments, native oil 26 can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, pumpkin, grape seed, and vegetable oil blends (or oils that can be purified into higher concentrations of different chain length and levels of unsaturation (i.e., 18:1)). In some embodiments, native oil 26 is a mixture of two or more native oils such as a mixture of palm and soybean oils, for example. In some embodiments, native oil 26 is a plant-derived oil. In some embodiments, the plant-derived oil can be, though not necessarily, derived from biomass that can be used in a fermentation process. The biomass can be the same or different source from which feedstock 12 is obtained. Thus, for example, in some embodiments, oil 26 can be derived from corn, whereas feedstock 12 can be cane. For example, in some embodiments, oil 26 can be derived from corn, and the biomass source of feedstock 12 is also corn. Any possible combination of different biomass sources for oil 26 versus feedstock 12 can be used, as should be apparent to one of skill in the art. In some embodiments, oil 26 is derived from the biomass used in the fermentation process. Thus, in some embodiments, as later described with reference to FIG. 3, oil 26 is derived directly from feedstock 12 as oil 26'. For example, when feedstock 12 is corn, then oil 26' is the feedstock's constituent corn oil.

In other embodiments, carboxylic acid 28 may comprise one or more of the following carboxylic acids: formic acid, acetic acid, lactic acid, propionic acid, butyric acid, valeric acid, caproic acid, oxalic acid, malonic acid, malic acid, succinic acid, maleic acid, fumaric acid, tartaric acid, oxaloacetic acid, citric acid, benzoic acid, salicyclic acid, toluic acid, phthalic acid as well as other dicarboxylic acids, tricarboxylic acids, and aromatic carboxylic acids, and mixtures thereof. In one embodiment, the concentration of the one or more carboxylic acids is in a range or ranges that is biocompatible with microorganism 32. In another embodiment, the concentration of the one or more carboxylic acids is in a range or ranges that is compatible with catalyst(s) and/or enzyme(s) of the claimed methods.

Optionally, ethanol 33 may be supplied to fermentation vessel 30 to be included in the fermentation broth. In some embodiments, when a recombinant microorganism having a butanol biosynthetic pathway and/or reduced or eliminated expression of pyruvate decarboxylase is used as microorganism 32, microorganism 32 may require supplementation of a 2-carbon substrate, for example, ethanol, for survival and growth. Thus, in some embodiments, ethanol 33 may be supplied to fermentation vessel 30.

However, it has been surprisingly found that methods of the present invention, in which carboxylic acid such as fatty acid, is present in the fermentation vessel, can allow reduction of the amount of ethanol 33 typically supplied for a given recombinant microorganism without detriment to the vitality of the recombinant microorganism. Further, in some embodiments of the methods of the present invention, the alcohol (e.g., butanol) production rate without ethanol supplementation can be comparable with the production rate that can be realized when ethanol 33 is supplemented. As further demonstrated by the comparative examples presented in the Examples 1-14 below, the butanol production rate when fatty acid but not ethanol is in the fermentation vessel can be comparable to or greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation or other alcohol fermentation that employs a microorganism that may require supplementation of a 2-carbon substrate to survive and grow.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which free fatty acids are produced at a step in the process and are contacted with microorganism cultures in a fermentation vessel for improving microorganism growth rate and glucose consumption are described in co-pending, commonly owned U.S. Provisional Application Ser. No. 61/368,451, filed on Jul. 28, 2010, which is incorporated herein in its entirety by reference thereto.

In fermentation vessel 30, alcohol produced by microorganism 32 is esterified with carboxylic acid 28 using catalyst 42 to form alcohol esters. For example, in the case of butanol production, butanol produced by microorganism 32 is esterified with carboxylic acid 28 using catalyst 42 to form butyl esters. In situ product removal (ISPR) can be utilized to remove the alcohol esters from the fermentation broth. As demonstrated herein, using catalyst to form esters in conjunction with ISPR can improve the performance of the fermentation. In some embodiments, using catalyst to form esters in conjunction with ISPR (such as, for example, liquid-liquid extraction) can increase the effective titer by at least about 10%, at least about 20%, at least about 30%, at least about 40%, at least about 50%, at least about 60%, at least about 70%, at least about 80%, at least about 90%, or at least about 100% as compared to the effective titer in an analogous fermentation using ISPR without a catalyst forming esters. Similarly, in some embodiments, using a catalyst to form esters in conjunction with ISPR (such as, for example, liquid-liquid extraction) can increase the effective rate by at least about 10%, at least about 20%, at least about 30%, at least about 40%, at least about 50%, at least about 60%, at least about 70%, at least about 80%, at least about 90%, or at least about 100% as compared to the effective rate in an analogous fermentation using ISPR without a catalyst forming esters (see, e.g., Examples 9 and 11-14, Table 3). In some embodiments, the effective yield is increased by at least about 10%, at least about 20%, at least about 30%, at least about 40%, or at least about 50%. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. In some embodiments, the ratio of alcohol ester to alcohol in the fermentation vessel may be about 1:1. In some embodiments, at least about 20%, at least about 30%, at least about 40%, at least about 50%, at least about 60%, at least about 70%, at least about 80%, or at least about 90% of the effective titer of alcohol is converted to alcohol ester.

In some embodiments, a grain load on water at a sufficient concentration to achieve a final effective titer of at least about 50 g/L, at least about 75 g/L, or at least about 100 g/L may be used in a grain mash fermentation comprising a microorganism capable of producing an alcohol such as butanol. In other embodiments, the grain mash fermentation may use simultaneous saccharification and fermentation (SSF), and the concentration of glucose may remain relatively low, for example, at least about 75 g/L glucose in the fermentation broth phase over the course of the fermentation.

In some embodiments, fatty acids may be added to the fermentor in an amount that is less than about 70% of the volume of the fermentor, less than about 50% of the volume of the fermentor, or less than about 30% of the volume of the fermentor. The amount of fatty acid added to the fermentor may be a means to maintain the aqueous phase titer of butanol during fermentation. In other embodiments, the aqueous phase titer of butanol may be maintained at a level less than about 35 g/L of fermentation broth, less than about 25 g/L of fermentation broth, or less than about 20 g/L of fermentation broth. In other embodiments, the amount of active esterification enzyme in the fermentation broth may be less than about 100 ppm, less than about 50 ppm, or less than about 10 ppm active enzyme. In some embodiments, the cell mass employed in a fermentation broth may be less than about 50 g dcw/L, less than about 20 g dcw/L, or less than about 10 g dcw/L. In other embodiments, the fermentation process may run at least about 30 hours to at least about 100 hours, at least about 40 hours to at least about 80 hours, or at least about 50 hours to at least about 70 hours.

In some embodiments, a brix on water at a sufficient concentration to achieve a final effective titer of at least about 30 g of butanol per liter of fermentation broth phase, at least about 45 g of butanol per liter of fermentation broth phase, or at least about 60 g of butanol per liter of fermentation broth phase may be used in a sugarcane fermentation comprising a microorganism capable of producing butanol. In some embodiments, fatty acids may be added to the fermentor in an amount that is less than about 70% of the volume of the fermentor, less than about 50% of the volume of the fermentor, or less than about 30% of the volume of the fermentor. The amount of fatty acid added to the fermentor may be a means to maintain the aqueous phase titer of butanol during fermentation. In other embodiments, the aqueous phase titer of butanol may be maintained at a level less than about 35 g/L of fermentation broth, less than about 25 g/L of fermentation broth, or less than about 15 g/L of fermentation broth. In other embodiments, the amount of active esterification enzyme in the fermentation broth may be less than about 200 ppm, less than about 100 ppm, or less than about 20 ppm active enzyme. In some embodiments, the cell mass employed in a fermentation broth may initially be at least about 100 g of cell per liter of broth in the initial charge occupying at least about 30% of the fermentor volume. After 3-7 hours of fermentation, the cell mass may be diluted to at least about 25 g of cell per liter of fermentation broth by the addition of a sugarcane feed. The cells may continue to grow to at least about 30 g of cell per liter of fermentation broth over the 8 to 15 hours of total fermentation time.

In some embodiments, the fermentation broth is contacted during fermentation with an extractant to form a two-phase mixture comprising an aqueous phase and an organic phase. In such embodiments, ISPR including liquid-liquid extraction may be conveniently carried out. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, and mixtures thereof. For use with the processes described herein, the extractant(s) for ISPR are typically non-alcohol extractants, so as to avoid consuming carboxylic acid 28 in fermentation vessel 30 by catalytic esterification of carboxylic acid 28 with an alcohol extractant, whereby less carboxylic acid would be available for esterification with the product alcohol. For example, if oleyl alcohol is used as an ISPR extractant, then oleyl alcohol esters of the carboxylic acid can be produced in fermentation vessel due to the presence of active catalyst 42, as further demonstrated in the Example 24 below.

With reference to the embodiment of FIG. 1, the carboxylic acid 28 can also serve as an ISPR extractant 28 or a component thereof. As earlier noted, carboxylic acid 28 can be supplied, and/or formed in situ in the case when native oil 26 is supplied to fermentation vessel 30, and/or formed in situ in the case when feedstock 16 includes oil that can be hydrolyzed. In some embodiments, ISPR extractant 28 includes free fatty acids. In some embodiments, ISPR extractant 28 includes corn oil fatty acids (COFA). In some embodiments, oil 26 is corn oil, whereby ISPR extractant 28 is COFA. In some embodiment, COFA may be pretreated to remove degradation products (e.g., hydrogenation, distillation, and/or urea treatment to remove saturated acids). COFA may be ISPR extractant (carboxylic acid) 28 contacts the fermentation broth and forms a two-phase mixture comprising an aqueous phase 34 and an organic phase. The product alcohol ester formed in the fermentation vessel preferentially partitions into the organic phase to form an ester-containing organic phase 36. That is, the product alcohol esters are produced at a concentration in excess of the equilibrium concentration of alcohol ester present in the aqueous phase 34 and therefore, preferentially partition into the organic phase. Any free product alcohol in the fermentation broth also preferentially partitions into the ester-containing organic phase. The biphasic mixture can be removed from fermentation vessel 30 as stream 39 and introduced into a vessel 35, in which the ester-containing organic phase 36 is separated from aqueous phase 34. Separation of biphasic mixture 39 into ester-containing organic phase 36 and aqueous phase 34 can be achieved using any methods known in the art, including but not limited to, siphoning, aspiration, decantation, centrifugation, using a gravity settler, membrane-assisted phase splitting, hydroclyclone, and the like. All or part of aqueous phase 34 can be recycled into fermentation vessel 30 as fermentation medium (as shown), or otherwise discarded and replaced with fresh medium, or treated for the removal of any remaining product alcohol and then recycled to fermentation vessel 30.

With reference to FIG. 1, ester-containing organic phase 36 is introduced into vessel 50 in which the alcohol esters are reacted with one or more substances 52 to recover product alcohol 54. Product alcohol 54 can be recovered using any method known in the art for obtaining an alcohol from an alcohol ester. For example, in some embodiments, the product alcohol can be recovered from the alcohol ester by hydrolysis with base followed by acidification. In other embodiments the product alcohol esters can be hydrolyzed by water in the presence of a hydrolysis catalyst as substance 52. For example, in some embodiments, hydrolysis of the product alcohol esters to alcohol and carboxylic acid 28 (e.g., fatty acid when carboxylic acid 28 is a fatty acid) can be achieved using a lipase, a water soluble acid, an inorganic acid, an organic acid, or a solid acid catalyst as substance 52. For example, sulfuric acid can be used as an inorganic acid catalyst for alcohol ester hydrolysis. In some embodiments, the product alcohol can be recovered from the alcohol ester by transesterification with glycerol to make acylglycerols. Some suitable hydrolysis catalysts are lipase enzymes; esterase enzymes; inorganic acids such as sulfuric acid, hydrochloric acid, phosphoric acid, or strong inorganic acids; organic acids such as toluenesulfonic acid, naphthalenesulfonic acid, or strong organic acids; solid acid catalysts such as Amberlyst® sulfonated polystyrene resins, or zeolites; bases such as potassium hydroxide, sodium hydroxide, calcium hydroxide, or strong bases. Additional suitable hydrolysis catalysts include calcium stearate, calcium oleate, zinc stearate, zinc oleate (which may be formed in situ by adding calcium oxide, calcium hydroxide, zinc oxide, or zinc hydroxide, respectively, to the reaction) as well as other water insoluble fatty acid salts and multi-valent metal oxides. In some embodiments, hydrolysis of the alcohol esters can be achieved using steam as substance 52, by increasing temperature, and/or by application of pressure. In some embodiments, hydrolysis of the alcohol esters can be carried out in a column, for example, a reactive distillation column. Examples 45 to 54 and 56 to 58 demonstrate several methods to recover the product alcohol from an alcohol ester. In some embodiments, by-products 56 are obtained from recovering product alcohol 54. By-products 56 do not include carboxylic acid 28 that can be recovered from hydrolysis of the alcohol esters. Example 67 demonstrates the recovery of product alcohol using irreversible base hydrolysis. Suitable bases include, but are not limited to, sodium hydroxide, potassium hydroxide, calcium hydroxide, and sodium carbonate. The base hydrolysis generates the cation salt of the fatty acid, for example, the potassium or sodium salt of the corn oil fatty acid. This process may require neutralization with acid to return the fatty acid to acid form. Suitable acids for this neutralization include, but are not limited to, sulfuric acid, hydrochloric acid, and nitric acid.

In some embodiments, hydrolysis of the alcohol esters of fatty acids present in the ester-containing organic phase 36 into the product alcohol and free fatty acids occurs at a fatty acid to water ratio from about 10:1 to about 1:10 or in other embodiments, at a fatty acid to water ratio from about 100:1 to about 1:100. In some embodiments, the alcohol esters of fatty acids are hydrolyzed with water at a temperature less than about 100° C. In some embodiments, the hydrolysis occurs at a temperature greater than 100° C., greater than 150° C., greater than 200° C., or greater than 250° C.

For example, in some embodiments, the alcohol esters can be transesterified to produce product alcohol 54 and in some embodiments, a second alcohol ester 56, for example, fatty acid alkyl esters, can also be produced as by-product 56. To achieve such transesterification, the alcohol esters can be contacted with catalysts capable of transesterifying the alcohol esters to release butanol. In some embodiments, the alcohol esters can be transesterified using glycerol to produce product alcohol 54 and acyl glycerides as by-product 56. The acyl glycerides produced may comprise mono- and diacylglycerides. Some suitable catalysts for transesterification reactions are, for example, lipase enzymes, alkoxide salts particularly of the second alcohol, alkyl titanates, soluble inorganic acids such as sulfuric acid and phosphoric acid, soluble organic acids such as toluenesulfonic acid and naphthalenesulfonic acid, and solid acids such as Amberlyst® sulfonated polystyrene resins, or zeolites. Suitable lipases for transesterifications or hydrolysis include, but are not limited to, lipases derived from *Burkholderia cepacia, Thermomyces lanuginosa*, or *Candida antarctica*. In some embodiments, the lipases are immobilized on a soluble or insoluble support using methods well-known to those skilled in the art (see, e.g., Immobilization of Enzymes and Cells; Gordon F. Bickerstaff, Editor; Humana Press, Totowa, N.J., USA, 1997). The immobilization of enzymes may be performed using a variety of techniques including 1) binding of the enzyme to a porous or non-porous carrier support, via covalent support, physical adsorption, electrostatic binding, or affinity binding; 2) crosslinking with bifunctional or multifunctional reagents; 3) entrapment in gel matrices, polymers, emulsions, or some form of membrane; and 4) a combination of any of these methods. In other embodiments, the lipases may not be immobilized. In some embodiments, the lipases are soluble. Fatty acid alkyl esters 56 can include fatty acid methyl esters, for example. Other fatty acid alkyl esters 56 can include $C_2$ to $C_{12}$ linear, branched, and cyclic alcohol esters, for example. Product alcohol 54 can then be separated from the reaction mixture including by-products 56 using any separation means known in the art such as distillation, for example. Other suitable separation mechanisms can include extraction and membrane separation, for example.

In some embodiments, at least about 5%, at least about 10%, at least about 20%, at least about 30%, at least about 40%, at least about 50%, at least about 60%, at least about 70%, at least about 80%, at least about 90%, or at least about 99% of the product alcohol is recovered from the alcohol esters.

ISPR extractant (carboxylic acid) 28 can be separated from the alcohol esters before reaction of the alcohol esters for recovery of product alcohol 54. Alternatively, ISPR extractant 28 can be separated from the product alcohol and any by-products after the reaction of the alcohol esters. The resulting recovered lean extractant 27 can then be recycled back into fermentation vessel 30, usually in combination with fresh make-up extractant 28 (which can be derived from oil 26, if supplied) for further production and/or extraction of alcohol esters. Alternatively, fresh extractant 28 (or oil 26)

can be continuously added to the fermentation vessel to replace the extractant removed in biphasic mixture stream 39.

In some embodiments, catalyst 42 can be recovered from biphasic mixture 39 and reused at a step in the fermentation process such as in the fermentation itself or in recovery of the product alcohol.

In some embodiments, one or more additional ISPR extractants 29 (see FIG. 2) can be introduced into fermentation vessel 30 to form a two-phase mixture comprising an aqueous phase and an organic phase. In such embodiments, ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. However, for the reasons noted above, ISPR extractant 29 is preferably not an alcohol. Rather, ISPR extractant 29 is preferably a carboxylic acid (e.g. free fatty acids). In some embodiments, ISPR extractant 29 is COFA. In some embodiments, ISPR extractant 29 is linseed oil fatty acid, soybean oil fatty acid, jatropha oil fatty acid, or fatty acids derived from palm oil, castor oil, olive oil, coconut oil, peanut oil, or any seed oil. In some embodiments, ISPR extractant 29 can be a fatty acid extractant selected from the group consisting of fatty acids, fatty alcohols, fatty amides, fatty esters (particularly those comprising 1 to 8 carbon atoms in the alcohol portion, e.g., fatty acid methyl esters and lower alcohol esters of fatty acids), fatty acid glycol esters, hydroxylated triglycerides, and mixtures thereof, obtained from chemical conversion of native oil such as biomass lipids as described, for example, in co-pending, commonly owned U.S. Provisional Application Ser. No. 61/368,436, filed on Jul. 28, 2010, herein incorporated by reference. In some embodiments, ISPR extractant 29 is free fatty acids obtained by chemical hydrolysis of biomass lipids. In some embodiments, ISPR extractant 29 can be free fatty acids produced from enzymatic hydrolysis of native oil such as biomass lipids as described, for example, in co-pending, commonly owned U.S. Provisional Application Ser. No. 61/368,444, filed on Jul. 28, 2010, herein incorporated by reference.

In situ product removal can be carried out in a batch mode or a continuous mode in fermentation vessel 30. In a continuous mode of in situ product removal, product is continually removed from the vessel (or reactor). In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth which can be determined by measuring the optical density of the culture. Further, the organic extractant can contact the fermentation medium at a time at which the product alcohol level in the fermentation medium reaches a preselected level. In the case of butanol production according to some embodiments of the present invention, at a time before the butanol concentration reaches a toxic level, the carboxylic acid extractant can contact the fermentation medium to esterify the butanol with the carboxylic acid to produce butyl esters and in some embodiments, produce a two-phase mixture comprising an aqueous phase and an organic phase comprising the butyl esters. Consequently, the concentration of butanol is reduced in the fermentation vessel and as a result, minimizes the toxic effects of butanol on the microorganism. The ester-containing organic phase can then be removed from the fermentation vessel (and separated from the fermentation broth which constitutes the aqueous phase) after a desired effective titer of the butyl esters is achieved. For example, in some embodiments, the ester-containing organic phase can be separated from the fermentation broth after the effective titer of butyl esters is greater than about 10 g/kg of fermentation broth. In other embodiments, the ester-containing organic phase can be separated from the fermentation medium after the effective titer of butyl esters is greater than about 230 g/kg fermentation broth, greater than about 300 g/kg fermentation broth, greater than about 400 g/kg fermentation broth, greater than about 500 g/kg fermentation broth, or greater than about 600 g/kg fermentation broth. In another embodiment, the ester-containing organic phase can be separated from the fermentation medium after the % conversion of COFA is at least about 10%, at least about 25%, at least about 50%, at least about 75%, or at least about 100%. In some embodiments, the ester-containing organic phase is separated from the aqueous phase after fermentation of the available fermentable sugar in the fermentation vessel is substantially complete.

In the example embodiment depicted in FIG. 1, the alcohol ester is extracted from the fermentation broth in situ, with the separation of the biphasic mixture 39 occurring in a separate vessel 35. In some embodiments, separation of the biphasic mixture can occur in the fermentation vessel, as shown in the example embodiments of later described FIGS. 3 and 4 in which the ester-containing organic phase stream 36 exits directly from fermentation vessel 30. Aqueous phase stream 34 can also exit directly from fermentation vessel 30, be treated for the removal of any remaining alcohol ester or product alcohol, and recycled, or discarded and replaced with fresh fermentation medium. The extraction of the alcohol ester and the product alcohol by the organic extractant can be done with or without the removal of microorganism 32 from the fermentation broth. Microorganism 32 can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

Figure 4:
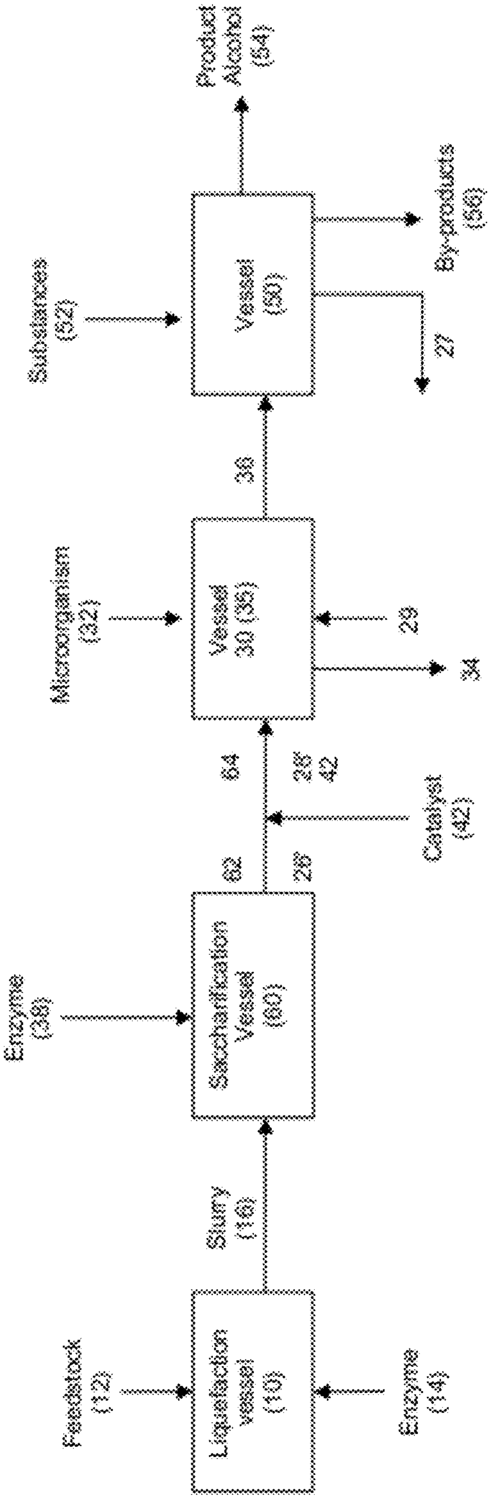

In some embodiments, the system and processes of FIG. 1 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 4).

Figure 2:
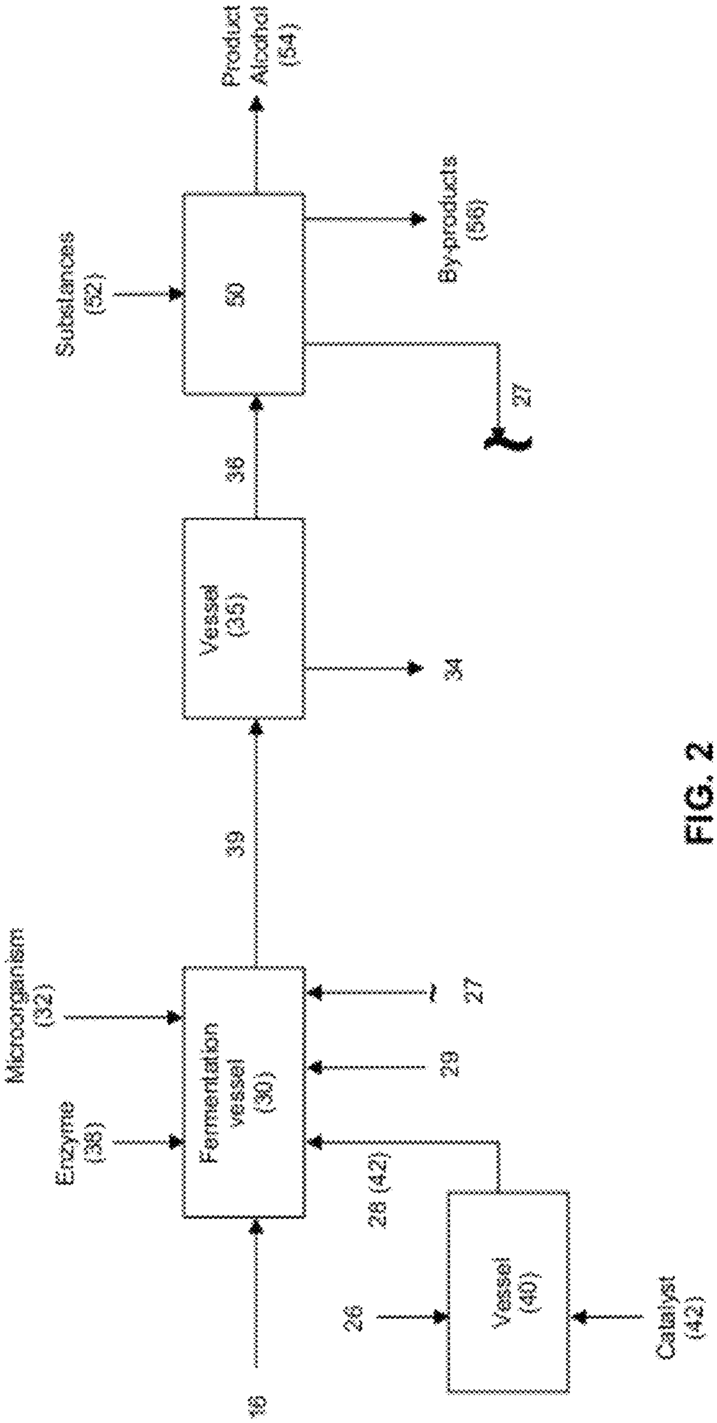

In still other embodiments, as shown, for example, in the example embodiment of FIG. 2, native oil 26 (instead of being supplied directly to fermentation vessel 30) is supplied to a vessel 40 to which catalyst 42 is also supplied, whereby at least a portion of the acyl glycerides in oil 26 are hydrolyzed to form carboxylic acid 28. A product stream from vessel 40 containing carboxylic acid 28 and catalyst 42 are then introduced into fermentation vessel 30. Carboxylic acid 28 and catalyst 42 contact the product alcohol produced in the fermentation medium whereby alcohol esters of the product alcohol are formed in situ from catalyzed esterification of the carboxylic acid with the product alcohol, in a same manner as described above with reference to FIG. 1. Carboxylic acid 28 can also serve as an ISPR extractant and in some embodiments, sufficient carboxylic acid 28 and/or one or more additional ISPR extractants 29 can be introduced into fermentation vessel 30 to form a two-phase mixture comprising an aqueous phase and an organic phase, with the alcohol ester partitioning into the organic phase. The remaining process operations of the embodiment of FIG. 2 are identical to FIG. 1 and therefore, will not be described in detail again.

Figure 3:
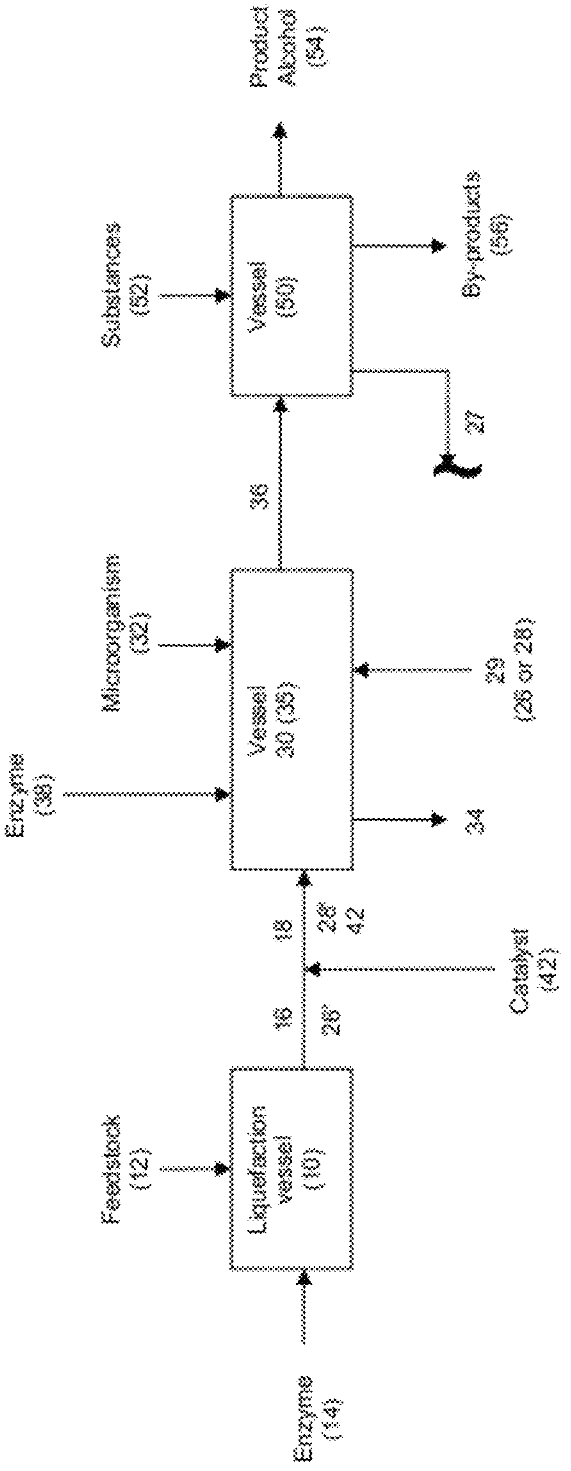

In some embodiments of the present invention, as shown, for example, in the embodiment of FIG. 3, catalyst 42 can be added to feedstock slurry 16 comprising oil 26' derived from the biomass from which feedstock 12 was formed. In the embodiment shown, catalyst 42 is capable of hydrolyzing the glycerides in oil 26' to free fatty acids 28'. Thus, after introduction of catalyst 42 to feedstock slurry 16, at least a portion of the glycerides in oil 26' are hydrolyzed, resulting in a feedstock slurry 18 having free fatty acids 28' and catalyst 42. For example, when feedstock 12 is corn, then oil 26' is the feedstock's constituent corn oil and the free fatty acids 28' are corn oil fatty acids (COFA).

Feedstock slurry 18 is introduced to fermentation vessel 30 along with alcohol-producing microorganism 32 to be included in a fermentation medium. In some embodiments, an enzyme 38 such as glucoamylase, can also be introduced into fermentation vessel for simultaneous saccharification of sugars in slurry 18 and fermentation of alcohol inside fermentation vessel 30. The presence of catalyst 42 in fermentation vessel (introduced via slurry 18) catalyzes the esterification of the alcohol with the free fatty acids 28' (introduced via slurry 18) to form fatty acid alcohol esters in situ, in a same manner as described above with reference to FIG. 1. In some embodiments, for butanol production, butanol-producing microorganism 32 is introduced in fermentation vessel 30 along with feedstock slurry 18. Catalyst 42 in fermentation vessel (introduced via slurry 18) catalyzes the esterification of the butanol with the free fatty acids 28' (introduced via slurry 18) to form fatty acid butyl esters (FABE) in situ. Free fatty acids 28' can also serve as an ISPR extractant. For example, when free fatty acids 28' are COFA, then alcohol esters of COFA are formed in situ, and COFA serves as an ISPR extractant or a portion thereof.

In some embodiments, one or more additional ISPR extractants 29 can be introduced into fermentation vessel 30 for preferentially partitioning the alcohol ester (and any free alcohol) from the aqueous phase. In some embodiments, ISPR extractant 29 can be carboxylic acid 28 described with reference to the embodiments of FIGS. 1 and 2. In some embodiments, ISPR extractant 29 is introduced in fermentation vessel 30 as oil 26 which is then hydrolyzed into fatty acids by catalyst 42 so as to become ISPR extractant 29. In some embodiments, oil 26 is corn oil, whereby ISPR extractant 29 is COFA. In some embodiments, ISPR extractant 29 can be a fatty acid extractant selected from the group consisting of fatty acids, fatty alcohols, fatty amides, fatty esters (particularly those comprising 1 to 8 carbon atoms in the alcohol portion, e.g., fatty acid methyl esters and lower alcohol esters of fatty acids), fatty acid glycol esters, hydroxylated triglycerides, and mixtures thereof, as described above with reference to the embodiments of FIGS. 1 and 2. In still other embodiments, ISPR extractant 29 can be free fatty acids obtained by chemical or enzymatic hydrolysis of biomass lipids. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. The remaining process operations of the embodiment of FIG. 2 are identical to FIG. 1 and therefore, will not be described in detail again.

As a non-limiting prophetic example, with reference to the embodiment of FIG. 3, an aqueous suspension of ground whole corn (as feedstock 12) which can nominally contain ca. 4 wt % corn oil, can be treated with amylase (as liquefaction enzyme 14) at ca. 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. The liquefied and lipase-treated mash 18 can be cooled to ca. 30° C. (e.g., using a heat-exchanger) and loaded to fermentation vessel 30 at ca. 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a broth using a liquefied mash that has not been treated with lipase 42. In particular, the lipase treatment 42 can result in the conversion of corn oil lipids 26' (triglycerides (TG)) into COFA 28' (and some diglycerides (DG) or monoglycerides (MG)), decreasing the rate of build-up of lipids 26' in the COFA ISPR extraction solvent 28' or 29. The lipase treatment 42 can also result in the conversion of butanol produced during fermentation to butyl esters of COFA, where the butyl esters of COFA have a high partition coefficient for dissolution into the COFA phase 36 during liquid-liquid extraction ISPR. At the end of fermentation, the COFA phase 36 containing butyl esters of COFA can be separated from the fermentation broth (at vessel 30/35), and the butanol 54 can be recovered (at vessel 50) from this organic mixture 36 using one of several methods including, but not limited to, hydrolysis of the ester using, for example, a lipase 52, a solid acid catalyst 52, or steam 52, to produce butanol 54 and COFA 27.

In still other embodiments, as shown, for example, in the embodiment of FIG. 4, the system and processes of FIG. 3 can be modified such that simultaneous saccharification and fermentation (SSF) in fermentation vessel 30 is replaced with a separate saccharification vessel 60 prior to fermentation vessel 30. FIG. 4 is substantially identical to FIG. 3 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, and oil 26' and undissolved solids derived from the feedstock. Oil 26' is hydrolyzed by the introduction of catalyst 42, resulting in a liquefied, saccharified feedstock slurry 64 having free fatty acids 28' and catalyst 42.

Alternatively, in some embodiments, catalyst 42 can be added along with saccharification enzyme 38 to simultaneously produce glucose and hydrolyze oil lipids 26' to free fatty acids 28', in a like manner as the introduction of catalyst 42 with enzyme 38 to the fermentation vessel 30 for SSF in the embodiment of FIG. 1. The addition of enzyme 38 and catalyst 42 can be stepwise (e.g., catalyst 42, then enzyme 38, or vice versa), or simultaneous. However, in contrast with the embodiment of FIG. 1 in which the addition of catalyst 42 into fermentation vessel 30 during SSF also substantially simultaneously converts the product alcohol to the alcohol esters, alcohol esters are not formed until slurry 64 containing catalyst 42 is introduced to fermentation vessel 30. Alternatively, in some embodiments, slurry 62 can be introduced to fermentation vessel 30, with catalyst 42 being added directly to the fermentation vessel 30.

In the embodiment of FIG. 4, slurry 64 is introduced to fermentation vessel 30 along with alcohol-producing microorganism 32 which metabolizes the monosaccharides to produce product alcohol. The presence of catalyst 42 in fermentation vessel (introduced via slurry 64) catalyzes the esterification of the alcohol with the free fatty acids 28' (introduced via slurry 62) to form fatty acid alcohol esters in situ, in the same manner as described above with reference to FIG. 1. Free fatty acids 28' can also serve as an ISPR extractant for preferentially partitioning the alcohol ester (and any free alcohol) from the aqueous phase. In some embodiments, one or more additional ISPR extractants 29 can also be introduced into fermentation vessel 30 as described above with reference to FIG. 3. The remaining process operations of the embodiment of FIG. 4 are identical to FIG. 3 and therefore, will not be described in detail again.

Figure 5:
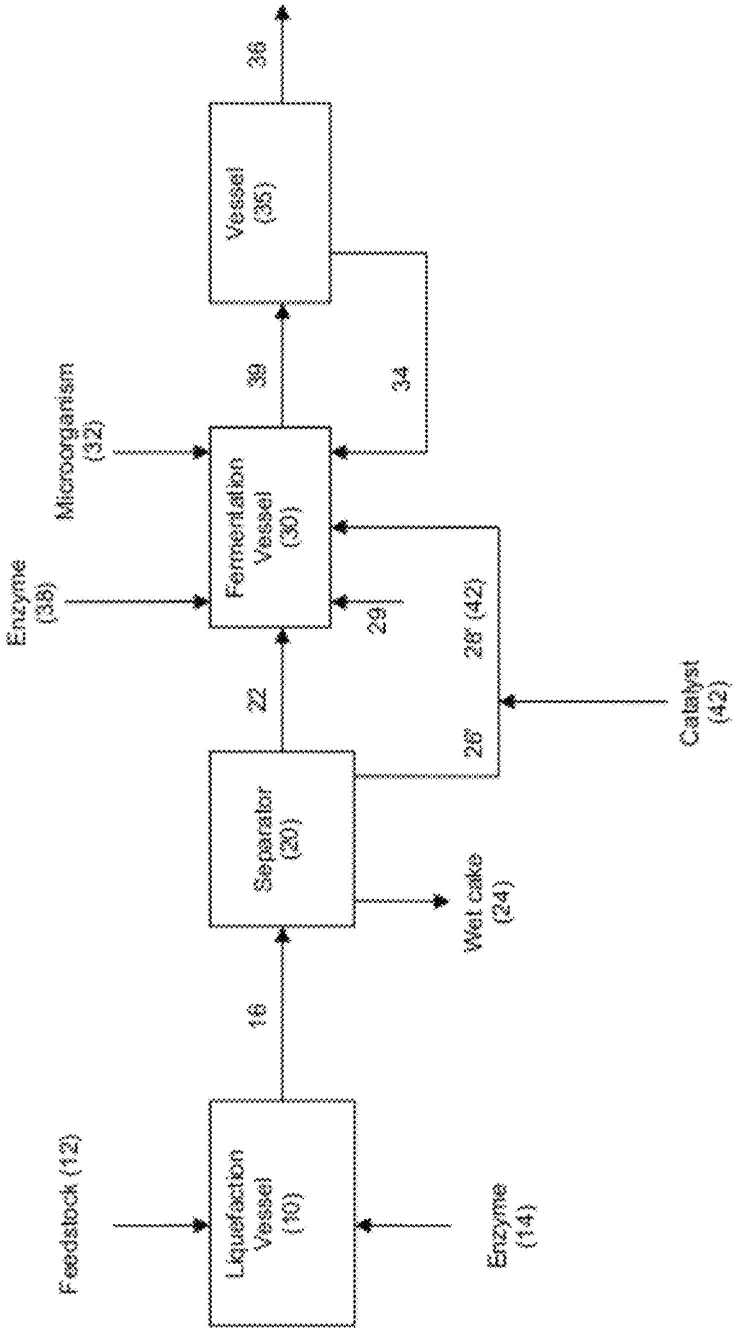

In some embodiments, including any of the earlier described embodiments with respect to FIGS. 1-4, undissolved solids can be removed from feedstock slurry 16 prior to introduction into fermentation vessel 30. For example, as shown in the embodiment of FIG. 5, feedstock slurry 16 is introduced into an inlet of a separator 20 which is configured to discharge the undissolved solids as a solid phase or wet cake 24. For example, in some embodiments, separator 20 can include a filter press, vacuum filtration, mechanical pressure filtration, or a centrifuge (e.g., decanter centrifuge) for separating the undissolved solids from feedstock slurry 16. In some embodiments, any conventional centrifuge utilized in the industry, including, for example, a decanter bowl centrifuge, tricanter centrifuge, disk stack centrifuge, filtering centrifuge, or decanter centrifuge may be used to separate the undissolved solids. In some embodiments, removal of the undissolved solids from feedstock slurry 16 can be accomplished by filtration, vacuum filtration, beltfilter, pressure filtration, filtration using a screen, screen separation, grates or grating, porous grating, flotation, hydroclone, filter press, screwpress, gravity settler, vortex separator, or any method that may be used to separate solids from liquids. Optionally, in some embodiments, separator 20 can also be configured to remove some or substantially all of oil 26' present in feedstock slurry 16. In such embodiments, separator 20 can be any suitable separator known in the art for removing oil from an aqueous feedstream including, but not limited to, siphoning, decantation, centrifugation, using a gravity settler, membrane-assisted phase splitting, and the like. The remaining feedstock including sugar and water is discharged as an aqueous stream 22 to fermentation vessel 30.

For example, in some embodiments, separator 20 includes a tricanter centrifuge 20 that agitates or spins feedstock slurry 16 to produce a centrifuge product comprising an aqueous layer containing sugar and water (i.e., stream 22), a solids layer containing the undissolved solids (i.e., wet cake 24), and an oil layer (i.e., oil stream 26'). In such a case, catalyst 42 can be contacted with the removed oil 26' to produce a stream of free fatty acid 28' and catalyst 42. The stream of free fatty acid 28' and catalyst 42 can then be introduced into fermentation vessel 30 to contact with the fermentation medium, whereby catalytic esterification of product alcohol in the fermentation medium into fatty acid alcohol esters can be achieved in situ, in a same manner as described above with reference to FIG. 1.

Free fatty acids 28' can also serve as an ISPR extractant 28', and one or more additional ISPR extractants 29 can also be introduced into fermentation vessel 30. Thus, feedstock oil 26' can be catalytically hydrolyzed to carboxylic acid, thereby decreasing the amount of lipids present in an ISPR extractant while also producing an ISPR extractant. The ester-containing organic phase 36 can be separated from the aqueous phase 34 of the biphasic mixture 39 at vessel 35, and the product alcohol can be recovered from the alcohol esters in vessel 50 (see FIG. 1). The remaining process operations of the embodiment of FIG. 5 are identical to FIG. 3 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 24 may be combined with solubles and then dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, the DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26' is not discharged separately from wet cake 24, but rather oil 26' is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock slurry 16 via centrifugation are described in detail in co-pending, commonly owned U.S. Provisional Application Ser. No. 61/356,290, filed Jun. 18, 2010, which is incorporated herein in its entirety by reference thereto.

As described above, oil 26' may be separated from DDGS using any suitable known process including, for example, a solvent extraction process. In one embodiment of the invention, DDGS are loaded into an extraction vessel and washed with a solvent such as hexane to remove oil 26'. Other solvents that may be utilized include, for example, isobutanol, isohexane, ethanol, petroleum distillates such as petroleum ether, or mixtures thereof. After oil 26' extraction, DDGS may be treated to remove any residual solvent. For example, DDGS may be heated to vaporize any residual solvent using any method known in the art. Following solvent removal, DDGS may be subjected to a drying process to remove any residual water. The processed DDGS may be used as a feed supplement for animals such as poultry, livestock, and domestic pets.

After extraction from DDGS, the resulting oil 26' and solvent mixture may be collected for separation of oil 26' from the solvent. In one embodiment, the oil 26'/solvent mixture may be processed by evaporation whereby the solvent is evaporated and may be collected and recycled. The recovered oil may be converted to an ISPR extractant 29 for subsequent use in the same or different alcohol fermentation process.

In addition to the recovery of solids, it may be desired to recover other by-products of the fermentation process. In one embodiment, fatty acid esters (e.g., fatty acid isobutyl esters) may be recovered, for example, to increase the yield of carbohydrate to product alcohol (e.g., butanol). This may be accomplished, for example, by using a solvent to extract fatty acid isobutyl esters from, for example, the by-product formed by combining and mixing several by-product streams and drying the product of the combining and mixing steps. Such a solvent-based extraction system for recovering corn oil triglyceride from DDGS is described in U.S. Patent Application Publication No. 2010/0092603, the teachings of which are incorporated by reference herein.

In one embodiment of solvent extraction of fatty acid esters, solids may be separated from whole stillage ("separated solids") since that stream would contain the largest portion, by far, of fatty acid esters in uncombined byproduct streams. These separated solids may then be fed into an extractor and washed with solvent. In one embodiment, the separated solids are turned at least once in order to ensure that all sides of the separated solids are washed with solvent. After washing, the resulting mixture of lipid and solvent, known as miscella, is collected for separation of the extracted lipid from the solvent. For example, the resulting mixture of lipid and solvent may be deposited to a separator for further processing. During the extraction process, as the solvent washes over the separated solids, the solvent not only brings lipid into solution, but it collects fine, solid particles. These "fines" are generally undesirable impurities in the miscella and in one embodiment, the miscella may be discharged from the extractor or separator through a device that separates or scrubs the fines from the miscella.

In order to separate the lipid and the solvent contained in the miscella, the miscella may be subjected to a distillation step. In this step, the miscella can, for example, be processed through an evaporator which heats the miscella to a temperature that is high enough to cause vaporization of the solvent, but is not sufficiently high to adversely affect or vaporize the extracted lipid. As the solvent evaporates, it may be collected, for example, in a condenser, and recycled for future use. Separation of the solvent from the miscella results in a stock of crude lipid which may be further processed to separate water, fatty acid esters (e.g., fatty acid isobutyl esters), fatty acids, and triglycerides.

After extraction of the lipids, the solids may be conveyed out of the extractor and subjected to a stripping process that removes residual solvent. Recovery of residual solvent is important to process economics. In one embodiment, the wet solids can be conveyed in a vapor tight environment to preserve and collect solvent that transiently evaporates from the wet solids as it is conveyed into the desolventizer. As the solids enter the desolventizer, they may be heated to vaporize and remove the residual solvent. In order to heat the solids, the desolventizer may include a mechanism for distributing the solids over one or more trays, and the solids may be heated directly, such as through direct contact with heated air or steam, or indirectly, such as by heating the tray carrying the meal. In order to facilitate transfer of the solids from one tray to another, the trays carrying the solids may include openings that allow the solids to pass from one tray to the next. From the desolventizer, the solids may be conveyed to, optionally, a mixer where the solids are mixed with other by-products before being conveyed into a dryer. An example of solids extraction is described in Example 63. In this example, the solids are fed to a desolventizer where the solids are contacted by steam. In one embodiment, the flows of steam and solids in the desolventizer may be countercurrent. The solids may then exit the desolventizer and may be fed to a dryer or optionally a mixer where various by-products may be mixed. Vapor exiting the desolventizer may be condensed and optionally mixed with miscella and then fed to a decanter. The water-rich phase exiting the decanter may be fed to a distillation column where hexane is removed from the water-rich stream. In one embodiment, the hexane-depleted water rich stream exits the bottom of the distillation column and may be recycled back to the fermentation process, for example, it may be used to slurry the ground corn solids. In another embodiment, the overhead and bottom products may be recycled to the fermentation process. For example, the lipid-rich bottoms may be added to the feed of a hydrolyzer. The overheads may be, for example, condensed and fed to a decanter. The hexane rich stream exiting this decanter can optionally be used as part of the solvent feed to the extractor. The water-rich phase exiting this decanter may be fed to the column that strips hexane out of water. As one skilled in the art can appreciate, the methods of the present invention may be modified in a variety of ways to optimize the fermentation process for the production of a product alcohol such as butanol.

In another embodiment of solvent extraction of fatty acid esters, solids may be separated from beer and solvent discharged from fermentation before they are introduced into a preflash column as a heterogeneous mixture. A wet cake of these solids can be formed using a separation device such as a screen filter or a centrifuge. A screened cake of solids can be displacement washed using hydrous isobutanol to remove fatty acid esters that were retained in the wet solids. Alternatively, a centrifuged cake of solids can be re-pulped in hydrous isobutanol and separated again to effect the removal of fatty acid esters that were retained in the wet solids. An example of this embodiment of solids extraction is described in Example 63.

In a further embodiment, by-products (or co-products) may be derived from the mash used in the fermentation process. For example, corn oil may be separated from mash and this corn oil may contain triglycerides, free fatty acids, diglycerides, monoglycerides, and phospholipids (see, e.g., Example 66). The corn oil may optionally be added to other by-products (or co-products) at different rates and thus, for example, creating the ability to vary the amount of triglyceride in the resulting byproduct. In this manner, the fat content of the resulting by-product could be controlled, for example, to yield a lower fat, high protein animal feed that would better suit the needs of dairy cows compared to a high fat product.

In one embodiment, crude corn oil separated from mash may be further processed into edible oil for consumer use, or it could also be used as a component of animal feed because its high triglyceride content would make it an excellent source of metabolizable energy. In another embodiment, it could also be used as feedstock for biodiesel or renewable diesel.

In one embodiment, extractant by-product may be used, all or in part, as a component of an animal feed by-product or it can be used as feedstock for biodiesel or renewable diesel.

In a further embodiment, solids may be separated from mash and may comprise triglycerides and free fatty acids. These solids (or stream) may be used as an animal feed, either recovered as discharge from centrifugation or after drying. The solids (or wet cake) may be particularly suited as feed for ruminants (e.g., dairy cows) because of its high content of available lysine and by-pass or rumen undegradable protein. For example, these solids may be of particular value in a high protein, low fat feed. In another embodiment, these solids may be used as a base, that is, other by-products such as syrup may be added to the solids to form a product that may be used as an animal feed. In another embodiment, different amounts of other by-products may be added to the solids to tailor the properties of the resulting product to meet the needs of a certain animal species.

The composition of solids separated from whole stillage as described in Example 62 may include, for example, crude protein, fatty acid, and fatty acid isobutyl esters. In one embodiment, this composition (or by-product) may be used, wet or dry, as an animal feed where, for example, a high protein (e.g., high lysine), low fat, and high fiber content is desired. In another embodiment, fat may be added to this composition, for example, from another by-product stream if a higher fat, low fiber animal feed is desired. In one embodiment, this higher fat, low fiber animal feed may be used for swine or poultry. In a further embodiment, a non-aqueous composition of Condensed Distillers Solubles (CDS) (see, e.g., Example 66) may include, for example, protein, fatty acids, and fatty acid isobutyl esters as well as other dissolved and suspended solids such as salts and carbohydrates. This CDS composition may be used, for example, as animal feed, either wet or dry, where a high protein, low fat, high mineral salt feed component is desired. In one embodiment, this composition may be used as a component of a dairy cow ration.

In another embodiment, oil from the fermentation process may be recovered by evaporation. This non-aqueous composition may comprise fatty acid isobutyl esters and fatty acids (see, e.g., Example 66) and this composition (or stream) may be fed to a hydrolyser to recover isobutanol and fatty acids. In a further embodiment, this stream may be used as feedstock for biodiesel production.

The various streams generated by the production of an alcohol (e.g., butanol) via a fermentation process may be combined in many ways to generate a number of co-products. For example, if crude corn from mash is used to generate fatty acids to be utilized as extractant and lipid is extracted by evaporators for other purposes, then the remaining streams may be combined and processed to create a co-product composition comprising crude protein, crude fat, triglycerides, fatty acid, and fatty acid isobutyl ester. In one embodiment, this composition may comprise at least about 20-35 wt % crude protein, at least about 1-20 wt % crude fat, at least about 0-5 wt % triglycerides, at least about 4-10 wt % fatty acid, and at least about 2-6 wt % fatty acid isobutyl ester. In one particular embodiment, the co-product composition may comprise about 25 wt % crude protein, about 10 wt % crude fat, about 0.5 wt % triglycerides, about 6 wt % fatty acid, and about 4 wt % fatty acid isobutyl ester.

In another embodiment, the lipid is extracted by evaporators and the fatty acids are used for other purposes and about 50 wt % of the crude corn from mash and the remaining streams are combined and processed, the resulting co-product composition may comprise crude protein, crude fat, triglycerides, fatty acid, and fatty acid isobutyl ester. In one embodiment, this composition may comprise at least about 25-31 wt % crude protein, at least about 6-10 wt % crude fat, at least about 4-8 wt % triglycerides, at least about 0-2 wt % fatty acid, and at least about 1-3 wt % fatty acid isobutyl ester. In one particular embodiment, the co-product composition may comprise about 28 wt % crude protein, about 8 wt % crude fat, about 6 wt % triglycerides, about 0.7 wt % fatty acid, and about 1 wt % fatty acid isobutyl ester.

In another embodiment, the solids separated from whole stillage and 50 wt % of the corn oil extracted from mash are combined and the resulting co-product composition may comprise crude protein, crude fat, triglycerides, fatty acid, fatty acid isobutyl ester, lysine, neutral detergent fiber (NDF), and acid detergent fiber (ADF). In one embodiment, this composition may comprise at least about 26-34 wt % crude protein, at least about 15-25 wt % crude fat, at least about 12-20 wt % triglycerides, at least about 1-2 wt % fatty acid, at least about 2-4 wt % fatty acid isobutyl ester, at least about 1-2 wt % lysine, at least about 11-23 wt % NDF, and at least about 5-11 wt % ADF. In one particular embodiment, the co-product composition may comprise about 29 wt % crude protein, about 21 wt % crude fat, about 16 wt % triglycerides, about 1 wt % fatty acid, about 3 wt % fatty acid isobutyl ester, about 1 wt % lysine, about 17 wt % NDF, and about 8 wt % ADF. The high fat, triglyceride, and lysine content and the lower fiber content of this co-product composition may be desirable as feed for swine and poultry.

As described above, the various streams generated by the production of an alcohol (e.g., butanol) via a fermentation process may be combined in many ways to generate a co-product composition comprising crude protein, crude fat, triglycerides, fatty acid, and fatty acid isobutyl ester. For example, a composition comprising at least about 6% crude fat and at least about 28% crude protein may be utilized as an animal feed product for dairy animals. A composition comprising at least about 6% crude fat and at least about 26% crude protein may be utilized as an animal feed product for feedlot cattle whereas a composition comprising at least about 1% crude fat and at least about 27% crude protein may be utilized as an animal feed product for wintering cattle. A composition comprising at least about 13% crude fat and at least about 27% crude protein may be utilized as an animal feed product for poultry. A composition comprising at least about 18% crude fat and at least about 22% crude protein may be utilized as an animal feed product for monogastric animals. Thus, the various streams may be combined in such a way as to customize a feed product for a specific animal species.

In one embodiment, one or more streams generated by the production of an alcohol (e.g., butanol) via a fermentation process may be combined in many ways to generate a composition comprising at least about 90% COFA which may be used as fuel source such as biodiesel.

As an example of one embodiment of the methods of the invention, milled grain (e.g., corn processed by hammer mill) and one or more enzymes are combined to generate a slurried grain. This slurried grain is cooked, liquified, and optionally flashed with flash vapor resulting in a cooked mash. The cooked mash is then filtered to remove suspended solids, generating a wet cake and a filtrate. The filtration may be accomplished by several methods such as centrifugation, screening, or vacuum filtration and this filtration step may remove at least about 80% to at least about 99% of the suspended solids from the mash.

The wet cake is reslurried with water and refiltered to remove additional starch, generating a washed filter cake. The reslurry process may be repeated a number of times, for example, one to five times. The water used to reslurry the wet cake may be recycled water generated during the fermentation process. The filtrate produced by the reslurry/refiltration process may be returned to the initial mix step to form a slurry with the milled grain. The filtrate may be heated or cooled prior to the mix step.

The washed filter cake may be reslurried with beer at a number of stages during the production process. For example, the washed filter cake may be reslurried with beer after the fermentor, before the preflash column, or at the feedpoint to the distillers grain dryer. The washed filter cake may be dried separately from other by-products or may be used directly as wet cake for generation of DDGS or an animal feed product.

The filtrate produced as a result of the initial mix step may be further processed as described herein. For example, the filtrate may be heated with steam or process to process heat exchange. A saccharification enzyme may be added to the filtrate and the dissolved starch of the filtrate may be partially or completely saccharified. The saccharified filtrate may be cooled by a number of means such as process to process exchange, exchange with cooling water, or exchange with chilled water.

The cooled filtrate may then be added to a fermentor as well as a microorganism that is suitable for alcohol production, for example, a recombinant yeast capable of producing butanol. In addition, ammonia and recycle streams may also be added to the fermentor. This process may include at least one fermentor, at least two fermentors, at least three fermentors, or at least four fermentors. Carbon dioxide generated during the fermentation may be vented to a scrubber in order to reduce air emissions (e.g., butanol air emissions) and to increase product yield.

Solvent may be added to the fermentor via a recycled loop or may be added directly into the fermentor. The solvent may be one or more organic compounds which have the ability to dissolve or react with the alcohol (e.g., butanol) and may have limited solubility in water. The solvent may be taken from the fermentor continually as a single liquid phase or as a two liquid phase material, or the solvent may be withdrawn batch-wise as a single or two liquid phase material.

Beer may be degassed. The beer may be heated before degassing, for example, by process to process exchange with hot mash or process to process exchange with preflash column overheads. Vapors may be vented to a condenser and then, to a scrubber. Degassed beer may be heated further, for example, by process to process heat exchange with other streams in the distillation area.

Preheated beer and solvent may enter a preflash column which may be retrofit from a beer column of a conventional dry grind fuel ethanol plant. This column may be operated at sub-atmospheric pressure, driven by water vapor taken from an evaporator train or from the mash cook step. The overheads of the preflash column may be condensed by heat exchange with some combination of cooling water and process to process heat exchange including heat exchange with the preflash column feed. The liquid condensate may be directed to an alcohol/water decanter (e.g., butanol/water decanter).

The preflash column bottoms may be advanced to a solvent decanter. The preflash column bottoms may be substantially stripped of free alcohol (e.g., butanol). The decanter may be a still well, a centrifuge, or a hydroclone. Water is substantially separated from the solvent phase in this decanter, generating a water phase. The water phase including suspended and dissolved solids may be centrifuged to produce a wet cake and thin stillage. The wet cake may be combined with other streams and dried to produce DDGS, it may be dried and sold separate from other streams which produce DDGS, or it may be sold as a wet cake. The water phase may be split to provide a backset which is used in part to reslurry the filter cake described above. The split also provides thin stillage which may be pumped to evaporators for further processing.

The organic phase produced in the solvent decanter may be an ester of an alcohol (e.g., butanol). The solvent may be hydrolyzed to regenerate reactive solvent and to recover additional alcohol (e.g., butanol). Alternatively, the organic phase may be filtered and sold as a product. Hydrolysis may be thermally driven, homogeneously catalyzed, or heterogeneously catalyzed. Hydrolysis may also occur by enzymatic reaction. The heat input to this process may be a fired heater, hot oil, electrical heat input, or high pressure steam. Water added to drive the hydrolysis may be from a recycled water stream, fresh water, or steam.

Cooled hydrolyzed solvent may be pumped into a sub-atmospheric solvent column where it may be substantially stripped of alcohol (e.g., butanol) with steam. This steam may be water vapor from evaporators, it may be steam from the flash step of the mash process, or it may be steam from a boiler (see, e.g., U.S. Patent Application Publication No. 2009/0171129, incorporated herein by reference). A rectifier column from a conventional dry grind ethanol plant may be suitable as a solvent column. The rectifier column may be modified to serve as a solvent column. The bottoms of the solvent column may be cooled, for example, by cooling water or process to process heat exchange. The cooled bottoms may be decanted to remove residual water and this water may be recycled to other steps with the process or recycled to the mash step.

The solvent column overheads may be cooled by exchange with cooling water or by process to process heat exchange, and the condensate may be directed to a vented alcohol/water decanter (e.g., butanol/water decanter) which may be shared with the preflash column overheads. Other mixed water and alcohol (e.g., butanol) streams may be added to this decanter including the scrubber bottoms and condensate from the degas step. The vent which comprises carbon dioxide, may be directed to a water scrubber. The aqueous layer of this decanter may also be fed to the solvent column or may be stripped of alcohol (e.g., butanol) in a small dedicated distillation column. The aqueous layer may be preheated by process to process exchange with the preflash column overheads, solvent column overheads, or solvent column bottoms. This dedicated column may be modified from the side stripper of a conventional dry grind fuel ethanol process.

The organic layer of the alcohol/water decanter (e.g., butanol/water decanter) may be pumped to an alcohol (e.g., butanol) column. This column may be a super-atmospheric column and may be driven by steam condensation within a reboiler. The feed to the column may be heated by process to process heat exchange in order to reduce the energy demand to operate the column. This process to process heat exchanger may include a partial condenser of the preflash column, a partial condenser of a solvent column, the product of the hydrolyzer, water vapor from the evaporators, or the butanol column bottoms. The condensate of the alcohol (e.g., butanol) column vapor may be cooled and may be returned to the alcohol/water decanter (e.g., butanol/water decanter). The alcohol (e.g., butanol) column bottoms may be cooled by process to process heat exchange including exchange with the alcohol (e.g., butanol) column feed and may be further cooled with cooling water, filtered, and are sold as product alcohol (e.g., butanol).

Thin stillage generated from the preflash column bottoms as described above may be directed to a multiple effect evaporator. This evaporator may have two, three, or more stages. The evaporator may have a configuration of four bodies by two effects similar to the conventional design of a fuel ethanol plant, it may have three bodies by three effects, or it may have other configurations. Thin stillage may enter at any of the effects. At least one of the first effect bodies may be heated with vapor from the super-atmospheric alcohol (e.g., butanol) column. The vapor may be taken from the lowest pressure effect to provide heat in the form of water vapor to the sub-atmospheric preflash column and solvent column. Syrup from the evaporators may be added to the distiller's grain dryer.

Carbon dioxide emissions from the fermentor, degasser, alcohol/water decanter (e.g., butanol/water decanter) and other sources may be directed to a water scrubber. The water supplied to the top of this scrubber may be fresh makeup water or may be recycled water. The recycled water may be treated (e.g., biologically digested) to remove volatile organic compounds and may be chilled. Scrubber bottoms may be sent to the alcohol/water decanter (e.g., butanol/water decanter), to the solvent column, or may be used with other recycled water to reslurry the wet cake described above. Condensate from the evaporators may be treated with anaerobic biological digestion or other processes to purify the water before recycling to reslurry the filter cakes.

If corn is used as the source of the milled grain, corn oil may be separated from the process streams at any of several points. For example, a centrifuge may be operated to produce a corn oil stream following filtration of the cooked mash or the preflash column water phase centrifuge may be operated to produce a corn oil stream. Intermediate concentration syrup for final syrup may be centrifuged to produce a corn oil stream.

In another example of an embodiment of the methods of the invention, the material discharged from the fermentor may be processed in a separation system that involves devices such as a centrifuge, settler, hydrocyclone, etc., and combinations thereof to effect the recovery of live yeast in a concentrated form that can be recycled for reuse in a subsequent fermentation batch either directly or after some re-conditioning. This separation system may also produce an organic stream that comprises fatty esters (e.g. isobutyl fatty esters) and an alcohol (e.g., isobutanol) produced from the fermentation and an aqueous stream containing only trace levels of immiscible organics. This aqueous stream may be used either before or after it is stripped of the alcohol (e.g., isobutanol) content to re-pulp and pump the low starch solids that was separated and washed from liquefied mash. This has the advantage of avoiding what might otherwise be a long belt-driven conveying system to transfer these solids from the liquefaction area to the grain drying and syrup blend area. Furthermore, this whole stillage that results after the alcohol (e.g., isobutanol) has been stripped will need to be separated into thin stillage and wet cake fractions either using existing or new separation devices and this thin stillage will form in part the backset that returns to combine with cook water for preparing a new batch of fermentable mash. Another advantage of this embodiment is that any residual dissolved starch that was retained in the moisture of the solids separated from the liquefied mash would in part be captured and recovered through this backset. Alternatively, the yeast contained in the solids stream may be considered nonviable and may be redispersed in the aqueous stream and this combined stream distilled of any alcohol (e.g., butanol) content remaining from fermentation. Non viable organisms may further be separated for use as a nutrient in the propagation process.

In another embodiment, the multi-phase material may leave the bottom of the pre-flash column and may be processed in a separation system as described above. The concentrated solids may be redispersed in the aqueous stream and this combined stream may be used to re-pulp and pump the low starch solids that were separated and washed from liquefied mash.

The process described above as well as other processes described herein may be demonstrated using computational modeling such as Aspen modeling (see, e.g., U.S. Pat. No. 7,666,282). For example, the commercial modeling software Aspen Plus® (Aspen Technology, Inc., Burlington, Mass.) may be use in conjunction with physical property databases such as DIPPR, available from American Institute of Chemical Engineers, Inc. (New York, N.Y.) to develop an Aspen model for an integrated butanol fermentation, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, preflash columns, condensers, evaporators, centrifuges, etc.

The present invention provides systems and methods for producing a fermentative product such as a product alcohol, through fermentation as well as increasing biomass processing productivity and cost effectiveness. In some embodiments, the product alcohol is butanol. A feedstock can be liquefied to create a feedstock slurry, wherein the feedstock slurry includes soluble sugar and undissolved solids. If the feedstock slurry is fed directly to the fermentor, the undissolved solids may interfere with efficient removal and recovery of a product alcohol such as butanol from the fermentor. In particular, when liquid-liquid extraction is utilized to extract butanol from the fermentation broth, the presence of the undissolved particulates may cause system inefficiencies including, but not limited to, decreasing the mass transfer rate of the butanol to the extractant by interfering with the contact between the extractant and the fermentation broth; creating an emulsion in the fermentor and thereby interfering with good phase separation of the extractant and the fermentation broth; reducing the efficiency of recovering and recycling the extractant because at least a portion of the extractant and butanol becomes "trapped" in the solids which are ultimately removed as DDGS; a lower fermentor volume efficiency because there are solids taking up volume in the fermentor and because there is a slower disengagement of the extractant from the fermentation broth; and shortening the life cycle of the extractant by contamination with corn oil. All of these effects result in higher capital and operating costs. In addition, the extractant "trapped" in the DDGS may detract from DDGS value and qualification for sale as animal feed. Thus, in order to avoid and/or minimize these problems, at least a portion of the undissolved particles (or solids) are removed from the feedstock slurry prior to the addition of sugar present in the feedstock slurry to the fermentor. Extraction activity and the efficiency of the butanol production are increased when extraction is performed on a fermentation broth containing an aqueous solution wherein undissolved particles have been removed relative to extraction performed on a fermentation broth containing an aqueous solution wherein undissolved particles have not been removed.

Extractive fermentation without the presence of the undissolved solids can lead to higher mass transfer rate of the product alcohol from the fermentation broth to the extractant, better phase separation of the extractant from the fermentation inside or external to the fermentor, and lower hold up of the extractant as a result of higher extractant droplet rise velocities. Also, for example, the extractant droplets held up in the fermentation broth during fermentation will disengage from the fermentation broth faster and more completely, thereby resulting in less free extractant in the fermentation broth and can decrease the amount of extractant lost in the process. In addition, for example, the microorganism can be recycled and additional equipment in the downstream processing can be eliminated, such as for example, a beer column and/or some or all of the whole stillage centrifuges. Further, for example, the possibility of extractant being lost in the DDGS is removed. Also, for example, the ability to recycle the microorganism can increase the overall rate of product alcohol production, lower the overall titer requirement, and/or lower the aqueous titer requirement, thereby leading to a healthier microorganism and a higher production rate. In addition, for example, it can be possible to eliminate an agitator in the fermentor to reduce capital costs; to increase the fermentor productivity since the volume is used more efficiently because the extractant hold up is minimized and the undissolved solids are not present; and/or to use continuous fermentation or smaller fermentors in a greenfield plant.

Examples of increased extraction efficiency can include, for example, a stabilized partition coefficient, enhanced (e.g., quicker or more complete) phase separation, enhanced liquid-liquid mass transfer coefficient, operation at a lower titer, increased process stream recyclability, increased fermentation volume efficiency, increased feedstock (e.g., corn) load feeding, increased butanol titer tolerance of the microorganism (e.g., a recombinant microorganism), water recycling, reduction in energy, increased recycling of extractant, and/or recycling of the microorganism.

For example, the volume of the fermentor taken up by solids will be decreased. Thus, the effective volume of the fermentor available for the fermentation can be increased. In some embodiments, the volume of the fermentor available for the fermentation is increased by at least about 10%.

For example, there can be a stabilization in partition coefficient. Because the corn oil in the fermentor can be reduced by removing the solids from the feedstock slurry prior to fermentation, the extractant is exposed to less corn oil which combines with the extractant and may lower the partition coefficient if present in sufficient amount. Therefore, reduction of the corn oil introduced into the fermentor results in a more stable partition coefficient of the extractant phase in the fermentor. In some embodiments, the partition coefficient is decreased by less than about 10% over 10 fermentation cycles.

For example, there can be an increase in the extraction efficiency of the butanol with extractant because there will be a higher mass transfer rate (e.g., in the form of a higher mass transfer coefficient) of the product alcohol from the fermentation broth to the extractant, thereby resulting in an increased efficiency of product alcohol production. In some embodiments, the mass transfer coefficient is increased at least 2-fold (see Examples 4 and 5).

In addition, there can be an increase in phase separation between the fermentation broth and the extractant that reduces the likelihood of the formation of an emulsion, thereby resulting in an increased efficiency of product alcohol production. For example, the phase separation can occur more quickly or can be more complete. In some embodiments, a phase separation may occur where previously no appreciable phase separation was observed in 24 hours. In some embodiments, the phase separation occurs at least about 2× as quickly, at least about 5× as quickly, or at least about 10× as quickly as compared to the phase separation where solids have not been removed (see Examples 6 and 7).

Further, there can be an increase in the recovery and recycling of the extractant. The extractant will not be "trapped" in the solids which may ultimately be removed as DDGS, thereby resulting in an increased efficiency of product alcohol production (see Examples 8 and 9). Also, there will be less dilution of the extractant with corn oil, and there may be less degradation of the extractant (see Example 10).

Also, the flow rate of the extractant can be reduced which will lower operating costs, thereby resulting in an increased efficiency of product alcohol production.

Further still, hold up of the extractant will be decreased as a result of extractant droplets rising at a higher velocity, thereby resulting in an increased efficiency of product alcohol production. Reducing the amount of undissolved solids in the fermentor will also result in an increased efficiency of product alcohol production.

In addition, an agitator can be removed from the fermentor because it is no longer needed to suspend the undissolved solids, thereby reducing capital costs and energy, and increasing the efficiency of the product alcohol production.

FIGS. 1-5 provide various non-limiting embodiments of methods and systems involving fermentation processes in which alcohol esters are produced in situ, extracted from the fermentation medium, and reacted to recover product alcohol. FIGS. 1-5 also provide various non-limiting embodiments of methods and systems of using carboxylic acid that can be esterified with product alcohol and can contemporaneously serve as an ISPR extractant. FIGS. 1-5 also provide various non-limiting embodiments of methods and systems of converting lipids in a feedstock to carboxylic acid that can be esterified with product alcohol and can contemporaneously serve as an ISPR extractant.

In some embodiments, including any of the aforementioned embodiments described with reference to FIGS. 1-5, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose and galactose; oligosaccharides such as lactose maltose, or sucrose; polysaccharides such as starch or cellulose; or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

Additionally, the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C*1 *Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489, 1990). Hence, it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch-based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, U.S. Patent Application Publication No. 2007/0031918 A1, which is herein incorporated by reference. In addition to an appropriate carbon source (from aqueous stream 22), fermentation broth must contain suitable minerals, salts, cofactors, buffers, and other components, known to those skilled in the art, suitable for the growth of the cultures and promotion of an enzymatic pathway for production of a product alcohol.

From the above discussion and the Examples, one skilled in the art can ascertain essential characteristics of the present invention and can make various changes and modifications of the invention to adapt to various uses and conditions without departing from the present invention. For example, in some embodiments, alcohol esterification and extraction according to the present invention can be employed pre-fermentation, that is, during seed culturing of microorganisms 32 prior to fermentation in fermentation vessel 30. Typically, microorganisms 32 such as yeast can be grown from a seed culture to a desired cell concentration before being harvested and inoculated into fermentation vessel 30, as known in the art.

The carbon source feedstock is an important cost factor in microorganism production such as yeast production and consequently, the biomass yield on sugar is an important optimization criterion. Because the ATP yield from the alcoholic fermentation is much lower than that from the respiratory sugar dissimilation, occurrence of alcoholic fermentation negatively affects the biomass yield and is sought to be avoided during the yeast production (i.e., seed culturing). Nonetheless, the culturing of microorganisms in a seed culture medium can produce an amount of fermentation product including alcohol. For example, in *S. cerevisiae* yeast, the alcoholic fermentation and respiration occur simultaneously whenever the specific growth rate (μ) and/or the sugar concentration in aerobic cultures exceed a critical value (see, e.g., van Hoek, et al., Biotechnol. Bioeng. 68:517-523, 2000). In order to achieve high biomass yield, the yeast growth is typically controlled, for example, by respiratory conditions using fed-batch fermentation technology for seed culturing. For example, sugar is fed at a low rate resulting in a low sugar concentration in the culture and a low rate of sugar uptake such that sugar metabolism can be substantially respiratory. Under these conditions, high biomass yields can be obtained and accumulation of toxic products can be minimized. In practice, in large scale fed-batch industrial processes, the cells can be exposed to concentration gradients due to an inefficient mixing (see, e.g., Enfors, et al., J. Biotechnol. 85:175-185, 2001). Production and reassimilation of fermentation by-products can be one of the reasons for reduction of biomass yield per glucose in large scale bioreactors compared to laboratory scale.

However, at these conditions, when culturing butanol-producing yeast, for example, the fermentation product including butanol cannot be reassimilated and may accumulate in the culture medium which can be toxic to the microorganisms at high concentration. If product accumulation exceeds critical cell growth inhibitory concentrations (e.g., cell growth is lower than the growth that may be limited by the feed), then a loss of fed-batch control may occur. According to the present invention, using alcohol esterification and extraction to remove butanol from the culture medium can allow the fed-batch fermentation to proceed despite the problems with inefficient mixing and butanol toxicity.

Thus, according to some embodiments, the seed culture medium can be contacted with catalyst 42 and carboxylic acid 28 leading to the production of alcohol esters by esterification of the product alcohol and ultimately, an improved biomass yield per glucose in large scale bioreactors. Furthermore, the concentration of product alcohol in the culture medium can be controlled by alcohol esterification and thus, minimizing or avoiding the deleterious effects of the product alcohol on the microorganisms. In some embodiments, alcohol esters can be extracted from the seed culture medium and the alcohol recovered from the alcohol esters in the same manner as described above with respect to extraction of alcohol esters from fermentation vessel 30 and recovery of product alcohol 54. In some embodiments, alcohol esterification according to the present invention can be employed to esterify the product alcohol in both the seed culture medium and the fermentation medium. In such embodiments, a higher yield of product alcohol can be achieved for the fermentation process as a whole by recovering not only alcohol esters (and free product alcohol) from the fermentation medium, but also recovering alcohol esters produced during the seed culturing (e.g., recovering alcohol esters and/or product alcohol from a propagation tank). In some embodiments, alcohol esterification according to the present invention can be employed pre-fermentation for removal of alcohol from the seed culture medium, while conventional ISPR of product alcohol can be employed for removal of product alcohol during fermentation in fermentation vessel 30.

Thus, it should be apparent that alcohol esterification and extraction according to the present invention can be employed at various stages in an alcohol fermentation process without departing from the present invention.

The alcohol products produced by the methods of the present invention have a number of applications, for example, as reagents, solvents, and fuel. Butanol produced by the claimed methods may be used directly as a fuel (e.g., biofuel), a fuel additive, an alcohol used for the production of esters that can be used as diesel or biodiesel fuel, a feedstock chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids. Thus, the present invention provides alternative methods to produce alcohols including butanol, which can support the high demand for these industrial chemicals. While not wishing to be bound by theory, it is believed that the processes described herein are useful in conjunction with any alcohol producing microorganism, particularly recombinant microorganisms which produce alcohol at titers above their tolerance levels.

Recombinant Microorganisms and Butanol Biosynthetic Pathways

Alcohol-producing microorganisms are known in the art. For example, fermentative oxidation of methane by methanotrophic bacteria (e.g., *Methylosinus trichosporium*) produces methanol, and contacting methanol (a $C_1$ alkyl alcohol) with a carboxylic acid and a catalyst capable of esterifying the carboxylic acid with methanol forms a methanol ester of the carboxylic acid. The yeast strain CEN.PK113-7D (CBS 8340, the Centraal Buro voor Schimmelculture; van Dijken, et al., Enzyme Microb. Techno. 26:706-714, 2000) can produce ethanol, and contacting ethanol with a carboxylic acid and a catalyst capable of esterifying the carboxylic acid with the ethanol forms ethyl ester (see, e.g., Example 36).

Recombinant microorganisms which produce alcohol are also known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38:

354-361, 1992; Zhang, et al., Science 267:240-243, 1995; U.S. Patent Application Publication No. 2007/0031918 A1; U.S. Pat. No. 7,223,575; U.S. Pat. No. 7,741,119; U.S. Patent Application Publication No. 2009/0203099 A1; U.S. Patent Application Publication No. 2009/0246846 A1; and PCT Application Publication No. WO 2010/075241, which are herein incorporated by reference).

Suitable recombinant microorganisms capable of producing butanol are known in the art, and certain suitable microorganisms capable of producing butanol are described herein. Recombinant microorganisms to produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia*, or *Saccharomyces*. In one embodiment, recombinant microorganisms can be selected from the group consisting of *Escherichia coli, Lactobacillus plantarum, Kluyveromyces lactis, Kluyveromyces marxianus*, and *Saccharomyces cerevisiae*. In one embodiment, the recombinant microorganism is yeast. In one embodiment, the recombinant microorganism is crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*.

In some embodiments, the host cell is *Saccharomyces cerevisiae. S. cerevisiae* yeast are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

The production of butanol utilizing fermentation with a microorganism, as well as microorganisms which produce butanol, is disclosed, for example, in U.S. Patent Application Publication No. 2009/0305370, herein incorporated by reference. In some embodiments, microorganisms comprise a butanol biosynthetic pathway. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in US Application Publication No. 2009/0305363, herein incorporated by reference. Microorganisms substantially free of an enzyme having NAD-dependent glycerol-3-phosphate dehydrogenase activity such as GPD2 are also described therein.

Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Certain suitable proteins having the ability to catalyze indicated substrate to product conversions are described herein and other suitable proteins are provided in the art. For example, U.S. Patent Application Publication Nos. 2008/0261230, 2009/0163376, and 2010/0197519, incorporated herein by reference, describe acetohydroxy acid isomeroreductases; U.S. Patent Application Publication No. 2010/0081154, incorporated by reference, describes dihydroxy-acid dehydratases; an alcohol dehydrogenase is described in U.S. Patent Application Publication No. 2009/0269823, incorporated herein by reference.

It is well understood by one skilled in the art that many levels of sequence identity are useful in identifying polypeptides from other species, wherein such polypeptides have the same or similar function or activity and are suitable for use in the recombinant microorganisms described herein. Useful examples of percent identities include, but are not limited to, 75%, 80%, 85%, 90%, or 95%, or any integer percentage from 75% to 100% may be useful in describing the present invention such as 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

1-Butanol Biosynthetic Pathway

A biosynthetic pathway for the production of 1-butanol as well as suitable polypeptides and polynucleotides encoding such polypeptides that may be used is described by Donaldson, et al., in U.S. Patent Application Publication No. 2008/0182308 A1, incorporated herein by reference. This biosynthetic pathway comprises the following substrate to product conversions:

a) acetyl-CoA to acetoacetyl-CoA, which may be catalyzed, for example, by acetyl-CoA acetyltransferase;
b) acetoacetyl-CoA to 3-hydroxybutyryl-CoA, which may be catalyzed, for example, by 3-hydroxybutyryl-CoA dehydrogenase;
c) 3-hydroxybutyryl-CoA to crotonyl-CoA, which may be catalyzed, for example, by crotonase;
d) crotonyl-CoA to butyryl-CoA, which may be catalyzed, for example, by butyryl-CoA dehydrogenase;
e) butyryl-CoA to butyraldehyde, which may be catalyzed, for example, by butyraldehyde dehydrogenase; and
f) butyraldehyde to 1-butanol, which may be catalyzed, for example, by 1-butanol dehydrogenase.

In some embodiments, the 1-butanol biosynthetic pathway comprises at least one gene, at least two genes, at least three genes, at least four genes, or at least five genes that is/are heterologous to the yeast cell. In some embodiments, the recombinant host cell comprises a heterologous gene for each substrate to product conversion of a 1-butanol biosynthetic pathway.

2-Butanol Biosynthetic Pathway

Biosynthetic pathways for the production of 2-butanol as well as suitable polypeptides and polynucleotides encoding such polypeptides that may be used are described by Donaldson, et al., in U.S. Patent Application Publication Nos. 2007/0259410 A1 and 2007/0292927A1, and in PCT Application Publication No. WO 2007/130521, all of which are incorporated herein by reference. One 2-butanol biosynthetic pathway comprises the following substrate to product conversions:

a) pyruvate to alpha-acetolactate, which may be catalyzed, for example, by acetolactate synthase;

b) alpha-acetolactate to acetoin, which may be catalyzed, for example, by acetolactate decarboxylase;

c) acetoin to 2,3-butanediol, which may be catalyzed, for example, by butanediol dehydrogenase;

d) 2,3-butanediol to 2-butanone, which may be catalyzed, for example, by butanediol dehydratase; and e) 2-butanone to 2-butanol, which may be catalyzed, for example, by 2-butanol dehydrogenase.

In some embodiments, the 2-butanol biosynthetic pathway comprises at least one gene, at least two genes, at least three genes, or at least four genes that is/are heterologous to the yeast cell. In some embodiments, the recombinant host cell comprises a heterologous gene for each substrate to product conversion of a 2-butanol biosynthetic pathway.

Isobutanol Biosynthetic Pathway

Biosynthetic pathways for the production of isobutanol as well as suitable polypeptides and polynucleotides encoding such polypeptides that may be used are described in U.S. Patent Application Publication No. 2007/0092957 A1 and PCT Application Publication No. WO 2007/050671, incorporated herein by reference. One isobutanol biosynthetic pathway comprises the following substrate to product conversions:

a) pyruvate to acetolactate, which may be catalyzed, for example, by acetolactate synthase;

b) acetolactate to 2,3-dihydroxyisovalerate, which may be catalyzed, for example, by acetohydroxy acid reductoisomerase;

c) 2,3-dihydroxyisovalerate to α-ketoisovalerate, which may be catalyzed, for example, by acetohydroxy acid dehydratase;

d) α-ketoisovalerate to isobutyraldehyde, which may be catalyzed, for example, by a branched-chain keto acid decarboxylase; and e) isobutyraldehyde to isobutanol, which may be catalyzed, for example, by a branched-chain alcohol dehydrogenase.

Suitable polypeptide sequences that encode enzymes which catalyze the substrate to product conversions of the isobutanol biosynthetic pathway as well as E.C. numbers corresponding to suitable enzymes for the indicated pathway steps include, but are not limited to, those in Tables AA and BB. Suitable enzymes associated with the given E.C. numbers will be readily available to those of skill in the art, for example, through the BRENDA database (http://www.brenda-enzymes.org/).

TABLE AA

Example polypeptides

| Pathway step | Enzyme | SEQ ID NO: |
|---|---|---|
| a) pyruvate to acetolactate | *Bacillus subtilis* alsS (acetolactate synthase, "ALS") | 144 |
| b) acetolactate to 2,3-dihydroxyisovalerate | *Lactococcus lactis* ilvC (ketol-acid reductoisomerase, "KARI") | 145 |
| c) 2,3-dihydroxyisovalerate to α-ketoisovalerate | *Streptococcus mutans* ilvD (dihydroxyacid dehydratase, "DHAD") | 146 |
| d) α-ketoisovalerate to isobutyraldehyde | *Lactococcus lactis* kivD (branched-chain α-keto acid decarboxylase), codon optimized | 147 |
| e) isobutyraldehyde to isobutanol | horse liver alcohol dehydrogenase ("ADH") | 148 |
| e) isobutyraldehyde to isobutanol | *Achromobacter xylosoxidans* sadB | 149 |

TABLE BB

E.C. numbers

| Pathway step | E.C. Number: |
|---|---|
| a) pyruvate to acetolactate | 2.2.1.6 |
| b) acetolactate to 2,3-dihydroxyisovalerate | 1.1.1.86 |
| c) 2,3-dihydroxyisovalerate to α-ketoisovalerate | 4.2.1.9 |
| d) α-ketoisovalerate to isobutyraldehyde | 4.1.1.72 or 4.1.1.1 |
| e) isobutyraldehyde to isobutanol | 1.1.1.265, 1.1.1.1 or 1.1.1.2 |

Provided herein are recombinant microorganisms comprising an isobutanol biosynthetic pathway comprising steps a)-e) (above) wherein at least one of the enzymes selected from the group of the enzyme catalyzing step c) and the enzyme catalyzing step e) is encoded by a heterologous polynucleotide integrated into the chromosome of the microorganism. In some embodiments, both an enzyme catalyzing step c) is encoded by a heterologous polynucleotide integrated into the chromosome of the microorganism, and enzyme catalyzing step e) is encoded by a heterologous polynucleotide integrated into the chromosome of the microorganism.

Provided herein are polynucleotides suitable for recombinant microorganisms comprising a butanol biosynthetic pathway such as an isobutanol biosynthetic pathway. Such polynucleotides include the coding region of the alsS gene from *Bacillus subtilis* (nt position 457-2172 of SEQ ID NO: 1) and the ilvC gene from *Lactococcus lactis* (nt 3634-4656 of SEQ ID NO: 1) as well as plasmids comprising either or both. Also suitable is a chimeric gene having the coding region of the alsS gene from *Bacillus subtilis* (nt position 457-2172 of SEQ ID NO: 1) expressed from the yeast CUP1 promoter (nt 2-449 of SEQ ID NO: 1) and followed by the CYC1 terminator (nt 2181-2430 of SEQ ID NO: 1) for expression of ALS, and a chimeric gene having the coding region of the ilvC gene from *Lactococcus lactis* (nt 3634-4656 of SEQ ID NO: 1) expressed from the yeast ILV5 promoter (2433-3626 of SEQ ID NO: 1) and followed by the ILV5 terminator (nt 4682-5304 of SEQ ID NO: 1) for expression of KARI, as well as plasmids comprising either or both chimeric genes.

Suitable polynucleotides include the coding region of the ilvD gene from *Streptococcus mutans* (nt position 3313-4849 of SEQ ID NO: 2), the coding region of codon optimized horse liver alcohol dehydrogenase (nt 6286-7413 of SEQ ID NO: 2), the coding region of the codon-optimized kivD gene from *Lactococcus lactis* (nt 9249-10895 of SEQ ID NO: 2) as well as plasmids comprising any or all or any combination thereof. Also suitable is a chimeric gene having the coding region of the ilvD gene from *Streptococcus mutans* (nt position 3313-4849 of SEQ ID NO: 2) expressed from the *S. cerevisiae* FBA1 promoter (nt 2109-3105 of SEQ ID NO: 2)

followed by the FBA1 terminator (nt 4858-5857 of SEQ ID NO: 2) for expression of DHAD; a chimeric gene having the coding region of codon optimized horse liver alcohol dehydrogenase (nt 6286-7413 of SEQ ID NO: 2) expressed from the *S. cerevisiae* GPM1 promoter (nt 7425-8181 of SEQ ID NO: 2) followed by the ADH1 terminator (nt 5962-6277 of SEQ ID NO: 2) for expression of ADH; and a chimeric gene having the coding region of the codon-optimized kivD gene from *Lactococcus lactis* (nt 9249-10895 of SEQ ID NO: 2) expressed from the TDH3 promoter (nt 10896-11918 of SEQ ID NO: 2) followed by the TDH3 terminator (nt 8237-9235 of SEQ ID NO: 2) for expression of KivD as well as plasmids containing any, all, or any combination of such chimeric genes. In addition, suitable polynucleotides include those having at least about 75% identity to the coding regions and chimeric genes specified, as well as plasmids comprising such polynucleotides.

In some embodiments, the isobutanol biosynthetic pathway comprises at least one gene, at least two genes, at least three genes, or at least four genes that is/are heterologous to the yeast cell. In some embodiments, the recombinant host cell comprises a heterologous gene for each substrate to product conversion of an isobutanol biosynthetic pathway.

Suitable strains include those described in certain applications cited and incorporated by reference herein as well as in U.S. Provisional Application Ser. No. 61/380,563, filed on Sep. 7, 2010. Construction of certain suitable strains including those used in the Examples, is provided herein.

Construction of *Saccharomyces cerevisiae* Strain BP1083 ("NGCI-070"; PNY1504)

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-IoxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 μg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 genomic DNA as template, prepared with a Gentra® Puregene® Yeast/Bact. kit (Qiagen, Valencia, Calif.). NYLA83 is a strain (construction described in U.S. Patent Application Publication No. 2011/0124060, incorporated herein by reference in its entirety) which carries the PDC1 deletion-ilvDSm integration described in U.S. Patent Application Publication No. 2009/0305363, herein incorporated by reference in its entirety). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1°)/0) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccharomyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccharomyces cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 150) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 143) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 151) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of *Saccharomyces cerevisiae* Strain PNY2205

The strain, PNY2205, was derived from PNY1503 (BP1064) which is described above.

Deletions, which generally removed the entire coding sequence, were created by homologous recombination with PCR fragments containing regions of homology upstream and downstream of the target gene and the URA3 gene for selection of transformants. The URA3 gene was removed by homologous recombination to create a scarless deletion. Gene integrations were generated in a similar manner.

The scarless deletion procedure was adapted from Akada et al., (Yeast, 23:399, 2006). In general, the PCR cassette for each scarless deletion was made by combining four fragments, A-B-U-C, by overlapping PCR. In some instances, the individual fragments were first cloned into a plasmid prior to the entire cassette being amplified by PCR for the deletion/integration procedure. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene) regions. Fragments A and C, each generally 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome.

Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

FRA2 Deletion

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). FRA2 Fragment A was amplified with primer oBP594 (SEQ ID NO: 152) and primer oBP595 (SEQ ID NO: 153), containing a 5' tail with homology to the 5' end of FRA2 Fragment B. FRA2 Fragment B was amplified with primer oBP596 (SEQ ID NO: 154), containing a 5' tail with homology to the 3' end of FRA2 Fragment A, and primer oBP597 (SEQ ID NO: 155), containing a 5' tail with homology to the 5' end of FRA2 Fragment U. FRA2 Fragment U was amplified with primer oBP598 (SEQ ID NO: 156), containing a 5' tail with homology to the 3' end of FRA2 Fragment B, and primer oBP599 (SEQ ID NO: 157), containing a 5' tail with homology to the 5' end of FRA2 Fragment C. FRA2 Fragment C was amplified with primer oBP600 (SEQ ID NO: 158), containing a 5' tail with homology to the 3' end of FRA2 Fragment U, and primer oBP601 (SEQ ID NO: 159). PCR products were purified with a PCR Purification kit (Qiagen, Valencia, Calif.). FRA2 Fragment AB was created by overlapping PCR by mixing FRA2 Fragment A and FRA2 Fragment B and amplifying with primers oBP594 (SEQ ID NO: 152) and oBP597 (SEQ ID NO: 155). FRA2 Fragment UC was created by overlapping PCR by mixing FRA2 Fragment U and FRA2 Fragment C and amplifying with primers oBP598 (SEQ ID NO: 156) and oBP601 (SEQ ID NO: 159). The resulting PCR products were purified on an agarose gel followed by a Gel Extraction kit (Qiagen, Valencia, Calif.). The FRA2 ABUC cassette was created by overlapping PCR by mixing FRA2 Fragment AB and FRA2 Fragment UC and amplifying with primers oBP594 (SEQ ID NO: 152) and oBP601 (SEQ ID NO: 159). The PCR product was purified with a PCR Purification kit (Qiagen, Valencia, Calif.).

Competent cells of PNY1503 were made and transformed with the FRA2 ABUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol at 30° C. Transformants with a fra2 knockout were screened for by PCR with primers oBP602 (SEQ ID NO: 160) and oBP603 (SEQ ID NO: 161) using genomic DNA prepared with a Gentra® Puregene® Yeast/Bact. kit (Qiagen, Valencia, Calif.). A correct transformant was grown in YPE (yeast extract, peptone, 1% ethanol) and plated on synthetic complete medium containing 5-fluoro-orotic acid (0.1%) at 30° C. to select for isolates that lost the URA3 marker. The deletion and marker removal were confirmed by PCR with primers oBP602 (SEQ ID NO: 160) and oBP603 (SEQ ID NO: 161) using genomic DNA prepared with a Gentra® Puregene® Yeast/Bact. kit (Qiagen, Valencia, Calif.). The absence of the FRA2 gene from the isolate was demonstrated by a negative PCR result using primers specific for the deleted coding sequence of FRA2, oBP605 (SEQ ID NO: 162) and oBP606 (SEQ ID NO: 163). The correct isolate was selected as strain CEN.PK 113-7D MATa ura3Δ::loxP his3Δ pdc6Δ pdc1Δ::P[PDC1]-DHAD|ilvD_Sm-PDC1t pdc5Δ::P[PDC5]-ADH|sadB_Ax-PDC5t gpd2Δ::loxP fra2Δ and designated as PNY1505 (BP1135).

ADH1 Deletion and kivD LI(y) Integration

The ADH1 gene was deleted and replaced with the kivD coding region from *Lactococcus lactis* codon optimized for expression in *Saccharomyces cerevisiae*. The scarless cassette for the ADH1 deletion-kivD_LI(y) integration was first cloned into plasmid pUC19-URA3MCS, as described in U.S. Provisional Application Ser. No. 61/356,379, filed Jun. 18, 2010, incorporated herein by reference. The vector is pUC19 based and contains the sequence of the URA3 gene from *Saccharomyces cerevisiae* CEN.PK 113-7D situated within a multiple cloning site (MCS). pUC19 contains the pMB1 replicon and a gene coding for beta-lactamase for replication and selection in *Escherichia coli*. In addition to the coding sequence for URA3, the sequences from upstream (250 bp) and downstream (150 bp) of this gene are present for expression of the URA3 gene in yeast.

The kivD coding region from *Lactococcus lactis* codon optimized for expression in *Saccharomyces cerevisiae* was amplified using pLH468 (U.S. Provisional Application Ser. No. 61/246,709, filed Sep. 29, 2009) as template with primer oBP562 (SEQ ID NO: 164), containing a PmeI restriction site, and primer oBP563 (SEQ ID NO: 165), containing a 5' tail with homology to the 5' end of ADH1 Fragment B. ADH1 Fragment B was amplified from genomic DNA prepared as above with primer oBP564 (SEQ ID NO: 166), containing a 5' tail with homology to the 3' end of kivD_LI(y), and primer oBP565 (SEQ ID NO: 167), containing a FseI restriction site. PCR products were purified with a PCR Purification kit (Qiagen, Valencia, Calif.). kivD_LI(y)-ADH1 Fragment B was created by overlapping PCR by mixing the kivD_LI(y) and ADH1 Fragment B PCR products and amplifying with primers oBP562 (SEQ ID NO: 164) and oBP565 (SEQ ID NO: 167). The resulting PCR product was digested with PmeI and FseI and ligated with T4 DNA ligase into the corresponding sites of pUC19-URA3MCS after digestion with the appropriate enzymes. ADH1 Fragment A was amplified from genomic DNA with primer oBP505 (SEQ ID NO: 168) containing a SacI restriction site, and primer oBP506 (SEQ ID NO: 169), containing an AscI restriction site. The ADH1 Fragment A PCR product was digested with SacI and AscI and ligated with T4 DNA ligase into the corresponding sites of the plasmid containing kivD_LI(y)-ADH1 Fragment B. ADH1 Fragment C was amplified from genomic DNA with primer oBP507 (SEQ ID NO: 170), containing a PacI restriction site, and primer oBP508 (SEQ ID NO: 171), containing a SalI restriction site. The ADH1 Fragment C PCR product was digested with PacI and SalI and ligated with T4 DNA ligase into the corresponding sites of the plasmid containing ADH1 Fragment A-kivD_LI(y)-ADH1 Fragment B. The hybrid promoter UAS(PGK1)—$P_{FBA1}$ was amplified from vector pRS316-UAS(PGK1)-$P_{FBA1}$-GUS (SEQ ID NO: 172) with primer oBP674 (SEQ ID NO: 173), containing an AscI restriction site, and primer oBP675 (SEQ ID NO: 174), containing a PmeI restriction site. The UAS(PGK1)—$P_{FBA1}$ PCR product was digested with AscI and PmeI and ligated with T4 DNA ligase into the corresponding sites of the plasmid containing kivD_LI(y)-ADH1 Fragments ABC. The entire integration cassette was amplified from the resulting plasmid with primers oBP505 (SEQ ID NO: 168) and oBP508 (SEQ ID NO: 171) and purified with a PCR Purification kit (Qiagen, Valencia, Calif.).

Competent cells of PNY1505 were made and transformed with the ADH1-kivD_LI(y) PCR cassette constructed above using a Frozen-EZ Yeast Transformation II™ kit (Zymo Research Corporation, Irvine, Calif.). Transformation mixtures were plated on synthetic complete media lacking uracil supplemented with 1% ethanol at 30° C. Transformants were grown in YPE (1% ethanol) and plated on synthetic complete medium containing 5-fluoro-orotic acid (0.1%) at 30° C. to select for isolates that lost the URA3 marker. The deletion of ADH1 and integration of kivD_LI(y) were confirmed by PCR with external primers oBP495 (SEQ ID NO: 175) and oBP496 (SEQ ID NO: 176) and with kivD_LI(y) specific primer oBP562 (SEQ ID NO: 164) and external primer oBP496 (SEQ ID NO: 176) using genomic DNA prepared with a Gentra® Puregene® Yeast/Bact. kit (Qiagen, Valencia, Calif.). The correct isolate was selected as strain CEN.PK 113-7D MATa ura3Δ::loxP his3Δ pdc6Δ pdc1Δ::P[PDC1]-DHAD|ilvD_Sm-PDC1tpdc5Δ::P[PDC5]-ADH|sadB_Ax-PDC5t gpd2Δ::loxP fra2Δ adh1Δ::UAS(PGK1)P[FBA1]-kivD_LI(y)-ADH1t and designated as PNY1507 (BP1201). PNY1507 was transformed with isobutanol pathway plasmids pYZ090 (SEQ ID NO: 1) and pBP915 (described below).

Construction of the pRS316-UAS(PGK1)—FBA1p-GUS Vector

To clone a cassette UAS(PGK1)—FBA1p (SEQ ID NO: 177, first a 602 bp FBA1 promoter (FBA1p) was PCR-amplified from genomic DNA of CEN.PK with primers T-FBA1 (SalI) (SEQ ID NO: 178) and B-FBA1 (SpeI) (SEQ ID NO: 179), and cloned into SalI and SpeI sites on the plasmid pWS358-PGK1p-GUS (SEQ ID NO: 180) after the PGK1p promoter was removed with a SalI/SpeI digest of the plasmid, yielding pWS358-FBA1p-GUS. The pWS358-PGK1p-GUS plasmid was generated by inserting a PGK1p and beta-glucuronidase gene (GUS) DNA fragments into multiple cloning site of pWS358, which was derived from pRS423 vector (Christianson, et al., Gene 110:119-122, 1992). Secondly, the resulting pWS358-FBA1p-GUS plasmid was digested with SalI and SacI, a DNA fragment containing a FBA1p promoter, GUS gene, and FBAt terminator gel-purified, and cloned into SalI/SacI sites on pRS316 to create pRS316-FBA1p-GUS. Thirdly, a 118 bp DNA fragment containing an upstream activation sequence (UAS) located between positions −519 and −402 upstream of the 3-phosphoglycerate kinase (PGK1) open reading frame, namely UAS(PGK1), was PCR-amplified from genomic DNA of CEN.PK with primers T-U/PGK1 (KpnI) (SEQ ID NO: 181) and B-U/PGK1 (SalI) (SEQ ID NO: 182). The PCR product was digested with KpnI and SalI and cloned into KpnI/SalI sites on pRS316-FBA1p-GUS to create pRS316-UAS(PGK1)-FBA1p-GUS.

Construction of Integration Vector pUC19-kan::pdc1::FBA-alsS::TRX1

The FBA-alsS-CYCt cassette was constructed by moving the 1.7 kb BbvCI/PacI fragment from pRS426::GPD::alsS::

CYC (U.S. Patent Application Publication No. 2007/0092957) to pRS426::FBA::ILV5::CYC (U.S. Patent Application Publication No. 2007/0092957, previously digested with BbvCI/PacI to release the ILV5 gene). Ligation reactions were transformed into *E. coli* TOP10 cells and transformants were screened by PCR using primers N98SegF1 (SEQ ID NO: 183) and N99SeqR2 (SEQ ID NO: 184). The FBA-alsS-CYCt cassette was isolated from the vector using BglII and NotI for cloning into pUC19 URA3::ilvD-TRX1 (as described in U.S. Provisional Application Ser. No. 61/356,379, filed Jun. 18, 2010, incorporated herein by reference, clone "B") at the AflII site (Klenow fragment was used to make ends compatible for ligation). Transformants containing the alsS cassette in both orientations in the vector were obtained and confirmed by PCR using primers N98SeqF4 (SEQ ID NO: 185) and N1111 (SEQ ID NO: 186) for configuration "A" and N98SeqF4 (SEQ ID NO: 185) and N1110 (SEQ ID NO: 187) for configuration "B". A geneticin selectable version of the "A" configuration vector was then made by removing the URA3 gene (1.2 kb NotI/NaeI fragment) and adding a geneticin cassette previously described (SEQ ID NO: 655 of U.S. Provisional Application Ser. No. 61/356,379, filed Jun. 18, 2010, incorporated herein by reference). Klenow fragment was used to make all ends compatible for ligation, and transformants were screened by PCR to select a clone with the geneticin resistance gene in the same orientation as the previous URA3 marker using primers BK468 (SEQ ID NO: 188) and N160SeqF5 (SEQ ID NO: 189). The resulting clone was called pUC19-kan::pdc1::FBA-alsS::TRX1 (clone A) (SEQ ID NO: 190).

The pUC19-kan::pdc1::FBA-alsS integration vector described above was linearized with PmeI and transformed into PNY1507 (described above). PmeI cuts the vector within the cloned pdc1-TRX1 intergenic region and thus, leads to targeted integration at that location (Rothstein, Methods Enzymol. 194:281-301, 1991). Transformants were selected on YPE plus 50 μg/ml G418. Patched transformants were screened by PCR for the integration event using primers N160SeqF5 (SEQ ID NO: 189) and oBP512 (SEQ ID NO: 47). Two transformants were tested indirectly for acetolactate synthase function by evaluating the strains ability to make isobutanol. To do this, additional isobutanol pathway genes were supplied on *E. coli*-yeast shuttle vectors (pYZ090ΔalsS and pBP915, described below). One clone, strain MATa ura3Δ::loxP his3Δ pdc6Δ pdc1Δ::P[PDC1]-DHAD|ilvD_Sm-PDC1t-pUC19-loxP-kanMX-IoxP-P [FBA1]-ALS|alsS_Bs-CYC1t pdc5Δ::P[PDC5]-ADH|sadB_Ax-PDC5t gpd2Δ::loxP fra2Δ adh1Δ::UAS(PGK1)P [FBA1]-kivD_LI(y)-ADH1t was designated as PNY2204. PNY2205 is PNY2204 transformed with pYZ090ΔalsS and pBP915 plasmids.

Isobutanol Pathway Plasmids (pYZ090ΔalsS and pBP915)

pYZ090 (SEQ ID NO: 1) was digested with SpeI and NotI to remove most of the CUP1 promoter and all of the alsS coding sequence and CYC terminator. The vector was then self-ligated after treatment with Klenow fragment and transformed into *E. coli* StbI3 cells, selecting for ampicillin resistance. Removal of the DNA region was confirmed for two independent clones by DNA sequencing across the ligation junction by PCR using primer N191 (SEQ ID NO: 191). The resulting plasmid was named pYZ090ΔalsS (SEQ ID NO: 192).

pBP915 was constructed from pLH468 (SEQ ID NO: 2; U.S. Provisional Application Ser. No. 61/246,709, filed Sep. 29, 2009) by deleting the kivD gene and 957 base pairs of the TDH3 promoter upstream of kivD. pLH468 was digested with SwaI and the large fragment (12896 bp) was purified on an agarose gel followed by a Gel Extraction kit (Qiagen, Valencia, Calif.). The isolated fragment of DNA was self-ligated with T4 DNA ligase and used to transform electrocompetent TOP10 *Escherichia coli* (Invitrogen, Carlsbad, Calif.). Plasmids from transformants were isolated and checked for the proper deletion by restriction analysis with the SwaI restriction enzyme. Isolates were also sequenced across the deletion site with primers oBP556 (SEQ ID NO: 193) and oBP561 (SEQ ID NO: 194). A clone with the proper deletion was designated pBP915 (pLH468ΔkivD) (SEQ ID NO: 195).

Construction of Strains NYLA74, NYLA83, and NYLA84

Insertion-inactivation of endogenous PDC1 and PDC6 genes of *S. cerevisiae*. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from *Achromobacter xylosoxidans* (disclosed in U.S. Patent Application Publication No. 2009/0269823) was cloned. The coding region of this gene called sadB for secondary alcohol dehydrogenase (SEQ ID NO: 69) was amplified using standard conditions from *A. xylosoxidans* genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in *Saccharomyces cerevisiae* (Ma, et al., Gene 58:201-216, 1987) as follows. The yeast-*E. coli* shuttle vector pRS425::GPM::kivD::ADH which contains the GPM1 promoter (SEQ ID NO: 72), kivD coding region from *Lactococcus* lactis (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 g of the remaining vector fragment was transformed into *S. cerevisiae* strain BY4741 along with 1 g of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6:: PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO: 80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117A-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH1t.

Construction of pdc1::PPDC1-ilvD Integration Cassette and PDC1 Deletion:

A pdc1::PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::PGPM1-sadB-ADH1t pdc1::PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6::PGPM1-sadB-ADH1t pdc1::PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 μg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6::PGPM1-sadB-ADH1t pdc1::PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (Hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6:: PGPM1-sadB-ADH1t pdc1::PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6::PGPM1-sadB-ADH1t pdc1::PPDC1-ilvD-FBA1t Δhis3 Δhxk2 pdc5::kanMX4.

Plasmid vectors pLH468 and pLH532 were simultaneously transformed into strain NYLA84 (BY4700 pdc6:: PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus lactis* (nt 9249-10895) expressed from the TDH3 promoter (nt 10896-11918) followed by the TDH3 terminator (nt 8237-9235) for expression of KivD.

Coding regions for *Lactococcus lactis* ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058,970, Example 3, which is herein incorporated by reference. pRS425::GPM-sadB is the pRS425 vector (ATCC No. 77106) with a chimeric gene containing the GPM1 promoter (SEQ ID NO: 72), coding region from a butanol dehydrogenase of *Achromobacter xylosoxidans* (sad B; DNA SEQ ID NO: 69; protein SEQ ID NO: 70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-Nott fragment from pLH435 that contains the PGPM1-Hadhy-ADH1t cassette in a triple ligation reaction. This yielded the vector pRS411:: PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the IlvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-IlvD (*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::PFBA1-ilvD(Strep) Lumio-FBA1t-PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KAR1 in yeast. pLH532 is a pHR81 vector (ATCC No. 87541) containing the following chimeric genes: 1) the CUP1 promoter (SEQ ID NO: 139), acetolactate synthase coding region from *Bacillus subtilis* (AlsS; SEQ ID NO: 137; protein SEQ ID NO: 138) and CYC1 terminator2 (SEQ ID NO: 133); 2) an ILV5 promoter (SEQ ID NO: 134), Pf5.IlvC coding region (SEQ ID NO: 132) and ILV5 terminator (SEQ ID NO: 135); and 3) the FBA1 promoter (SEQ ID NO: 136), *S. cerevisiae* KAR1 coding region (ILV5; SEQ ID NO: 131); and CYC1 terminator.

The Pf5.IlvC coding region is a sequence encoding KARI derived from *Pseudomonas fluorescens* that was described in U.S. Patent Application Publication No. 2009/0163376, which is herein incorporated by reference.

The Pf5.1IvC coding region was synthesized by DNA2.0, Inc. (Menlo Park, Calif.; SEQ ID NO: 132) based on codons that were optimized for expression in *Saccharomyces cerevisiae.* pYZ090 Construction pYZ090 (SEQ ID NO: 1) is based on the pHR81 (ATCC No. 87541) backbone and was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 Construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Construction of *Saccharomyces cerevisiae* Strain PNY2242

Strain PNY2242 was constructed in several steps from PNY1507 (described above). First, a chimeric gene comprised of the FBA1 promoter, the alsS coding region, and the CYC1 terminator was integrated into Chromosome XII, upstream of the TRX1 gene. The sequence of the modified locus is provided as SEQ ID NO: 196. Next, two copies of a gene encoding horse liver alcohol dehydrogenase were integrated into Chromosomes VII and XVI. On Chromosome VII, a chimeric gene comprised of the PDC1promoter, the hADH coding region, and the ADH1 terminator were placed into the fra2Δ locus (the original deletion of FRA2 is described above). The sequence of the modified locus is provided as SEQ ID NO: 197. On Chromosome XVI, a chimeric gene comprised of the PDC5 promoter, the hADH coding region, and the ADH1 terminator were integrated in the region formerly occupied by the long term repeat element YPRCdelta15. The sequence of the modified locus is provided as SEQ ID NO: 198. Then the native genes YMR226c and ALD6 were deleted. Elimination of YMR226c was a scarless deletion of only the coding region. The sequence of the modified locus is provided as SEQ ID NO: 199. The ALD6 coding region plus 700 bp of upstream sequence were deleted using CRE-lox mediated marker removal (methodology described above), so the resulting locus contains one loxP site. The sequence of the modified locus is provided as SEQ ID NO: 200. Finally, plasmids were introduced into the strain for expression of KARI (pLH702, SEQ ID NO: 201) and DHAD (pYZ067DkivDDhADH, SEQ ID NO: 202), resulting in strain PNY2242.

Where the recombinant microorganism produces isobutanol, under certain embodiments, smicroorganisms show higher specific productivity. Further, the volumetric rate was improved by about 50%.

While not wishing to be bound by theory, it is believed that the methods described herein provide extractive fermentation methods with improved production yields of product alcohol. As discussed above, alcohol production utilizing fermentation by microorganisms may be inefficient due to the alcohol toxicity thresholds of the microorganism. In some embodiments, the methods herein provide a means to convert the product alcohol into a substance less toxic to the microorganism. For example, the product alcohol may be contacted with carboxylic acid in the presence of a catalyst which esterifies the alcohol with the carboxylic acid and thereby, produces alcohol esters which are less toxic to the microorganism. In addition, the generation of alcohol esters from the product alcohol results in a lower concentration of the product alcohol in the fermentation medium. The reduced concentration of product alcohol minimizes the toxic effects of the product alcohol on the microorganism and thus, leads to improved production yields of product alcohol.

Carboxylic acid may serve as an extractant, and alcohol esters can partition into the extractant. However, the partition coefficient of the extractant may be degraded by lipid contamination. To reduce the degradation of the partition coefficient of the extractant, lipids present in the fermentation medium may be converted to extractant and consequently, minimize lipid contamination. In some embodiments, the methods herein provide a means to convert the lipids present in the feedstock or biomass into an extractant by catalytically hydrolyzing the lipids to carboxylic acid. The carboxylic acid produced by this hydrolysis may serve as an extractant or esterified with the product alcohol to form alcohol esters. Thus, the methods described herein provide a means to preserve the partition coefficient of the extractant (e.g., lipid hydrolysis) as well as minimize the toxic effects of the product alcohol (e.g., esterification of the product alcohol.

Carboxylic acid may be supplied to the fermentation vessel or derived by hydrolysis from lipids (e.g., biomass) supplied to the fermentation vessel. The amount of carboxylic acid should be sufficient to form a two-phase mixture comprising an organic phase and an aqueous phase. That is, carboxylic acid (i.e., extractant) in an appropriate concentration contacts the fermentation broth and forms the two-phase mixture. The alcohol esters formed in the fermentation broth will preferentially partition into the organic phase because these esters are formed at a concentration in excess of the equilibrium concentration of the aqueous phase. The alcohol ester-containing organic phase may be separated from the fermentation broth, the product alcohol may be recovered from organic phase, and the extractant may be recycled to the fermentation vessel.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "μL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods

Seed Flask Growth

A *Saccharomyces cerevisiae* strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 23-26° C. in an incubator rotating at 300 rpm. The frozen culture was previously stored at −80° C. The composition of the first seed flask medium was:

- 3.0-5.0 g/L dextrose
- 3.0-3.5 g/L ethanol, anhydrous
- 3.7 g/L ForMedium™ Synthetic Complete Amino Acid (Kaiser) Drop-Out: without HIS, without URA (Reference # DSCK162CK)
- 6.7 g/L Difco Yeast Nitrogen Base without amino acids (No. 291920).

Eight to twelve milliliters from the first seed flask culture was transferred to a 2 L flask and grown at 30° C. in an incubator rotating at 300 rpm. The second seed flask has 220 mL of the following medium:

- 30.0 g/L dextrose
- 5.0 g/L ethanol, anhydrous
- 3.7 g/L ForMedium™ Synthetic Complete Amino Acid (Kaiser) Drop-Out: without HIS, without URA (Reference # DSCK162CK)
- 6.7 g/L Difco Yeast Nitrogen Base without amino acids (No. 291920)
- 0.2 M MES Buffer titrated to pH 5.5-6.0.

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 250-300 mL of 0.2 uM filter sterilized HD OCENOL® 90/95 oleyl alcohol (Cognis, Monheim, Del.) was added to the flask. The culture continues to grow to >4 g/L dcw ($OD_{600}$>10) before being harvested and added to the fermentation.

Fermentation Preparation

Initial Fermentation Vessel Preparation

A glass jacked, 2 L fermentation vessel (Sartorius AG, Goettingen, Germany) was charged with house water to 66% of the liquefaction weight. A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 bp making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (7 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Operation

Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a α-amylase (glucoamylase). The glucose was kept excess (1-50 g/L) for as long as starch was available for saccharification.

Analytical

Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
|---|---|---|
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Cell Mass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 μL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 μL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 μL) was drawn of the final Trypan Blue dilution with an m20 Variable Channel BioHit pipette with 2-20 μL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 μL of sample was transferred with a m1000 Variable Channel BioHit pipette with 100-1000 μL BioHit pipette tips into a 0.2 um centrifuge filter (Nanosep® MF modified nylon centrifuge filter), then centrifuged using a Eppendorf, 5415C for five minutes at 14,000 rpm. Approximately 200 μL of filtered sample was transferred into a 1.8 auto sampler vial with a 250 μL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid at a flow rate of 0.6 mL/min for 40 minutes. Results are shown in Table 1.

TABLE 1

Retention times of fermentation products in aqueous phase

| HPLC 302/310 Normalized to 10 μL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 μL of sample was transferred using a m1000 Variable Channel BioHit pipette with 100-1000 μL BioHit pipette tips into a 1.8 auto sampler vial with a 250 μL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 μm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

Retention times of fermentation products in solvent phase

| GC 302/310 Normalized to 10 μL injections | FW | Solvent Retention Time, min | Range of Standards, g/L |
|---|---|---|---|
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 μm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, the Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, the Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post - liquefaction | 17.2 | 0.25 |
| 5 | 2010Y018 | 7.2 ppm | 16.2 | 5 | Oleyl alcohol | post - liquefaction | 45.8 | 0.66 |
| 6 | 2010Y019 | none | 17.5 | 5 | Oleyl alcohol | post - liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |
| 13 | 2010Y031 | 10 ppm | 12.8 | 0 | Corn Oil Fatty Acids | none | 18.86 | 0.35 |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume Examples 15 and 16 represent a comparison of fermentation and isobutanol production in the presence and absence of post-liquefaction lipase treatment. Results are shown in Tables 4 and 5.

Example 15

Experiment identifier 2010Y026 included: Seed Flask Growth method, Initial Fermentation vessel Preparation method, the Liquefaction method, the Lipase Treatment Post-Liquefaction method, the Nutrient Addition Prior to Inoculation method, Fermentation vessel Inoculation method, Fermentation vessel Operating Conditions method, and all of the Analytical methods. Corn oil fatty acids made from crude corn oil was added in a single batch between 0.1-1.0 hr after inoculation. The corn oil fatty acids extracting solvent was added in equal volume to the broth volume. The butanologen was PNY2205. Between 46 hrs and 61 hrs fermentation time, the addition of 274 g of a 50% w/w sterile, glucose solution was made because the glucose made from corn mash had been all but depleted.

Example 16

Experiment identifier 2010Y027 included: Seed Flask Growth method, Initial Fermentation vessel Preparation method, the Liquefaction method, the Nutrient Addition Prior to Inoculation method, Fermentation vessel Inoculation method, Fermentation vessel Operating Conditions method, and all of the Analytical methods. HD OCENOL® 90/95 (oleyl alcohol, CAS No. 143-28-2, Cognis, Monheim, Del.) was added in a single batch between 0.1-1.0 hr after inoculation. The oleyl alcohol extracting solvent was added in equal volume to the broth volume. The butanologen was PNY2205.

TABLE 4

| Experimental ID | Lipase Addition | Extracting Solvent | Glucose Consumed (g) | Biomass produced (cfu/mL) |
|---|---|---|---|---|
| 2010Y026 | Yes | corn oil fatty acids | 326.3 | 34.2 × $10^7$ |
| 2010Y027 | No | oleyl alcohol | 234.9 | 33.0 × $10^7$ |

TABLE 5

| Exp. ID | Lipase Addition | Maximum residual i-BuOH in aqueous (g/L) | Effective i-BuOH titer (g/L) | Maximum effective i-BuOH production rate g/L/hr (aqueous volume) | Yield g i-BuOH/ g glucose |
|---|---|---|---|---|---|
| 2010Y026 | Yes | 4.7 | 72.2 | 1.41 | 0.26 |
| 2010Y026 | No | 10.0 | 55.4 | 1.19 | 0.25 |

Examples 17 to 22 represent a comparison of the effect of fresh extractant versus recycled extractant on fermentation and isobutanol production. Results are shown in Table 6. For these examples, 2 L and 10 L fermentations were prepared as described below.

10 L Pre-Seed Flask Growth

A *Saccharomyces cerevisiae* strain (strain PNY2242 described above) that was engineered to produce isobutanol from a carbohydrate source, with pdc1 deleted, pdc5 deleted, and pdc6, deleted was grown to 0.6-0.7 g/L dcw ($OD_{600}$ 1.5-2.5—Thermo Helios a Thermo Fisher Scientific Inc., Waltham, Mass.) in seed flasks (10 mL synthetic medium in a 125 mL, vented flask) from a frozen culture. The culture was grown at 29-31° C. in an incubator rotating at 260 rpm. The frozen culture was previously stored at −80° C. The composition synthetic seed flask medium was:

10.0 g/L dextrose 3.5 mL/L ethanol, anhydrous 3.7 g/L ForMedium™ Synthetic Complete Amino Acid (Kaiser) Drop-Out: without HIS, without URA (Reference No. DSCK162CK)

6.7 g/L Difco Yeast Nitrogen Base without amino acids (No. 291920)

1% Ergersterol in 1:1::Tween 80:Ethanol

Two milliliters from the first seed flask culture was transferred to 25 mL in a 250 mL, vented flask and grown at 29-31° C. in an incubator rotating at 260 rpm. The second seed flask uses the same synthetic medium as used above.

The culture was grown to 0.6-0.7 g/L dcw ($OD_{600}$ 1.0-3.0). Then, 8 mL of this second flask culture was added to three flasks (2 L, vented, baffled flasks) with 200 mL of synthetic medium. The culture was grown in an incubator at 29-31° C. for 18-24 hrs. The three seed flasks use the same synthetic medium as used in the first two seed flasks. These three flasks (600 mL of flask broth) are used to inoculate the propagation tank at a final aqueous volume of 6 L.

10 L Propagation Tank Liquefaction

A 10 L, B. Braun BioStat C fermentor was prepared for use. An inline pH probe was placed in the fermentor. The zero was calibrated at pH=7. The span was calibrated at pH=4. The probe was then placed into the fermentation vessel, through a side port. A dissolved oxygen probe ($pO_2$ probe) was also placed into the fermentor through a side port. Tubing used for delivering nutrients, seed culture, extracting solvent, and base were attached to the head plate and the ends were foiled. The valve for harvesting and sampling were sterilized with low pressure steam and a steam trap at >121° C. for >20 minutes.

The fermentation vessel temperature was controlled at 30° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 10-20% (dry corn solids weight) of the liquefaction reaction mass. Difco Yeast Extract was added to the fermentor at 0.5% w/w of the total batch weight.

An alpha-amylase was added to the fermentation vessel per its specification sheet while the fermentation vessel was mixing at 300-1500 rpm, with sterile, house $N_2$ being added at 1-2 slpm through the sparger. The temperature set-point was changed from 55° C. to 95° C. in 5° C. step changes with a 5-15 minute hold at each step to ensure good mixing. When the temperature was >90° C., the liquefaction cook time was started and the liquefaction cycle was held at >90° C. for 60 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

10 L Propagation Tank Operation

The fermentation vessels $pO_2$ probe was calibrated to zero while $N_2$ was being added to the fermentation vessel. The fermentation vessels $pO_2$ probe was calibrated to its span with sterile air sparging at 400 rpm. The fermentation vessel was inoculated from the final stage of the Pre-Seed Flask Growth step. The three shake flasks were removed from the incubator/shaker and added to a sterile vessel. The content of the sterile vessel was added to 5.3-5.5 L of the liquefied mash that was made during the Propagation Tank Liquefaction method.

The fermentation temperature was controlled between 29-31° C. The agitation speed was fixed at 400 rpm. Air was sparged for the entire fermentation at 2.0 slpm. The pH was controlled at 5.4-5.5 bp using $NH_4OH$ and the PID control loop for the fermentor. There was 0.3-0.5 bar of back pressure set on the fermentor, controlled by a PID loop that controlled a back pressure control valve.

At 16-20 hrs after inoculation, a glucoamylase (1.8 mL of Distillase® L-400, Genencor, Palo Alto, Calif.) was added to start simultaneous saccharification and fermentation, releasing glucose from the dissolved starch. Also, 5.5 L of HD OCENOL® 90/95 (oleyl alcohol, Cognis, Monheim, Del.) was added to the fermentor. At 34-36 hrs, the agitator speed was reduced to 100 rpm. After 10 minutes, the agitator was turned off and the airflow to the fermentor was changed from sparge mode to overlay mode.

10 L Production Tank Liquefaction

A 10 L Production Tank Liquefaction was performed as described above. The fermentation vessel temperature was controlled at 30° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 25-35% (dry corn solids weight) of the liquefaction reaction mass. A 75 mL addition of a 100× Vitamin Solution (2 g/L thiamine and 10 g/L nicotinic acid) was made to the fermentor. An alpha-amylase was added to the fermentation vessel was added as described above. Also, an addition of 6-7 mL/L anhydrous ethanol was made to the fermentor after the fermentor was returned to 30° C.

10 L Production Tank Operation

The fermentation vessels $pO_2$ probe was calibrated to zero while $N_2$ was being added to the fermentation vessel. The fermentation vessels $pO_2$ probe was calibrated to its span with sterile air sparging at 400 rpm. The fermentation vessel was inoculated from Propagation Tank. An aseptic transfer was made from the Propagation Tank after 36 hrs of growth time in the propagation tank and the fermentation agitation was turned off for >10 minutes. This allowed for significant separation of the oleyl alcohol and the aqueous phase. The aseptic transfer was made from the harvest valve on the Propagation Tank, which is located at the bottom of this fermentor. Approximately 10% v/v was added to the Production Tank, based on the tanks final non-solvent volume after transfer.

The fermentation temperature was controlled between 29-31° C. The agitation speed was fixed at 400 rpm. Air was sparged for the entire fermentation at 2.0 slpm. The pH was controlled at 5.2-5.3 bp using $NH_4OH$ and the PID control loop for the fermentor. There was 0.3-0.5 bar of back pressure set on the fermentor, controlled by a PID loop that controlled a back pressure control valve.

Just prior to inoculation, 25-35% v/v Cognis Emery® 610 SOYA Fatty Acid was aseptically added to the fermentor. The fermentor was inoculated with 10% v/v fermentation broth after the completion of the 10 L Propagation Tank Operation method. Just after inoculation, a glucoamylase (Distillase® L-400) was added to release glucose from the starch. Additional glucoamylase additions were made when needed to maintain the glucose excess. Just after inoculation, a lipase (Novozymes Lipolase® 100L) was added to the fermentor at 4-15 ppm.

2 L Pre-Seed Flask Growth

A 2 L pre-seed flask growth was prepared using a *Saccharomyces cerevisiae* strain (strain PNY2242 described above) and was grown to 0.6-0.7 g/L dcw ($OD_{600}$ 1.5-2.5—Thermo Helios α Thermo Fisher Scientific Inc., Waltham, Mass.) in seed flasks (10 mL synthetic medium in a 125 mL, vented flask) from a frozen culture. The culture was grown at 29-31° C. in an incubator rotating at 260 rpm. The frozen culture was previously stored at −80° C. The composition synthetic seed flask medium was:

10.0 g/L dextrose
3.5 mL/L ethanol, anhydrous
3.7 g/L ForMedium Synthetic Complete Amino Acid (Kaiser) Drop-Out: without HIS, without URA (Reference No. DSCK162CK)
6.7 g/L Difco Yeast Nitrogen Base without amino acids (No. 291920)
1% Ergersterol in 1:1::Tween 80:Ethanol.

Two milliliters from the first seed flask culture was transferred to 25 mL in a 250 mL, vented flask and grown at 29-31° C. in an incubator rotating at 260 rpm. The second seed flask uses the same synthetic medium as used above.

The culture was grown to 0.6-0.7 g/L dcw ($OD_{600}$ 1.0-3.0). Then 4 mL of this second flask culture was added to 100 mL of corn mash centrate in a 2 L flask. The culture was grown in an incubator at 29-31° C. for 18-24 hrs. Then 500 mL of HD OCENOL® 90/95 (oleyl alcohol, Cognis, Monheim, Del.) was added to the flask. The flask was allowed to grow for 6-8 hrs. Then 2 mL of a 1.2 g Distillase® L-400, (Genencor, Palo Alto, Calif.) in 80 mL of deionized water was added to the centrate to release glucose from the dissolved starch in the centrate. The culture continued to grow for 18-24 hrs. The final biomass concentration was 6-12 g/L dcw.

The corn mash centrate was made by liquefying corn in the following recipe:

1150 g tap water
340.5 g 1 mm screened ground corn
13.5 g yeast extract (Difco No. 9102333, low dusting)
27 g peptone
4.1 g urea
40.5 mg nicotinic acid
40.5 mg thiamine.

Then the material was centrifuged for 30 minutes in a Sorval RC5C centrifuge. The supernatant was separated from the solids pellet. The supernatant was heated in a Steris autoclave for a 5 minute liquid cycle and is defined as centrate.

2 L Fermentation Preparation

2 L Initial Fermentation Vessel Preparation

A 2 L Initial Fermentation Vessel Preparation was prepared as described above. The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 25-30% (dry corn solids weight) of the liquefaction reaction mass. In addition, Liquefaction was conducted as described above. An alpha-amylase was added to the fermentation vessel per its specification sheet while the fermentation vessel was mixing at 300-1200 rpm, with sterile, house $N_2$ being added at 0.3 slpm through the sparger.

2 L Additions Prior to Inoculation

The following nutrients were added to the fermentation vessel prior to inoculation, after liquefaction, on a post-inoculation volume basis:

30 mg/L of nicotinic acid
30 mg/L of thiamine
1 mL/L of a 1% ergersterol w/v solution in 1:1:Tween 80:Ethanol
6.3 mL/L ethanol
2 g/L urea.

2 L Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated from the final stage of the Pre-Seed Flask Growth step. The shake flask was removed from the incubator/shaker and centrifuged for 30 minutes. The liquid (oleyl alcohol and aqueous supernatant) was discarded and the cell pellet was re-suspended in the Pre-Seed Flask Growth medium (synthetic medium). The 100 mL of the aqueous phase was transferred to a sterile inoculation bottle. The inoculum was pumped into the fermentation vessel through a peristaltic pump.

2 L Lipase Addition After Inoculation

A Lipolase® solution (100 L stock solution) was prepared to an enzyme concentration of 1.2-1.4 mg/mL. The solution was added to the fermentation after inoculating the fermentor to the desired part per million concentration based on the non-solvent volume. The addition time occurred <1 hr after inoculating the fermentor.

2 L Soy Bean Oil Fatty Acid Addition

To the fermentation vessel was added 0.1-0.5 L/L (post-inoculation volume) of either virgin Cognis Emery® 610 SOYA Fatty Acid or recycled Cognis Emery® 610 SOYA Fatty Acids that contains 0-30 weight percent fatty acid butyl ester.

2 L Fermentation Vessel Operating Conditions

The fermentation vessel was operated at 30° C. for the entire growth and production stages. The pH was allowed to drop from a pH between 5.7-5.9 to a control set-point of 5.25 without adding any acid. The pH was controlled for the remainder of the growth and production stage at a pH=5.2 with ammonium hydroxide. Sterile air was added to the fermentation vessel, through the sparger, at 0.2-0.3 slpm for the remainder of the growth and production stages. The $pO_2$ was not controlled. The agitator was set to a fixed rpm at 300 rpm. The stir shaft had two Rushton impellers below the aqueous level and one pitched blade impeller above the aqueous level. The glucose was supplied through simultaneous saccharification and fermentation of the liquified corn mash by adding a glucoamylase. The glucose was kept excess (1-50 g/L) for as long as starch was available for saccharification.

A 5-20 mL sample was pulled from a fermentation vessel and placed in a centrifuge tube and centrifuged for cell mass measurement using the procedure described above. In addition, Analytical methods such as gas analyses as well as LC analyses of fermentation products in the aqueous phase and GC analyses of fermentation products in the solvent phase were conducted as described above.

The fermentation conditions for Examples 17 to 22 are provided below and a summary of the results (virgin soy bean oil fatty acids and recycled soy bean fatty acids with fatty acid butyl esters) are shown in Table 6.

Example 17

Experimental Identifier GLNOR1050 included: 10 L Pre-Seed Flask Growth, 10 L Propagation Tank Liquefaction, 10 L Propagation Tank Operation, 10 L Production Tank Liquefaction, 10 L Production Tank Operation with 10 ppm Lipolase® 100L (Genencor) added to the fermentor, extractant: Virgin Cognis Emery® 610 SOYA Fatty Acid (virgin soy bean oil fatty acid). The liquid solvent and non-solvent material was separated in a Sorval RC-12 centrifuge, and all Analytical methods.

Example 18

Experimental Identifier GLNOR1051 included: 10 L Pre-Seed Flask Growth, 10 L Propagation Tank Liquefaction, 10 L Propagation Tank Operation, 10 L Production Tank Liquefaction, 10 L Production Tank Operation with 4 ppm Lipolase® 100L (Genencor) added to the fermentor, extractant: Virgin Cognis Emery® 610 SOYA Fatty Acid (virgin soy bean oil fatty acid). The liquid solvent and non-solvent material was separated in a Sorval RC-12 centrifuge, and all Analytical methods.

Example 19

Identifier 2011Y029 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, 2 L Recycled Soy Bean Oil Fatty Acid Addition (Recycled Cognis Emery® 610 SOYA Fatty Acid and fatty acid butyl ester from Example 56A—50% v/v solvent load), 2 L Fermentation Vessel Operating Conditions, and all Analytical methods.

Example 20

Identifier 2011Y030 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, added 0.4 L/L (post-inoculation volume) Virgin Cognis Emery® 610 SOYA Fatty Acids that included 20-30% fatty acid butyl esters, 2 L Fermentation Vessel Operating Conditions, and all Analytical methods.

Example 21

Identifier 2011Y031 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, 2 L Recycled Soy Bean Oil Fatty Acid Addition (Recycled Cognis Emery® 610 SOYA Fatty Acid and fatty acid butyl ester from Example 56B—10% v/v solvent load), 2 L Fermentation Vessel Operating Conditions, and all Analytical methods.

Example 22

Identifier 2011Y032 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, added 0.4 L/L (post-inoculation volume) Virgin Cognis Emery® 610 SOYA Fatty Acids, 2 L Fermentation Vessel Operating Conditions, and all Analytical methods.

TABLE 6

| Exp. ID | Lipase ppm | Max Cell Count × $10^7$ | Solvent Loading Vol % | Max i-BuOH (aq) g/L | EOR Volumetric Rate g/L/hr | Extractant |
|---|---|---|---|---|---|---|
| GLNOR 1050 | 10 | 21.3 | 28% | 6.9 | 0.97 | Virgin Soy Bean Oil Fatty Acid |
| GLNOR 1051 | 4 | 20.9 | 28% | 8.9 | 0.83 | Virgin Soy Bean Oil Fatty Acid |
| 2011Y029 | 10 | 20.9 | 50% | 8.2 | 0.85 | Recycled Soy Bean Oil Fatty Acid and Fatty Acid Butyl Ester |
| 2011Y030 | 10 | 24.4 | 40% | 9.8 | 0.88 | Virgin Soy Bean Oil Fatty Acid and Fatty Acid Butyl Ester |
| 2011Y031 | 10 | 9.8 | 10% | 12.7 | 0.42 | Recycled Soy Bean Oil Fatty Acid and Fatty Acid Butyl Ester |
| 2011Y032 | 10 | 26.5 | 40% | 6.8 | 0.94 | Virgin Soy Bean Oil Fatty Acid |

Example 23

The following example describes the production of isobutanol by fermentation using sucrose as a fermentable carbon source.

Generation of Biomass

Inoculum: A seed medium was prepared to initiate the growth of the isobutanologen. The composition of the seed medium was as follows: ammonium sulfate, 5 g/L; potassium phosphate monobasic, 3 g/L; magnesium sulfate heptahydrate, 0.5 g/L; ethanol, 3.2 g/L; yeast extract (BBL), 5 g/L; glucose, 10 g/L; MES buffer, 150 mmol/L; biotin, 50 µg/L; and a trace element solution, 1 mL/L, which contains in 1 L water, 15 g EDTA, 4.5 g zinc sulfate heptahydrate, 0.8 g manganese chloride dehydrate, 0.3 g cobalt chloride hexahydrate, 0.3 g copper sulfate pentahydrate, 0.4 g disodium molybdenum dehydrate, 4.5 g calcium chloride dihydrate, 3 g iron sulfate heptahydrate, 1 g boric acid, 0.1 g potassium iodide. The pH was adjusted to 5.5, and then the medium filter sterilized through an 0.22µ sterile filter apparatus.

Preparation of the 10 L Fermentor for Biomass Production

A single vial of the isobutanologen PNY2205 was aseptically transferred to 15 mL seed medium in a 125 mL vented flask for over night growth at 30° C. and 260 rpm shaking. The culture was aseptically transferred to 500 mL of the same medium in a 2 L baffled, vented flask for over night growth at 30° C. and 260 rpm shaking, and transferred to a prepared 10 L Sartorius C fermentor (Sartorius AG, Goettingen, Germany) when the culture reached $OD_{600}$ 7.

A 10 L Sartorius C fermentor was prepared with 6 L initial volume of growth medium. The growth medium composition and preparation was as follows: prior to sterilization, ammonium sulfate, 1 g/L; potassium phosphate monobasic, 5 g/L; magnesium sulfate, heptahydrate, 2 g/L; yeast extract (Amberex™ 695), 2 g/L; Antifoam Sigma 204, 0.5 mL/L; biotin, 100 µg/L; and 1 mL/L trace element solution (prepared in 1 L water: 15 g EDTA, 4.5 g zinc sulfate heptahydrate, 0.8 g manganese chloride dehydrate, 0.3 g cobalt chloride hexahydrate, 0.3 g copper sulfate pentahydrate, 0.4 g disodium molybdenum dehydrate, 4.5 g calcium chloride dihydrate, 3 g iron sulfate heptahydrate, 1 g boric acid, 0.1 g potassium iodide). After steam sterilization at 121° C. in place, the vessel was cooled, and 60 g of the feed medium was added. The feed medium was prepared as follows: sucrose, 50% solution, 2.97 L; biotin, 1.4 mg; 34 mL of the trace mineral solution; titrated to pH 7.5 with 5N sodium hydroxide and steam sterilized; post sterilization and cooling, 130 mL ethanol and 320 mL of a 20% (w/v) filter sterilized solution of yeast extract (Amberex™ 695) was added. The initial sugar concentration in the 10 L fermentor was thus 3.7 g/L sucrose, 0.8 g/L glucose, and 0.8 g/L fructose.

The fermentation was controlled at pH 5.5 (with ammonium hydroxide addition), 30° C., airflow at 2.0 standard liters per minute, dissolved oxygen at 30% by agitation control, and 0.5 barg back pressure. After inoculation, the sugar was consumed until the residual measurement of glucose was less than 0.1 g/L, and then the feed program began; this occurred at 11 hours elapsed fermentation time. The program was established to maintain sucrose limitation until $OD_{600}$ of 20 (approximately 8 g/L dry cell weight) was achieved, with a programmed growth rate of 0.1/hr. The actual measured growth rate in this experiment was 0.18/hr. The targeted $OD_{600}$ was reached after 20 hours fermentation time.

Once the target was achieved, the culture was harvested aseptically, and centrifuged in a Sorvall RC12BP centrifuge. The resulting pellet was resuspended to a final volume of 300 mL with isobutanol production medium, described below. This culture was used as the inoculum for the isobutanol production fermentors.

Isobutanol Production

Preparation of production fermentors: Two one liter glass Applikon (Applikon, Inc, Holland) fermentors associated with a Sartorius BioStat B Plus Twin control unit (Sartorius AG, Goettingen, Germany) were used for the isobutanol production. The fermentors were prepared with 1 L deionized water, and sterilized by autoclaving at 121° C. for 30 minutes. Once the fermentors cooled, the water was aseptically removed, and the volume of filter sterilized production medium, as indicated in Table 7, was added. The production medium composition was as follows: yeast nitrogen base without amino acids (Difco), 6.7 g/L; Yeast Synthetic Drop-out Medium Supplements without histidine, leucine, tryptophan, and uracil (Sigma), 2.70 g/L; tryptophan, 1.6 mg/L; leucine, 8 mg/L; ethanol, 2.8 g/L; Antifoam Sigma 204, 0.2 mL/L; sucrose, 25 g/L. Just before inoculation, filter sterilized lipase solution was as indicated in Table 7. The lipase solution was prepared by dilution of Lipolase® L100 (Sigma) in 10 mM potassium phosphate buffer, pH 7, to a final concentration of 1.25 mg protein/mL. The solution was prepared and stored for one day at 5° C. before addition to the fermentors.

TABLE 7

| Fermentor | Fermentation Broth (mL) | SOFA (mL) | lipase (mg/L) |
|---|---|---|---|
| A | 440 | 320 | 0 |
| B | 440 | 320 | 10 |
| C | 520 | 240 | 10 |
| D | 520 | 240 | 25 |

The fermentors were controlled at pH 5.2 (by addition of 20% potassium hydroxide), 30° C., airflow at 0.2 standard liters per minute, and dissolved oxygen at 3% by agitation control.

The fermentors were each inoculated with 40 mL of the concentrated biomass, to initial $OD_{600}$ 20-25 (approximately 8-10 g/L dry cell weight). An addition 4 mL of a filter sterilized vitamin solution (thiamine-HCl, 1 mg/mL; nicotinic acid, 1 mg/mL, in water) was added at inoculation, as was the volume of filter sterilized Soya Oil Fatty Acids (SOFA) indicated in Table 7. Samples (5-10 mL) were drawn every 2-3 hours, and assayed for glucose and sucrose by a YSI Select Biochemistry Analyzer (YSI, Inc., Yellow Springs, Ohio). As sucrose was consumed, a feed of 50% sucrose (w/w) was added to maintain a concentration of 5-30 g/L. The aqueous and organic phases of the samples were separated and analyzed by the HPLC method described above via an Agilent 1100 HPLC. For analysis of organic acids and alcohols, a Shodex® Sugar SH1011 column was used with 0.01 N sulfuric acid mobile phase. For analysis of sucrose, glucose, and fructose, a BioRad Aminex® HPX-87N column with 0.01 M $Na_2HPO_4$ (pH 8) mobile phase was used.

Figure 6:
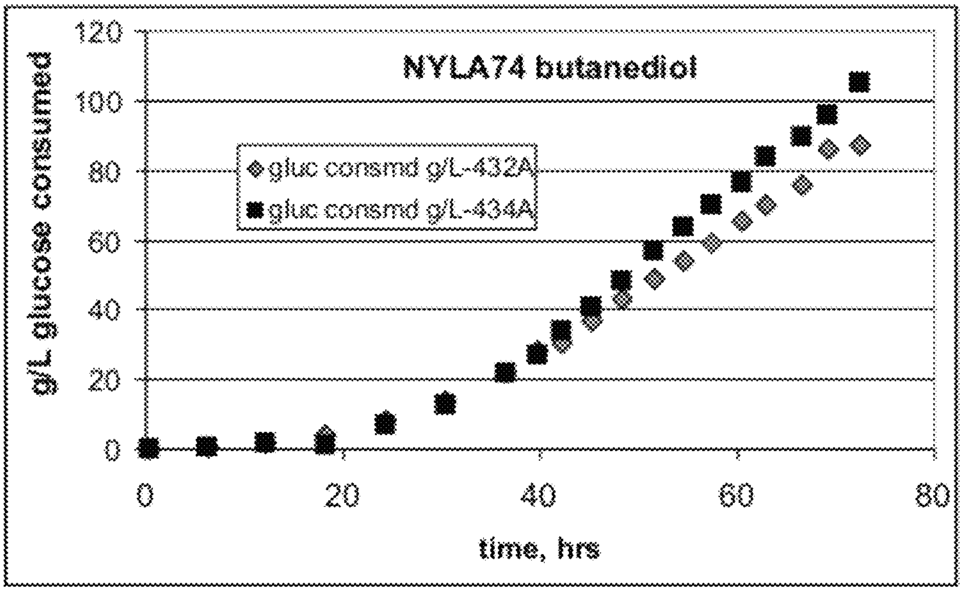

Each of the fermentors with lipase added had lower concentrations of isobutanol in the aqueous phase and free isobutanol in the solvent phase. The aqueous and solvent phase concentrations of isobutanol are shown in FIG. 6. Addition of more lipase at the same solvent loading also resulted in lower aqueous titers of isobutanol and lower free isobutanol in the solvent, and more isobutanol as FABE.

Figure 7:
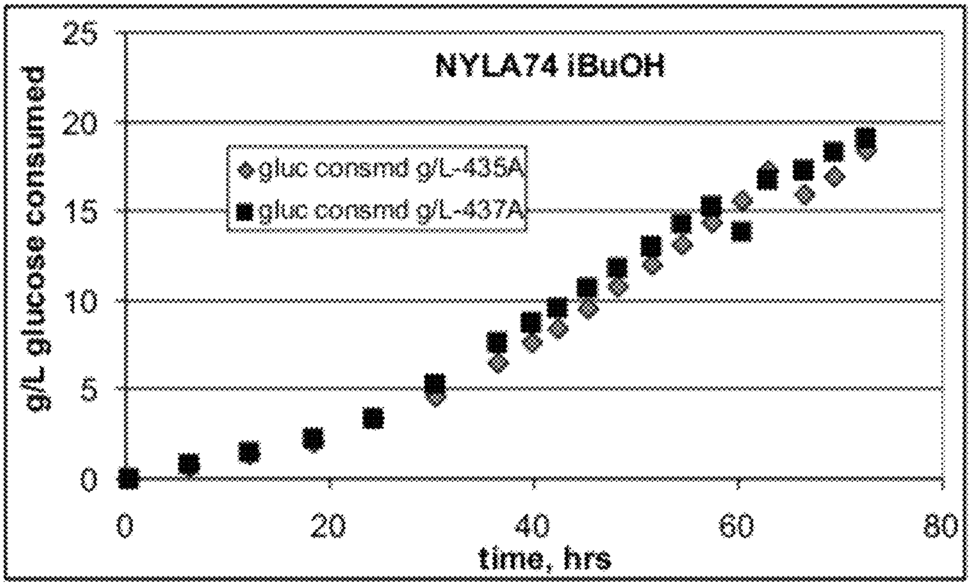
FIG. 7 shows the effective titer of isobutanol, g/L, over time. Effective titer in this example was calculated as described in the text, based on the initial volume of aqueous fermentor broth after inoculation.

The cultivations which included lipase resulted in a higher effective titer of isobutanol than the control fermentor without lipase. FIG. 7 shows the effective titer of isobutanol. In this example, the effective titer was calculated based on the initial measured weight of broth in the fermentor after inoculation and the initial measured weight of solvent charged to the fermentor. The solvent density was assumed to be 0.88 g/mL and the aqueous broth density 1.00 g/mL throughout the fermentation. Addition of more lipase at the lower solvent loading did result in higher effective titers of isobutanol (D vs C), but not as much as increasing the relative volume of solvent (C vs B).

Figure 8:
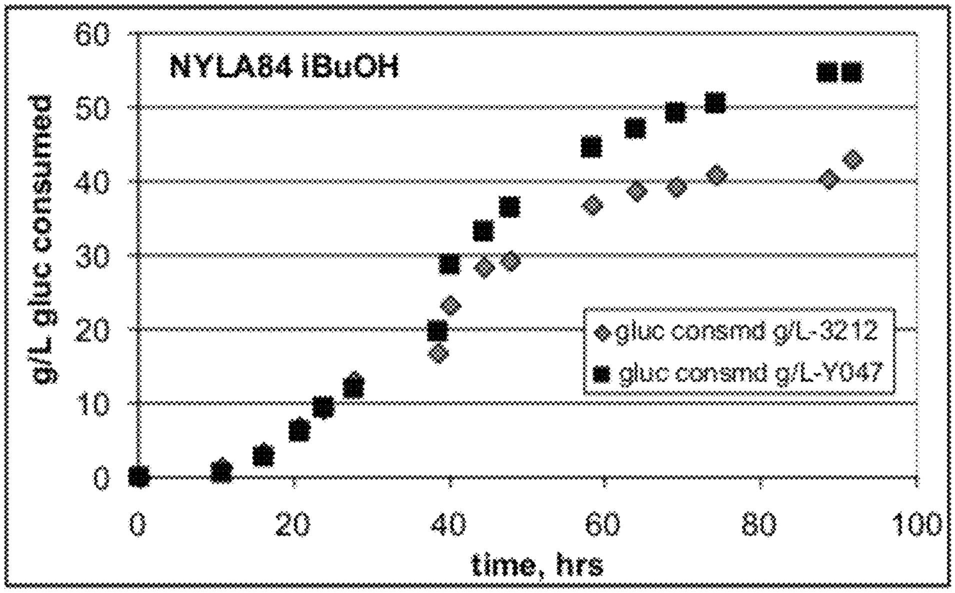
FIG. 8 shows the consumption of sugars, reported in glucose equivalents, over time.

Sugar consumed, calculated in glucose equivalents, was higher in fermentors with lipase added, shown in FIG. 8. Glucose equivalents consumed is calculated from the measured sugars fed and remaining in the fermentor, with each mole of sucrose counted as two moles of glucose and each mole of fructose counted as one mole of glucose, then converted to grams via the molecular weight of glucose. The concentration of glucose equivalents consumed is also calculated on the basis of the initial volume of fermentation broth after inoculation.

Example 24

Lipase Treatment of Liquefied Corn Mash for Simultaneous Saccharification and Fermentation with In-situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash; the production of oleyl palmitate, oleyl stearate, and oleyl oleate was confirmed by GC/MS, and a fourth ester was tentatively identified as oleyl linoleate. Results for FFA and lipid analysis are shown in Table 8.

TABLE 8

Lipid and free fatty acid content of fermentations containing oleyl alcohol as ISPR extractant and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 25

Heat Inactivation of Lipase in Lipase-Treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 9.

TABLE 9

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, | 6 h, liq. mash | 0.08 | 0.71 | 41 | 345 | 386 | 89 |
| no 85° C. heat treatment | 25 h, liq. mash | 0.22 | 0.06 | 105 | 27 | 132 | 20 |
| | 25 h, OA | 0.58 | 0.39 | 212 | 143 | 355 | 40 |
| | 73 h, liq. mash | 0.25 | 0.05 | 121 | 22 | 143 | 18 |
| | 73 h, OA | 0.91 | 0.24 | 333 | 88 | 420 | 21 |
| 10 ppm inactive lipase, | 6 h, liq. mash | 0.06 | 0.45 | 28 | 224 | 252 | 89 |
| 85° C. heat treatment | 25 h, liq. mash | 0.10 | 0.11 | 49 | 54 | 103 | 53 |
| | 25 h, OA | 0.02 | 0.96 | 8 | 366 | 374 | 99 |
| | 73 h, liq. mash | 0.24 | 0.15 | 117 | 72 | 189 | 62 |
| | 73 h, OA | 0.06 | 1.11 | 23 | 424 | 447 | 95 |
| no lipase, | 6 h, liq. mash | 0.80 | 0.40 | 401 | 199 | 599 | 33 |
| no 85° C. heat treatment | 25 h, liq. mash | 0.30 | 0.05 | 147 | 25 | 173 | 15 |
| | 25 h, OA | 0.55 | 0.36 | 212 | 139 | 351 | 40 |
| | 73 h, liq. mash | 0.23 | 0.05 | 117 | 26 | 143 | 23 |
| | 73 h, OA | 0.79 | 0.42 | 305 | 162 | 467 | 34 |
| no lipase, | 6 h, liq. mash | 0.74 | 0.36 | 370 | 183 | 553 | 33 |
| 85° C. heat treatment | 25 h, liq. mash | 0.31 | 0.05 | 156 | 27 | 183 | 15 |
| | 25 h, OA | 0.60 | 0.35 | 233 | 136 | 369 | 37 |
| | 73 h, liq. mash | 0.20 | 0.05 | 99 | 23 | 121 | 23 |
| | 73 h, OA | 0.84 | 0.41 | 326 | 159 | 486 | 33 |

Example 26

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 10.

TABLE 10

Lipid and free fatty acid content of fermentations containing oleyl alcohol as ISPR extractant and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |

TABLE 10-continued

Lipid and free fatty acid content of fermentations containing oleyl alcohol as ISPR extractant and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

Example 27

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100L Solution (21 mg total soluble protein, 10 ppm lipase final concentration) and to the second mixture was added 1.05 mL of aqueous solution of Lipolase® 100L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 11.

TABLE 11

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase | 1 h, pre-liquefaction | 0.226 | 0.627 | 112 | 311 | 424 | 74 |
| at 55° C. prior to | 2 h, pre-liquefaction | 0.199 | 0.650 | 99 | 323 | 422 | 77 |
| liquefaction at | 4 h, pre-liquefaction | 0.151 | 0.673 | 75 | 334 | 410 | 82 |
| 85° C., mix with | 6 h, pre-liquefaction | 0.101 | 0.700 | 50 | 348 | 398 | 87 |
| OA for 20 h | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase | 1 h, pre-liquefaction | 0.408 | 0.480 | 226 | 266 | 492 | 54 |
| at 55° C. prior to | 2 h, pre-liquefaction | 0.401 | 0.424 | 222 | 235 | 457 | 51 |
| liquefaction at | 4 h, pre-liquefaction | 0.299 | 0.433 | 165 | 240 | 405 | 58 |
| 85° C., mix with | 6 h, pre-liquefaction | 0.346 | 0.453 | 192 | 251 | 442 | 57 |
| OA for 20 h | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

Example 28

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 12.

TABLE 12

Percent free fatty acid content (% FFA) of a mixture of ground whole corn kernels using lipase treatment at 55° C. prior to liquefaction

| | % FFA time | | | | |
|---|---|---|---|---|---|
| | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |
| Novozyme ® CALA L | 37 | 40 | 44 | 44 | 45 |
| Palatase ® 20000L | 37 | 49 | 59 | 62 | 66 |
| no enzyme | 38 | 33 | 37 | 41 | 42 |

Example 29

Lipase Treatment of Ground Whole Corn Kernels Prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The FFA in the OA phase of the fermentation run according to Examples 7 and 10 (with heat inactivation of lipase prior to fermentation) were each 97% at 70 h (end of run (EOR)), compared to only 49% FFA for the fermentation run according to Example 8 where ground whole corn kernels had not been treated with lipase prior to liquefaction. Results are shown in Table 13.

TABLE 13

Lipid and free fatty acid content of fermentations containing oleyl alcohol as ISPR extractant and heat-inactivated lipase (lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 30

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH (including i-BuOH present as FABE) present in the COFA phase of the fermentations containing inactive lipase. The final total grams of isobutanol (i-BuOH) present in the fermentation broths (aqueous phase) containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 14 and 15.

TABLE 14

Dependence of the production of free isobutanol (i-BuOH) and isobutyl esters of COFA (FABE) in fermentations containing corn oil fatty acids (COFA) as ISPR extractant in presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9 | 4.5 | 2.4 | 0.0 | 0 | 2.4 |
| Example 9 | 28.8 | 5.4 | 70.9 | 16.5 | 22.0 |
| Example 9 | 52.4 | 8.9 | 199.0 | 46.4 | 55.3 |
| Example 9 | 69.3 | 4.9 | 230.9 | 53.9 | 69.3 |
| Example 11 | 6.6 | 2.3 | 0.0 | 0.0 | 2.3 |
| Example 11 | 53.5 | 25.1 | 2.9 | 0.6 | 25.7 |
| Example 11 | 71.1 | 24.4 | 6.3 | 1.4 | 25.8 |
| Example 12 | 6.6 | 2.3 | 0.0 | 0.0 | 2.3 |
| Example 12 | 53.5 | 12.8 | 1.6 | 0.4 | 13.2 |
| Example 12 | 71.1 | 12.8 | 3.0 | 0.7 | 13.5 |
| Example 13 | 6.6 | 2.3 | 0.0 | 0.0 | 2.3 |
| Example 13 | 53.5 | 4.9 | 72.1 | 16.0 | 20.9 |
| Example 13 | 71.1 | 4.6 | 91.4 | 20.3 | 24.9 |
| Example 14 | 6.6 | 2.1 | 0.0 | 0.0 | 2.1 |
| Example 14 | 53.5 | 9.8 | 197.2 | 43.8 | 53.6 |
| Example 14 | 71.1 | 4.9 | 244.5 | 54.3 | 59.2 |

TABLE 15

Dependence of the production of free isobutanol (i-BuOH) and isobutyl esters of COFA (FABE) in fermentations containing corn oil fatty acids (COFA) as ISPR extractant on presence (Examples 9, 13 and 14) or absence (Examples 11 and 12) of active lipase (fermentation broth analysis)

| sample | fermentation time (h) | g i-BuOH/ kg broth | g FABE/ kg broth | g i-BuOH from FABE/ kg broth | total g i-BuOH/ kg broth |
|---|---|---|---|---|---|
| Example 9 | 4.5 | 0.0 | 0.0 | 0 | 0 |
| Example 9 | 28.8 | 0.0 | 12.6 | 2.9 | 2.9 |
| Example 9 | 52.4 | 0.0 | 30.3 | 7.1 | 7.1 |
| Example 9 | 69.3 | 0.0 | 24.7 | 5.8 | 5.8 |
| Example 11 | 6.6 | 0.0 | 0.0 | 0 | 0.0 |
| Example 11 | 53.5 | 9.8 | 0.0 | 0 | 9.8 |
| Example 11 | 71.1 | 9.5 | 0.0 | 0 | 9.5 |
| Example 12 | 6.6 | 0.0 | 0.0 | 0 | 0 |
| Example 12 | 53.5 | 3.8 | 0.0 | 0.0 | 3.8 |
| Example 12 | 71.1 | 5.1 | 0.0 | 0.0 | 5.1 |
| Example 13 | 6.6 | 0.0 | 0.0 | 0 | 0 |
| Example 13 | 53.5 | 2.1 | 3.0 | 0.7 | 2.8 |
| Example 13 | 71.1 | 2.1 | 7.4 | 1.6 | 3.7 |
| Example 14 | 6.6 | 0.0 | 0.0 | 0 | 0.0 |
| Example 14 | 53.5 | 2.9 | 22.4 | 5.0 | 7.9 |
| Example 14 | 71.1 | 3.3 | 19.3 | 4.3 | 7.6 |

Example 31

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 16), and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 17).

TABLE 16

Reaction conditions for conversion of isobutanol (i-BuOH) to isobutyl esters of corn oil fatty acids (i-BuO-COFA)

| reaction | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 17

Weights of isobutanol (i-BuOH) and isobutyl esters of corn oil fatty acids (i-BuO-COFA) present in the aqueous fraction (AQ) and organic fraction (ORG) for reactions described in Table 16.

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |
| 1 | 20 | 1.25 | 2.43 | 2.22 | 0.21 | 0.96 |

TABLE 17-continued

Weights of isobutanol (i-BuOH) and isobutyl esters of corn oil fatty acids (i-BuO-COFA) present in the aqueous fraction (AQ) and organic fraction (ORG) for reactions described in Table 16.

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 32

Dependence of Isobutyl-COFA Ester Concentration on Aqueous/COFA Ratio in Lipase-Catalyzed Reactions Reaction mixtures containing aqueous 2-(N-morpholino) ethanesulfonic acid buffer (0.20 M, pH 5.2), isobutanol (2-methyl-1-propanol), lipase (Lipolase® 100 L; Novozymes) and corn oil fatty acids prepared from corn oil (Table 18) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 19).

TABLE 18

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 45.96 | 3.6 | 43.4 | 10 |
| 2 | 45.96 | 3.6 | 21.7 | 10 |
| 3 | 45.96 | 3.6 | 10.85 | 10 |
| 4 | 45.96 | 3.6 | 43.4 | 4 |
| 5 | 45.96 | 3.6 | 43.4 | 0 |

TABLE 19

Weights of isobutanol (i-BuOH) and isobutyl esters of corn oil fatty acids (i-BuO-COFA) present in the aqueous fraction (AQ) and organic fraction (ORG) for reactions described in Table 18

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1 | 0.76 | 2.84 | 2.58 | 0.25 | 1.13 |
| 1 | 2 | 0.74 | 2.86 | 2.41 | 0.44 | 2.00 |
| 1 | 4 | 0.66 | 2.94 | 2.05 | 0.89 | 4.03 |
| 1 | 6 | 0.63 | 2.97 | 1.43 | 1.54 | 6.93 |

TABLE 19-continued

Weights of isobutanol (i-BuOH) and isobutyl esters of corn oil fatty acids (i-BuO-COFA) present in the aqueous fraction (AQ) and organic fraction (ORG) for reactions described in Table 18

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 33

Dependence of Butyl-COFA Ester Concentration on Esterification Alcohol in Lipase-Catalyzed Reactions Reaction mixtures containing aqueous 2-(N-morpholino) ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 20) were stirred at 30° C., and samples were withdrawn from each reaction mixture at predetermined times, immediately centrifuged, and the aqueous and organic layers separated and analyzed for isobutanol (1-BuOH) or n-butanol (n-BuOH) and isobutyl- or butyl esters of corn oil fatty acids (BuO-COFA) (Table 21).

TABLE 20

Reaction conditions for conversion of isobutanol (i-BuOH) or n-butanol (n-BuOH) to butyl esters of corn oil fatty acids (BuO-COFA)

| Reaction | butanol | MES buffer (0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 21

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 20

| reaction | time (h) | | | | | |
|---|---|---|---|---|---|---|
| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
| 6 | 0.1 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |
| | | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
| 7 | 0.1 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |
| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
| 8 | 0.1 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |
| | | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
| 9 | 0.1 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 34

Production of Iso-Butyl Oleate by Lipase-Catalyzed Reaction of Isobutanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 22) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 23).

TABLE 22

Reaction conditions for conversion of isobutanol (i-BuOH) to iso-butyl oleate (i-BuO-oleate)

| reaction # | MES buffer (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 23

Weights of isobutanol (i-BuOH) and iso-butyl oleate (i-BuO-COFA) present in the aqueous fraction (AQ) and organic fraction (ORG) for reactions described in Table 22

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0.1 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |
| 10 | 51 | 0.82 | 2.83 | 0.54 | 2.29 | 10.5 |
| 11 | 0.1 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 35

Comparison of Production of Iso-Butyl Oleate by Lipase-Catalyzed Reactions of Isobutanol and Oleic Acid Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100L, Lipex® 100L, Lipozyme® CALB L, Novozyme® CALA L, Palatase® from Novozymes, or lipase (10 ppm) from *Pseudomonas fluorescens, Pseudomonas cepacia, Mucor miehei*, hog pancreas, *Candida cylindracea, Rhizopus niveus, Candida antarctica, Rhizopus arrhizus* or *Aspergillus* from SigmaAldrich (Table 24), were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 25).

TABLE 24

Reaction conditions for conversion of isobutanol (i-BuOH) to iso-butyl oleate (i-BuO-oleate)

| MES buffer (0.2M) (g) | i-BuOH (g) | oleic acid (g) | lipase (ppm) |
|---|---|---|---|
| 46.105 | 3.601 | 13.72 | 10 |

TABLE 25

Weights of isobutanol (i-BuOH) and iso-butyl oleate (i-BuO-oleate) present in the aqueous fraction (AQ) and organic fraction (ORG) for reactions described in Table 24

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100 L | 23 | 0.92 | 2.72 | 0.71 | 2.01 | 9.20 |
| Lipex ® 100 L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| *Pseudomonas fluorescens* | 23 | 1.38 | 2.22 | 1.97 | 0.25 | 1.14 |
| *Pseudomonas cepacia* | 23 | 1.39 | 2.21 | 1.95 | 0.26 | 1.20 |
| *Mucor miehei* | 23 | 1.29 | 2.31 | 1.57 | 0.75 | 3.42 |
| hog pancreas | 23 | 1.40 | 2.20 | 2.19 | 0.01 | 0.04 |
| *Candida cylindracea* | 23 | 1.15 | 2.45 | 1.08 | 1.37 | 6.25 |
| *Rhizopus niveus* | 23 | 1.39 | 2.21 | 2.19 | 0.02 | 0.11 |
| *Candida antarctica* | 23 | 1.37 | 2.24 | 2.08 | 0.15 | 0.69 |
| *Rhizopus arrhizus* | 23 | 1.01 | 2.59 | 0.81 | 1.78 | 8.12 |
| *Aspergillus* | 23 | 1.36 | 2.24 | 2.06 | 0.18 | 0.82 |
| no lipase | 23 | 1.49 | 2.10 | 2.10 | 0.01 | 0.02 |

Example 36

Production of Ethyl-COFA Ester by Lipase-Catalyzed Reaction of Ethanol and Corn Oil Fatty Acids (COFA)

Reaction mixtures containing aqueous 2-(N-morpholino) ethanesulfonic acid buffer (0.20 M, pH 5.5), ethanol, lipase (Lipolase® 100 L or Lipozyme® CALB L; Novozymes) and corn oil fatty acids prepared from corn oil (Table 26) were stirred at 30° C., and samples were withdrawn while stirring from each reaction mixture at predetermined times, immediately centrifuged, and the aqueous and organic layers separated and analyzed for ethanol and ethyl esters of corn oil fatty acids (EtO-COFA) (Table 27).

TABLE 26

Reaction conditions for conversion of ethanol (EtOH) to ethyl esters of corn oil fatty acids (EtO-COFA)

| Reaction | MES buffer (0.2M) (g) | ethanol (g) | COFA (g) | lipase | lipase (ppm) |
|---|---|---|---|---|---|
| 12 | 46.11 | 3.60 | 14.48 | Lipolase ® 100L | 10 |
| 13 | 46.10 | 3.60 | 14.47 | Lipozyme ® CALB L | 10 |
| 14 | 46.11 | 3.61 | 14.47 | no lipase | 0 |

TABLE 27

Weights of ethanol (EtOH) and ethyl esters of corn oil fatty acids (EtO-COFA) present in the aqueous fraction (AQ) and organic fraction (ORG) for reactions described in Table 26

| reaction | time (h) | total EtOH (g) (AQ) | total EtOH (g) (ORG) | EtOH (g) (ORG) | EtOH from EtO-COFA (g) (ORG) | ETO-COFA (g) (ORG) |
|---|---|---|---|---|---|---|
| 12 | 0 | 2.94 | 0.655 | 0.634 | 0.021 | 0.01 |
| 12 | 2 | 3.09 | 0.504 | 0.105 | 0.398 | 0.81 |
| 12 | 20 | 2.74 | 0.854 | 0.030 | 0.824 | 4.46 |
| 12 | 24 | 2.43 | 1.167 | 0.032 | 1.135 | 5.25 |
| 12 | 44 | 2.37 | 1.230 | 0.022 | 1.208 | 7.28 |
| 12 | 48 | 2.24 | 1.360 | 0.022 | 1.338 | 7.63 |
| 13 | 0 | 2.94 | 0.659 | 0.635 | 0.024 | 0.01 |
| 13 | 2 | 2.83 | 0.773 | 0.074 | 0.699 | 1.88 |

TABLE 27-continued

Weights of ethanol (EtOH) and ethyl esters of corn oil fatty acids (EtO-COFA) present in the aqueous fraction (AQ) and organic fraction (ORG) for reactions described in Table 26

| reaction | time (h) | total EtOH (g) (AQ) | total EtOH (g) (ORG) | EtOH (g) (ORG) | EtOH from EtO-COFA (g) (ORG) | ETO-COFA (g) (ORG) |
|---|---|---|---|---|---|---|
| 13 | 20 | 2.10 | 1.501 | 0.000 | 1.501 | 9.72 |
| 13 | 24 | 2.07 | 1.532 | 0.000 | 1.532 | 10.14 |
| 13 | 44 | 1.94 | 1.673 | 0.014 | 1.659 | 10.93 |
| 13 | 48 | 1.72 | 1.882 | 0.016 | 1.865 | 11.05 |
| 14 | 0 | 2.96 | 0.646 | 0.624 | 0.023 | 0.01 |
| 14 | 2 | 2.93 | 0.679 | 0.661 | 0.018 | 0.01 |
| 14 | 20 | 2.75 | 0.857 | 0.779 | 0.079 | 0.02 |
| 14 | 24 | 2.87 | 0.738 | 0.662 | 0.075 | 0.03 |
| 14 | 44 | 2.79 | 0.813 | 0.688 | 0.126 | 0.04 |
| 14 | 48 | 2.82 | 0.785 | 0.671 | 0.114 | 0.05 |

Example 37

Production of Ethyl-COFA Ester by Lipase-Catalyzed Reaction of Ethanol and Corn Oil Fatty Acids (COFA) During Fermentation of Yeast The wild-type yeast strain CEN.PK113-7D was propagated overnight in medium containing yeast nitrogen base without amino acids (6.7 g/L), dextrose (25 g/L), and MES buffer (0.1 M at pH 5.5). The overnight culture was diluted into fresh medium such that the resulting optical density at 600 nm was 0.1. The diluted culture was aliquoted, 25 mL per flask, into six 250 mL sealed-cap shake flasks. Four of the cultures were supplemented with either of two lipase enzyme stock solutions (2 mg protein/mL 10 mM phosphate buffer (pH 7.0) of Lipozyme® CALB L or Lipolase® 100L) to a final lipase concentration of 10 ppm in the media. Corn oil fatty acids (COFA) were added at a 1:1 volume ratio to the aqueous culture in three of the flasks (no enzyme, CALB L, or Lipolase® 100L). One flask had no supplements. The cultures were grown in a temperature-controlled shaking incubator at 30° C. and a shaking speed of 250 rpm for 23 hours. Samples for cell mass determination were allowed to phase separate in 15 mL conical bottom tubes. The sample's optical density at 600 nm was measured at a 20-fold dilution in saline.

Samples (5 mL aqueous or 10 mL culture/COFA emulsion) for chromatographic analysis were immediately centrifuged for 5 minutes at 4000 rpm in a TX-400 swinging bucket rotor in 15 mL conical bottom tubes. For aqueous samples, a 0.22 m spin filter was used prior to analysis. Aqueous samples were analyzed on a Shodex SH1011 column with a SH-G guard column using 0.01 M sulfuric acid mobile phase at 50° C. and a flow rate of 0.5 mL per minute. Detection of sugars and alcohols was by Refractive Index and 210 nm absorption, and quantitation was performed using standard curves. Samples were taken of the aqueous culture (no added COFA) or culture/COFA emulsion, and analyzed as described in previous Examples for ethyl esters of COFA. Results are shown in Tables 28 and 29.

TABLE 28

Weights of ethanol (EtOH), glucose and fermentation byproducts present in the aqueous media (AQ) from 23 h fermentations

| | glucose (g/L) | glycerol (g/L) | acetate (g/L) | acetoin (g/L) | EtOH (g/L) |
|---|---|---|---|---|---|
| Media | 0 | 0.62 | 1.01 | 0.08 | 9.98 |
| media + CALB L | 0 | 0.72 | 0.94 | 0.06 | 9.94 |
| media + Lipolase ® 100L | 0 | 0.61 | 0.99 | 0.05 | 9.87 |
| media + COFA | 0 | 0.68 | 0.32 | 0.15 | 7.73 |
| media + COFA + CALB L | 0 | 0.74 | 0.09 | 0.11 | 3.92 |
| media + COFA + Lipolase ® 100L | 0 | 0.63 | 0.23 | 0.18 | 7.19 |

TABLE 29

Weights of ethanol (EtOH) and ethyl esters of corn oil fatty acids (EtO-COFA) present in the aqueous fraction (AQ) and the organic fraction (ORG) for 23 h fermentations

| Reaction | EtOH (g/L) (AQ) | EtOH (g/L) (ORG) | EtOH from EtO-COFA (g/L) (ORG) | ETO-COFA (g/L) (ORG) |
|---|---|---|---|---|
| media + COFA | 6.7 | 0 | 0.18 | 1.2 |
| media + COFA + CALB L | 3.4 | 0 | 4.52 | 30.0 |
| media + COFA + Lipolase ® 100L | 6.1 | 0 | 0.72 | 4.8 |

Example 38

Production of Methyl-COFA Ester by Lipase-Catalyzed Reaction of Methanol and Corn Oil Fatty Acids (COFA)

Reaction mixtures containing aqueous 2-(N-morpholino) ethanesulfonic acid buffer (0.20 M, pH 5.5), methanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 30) were stirred at 30° C., and samples were withdrawn while stirring from each reaction mixture at predetermined times, immediately centrifuged, and the aqueous and organic layers separated and analyzed for ethanol and ethyl esters of corn oil fatty acids (EtO-COFA) (Table 31).

TABLE 30

Reaction conditions for conversion of methanol (MeOH) to methyl esters of corn oil fatty acids (MeO-COFA)

| Reaction | MES buffer (0.2M) (g) | methanol (g) | COFA (g) | lipase | lipase (ppm) |
|---|---|---|---|---|---|
| 15 | 46.11 | 3.60 | 14.51 | Lipolase ® 100L | 10 |
| 16 | 46.10 | 3.59 | 14.49 | Lipozyme ® CALB L | 10 |
| 17 | 46.11 | 3.60 | 14.49 | *R. arrhizus* | 10 |
| 18 | 46.10 | 3.60 | 14.48 | *C. cylindracea* | 10 |
| 19 | 46.10 | 3.60 | 14.51 | no lipase | 10 |

TABLE 31

Weights of methanol (MeOH) and methyl esters of corn oil fatty acids (MeO-COFA) present in the aqueous fraction (AQ) and organic fraction (ORG) for reactions described in Table 30

| reac-tion | time (h) | total MeOH (g) (AQ) | total MeOH (g) (ORG) | MeOH (g) (ORG) | MeOH from MeO-COFA (g) (ORG) | MeO-COFA (g) (ORG) |
|---|---|---|---|---|---|---|
| 15 | 0 | 3.33 | 0.26 | 0.05 | 0.01 | 0.02 |
| 15 | 2 | 3.09 | 0.50 | 0.05 | 0.13 | 0.16 |
| 15 | 4 | 3.09 | 0.51 | 0.04 | 0.33 | 0.73 |
| 15 | 20 | 2.81 | 0.79 | 0.04 | 0.70 | 3.03 |
| 15 | 24 | 2.72 | 0.87 | 0.04 | 0.79 | 3.47 |
| 15 | 44 | 2.53 | 1.06 | 0.03 | 1.00 | 4.97 |
| 15 | 48 | 2.48 | 1.12 | 0.03 | 1.05 | 5.18 |
| 16 | 0 | 3.07 | 0.53 | 0.04 | 0.02 | 0.02 |
| 16 | 2 | 3.01 | 0.59 | 0.04 | 0.20 | 0.22 |
| 16 | 4 | 2.92 | 0.67 | 0.03 | 0.56 | 1.32 |
| 16 | 20 | 2.54 | 1.06 | 0.03 | 0.99 | 5.25 |
| 16 | 24 | 2.43 | 1.16 | 0.03 | 1.09 | 5.90 |
| 16 | 44 | 2.28 | 1.32 | 0.02 | 1.27 | 7.63 |
| 16 | 48 | 2.22 | 1.37 | 0.03 | 1.32 | 7.89 |
| 17 | 0 | 3.09 | 0.52 | 0.04 | 0.02 | 0.02 |
| 17 | 2 | 3.05 | 0.56 | 0.06 | 0.05 | 0.06 |
| 17 | 4 | 2.98 | 0.63 | 0.04 | 0.25 | 0.24 |
| 17 | 20 | 3.03 | 0.57 | 0.04 | 0.32 | 0.49 |
| 17 | 24 | 2.98 | 0.63 | 0.04 | 0.35 | 0.52 |
| 17 | 44 | 2.99 | 0.62 | 0.04 | 0.38 | 0.62 |
| 17 | 48 | 2.94 | 0.67 | 0.04 | 0.40 | 0.61 |
| 18 | 0 | 3.17 | 0.43 | 0.05 | 0.02 | 0.02 |
| 18 | 2 | 3.12 | 0.49 | 0.04 | 0.02 | 0.02 |
| 18 | 4 | 2.96 | 0.64 | 0.00 | 0.64 | 1.24 |
| 18 | 20 | 2.64 | 0.96 | 0.03 | 0.89 | 3.97 |
| 18 | 24 | 2.58 | 1.03 | 0.03 | 0.95 | 4.49 |
| 18 | 44 | 2.37 | 1.23 | 0.03 | 1.18 | 6.40 |
| 18 | 48 | 2.30 | 1.30 | 0.03 | 1.25 | 6.71 |
| 19 | 0 | 3.08 | 0.52 | 0.04 | 0.03 | 0.02 |
| 19 | 2 | 3.08 | 0.52 | 0.04 | 0.02 | 0.02 |
| 19 | 4 | 3.04 | 0.56 | 0.04 | 0.03 | 0.02 |
| 19 | 20 | 3.08 | 0.53 | 0.04 | 0.03 | 0.03 |
| 19 | 24 | 3.04 | 0.56 | 0.05 | 0.03 | 0.04 |
| 19 | 44 | 3.01 | 0.59 | 0.04 | 0.06 | 0.04 |
| 19 | 48 | 2.95 | 0.65 | 0.05 | 0.06 | 0.04 |

Example 39

Production of 1-Propyl-COFA Ester by Lipase-Catalyzed Reaction of 1-Propanol and Corn Oil Fatty Acids (COFA)

Reaction mixtures containing aqueous 2-(N-morpholino) ethanesulfonic acid buffer (0.20 M, pH 5.5), 1-propanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 32) were stirred at 30° C., and samples were withdrawn while stirring from each reaction mixture at predetermined times, immediately centrifuged, and the aqueous and organic layers separated and analyzed for 1-propanol and 1-propyl esters of corn oil fatty acids (PrO-COFA) (Table 33).

TABLE 32

Reaction conditions for conversion of 1-propanol (PrOH) to 1-propyl esters of corn oil fatty acids (PrO-COFA)

| Reaction | MES buffer (0.2M) (g) | 1-propanol (g) | COFA (g) | lipase | lipase (ppm) |
|---|---|---|---|---|---|
| 20 | 46.11 | 3.60 | 14.47 | Lipolase ® 100L | 10 |
| 21 | 46.12 | 3.60 | 14.48 | Lipozyme ® CALB L | 10 |
| 22 | 46.10 | 3.60 | 14.48 | *R. arrhizus* | 10 |
| 23 | 46.13 | 3.62 | 14.49 | *C. cylindracea* | 10 |
| 24 | 46.13 | 3.60 | 14.48 | no lipase | 0 |

TABLE 33

Weights of 1-propanol (PrOH) and 1-propyl esters of corn oil fatty acids (PrO-COFA) present in the aqueous fraction (AQ) and organic fraction (ORG) for reactions described in Table 32

| reaction | time (h) | total PrOH (g) (AQ) | total PrOH (g) (ORG) | PrOH (g) (ORG) | PrOH from PrO-COFA (g) (ORG) | PrO-COFA (g) (ORG) |
|---|---|---|---|---|---|---|
| 20 | 0 | 2.54 | 1.05 | 0.80 | 0.00 | 0.02 |
| 20 | 2 | 2.39 | 1.20 | 0.70 | 0.11 | 0.44 |
| 20 | 4 | 2.00 | 1.60 | 0.61 | 0.55 | 1.88 |
| 20 | 20 | 1.65 | 1.95 | 0.31 | 1.50 | 6.96 |
| 20 | 24 | 1.51 | 2.08 | 0.28 | 1.69 | 7.97 |
| 20 | 44 | 1.13 | 2.46 | 0.16 | 2.23 | 11.09 |
| 20 | 48 | 1.09 | 2.51 | 0.15 | 2.29 | 11.27 |
| 21 | 0 | 2.44 | 1.16 | 0.79 | 0.00 | 0.02 |
| 21 | 2 | 2.38 | 1.22 | 0.65 | 0.13 | 0.49 |
| 21 | 4 | 2.07 | 1.53 | 0.52 | 0.73 | 2.94 |
| 21 | 20 | 1.16 | 2.43 | 0.17 | 2.18 | 10.80 |
| 21 | 24 | 1.08 | 2.51 | 0.16 | 2.28 | 11.26 |
| 21 | 44 | 1.00 | 2.60 | 0.13 | 2.40 | 11.86 |
| 21 | 48 | 0.98 | 2.62 | 0.13 | 2.42 | 11.91 |
| 22 | 0 | 2.49 | 1.11 | 0.80 | 0.00 | 0.02 |
| 22 | 2 | 2.42 | 1.18 | 0.76 | 0.10 | 0.38 |
| 22 | 4 | 2.23 | 1.37 | 0.71 | 0.29 | 1.08 |
| 22 | 20 | 2.09 | 1.51 | 0.56 | 0.71 | 2.96 |
| 22 | 24 | 2.06 | 1.54 | 0.54 | 0.77 | 3.17 |
| 22 | 44 | 1.87 | 1.73 | 0.47 | 0.58 | 1.75 |
| 22 | 48 | 1.88 | 1.73 | 0.46 | 0.60 | 1.82 |
| 23 | 0 | 2.49 | 1.13 | 0.80 | 0.00 | 0.02 |
| 23 | 2 | 2.45 | 1.17 | 0.77 | 0.07 | 0.29 |
| 23 | 4 | 2.35 | 1.27 | 0.71 | 0.21 | 0.82 |
| 23 | 20 | 2.00 | 1.61 | 0.50 | 0.89 | 3.74 |
| 23 | 24 | 1.93 | 1.68 | 0.49 | 0.99 | 4.23 |
| 23 | 44 | 1.57 | 2.04 | 0.33 | 1.56 | 6.83 |
| 23 | 48 | 1.49 | 2.13 | 0.31 | 1.67 | 7.33 |
| 24 | 0 | 2.49 | 1.11 | 0.81 | 0.00 | 0.02 |
| 24 | 2 | 2.47 | 1.13 | 0.81 | 0.00 | 0.02 |
| 24 | 4 | 2.38 | 1.21 | 0.78 | 0.01 | 0.03 |
| 24 | 20 | 2.46 | 1.14 | 0.79 | 0.01 | 0.05 |
| 24 | 24 | 2.42 | 1.17 | 0.79 | 0.01 | 0.05 |
| 24 | 44 | 2.41 | 1.19 | 0.76 | 0.02 | 0.09 |
| 24 | 48 | 2.32 | 1.28 | 0.77 | 0.03 | 0.10 |

Example 40

Production of 1-Pentyl-COFA Ester by Lipase-Catalyzed Reaction of 1-Pentanol and Corn Oil Fatty Acids (COFA)

Reaction mixtures containing aqueous 2-(N-morpholino) ethanesulfonic acid buffer (0.20 M, pH 5.5), 1-pentanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 34) were stirred at 30° C., and samples were withdrawn while stirring from each reaction mixture at predetermined times, immediately centrifuged, and the aqueous and organic layers separated and analyzed for 1-pentanol and 1-pentyl esters of corn oil fatty acids (PenO-COFA) (Table 35).

TABLE 34

Reaction conditions for conversion of 1-pentanol (PenOH) to 1-pentyl esters of corn oil fatty acids (PenO-COFA)

| Reaction | MES buffer (0.2M) (g) | 1-pentanol (g) | COFA (g) | lipase | lipase (ppm) |
|---|---|---|---|---|---|
| 25 | 46.11 | 3.60 | 14.47 | Lipolase ® 100L | 10 |
| 26 | 46.12 | 3.60 | 14.48 | Lipozyme ® CALB L | 10 |
| 27 | 46.10 | 3.60 | 14.48 | *R. arrhizus* | 10 |
| 28 | 46.13 | 3.62 | 14.49 | *C. cylindracea* | 10 |
| 29 | 46.13 | 3.60 | 14.48 | no lipase | 0 |

TABLE 35

Weights of 1-pentanol (PenOH) and 1-pentyl esters of corn oil fatty acids (PenO-COFA) present in the aqueous fraction (AQ) and organic fraction (ORG) for reactions described in Table 34

| reaction | time (h) | total PenOH (g) (AQ) | total PenOH (g) (ORG) | PenOH (g) (ORG) | PenOH from PenO-COFA (g) (ORG) | PenO-COFA (g) (ORG) |
|---|---|---|---|---|---|---|
| 25 | 0 | 0.364 | 3.238 | 3.091 | 0.002 | 0.006 |
| 25 | 2 | 0.339 | 3.264 | 2.745 | 0.446 | 1.760 |
| 25 | 4 | 0.373 | 3.229 | 2.761 | 0.557 | 2.196 |
| 25 | 20 | 0.336 | 3.266 | 1.833 | 1.002 | 3.953 |
| 25 | 24 | 0.325 | 3.277 | 1.575 | 1.257 | 4.960 |
| 25 | 44 | 0.226 | 3.377 | 0.921 | 2.383 | 9.400 |
| 25 | 48 | 0.206 | 3.396 | 0.723 | 2.524 | 9.957 |
| 26 | 0 | 0.364 | 3.243 | 3.105 | 0.002 | 0.006 |
| 26 | 2 | 0.317 | 3.290 | 2.462 | 0.512 | 2.019 |
| 26 | 4 | 0.320 | 3.287 | 2.287 | 0.652 | 2.574 |
| 26 | 20 | 0.130 | 3.477 | 0.387 | 3.007 | 11.860 |
| 26 | 24 | 0.094 | 3.513 | 0.215 | 3.251 | 12.823 |
| 26 | 44 | 0.075 | 3.532 | 0.165 | 3.312 | 13.067 |
| 26 | 48 | 0.081 | 3.526 | 0.165 | 3.326 | 13.120 |
| 27 | 0 | 0.384 | 3.216 | 3.102 | 0.002 | 0.006 |
| 27 | 2 | 0.356 | 3.244 | 2.957 | 0.437 | 1.725 |
| 27 | 4 | 0.333 | 3.267 | 2.912 | 0.388 | 1.532 |
| 27 | 20 | 0.363 | 3.237 | 2.664 | 0.433 | 1.707 |
| 27 | 24 | 0.367 | 3.233 | 2.597 | 0.665 | 2.623 |
| 27 | 44 | 0.366 | 3.234 | 2.473 | 0.549 | 2.166 |
| 27 | 48 | 0.347 | 3.253 | 2.473 | 0.559 | 2.205 |
| 28 | 0 | 0.369 | 3.244 | 3.086 | 0.002 | 0.006 |
| 28 | 2 | 0.329 | 3.284 | 2.523 | 0.435 | 1.717 |
| 28 | 4 | 0.332 | 3.281 | 2.496 | 0.493 | 1.944 |
| 28 | 20 | 0.304 | 3.309 | 1.575 | 1.321 | 5.209 |
| 28 | 24 | 0.270 | 3.343 | 1.292 | 1.868 | 7.367 |
| 28 | 44 | 0.186 | 3.427 | 0.596 | 2.722 | 10.735 |
| 28 | 48 | 0.162 | 3.451 | 0.509 | 2.846 | 11.224 |
| 29 | 0 | 0.375 | 3.239 | 3.102 | 0.001 | 0.006 |
| 29 | 2 | 0.366 | 3.248 | 3.117 | 0.009 | 0.034 |
| 29 | 4 | 0.377 | 3.237 | 3.099 | 0.023 | 0.089 |
| 29 | 20 | 0.380 | 3.234 | 3.092 | 0.032 | 0.125 |
| 29 | 24 | 0.379 | 3.235 | 3.058 | 0.039 | 0.154 |
| 29 | 44 | 0.374 | 3.240 | 3.013 | 0.053 | 0.209 |
| 29 | 48 | 0.373 | 3.241 | 2.950 | 0.059 | 0.233 |

Example 41

Production of 2-Methyl-1-Butyl-COFA Ester by Lipase-Catalyzed Reaction of 2-Methyl-1-Butanol and Corn Oil Fatty Acids (COFA)

Reaction mixtures containing aqueous 2-(N-morpholino) ethanesulfonic acid buffer (0.20 M, pH 5.5), 2-methyl-1-butanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 36) were stirred at 30° C., and samples were withdrawn while stirring from each reaction mixture at predetermined times, immediately centrifuged, and the aqueous and organic layers separated and analyzed for 2-methyl-1-butanol and 2-methyl-1-butyl esters of corn oil fatty acids (MeBO-COFA) (Table 37).

TABLE 36

Reaction conditions for conversion of 2-methyl-1-butanol (MeBOH) to 2-methyl-1-butyl esters of corn oil fatty acids (MeBO-COFA)

| Reaction | MES buffer (0.2M) (g) | 2-methyl-1-butanol (g) | COFA (g) | lipase | lipase (ppm) |
|---|---|---|---|---|---|
| 30 | 46.27 | 3.60 | 14.48 | Lipolase ® 100L | 10 |
| 31 | 46.14 | 3.60 | 14.48 | Lipozyme ® CALB L | 10 |
| 32 | 46.12 | 3.60 | 14.47 | *R. arrhizus* | 10 |
| 33 | 46.11 | 3.49 | 14.47 | *C. cylindracea* | 10 |
| 34 | 46.18 | 3.60 | 14.47 | no lipase | 0 |

TABLE 37

Weights of 2-methyl-1-butanol (MeBOH) and 2-methyl-1-butyl esters of corn oil fatty acids (MeBO-COFA) present in the aqueous fraction (AQ) and organic fraction (ORG) for reactions described in Table 36

| reaction | time (h) | total MeBOH (g) (AQ) | total MeBOH (g) (ORG) | MeBOH (g) (ORG) | MeBOH from MeBO-COFA (g) (ORG) | MeBO-COFA (g) (ORG) |
|---|---|---|---|---|---|---|
| 30 | 0 | 0.000 | 3.603 | 3.103 | 0.002 | 0.008 |
| 30 | 2 | 0.009 | 3.593 | 2.919 | 0.630 | 2.484 |
| 30 | 4 | 0.058 | 3.545 | 2.766 | 0.673 | 2.653 |
| 30 | 20 | 0.005 | 3.598 | 2.041 | 1.331 | 5.250 |
| 30 | 24 | 0.029 | 3.574 | 1.967 | 1.418 | 5.594 |
| 30 | 44 | 0.017 | 3.585 | 1.218 | 2.174 | 8.577 |
| 30 | 48 | 0.008 | 3.595 | 1.099 | 2.085 | 8.224 |
| 31 | 0 | 0.000 | 3.595 | 3.129 | 0.003 | 0.010 |
| 31 | 2 | 0.003 | 3.592 | 2.665 | 0.692 | 2.730 |
| 31 | 4 | 0.012 | 3.583 | 2.510 | 0.839 | 3.308 |
| 31 | 20 | 0.001 | 3.594 | 1.408 | 1.932 | 7.622 |
| 31 | 24 | 0.005 | 3.590 | 1.293 | 2.082 | 8.214 |
| 31 | 44 | 0.006 | 3.589 | 0.970 | 2.437 | 9.612 |
| 31 | 48 | 0.007 | 3.588 | 0.918 | 2.495 | 9.840 |
| 32 | 0 | 0.000 | 3.597 | 3.100 | 0.003 | 0.011 |
| 32 | 2 | 0.017 | 3.580 | 2.855 | 0.588 | 2.321 |
| 32 | 4 | 0.000 | 3.597 | 2.783 | 0.675 | 2.664 |
| 32 | 20 | 0.000 | 3.597 | 2.392 | 1.027 | 4.051 |
| 32 | 24 | 0.000 | 3.597 | 2.337 | 1.081 | 4.266 |
| 32 | 44 | 0.001 | 3.596 | 2.209 | 1.191 | 4.697 |
| 32 | 48 | 0.000 | 3.597 | 2.174 | 1.216 | 4.798 |
| 33 | 0 | 0.000 | 3.597 | 3.093 | 0.002 | 0.008 |
| 33 | 2 | 0.001 | 3.596 | 1.756 | 1.398 | 5.514 |
| 33 | 4 | 0.003 | 3.594 | 2.116 | 1.026 | 4.046 |
| 33 | 20 | 0.027 | 3.570 | 0.607 | 2.865 | 11.302 |
| 33 | 24 | 0.000 | 3.597 | 0.429 | 3.097 | 12.216 |
| 33 | 44 | 0.007 | 3.590 | 0.205 | 3.345 | 13.194 |
| 33 | 48 | 0.003 | 3.594 | 0.202 | 3.353 | 13.228 |

TABLE 37-continued

Weights of 2-methyl-1-butanol (MeBOH) and 2-methyl-1-butyl esters of corn oil fatty acids (MeBO-COFA) present in the aqueous fraction (AQ) and organic fraction (ORG) for reactions described in Table 36

| reaction | time (h) | total MeBOH (g) (AQ) | total MeBOH (g) (ORG) | MeBOH (g) (ORG) | MeBOH from MeBO-COFA (g) (ORG) | MeBO-COFA (g) (ORG) |
|---|---|---|---|---|---|---|
| 34 | 0 | 0.000 | 3.485 | 3.014 | 0.003 | 0.011 |
| 34 | 2 | 0.000 | 3.485 | 2.991 | 0.021 | 0.083 |
| 34 | 4 | 0.000 | 3.485 | 3.020 | 0.012 | 0.046 |
| 34 | 20 | 0.000 | 3.485 | 2.970 | 0.029 | 0.115 |
| 34 | 24 | 0.002 | 3.483 | 2.949 | 0.037 | 0.148 |
| 34 | 44 | 0.000 | 3.485 | 2.912 | 0.047 | 0.185 |
| 34 | 48 | 0.000 | 3.485 | 2.909 | 0.051 | 0.200 |

Example 42

Production of Isopropyl-COFA Ester by Lipase-Catalyzed Reaction of Isopropanol and Corn Oil Fatty Acids (COFA)

Reaction mixtures containing aqueous 2-(N-morpholino) ethanesulfonic acid buffer (0.20 M, pH 5.5), isopropanol (2-propanol), lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 38) were stirred at 30° C., and samples were withdrawn while stirring from each reaction mixture at predetermined times, immediately centrifuged, and the aqueous and organic layers separated and analyzed for isopropanol and isopropyl esters of corn oil fatty acids (1-PrO-COFA) (Table 39).

TABLE 38

Reaction conditions for conversion of isopropanol (i-PrOH) to isopropyl esters of corn oil fatty acids (i-PrO-COFA)

| Reaction | MES buffer (0.2M) (g) | isopropanol (g) | COFA (g) | lipase | lipase (ppm) |
|---|---|---|---|---|---|
| 35 | 46.14 | 3.60 | 14.48 | Lipozyme ® CALB L | 10 |
| 36 | 46.11 | 3.49 | 14.47 | *C. cylindracea* | 10 |
| 37 | 46.18 | 3.60 | 14.47 | no lipase | 0 |

TABLE 39

Weights of isopropanol (i-PrOH) and isopropyl esters of corn oil fatty acids (i-PrO-COFA) present in the organic fraction (ORG) for reactions described in Table 38

| reaction | time (h) | i-PrOH from i-PRO-COFA (g) (ORG) | i-PrO-COFA (g) (ORG) |
|---|---|---|---|
| 35 | 0 | 0.001 | 0.00 |
| 35 | 2 | 0.013 | 0.07 |
| 35 | 4 | 0.038 | 0.20 |
| 35 | 20 | 0.132 | 0.71 |
| 35 | 24 | 0.177 | 0.94 |
| 35 | 44 | 0.291 | 1.55 |
| 35 | 48 | 0.301 | 1.61 |
| 36 | 0 | 0.001 | 0.01 |
| 36 | 2 | 0.051 | 0.27 |
| 36 | 4 | 0.163 | 0.87 |
| 36 | 20 | 0.532 | 2.84 |

TABLE 39-continued

| Weights of isopropanol (i-PrOH) and isopropyl esters of corn oil fatty acids (i-PrO-COFA) present in the organic fraction (ORG) for reactions described in Table 38 | | | |
|---|---|---|---|
| reaction | time (h) | i-PrOH from i-PRO-COFA (g) (ORG) | i-PrO-COFA (g) (ORG) |
| 36 | 24 | 0.652 | 3.48 |
| 36 | 44 | 0.916 | 4.89 |
| 36 | 48 | 0.959 | 5.12 |
| 37 | 0 | 0.001 | 0.01 |
| 37 | 2 | 0.001 | 0.01 |
| 37 | 4 | 0.003 | 0.02 |
| 37 | 20 | 0.009 | 0.05 |
| 37 | 24 | 0.011 | 0.06 |
| 37 | 44 | 0.016 | 0.09 |
| 37 | 48 | 0.023 | 0.12 |

Example 43

Comparison of Partition Coefficients for Isobutanol Between Water and Extractant Aqueous solutions of isobutanol (30 g/L) were mixed with corn oil fatty acids (COFA), or oleic acid or corn oil triglycerides, and their measured partition coefficients reported in the table relative to the measured partition coefficient for oleyl alcohol. Results are shown in Table 40.

TABLE 40

| Relative partition coefficients for isobutanol (30 g/L) between water and extractant | |
|---|---|
| extractant | isobutanol partition coefficient, relative to oleyl alcohol |
| oleyl alcohol | 100% |
| corn oil fatty acids | 91% |
| corn oil fatty acid isobutyl esters | 43% |
| corn oil triglycerides | 10% |

Example 44

Production of Corn Oil Fatty Acids

A five-liter (5 L) round bottom flask equipped with a mechanical stirrer, thermocouple, heating mantle, condenser and nitrogen tee was charged with 750 g of crude corn oil (non-food grade, recovered from an ethanol fermentation facility), 2112 g of water and 285 g of 50% sodium hydroxide solution. Mixture was heated to 90° C. and held for two hours, during which time it became a single thick, emulsion-like single phase. At the end of this time, TLC shows no remaining corn oil in the mixture. The mixture was then cooled to 74° C. and 900 g of 25% sulfuric acid was added to acidify the mixture. It was then cooled to 50° C. and the aqueous layer was drained. The oil layer was washed twice with 1500 mL of 40° C. water and then once with 1 liter of saturated brine. It was dried over magnesium sulfate and filtered through Celite. Yield was 610 g of clear red oil. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids.

Example 45

Chemical Synthesis of FABE

A 3L flask was equipped with a mechanical stirrer, thermocouple, nitrogen inlet, heating mantle and a condenser. The flask was charged with COFA (595 g) (prepared as in Example 44), isobutanol (595 g), and sulfuric acid (12 g). The mixture was refluxed for 1.5 hours at which time the condenser was removed and replaced with a still head. Distillate was collected over three hours with an initial head temperature of 90° C. and a final head temperature of 105° C. The mixture was then cooled to room temperature and 500 mL of DI water was added. The layers were separated and the organic layer was washed five times with 500 mL of DI water. It was then washed once with 500 mL of a 10% calcium chloride solution followed by six washings with 500 mL of DI water. The oil was then dried over magnesium sulfate and filtered through a bed of Celite yielding 601 g of a clear red oil. GC analysis shows the presence of 0.36 wt % of isobutanol. GC/MS analysis shows the presence of isobutyl palmitate, isobutyl stearate, isobutyl oleate, isobutyl linoleate, and isobutyl linolenate.

Example 46

Recovery of Butanol Using an Inorganic Acid Catalyst

A 1 liter round bottom flask with magnetic stirring and a 12" column packed with Rasching rings topped with a still head and nitrogen inlet was used. The flask was charged with 254 g FABE synthesized as in Example 45, 255 g COFA, 100 mL water, and 5 g sulfuric acid, and heated to a pot temperature of 93° C. Head temperature was equilibrated at 89.7° C. The first cut was collected with a reflux ratio that maintained the head temperature between 89 and 94° C.

The reaction was cooled and sat at room temperature for three days. GC analysis of the pot shows a total of 1 g of isobutanol in the pot. The distillation was restarted and three more cuts, each of 25 mL, were collected. One hundred (100) mL of water was added to the pot after collecting cut #2. Four cuts were collected and analyzed with the results shown in Table 41.

GC analysis was done using a Hewlett Packard 6890 GC using a 30 m FFAP column. Samples were dissolved in isopropanol and 1-pentanol was added as an internal standard. Standard curves were made for isobutanol, isobutyl palmitate, isobutyl stearate, isobutyl oleate, isobutyl linoleate, isobutyl linolenate, isobutyl arachidate, palmitic acid, stearic acid, oleic acid, linoleic acid and linolenic acid. FABE content is reported as the sum of the butyl esters and COFA content as the sum of the fatty acids.

TABLE 41

| Composition analysis of cuts collected | | | |
|---|---|---|---|
| | i-BuOH mg/ml | mL | wt of i-BuOH |
| Cut 1 | 60 | 43 | 2.6 |
| Cut 2 | 41 | 23.4 | 1 |

TABLE 41-continued

| Composition analysis of cuts collected | | | |
|---|---|---|---|
| | i-BuOH mg/ml | mL | wt of i-BuOH |
| Cut 3 | 29 | 24.2 | 0.7 |
| Cut 4 | 30 | 27 | 0.8 |
| Total | | 117.6 | 5.1 |

Example 47

Recovery of Butanol Using an Organic Acid Catalyst

A 1 liter 3 neck round bottom flask equipped with magnetic stirrer, thermocouple, addition funnel and still head was used. The flask charged with 100 g FABE synthesized as in Example 45, 100 g COFA, 5 g p-toluenesulfonic acid, and 25 mL water. Isobutanol analysis of initial pot shows 1.1 g of isobutanol present (contaminant in FABE). The pot was heated to 125° C. When the pot reached 116° C. head temperature was 96° C., and 125 mL water was added over 2.5 hours. Six cuts were collected over the time that the water was added and they were analyzed by GC as in Example 46. Results are provided in Table 42.

TABLE 42

| Composition analysis of cuts collected | | | | | | |
|---|---|---|---|---|---|---|
| cut | pot temp | head temp | mL of water added | mg/ml i-BuOH in cut | mL | g i-BuOH in cut |
| #1 | 116 | 96 | 25 | 53 | 13 | 0.7 |
| #2 | 117 | 98 | 47 | 52 | 26 | 1.4 |
| #3 | 117 | 99 | 70 | 37 | 24 | 0.9 |
| #4 | 117 | 99 | 95 | 30 | 22 | 0.7 |
| #5 | 117 | 99 | 125 | 23 | 31 | 0.7 |
| #6 | 117 | 99 | | 39 | 41 | 1.6 |
| Total | | | | | | 5.9 |

Butanol analysis of the remaining still pot shows 0.9 g of free isobutanol present. The initial COFA:FABE mixture analyzed was 45 wt % FABE. The final pot analyzed was 32 wt % FABE.

Example 48

Hydrolysis of FABE with Water at High Temperature

A 1 liter autoclave was charged with FABE synthesized as in Example 45, 300 mL and 300 mL water. It was sealed and purged with nitrogen. Stirring was started and it was then heated to 250° C. over 45 minutes and samples were removed every hour after reaching temperature. The samples were analyzed by GC as in Example 46. The oil phase samples showed the compositions as a function of time shown in Table 43.

TABLE 43

| Composition of organic phase of samples | | | |
|---|---|---|---|
| Time | wt % i-BuOH | wt % FABE | wt % COFA |
| 0 | 0 | 97 | 2 |
| 1 | 3 | 76 | 18 |
| 2 | 6 | 50 | 41 |
| 3 | 7 | 36 | 45 |
| 4 | 7 | 34 | 48 |
| 5 | 7 | 35 | 51 |

Example 49

Hydrolysis of FABE with Dilute Acid at High Temperature

A 1 liter autoclave was charged with 450 g of a 75/25 mixture of FABE synthesized as in Example 45 and COFA and with 150 g of 2% sulfuric acid. It was sealed and purged with nitrogen. Stirring was started and it was then heated to 225° C. over 45 minutes and samples were removed every hour after reaching temperature. The samples were analyzed by GC as in Example 46. The oil phase samples showed the compositions as a function of time shown in Table 44.

TABLE 44

| Composition analysis of cuts collected | | | |
|---|---|---|---|
| Time (h) | wt % i-BuOH | wt % FABE | wt % COFA |
| 0 | 2.2 | 61.8 | 34.1 |
| 1 | 3.8 | 47.8 | 42.0 |
| 2 | 5.2 | 38.4 | 48.2 |
| 3 | 5.3 | 38.4 | 53.5 |
| 4 | 5.1 | 33.4 | 48.2 |
| 5 | 5.1 | 31.9 | 43.3 |
| 6 | 5.5 | 35.2 | 51.7 |

Example 50

Hydrolysis of FABE with Sulfuric Acid in Solvent at 100° C.

A solution of 5 g FABE synthesized as in Example 45, 5 g of 25% sulfuric acid, and 60 g of diethyleneglycol dimethyl ether was prepared. Ten (10) g of the solution was added to each of five vials which were then sealed. All of the vials were heated to 100° C. and one vial was removed from the heater and analyzed every hour. The resulting compositions were determined by GC (as described in Example 46) and are reported in Table 45.

TABLE 45

| Composition analysis of cuts collected | | | |
|---|---|---|---|
| Time (h) | wt % i-BuOH | wt % FABE | wt % COFA |
| 0 | 0.11 | 5.74 | 0 |
| 1 | 1.1 | 1.72 | 1.23 |
| 2 | 1.32 | 0.96 | 1.77 |
| 3 | 1.35 | 0.76 | 1.8 |

TABLE 45-continued

| Composition analysis of cuts collected | | | |
|---|---|---|---|
| Time (h) | wt % i-BuOH | wt % FABE | wt % COFA |
| 4 | 1.38 | 0.7 | 1.81 |
| 5 | 1.37 | 0.72 | 1.82 |
| 15 | 1.37 | 0.84 | 2.12 |

Example 51

Hydrolysis of FABE by Reactive Distillation

A 12 liter flask was equipped with an insulated 2"×30" column topped with a feed inlet and a still head. The column was randomly packed with one liter of Pro-pak® (316 SS 0.16") still packing and 500 g of Amberlyst® 36 solid acid catalyst (Dow). The flask was charged with 6 liters of water and brought to a boil. The heat was controlled to have a water distillation rate of about 1.8 mL/min. FABE synthesized as per the method described in Example 45 was added to the top of the column at a rate of 2 g/min. The feed was continued for a total of 60 minutes. The distillation was continued for another 30 minutes. A total of 194 g of distillate was collected which contained 2.1 g of isobutanol. Based on the amount of FABE fed this represents a 9% conversion of FABE to butanol.

Example 52

Hydrolysis of FABE by Counter Current Steam

The apparatus as described in example 50 was modified by the addition of heat tape wrapped around the still column. The temperature in the upper half of the column was adjusted to 115° C. and the temperature in the lower half of the column was adjusted to 104° C. The pot was brought to a boil and the pot heat was adjusted until water was distilling at a rate of 1.5-2 mL/min. FABE (346 g) synthesized as per the method described in Example 45 was fed to the top of the packed column over a period of three hours while the distillation continued. After the feed period the distillation was continued for another 90 minutes. A total of 486 g of distillate was collected that contained 30.1 g of isobutanol. This represents a conversion of FABE to isobutanol of 39%.

Example 53

Hydrolysis Catalyzed by a Water Insoluble Organic Acid

A one liter 3n round bottom flask equipped with an oil bath, mechanical stirrer, nitrogen inlet, subsurface water inlet, and a still head was charged with 150 g of FABE, 50 g water, and 5 g dodecylbenzene sulfonic acid. An oil bath was heated to 95-100° C. and a slow nitrogen sweep started. Distillate cuts were collected every half hour for a total of five hours. After three hours, water was fed to the still pot at a rate of 15 mL/hr. Distillate cuts were analyzed for isobutanol content by the GC method described in Example 46 and the results are shown in Table 46. Approximately 44% of the isobutanol contained in the FABE was collected over five hours.

TABLE 46

| Sample | Cumulative i-BuOH collected (g) |
|---|---|
| 1 | 0.80 |
| 2 | 1.47 |
| 3 | 2.46 |
| 4 | 3.99 |
| 5 | 5.71 |
| 6 | 7.75 |
| 7 | 9.16 |
| 8 | 10.33 |
| 9 | 13.76 |
| 10 | 14.37 |

Example 54

Hydrolysis Catalyzed by Solid Acid Catalyst

A one liter 3n round bottom flask equipped with an oil bath, mechanical stirrer, subsurface nitrogen inlet, subsurface water inlet, and a still head was charged with 150 g of FABE and 50 g of dry Amberlyst 15 solid acid catalyst. The flask was heated to 110° C. with the oil bath and water was added via a syringe pump at a rate of 15 mL/hr. Distillation fractions were collected every half hour for a total of five hours. The fractions were analyzed for isobutanol content by the GC method described in Example 46 and the results are shown in Table 47. Approximately 44% of the theoretical amount of isobutanol contained in the FABE was collected over five hours.

TABLE 47

| Sample | Cumulative i-BuOH collected (g) |
|---|---|
| 1 | 0.3 |
| 2 | 0.9 |
| 3 | 2.3 |
| 4 | 3.4 |
| 5 | 4.4 |
| 6 | 5.5 |
| 7 | 6.3 |
| 8 | 6.9 |
| 9 | 7.4 |
| 10 | 8.0 |

Example 55

Hydrolysis Catalyzed by Water Soluble Organic Acid Catalyst

A one liter flask with mechanical stirrer, subsurface nitrogen inlet, subsurface water inlet, and a still head was charged with 200 g of FABE and 10 g of p-toluenesulfonic acid. The flask was stirred and heated to 110° C. with an oil bath at which time water was added at a rate of 20 mL/hr via a syringe pump. Still fractions were collected every half hour for a total of three hours. The fractions were analyzed for isobutanol content by the GC method described in Example 46 and the results are shown in Table 48. Approximately 30% of the theorectical amount of isobutanol contained in the FABE was collected over five hours.

TABLE 48

| Fraction | Cumulative amount of isobutanol |
|---|---|
| 1 | 1.0 |
| 2 | 4.0 |

TABLE 48-continued

| Fraction | Cumulative amount of isobutanol |
|---|---|
| 3 | 7.2 |
| 4 | 9.5 |
| 5 | 11.8 |
| 6 | 13.4 |

Example 56

Hydrolysis of Solvent Phases from Fermentation

A. Solvent Phase 1

The solvent phase from the fermentation shown in Example 17 was analyzed by the GC method shown in Example 46 and the results are shown in Table 49. The analysis shows primarily FABE and fatty acids with a small amount of material with a retention time consistent with FAEE. Analysis of just the butyl esters and acids shows a ratio of 62% FABE and 39% fatty acids.

The solvent phase (1.25 liters, 1090 g) and 1.25 liters of water were charged to a one gallon autoclave. The autoclave was sealed and heated to 250° C. and held at temperature for four hours. The autoclave was then cooled and opened, giving an emulsion. The mixture was filtered through a bed of Celite and the layers were separated. The organic layer was washed three times with one liter of water. The sample was then heated to 50° C. and purged with nitrogen for six hours. GC analysis shows no i-BuOH and a ratio of 33% FABE and 67% fatty acids. An amber oil (993.9 g) was obtained. A detailed compositional analysis of the original solvent phase from fermentation Example 17 and the post-hydrolysis solvent phase is shown in Table 50.

B. Solvent Phase 2

The solvent phase from the fermentation shown in Example 18 was analyzed by the GC method shown in Example 46 and the results are shown in Table 49. The analysis shows primarily FABE and fatty acids with a small amount of material with a retention time consistent with FAEE. Analysis of just the butyl esters and acids shows a ratio of 45% FABE and 55% fatty acids.

The solvent (1.25 liters, 1100 g) and 1.25 liters of water charged to a one gallon autoclave. The autoclave was sealed and heated to 250° C. and held at temperature for four hours. The autoclave was then cooled and opened, giving an emulsion. The mixture was filtered through a bed of Celite and the layers were separated. The organic layer was washed three times with one liter of water. The sample was then heated to 50° C. and purged with nitrogen for six hours. GC analysis shows no i-BuOH and a ratio of 28% FABE and 72% fatty acids. An amber oil (720.5 g) was obtained.

TABLE 49

| | Pre-hydrolysis | | Post-hydrolysis | |
|---|---|---|---|---|
| Sample | FABE (%) | Fatty Acid (%) | FABE (%) | Fatty Acid (%) |
| Solvent Phase 1 | 62 | 39 | 33 | 67 |
| Solvent Phase 2 | 45 | 55 | 28 | 72 |

TABLE 50

| | Solvent Phase 1 (wt %) | Post Hydrolysis Composition (wt %) |
|---|---|---|
| Isobutyl palmitate | 7.28 | 4.24 |
| Isobutyl stearate | 3.41 | 2.25 |
| Isobutyl oleate | 13.92 | 7.69 |
| Isobutyl linoleate | 33.09 | 17.73 |
| Isobutyl linolenate | 2.78 | |
| Palmitic acid | 3.79 | 7.3 |
| Stearic acid | 2.58 | 4.07 |
| Oleic acid | 9.14 | 16.61 |
| Linoleic acid | 19.06 | 33.54 |
| Linolenic acid | 2.3 | 2.65 |

Example 57

Recovery of Product Alcohol—Hydrolysis Using a Lipase Catalyst

FABE was synthesized from corn oil fatty acid as per the method described in Example 44. Novozyme 435 (Novo 435, *Candida antarctica* lipase B, immobilized on an acrylic resin) was purchased from Sigma Aldrich (St. Louis, Mo.). *Candida antarctica* Lipase B was purchased from Novozymes (Franklinton, N.C.). t-BuOH, acetone, ethanol, methanol, and glycerol were all purchased from Sigma Aldrich (St. Louis, Mo.). For gas chromatography (GC) analysis, the gas chromatograph used was Hewlett Packard 5890 Series II GC chromatogram and methyl pentadecanoate was used as an internal standard.

A. Atmospheric Pressure, 40° C.

To a mixture of 2 mL FABE and 5 mL water was added 40 mg Novozyme 435, and the reaction mixture was placed in a 20 mL vial and incubated at 40° C. in a rotary shaker (300 rpm). The reaction mixture was analyzed using GC during 24 h of the reaction, to generate the following % conversion profile given in Table 51:

TABLE 51

| % Conversion Profile for Example 57A | |
|---|---|
| Reaction time (h) | % FABE conversion |
| 0 | 0 |
| 1 | 6.7 |
| 1.5 | 10.5 |
| 2 | 15.1 |
| 4 | 17.0 |
| 6 | 17.4 |
| 8 | 17.7 |
| 24 | 18.2 |

B. Atmospheric Pressure, 40° C., 65° C. and 80° C., No Organic Solvent

Together with part A of this example, these data show how equilibrium changes with temperature To a mixture of 1 mL FABE and 2 mL water was added 20 mg Novozyme 435 and the reaction mixture was rotated at 40° C. for 45 h in a 6 mL septum-capped vial. The reaction mixture was analyzed using GC to reveal 18.2% conversion of FABE at equilibrium.

To a mixture of 1 g FABE and 2 mL water was added 20 mg Novozyme 435, and the reaction mixture was rotated at 65° C. for 42 h in a 6 mL septum-capped vial. The reaction mixture was analyzed using GC to reveal 19.8% conversion of FABE at equilibrium.

To a mixture of 1 g FABE and 2 mL water was added 20 mg Novozyme 435, and the reaction mixture was rotated at 80° C. for 42 h in a 6 mL septum-capped vial. The reaction mixture was analyzed using GC to reveal 21.4% conversion of FABE at equilibrium.

C. Example Showing the Effect of Organic Solvent (t-BuOH) on the Equilibrium

To three reaction mixtures containing 0.25 mL FABE, 0.75 mL t-BuOH, and 0.1-0.3 mL water was added 20 mg Novozyme 435, and the mixtures, in 6 mL septum-capped vials, were left rotating at 40° C. overnight, at which point they had reached equilibrium. The reaction mixtures were analyzed using GC after 24 h of the reaction, to generate 77-82% FABE conversions given in Table 52. Replacing t-BuOH with 3-Me-3-pentanol under similar reaction conditions gave FABE hydrolysis yields of 70-80%.

TABLE 52

% Conversion Profile for Example 57C

| Reaction mixture | Novozyme 435 loading | % FABE conversion |
|---|---|---|
| 0.75 mL t-BuOH, 0.25 mL FABE, 0.1 g $H_2O$ | 20 mg | 77% |
| 0.75 mL t-BuOH, 0.25 mL FABE, 0.2 g$H_2O$ | 20 mg | 81% |
| 0.75 mL t-BuOH, 0.25 mL FABE, 0.3 g $H_2O$ | 20 mg | 82% |

D. Acetone as Solvent

To three reaction mixtures containing 0.25 mL FABE, 0.75 mL acetone, and 0.1-0.3 mL water was added 20 mg Novozyme 435, and the mixtures, in 6 mL septum-capped vials, were left rotating at 40° C. overnight, at which point they had reached equilibrium. The reaction mixtures were analyzed using GC after 24 h of the reaction, to show 71-78% FABE conversions given in Table 53.

TABLE 53

% Conversion Profile for Example 57D

| Reaction mixture | Novozyme 435 loading | % FABE conversion |
|---|---|---|
| 0.75 mL acetone, 0.25 mL FABE, 0.1 g $H_2O$ | 20 mg | 71% |
| 0.75 mL acetone, 0.25 mL FABE, 0.2 g $H_2O$ | 20 mg | 74% |
| 0.75 mL acetone, 0.25 mL FABE, 0.3 g $H_2O$ | 20 mg | 78% |

E. Example Showing the Effect of Removing i-BuOH During Hydrolysis on FABE Conversion—Nitrogen Purge at Atmospheric Pressure A 25 mL round bottom flask was charged with 2 mL FABE, 5 mL water, and 40 mg Novozyme 435. The reaction mixture was heated to 95° C., and the i-BuOH that was forming in the reaction was removed by bubbling nitrogen through the reaction mixture. Samples were taken from the mixture during the reaction, and the organic phase was analyzed using GC. Conversion of 94% was achieved after 6 h as shown in Table 54:

TABLE 54

FABE Conversion Profile for Example 57E

| Reaction time (h) | Mole % COFA in COFA + FABE |
|---|---|
| 0 | 1 |
| 1 | 62 |
| 2 | 76 |
| 3 | 86 |
| 4 | 90 |
| 6 | 94 |

F. Example Showing the Effect of Removing i-BuOH During Hydrolysis on the Conversion-Vacuum Distillation A 25 mL round bottom flask was charged with 3 mL FABE, 7.5 mL of water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 91% was achieved after 10 h as shown in Table 55.

TABLE 55

% Conversion Profile for Example 57F

| Reaction time (h) | % FABE conversion |
|---|---|
| 0 | 0 |
| 1 | 16 |
| 2 | 37 |
| 3 | 57 |
| 5 | 72 |
| 7 | 83 |
| 10 | 91 |

G. Example Showing the Effect of Removing i-BuOH During Hydrolysis on the Conversion-Vacuum Distillation Example-Varying FABE/COFA Starting Ratio: 23% FABE:77% COFA v/v A 25 mL round bottom flask was charged with 0.69 mL FABE, 2.31 mL COFA, 7.5 mL water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 98% was achieved after 10 h as shown in Table 56.

TABLE 56

FABE Conversion Profile for Example 57G

| Reaction time (h) | Mole % COFA in COFA + FABE |
|---|---|
| 0 | 77 |
| 1 | 83 |
| 2 | 86 |
| 3 | 90 |
| 4 | 92 |
| 6 | 93 |
| 7 | 96 |
| 10 | 98 |

H. Example Showing the Effect of Removing i-BuOH During Hydrolysis on the Conversion-Vacuum Distillation Example-Varying FABE/COFA Starting Ratio: 70% FABE:30% COFA v/v A 25 mL round bottom flask was charged with 2.1 mL FABE, 0.9 mL COFA, 7.5 mL water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 96% was achieved after 10 h as shown in Table 57:

TABLE 57

FABE Conversion Profile for Example 57H

| Reaction time (h) | Mole % COFA in COFA + FABE |
|---|---|
| 0 | 30 |
| 1 | 52 |
| 2 | 64 |
| 5 | 84 |
| 7 | 89 |
| 10 | 96 |

I. Example Showing the Free Cal B Enzyme in FABE Hydrolysis Under Vacuum Distillation Conditions Two round bottom flasks were charged with 3 mL (2.7 g) FABE and 7.5 mL $H_2O$ each. To one mixture was added 5.9 mg *Candida antarctica* Lipase B, and to the other was added 0.59 mg enzyme. The reaction flasks were separately connected to the distillation apparatus and exposed to pressure of 91 mm Hg. The reaction mixtures were heated to 65-68° C. Samples were taken from the reaction mixtures over a ten-hour period, and analyzed using gas chromatography. The final FABE conversions were 96 and 78%, respectively. The experiments show that reducing the amount of enzyme concentration by a factor of ten reduces the rate and conversion by 3× and 18%, respectively. The results are shown in Table 58.

TABLE 58

FABE Conversion Profile for Example 57I

| Reaction time (h) | Mole % COFA in COFA + FABE with 5.9 mg CALB/2.7 g FABE | Mole % COFA in COFA + FABE with 0.59 mg CALB/2.7 g FABE |
|---|---|---|
| 0 | 0 | 0 |
| 1 | 44 | 21 |
| 2 | 62 | 31 |
| 6 | 89 | 61 |
| 10 | 96 | 78 |

Example 58

Recovery of Product Alcohol—Transesterification

FABE was synthesized from corn oil fatty acid as per the method described in Example 44; Novozyme 435 (*Candida antarctica* lipase B, immobilized on an acrylic resin) was purchased from Sigma Aldrich (St. Louis, Mo.). *Candida antarctica* Lipase B was purchased from Novozymes (Franklinton, N.C.). t-BuOH, acetone, ethanol, methanol, and glycerol were all purchased from Sigma Aldrich (St. Louis, Mo.). For GC analysis, the gas chromatograph used was Hewlett Packard 5890 Series II GC chromatogram and methyl pentadecanoate was used as an internal standard.

A. Testing Lipases—FABE to FAME

Reagents used were t-BuOH (Aldrich); MeOH (Aldrich); Novozyme 435 (Aldrich); PS30 (*Burkholderia cepacia*, Amano Enzymes, Inc, Elgin, Ill.); Lipolase® 100T (*Thermomyces lanuginosa*, immobilized on silica, Novozymes, Franklinton, N.C.); Lipolase® 100L (*Thermomyces lanuginosa*, Novozymes, Franklinton, N.C.); Lipozyme® TLIM (immobilized *Thermomyces lanuginosa*, Novozymes, Franklinton, N.C.); Lipoclean® 2000T (immobilized mixture of lipases; Novozymes, Franklinton, N.C.); NZL-103-LYO (Lipase from *Rhizomucor miehi*, Novozymes, Franklinton, N.C.

To a 6 mL vial was added 500 mg FABE (1.48 mmol), 400 μL t-BuOH, 60 μL MeOH (1.48 mmol), 3 μL water, and 2.5 mg lipase (see Table 57). The resulting mixture was placed in an incubator/shaker, and left at 40° C. overnight. GC analysis of the reaction mixture revealed the conversions from 9-56%. Results are shown in Table 59.

TABLE 59

Equilibrium concentrations [mg/mL] and % conversion of FABE→FAME using different lipases

| Lipase | FABE (mg/mL) | COFA (mg/mL) | i-BuOH (mg/mL) | % conversion |
|---|---|---|---|---|
| PS30 | 471 | 2.48 | 11.2 | 9.73% |
| NOVOZYME 435 | 224 | 16.8 | 63.7 | 56.30% |
| LTLIM | 266 | 15.9 | 67.7 | 53.50% |
| L100T | 455 | 1.8 | 8.9 | 8.80% |
| 2000T | 452 | 1.8 | 9.1 | 8.31% |
| NZL-103-LYO | 429 | 3.94 | 15.3 | 13.90% |

B. FABE to FAME Transformation—Optimizing the Amount of Methanol

To a 6 mL vial was added 500 mg FABE (1.48 mmol), 400 μL t-BuOH, 60-240 μL MeOH (1.48-5.92 mmol), 3 μL water, and 2.5 mg Novozyme 435. The resulting mixture was placed in an incubator/shaker, and left at 40° C. overnight. GC analysis of the reaction mixture revealed the conversions from 53-73% as shown in Table 60.

TABLE 60

% Conversion Profile for Example 58B

| MeOH eq's | FABE (mg/mL) | COFA (mg/mL) | i-BuOH (mg/mL) | % conversion |
|---|---|---|---|---|
| 1.2 | 232 | 2.4 | 66.9 | 56.64 |
| 1.4 | 168 | 2.4 | 70.4 | 65.50 |
| 1.6 | 167 | 0 | 72.1 | 66.17 |
| 1.8 | 184 | 0 | 80.3 | 66.41 |
| 2.0 | 131 | 0 | 72.4 | 71.46 |
| 2.2 | 134 | 1.2 | 81 | 73.25 |
| 2.4 | 136 | 0 | 80 | 72.71 |
| 2.6 | 161 | 0 | 78 | 68.70 |
| 2.8 | 168 | 0 | 73 | 66.31 |
| 3.0 | 155 | 0 | 74 | 68.38 |
| 3.2 | 180 | 0 | 73 | 64.75 |
| 3.4 | 161 | 0 | 78 | 68.70 |
| 3.6 | 192 | 0 | 66 | 60.89 |
| 3.8 | 236 | 0 | 63 | 54.74 |
| 4.0 | 243 | 0 | 61 | 53.21 |

C. Optimizing the Amount of Enzyme—FABE to FAME

To a 6 mL vial was added 500 mg FABE (1.48 mmol), 400 μL t-BuOH, 132 μL MeOH (3.26 mmol), and 5-25 mg Novozyme 435. The resulting mixture was placed in an incubator/shaker, and left at 40° C. overnight. GC analysis of the reaction mixture revealed the conversions from 76-79% as shown in Table 61.

TABLE 61

| % Conversion Profile for Example 58C | | | | |
|---|---|---|---|---|
| Novozyme 435 (mg) | FABE (mg/mL) | COFA (mg/mL) | i-BuOH (mg/mL) | % conversion |
| 5 mg | 129.4 | 0 | 88 | 75.49 |
| 7.5 mg | 119.3 | 0 | 89.2 | 77.21 |
| 10 mg | 110.9 | 0 | 89 | 78.43 |
| 12.5 mg | 109.2 | 0 | 84.9 | 77.89 |
| 15 mg | 112.4 | 0 | 86.1 | 77.63 |
| 17.5 mg | 108.4 | 0 | 87.4 | 78.51 |
| 20 mg | 115.6 | 0 | 91.8 | 78.25 |
| 22.5 mg | 108.6 | 0 | 87.7 | 78.53 |
| 25 mg | 111.6 | 0 | 89 | 78.32 |

D. Minimizing the Amount of Solvent (t-BuOH)—FABE to FAME

To a 6 mL vial was added 500 mg FABE (1.48 mmol), 0-300 μL t-BuOH, 132 μL MeOH (3.26 mmol), and 10 mg Novozyme 435. The resulting mixture was placed in an incubator/shaker, and left at 40° C. overnight. GC analysis of the reaction mixture revealed the conversions from 30-81% as shown in Table 62.

TABLE 62

| % Conversion Profile for Example 58D | | | | | |
|---|---|---|---|---|---|
| Amount | FABE (mg/mL) | COFA (mg/mL) | i-BuOH (mg/mL) | % conversion | FAME (mg/mL) |
| 300 μL t-BuOH | 94.3 | 0 | 83 | 79.95 | 295 |
| 200 μL t-BuOH | 94.1 | 0 | 83.2 | 80.02 | 295 |
| 100 μL t-BuOH | 91.7 | 0 | 84.2 | 80.62 | 300 |
| 50 μL t-BuOH | 92.9 | 0 | 81 | 79.80 | 290.8 |
| <50 μL t-BuOH | 137 | 0 | 70.5 | 69.98 | 249.4 |
| no t-BuOH | 322.7 | 1.39 | 30.2 | 29.77 | 98.1 |

E. Minimization of the Amount of Solvent (3-Me-3-Pentanol)—FABE to FAME

To a 6 mL vial was added 500 mg FABE (1.48 mmol), 0-300 μL 3-Me-3-pentanol, 132 μL MeOH (3.26 mmol), and 10 mg Novozyme 435. The resulting mixture was placed in an incubator/shaker, and left at 40° C. overnight. GC analysis of the reaction mixture revealed the conversions from 30-78% as shown in Table 63.

TABLE 63

| % Conversion Profile for Example 58E | | | | | |
|---|---|---|---|---|---|
| Amount | FABE (mg/mL) | COFA (mg/mL) | i-BuOH (mg/mL) | % Conversion | FAME (mg/mL) |
| 0.3 mL 3M3P | 115.6 | 3.75 | 81.4 | 76.13 | 296 |
| 0.2 mL 3M3P | 106.3 | 3.13 | 80 | 77.32 | 294 |
| 0.1 mL 3M3P | 104.8 | 2.36 | 80.8 | 77.74 | 296 |
| 0.05 mL 3M3P | 102.9 | 2.3 | 79.6 | 77.80 | 295 |
| soak 3M3P | 102.5 | 2.4 | 79.9 | 77.93 | 296 |
| no 3M3P | 322.7 | 1.39 | 30.2 | 29.77 | 98.1 |

F. Conversion of FABE to FAME without Solvent

To a mixture of FABE (500 mg, 1.48 mmol) and methanol (0.13 μL, 3.25 mmol) was added 40 mg Novozyme 435, and the reaction mixture was stirred at 40° C. overnight. The mixture was then filtered and analyzed by GC to reveal 76% conversion.

G. Enzyme Recycle—FABE to FAME

To a 6 mL vial was added 500 mg FABE (1.48 mmol), 400 μL t-BuOH, 132 μL MeOH (3.26 mmol), and 10 mg Novozyme 435. The resulting mixture was placed in an incubator/shaker, and left at 40° C. overnight. After that time, the reaction mixture was filtered and analyzed for conversion using GC, and the filter cake containing the immobilized enzyme, was used for another conversion of FABE to FAME. The process was repeated ten times (Table 64). The experiment shows that it is possible to recycle the enzyme up to ten times without the loss in conversion in the overnight reaction.

TABLE 64

| % Conversion Profile for Enzyme Recycle in Example 58G Concentrations are in mg/mL | | | | | |
|---|---|---|---|---|---|
| FABE to FAME | FABE | COFA | i-BuOH | % Conversion | FAME |
| 1st | 115.8 | 5.29 | 82.1 | 76.26 | 298.1 |
| 2nd | 124 | 5.36 | 82.7 | 75.13 | 293.2 |
| 3rd | 112 | 4.82 | 85 | 77.47 | 303.1 |
| 4th | 111 | 9.06 | 85.1 | 77.64 | 306.3 |
| 5th | 99.4 | 5.1 | 82.1 | 78.91 | 284.5 |
| 6th | 98.2 | 6 | 81.2 | 78.93 | 283.8 |
| 7th | 115.6 | 6.8 | 78.9 | 75.56 | 262.7 |
| 8th | 114.8 | 6.5 | 77.6 | 75.38 | 257.2 |
| 9th | 99 | 5.7 | 78 | 78.12 | 241 |
| 10th | 109 | 8.6 | 73.7 | 75.39 | 226.7 |

H. Conversion of FABE to FAEE

To 6 mL septum-capped vials were added 0.8 mL FABE (2.08 mmol) and 0.2 mL EtOH (3.43 mmol), forming a single phase. No enzyme or 20 mg Novozyme 435 was added to the vials. The vials were then incubated at 25° C. and 40° C. in an incubator shaker (300 rpm) for 17 h after which the solution was analyzed by gas chromatography, giving the contents and percent conversion of FABE to FAEE shown in Table 65.

TABLE 65

| Sample | FABE (mg/mL) | i-BuOH (mg/mL) | COFA (mg/mL) | % Conversion |
|---|---|---|---|---|
| EtOH/FABE + enzyme, 25° C. | 93.2 | 38.5 | 0 | 41.6 |
| EtOH/FABE, no enzyme, 25° C. | 159.6 | 3.5 | 0.75 | 0 |
| EtOH/FABE + enzyme, 40° C. | 90 | 35.7 | 0 | 43.3 |
| EtOH/FABE, no enzyme, 40° C. | 158.7 | 3.1 | 0.75 | 0 |

Example 59

Glycerolysis of FABE

To a septum-capped 6 mL vial was added 0.75 mL t-BuOH, 0.25 mL FABE, 0.1 mL (0.126 g) glycerol+4 μL $H_2O$, enzyme 20 mg each, forming a single phase. The reactions were incubated with various lipases at 40° C. on a rotary shaker at 300 rpm. After 20 h, the samples were analyzed by gas chromatography, giving the contents shown in Table 66. A comparison of the COFA and FABE contents indicates that the products are i-BuOH and a mixture of COFA and acyl glycerol (~64% acyl glycerol/36% COFA on molar basis).

TABLE 66

| Percent conversion of FABE to a mixture of COFA and acyl glycerol | | | | |
|---|---|---|---|---|
| Lipase | FABE (mg/mL) | COFA (mg/mL) | i-BuOH (mg/mL) | Percent conversion of FABE |
| Amano PS-30 powder | 73 | 43 | 32 | 64% |
| IM-20, powder | 162.4 | 10.2 | 10.9 | 19% |
| Lipolase ® 100T immobilized | 190 | 0 | 4 | ~0% |
| Novozyme 435 immobilized | 73 | 39.5 | 30.8 | 64% |
| Lipozyme ® TL IM immobilized | 101.7 | 29 | 26.1 | 49% |
| Lipoclean ® 2000T immobilized | 200.9 | 0 | 3.9 | ~0% |

A. Dependence on Water and Glycerol/FABE

To 6 mL septum capped vials were added 0.75 mL t-BuOH, 0.25 mL FABE, 0.1 or 0.2 g glycerol+20 mg each of either Amano PS-30 or Novozyme 435, forming a single phase. No water was added. The reactions were incubated at 40° C. on a rotary shaker at 300 rpm. After 20 h, the samples were analyzed by gas chromatography, giving the contents shown in Table 67. A comparison of the COFA and FABE contents indicates that the products are i-BuOH and primarily acyl glycerol (mostly monoglyceride). Relative to the previous example, the percent of product in the form of acyl glycerol increases with the absence of added water and with the increase in glycerol/FABE (~91% acyl glycerol/9% COFA on molar basis with 1.6 glycerol/FABE, mole/mole and ~95% acyl glycerol/5% COFA on molar basis with 3.2 glycerol/FABE, mole/mole). The absence of added water eliminates the enzyme activity of Amano PS-30. The Novozyme 435 which has water in the acrylic resin (~3% w/w) to which it is immobilized is, however, still active.

TABLE 67

| Percent conversion of FABE to acyl glyceride | | | | | |
|---|---|---|---|---|---|
| Lipase | Glycerol | FABE (mg/mL) | COFA (mg/mL) | i-BuOH (mg/mL) | Percent conversion of FABE |
| Amano PS-30 powder | 0.1 g | 209 | 1.2 | 4.4 | ~0% |
| Novozyme 435, immobilized | 0.1 g | 84.2 | 10.7 | 28.6 | 58% |
| Amano PS-30 powder | 0.2 g | 182 | 0.74 | 3.8 | ~0% |
| Novozyme 435 immobilized | 0.2 g | 61.5 | 7.1 | 30.6 | ~69% |

B. Dependence on Enzyme Concentration

To 6 mL septum capped vials was added 0.75 mL t-BuOH, 0.25 mL FABE, 0.2 g glycerol (glycerol/FABE 3.2/1, mole/mole)+2 or 20 mg of Novozyme 435 (Novo 435). No water was added. The reactions were incubated at 40° C. on a rotary shaker at 300 rpm and the reaction was followed as a function of time by gas chromatography. The yields are indicated in Table 68. Approximately 97% of the FABE that reacted was converted to acyl glycerol (mostly monoglyceride) on a mole basis.

TABLE 68

| Time (h) | % FABE conversion 2 mg Novo 435 | % FABE conversion 20 mg Novo 435 |
|---|---|---|
| 0 | 0 | 0 |
| 0.167 | | 13.2 |
| 0.333 | | 38 |
| 0.5 | 3.37 | 42.9 |
| 1 | 10.8 | 59.1 |
| 2 | 21.9 | 65.5 |
| 4 | 31.6 | 67.1 |
| 6.5 | 32.1 | |
| 7 | 45.7 | 67.1 |
| 24 | 64 | 67.3 |

The rate of the reaction is linear with enzyme concentration, with $t_{1/2}$ for 2 and 20 mg of Novozyme 435 of 208 and 20 minutes, respectively. The reaction, however, reaches nearly the same yield of FABE conversion after 24 h.

These last reactions were repeated with 0.75 mL of 3-methyl-3-pentanol replacing 0.75 mL of t-BuOH. The extent of FABE hydrolysis obtained after 24 h was the same for both solvents. The advantage of 3-methyl-3-pentanol is that with a boiling point of 122° C., the i-BuOH can be distilled off first in pure form (b.p. 108° C.). The 3-methyl-3-pentanol can then be distilled off and recycled for the hydrolysis reaction, leaving in the retentate acyl glycerol, COFA, and glycerol to be recycled to the fermentation tank for reuse in the generation of FABE. Tertiary alcohols act as a solvent alone and have the advantage of not reacting with the fatty acid to form fatty acid alkyl esters in the presence of CALB.

C. Glycerolysis of FABE (FABE to COFA+Acyl Glycerol) in the Absence of Organic Cosolvent—Dependence on Glycerol Concentration One gram (1 g) of FABE was mixed with 2 mL of 50, 70, 90, and 100% (w/w) glycerol and placed in a 6 mL septum-sealed vial in the presence of 20 mg Lipobond (Sprin Technologies, Trieste, Italy). The vial was tumbled end-over-end for 24 h at 62° C. With increasing glycerol concentration in the aqueous phase, the percent of the product in the form of acyl glycerol increases (Table 69, mostly monoglyceride). The extent of FABE conversion, however, does not show a dependence on the glycerol concentration.

TABLE 69

| Condition (% glycerol in aqueous phase) | % of FABE conversion | % of COFA in product (mole basis) | % of acyl glycerol in product (mole basis) |
|---|---|---|---|
| 50 | 18 | 100 | 0 |
| 70 | 17 | 84 | 16 |
| 90 | 17 | 34 | 66 |
| 100 | 17 | 3 | 97 |

Example 60

Conversion of COFA to FAEE and Monoacyl Glycerol

The following examples show that COFA can be esterified with EtOH or with glycerol at high yield under mild conditions using immobilized enzyme.

Novozyme 435 (*Candida antarctica* lipase B, immobilized on an acrylic resin) was purchased from Sigma Aldrich (St. Louis, Mo.). Acetone, t-BuOH, ethanol, methanol, and glycerol were all purchased from Sigma Aldrich (St. Louis, Mo). For GC analysis, the gas chromatograph used was Hewlett Packard 5890 Series II GC chromatogram and methyl pentadecanoate was used as an internal standard.

A. Conversion of COFA to FAEE+i-BuOH Using Ethanol

Corn oil fatty acid (COFA, 0.25 g) was dissolved in 2.0 mL EtOH forming a single phase. Twenty mg of *Candida antarctica* lipase B (CALB) immobilized on acrylic resin (Novozyme 435) was added (contains 1.7 mg of enzyme) and the suspension was incubated for 24 h on a rotary shaker (300 rpm) at 40° C. in a 6 mL glass vial sealed with a septum cap. The reaction went practically to completion with 98% of the COFA converted to FAEE (fatty acid ethyl ester). The GC analysis after 24 h showed 98% conversion of COFA to fatty acid ethyl ester as shown in Table 70.

TABLE 70

% Conversion Profile for Example 60A

| Reaction mix bp of EtOH = 78.1° C. | Novozyme 435 loading | % Conversion of COFA to FAEE | Phases |
|---|---|---|---|
| 2.0 mL EtOH + 0.25 g COFA Moles EtOH/moles COFA = 38.7 | 20 mg (contains 1.7 mg CALB) | 98 | 1 throughout |

B. Conversion of COFA to Monoacylglycerides (Mag)+i-BuOH Using Glycerol

Corn oil fatty acid (COFA, 0.25 g) plus 0.325 g of glycerol were dissolved in 2.0 mL acetone. There was a large upper phase in which most of the components were dissolved and a small residual glycerol-containing phase. Twenty mg of *Candida antarctica* lipase B (CALB) immobilized on acrylic resin (Novozyme 435) was added (contains 1.7 mg of enzyme) and the suspension was incubated for 24 h on a rotary shaker (300 rpm) at 40° C. in a 6 mL glass vial sealed with a septum cap. GC of the upper phase indicated that 87% of the COFA had been converted to acyl glyceride (expected to be mostly monoacylglyceride). Results are shown in Table 71.

TABLE 71

% Conversion Profile for Example 60B

| Reaction mix bp of acetone = 56° C. | Novozyme 435 loading | % Conversion of COFA to acyl glyceride (mostly MAG) | Phases |
|---|---|---|---|
| 2.0 mL acetone + 0.25 g COFA + 0.325 g glycerol Moles glycerol/moles COFA = 4 | 20 mg (contains 1.7 mg CALB) | 87 | Minor glycerol phase throughout at 40° C. |

Example 61

Conversion of COFA to FAME

The following examples show that COFA can be esterified with MeOH, with EtOH, and with glycerol at high yield under mild conditions using immobilized lipase.

A. Conversion of COFA to FAME without Solvent

To a 6 mL vial was added 500 mg COFA (1.48 mmol), 132 μL of MeOH (3.26 mmol), and 10 mg Novozyme 435. The resulting mixture was placed in an incubator/shaker, and left at 40° C. overnight. GC analysis of the reaction mixture revealed 95% conversion.

B. Time Course Measurement of COFA to FAME Reaction

To a 6 mL vial was added 500 mg COFA (1.48 mmol), 132 μL of MeOH (3.26 mmol), and 10 mg Novozyme 435. The samples were incubated at 40° C. in an incubator/shaker and time points were taken during the reaction, and analyzed using GC. Results are shown in Table 72.

TABLE 72

| Time | COFA [mg/mL] | FAME [mg/mL] | Conversion [%] |
|---|---|---|---|
| 0 min | 377 | 0 | 0% |
| 10 min | 242.2 | 135 | 35% |
| 20 min | 173.6 | 231.8 | 56% |
| 30 min | 122.8 | 274.3 | 68% |
| 1 hr | 59.2 | 373.2 | 86% |
| 2 hr | 18.2 | 389.9 | 95% |
| 3 hr | 16.8 | 406.2 | 96% |
| 4 hr | 15.6 | 404.4 | 96% |
| 7 hr | 16 | 411.2 | 96% |

C. Adding More MeOH to the COFA→FAME Reaction

To a 6 mL vial was added 500 mg COFA (1.48 mmol), 180, 240, 300, or 1320 μL of MeOH (4.44, 5.92, 7.41, and 14.82 mmol), and 10 mg Novozyme 435. The resulting mixture was placed in an incubator/shaker, and left at 40° C. overnight. GC analysis of the reaction mixture revealed 96-97% conversion. The results are shown in Table 73.

TABLE 73

| MeOH [eq] | COFA [mg/mL] | FAME [mg/mL] | % Conversion |
|---|---|---|---|
| 3 | 13.26 | 377 | 96.44% |
| 4 | 13.15 | 398.9 | 96.65% |
| 5 | 12.12 | 391.8 | 96.85% |
| 10 | 12.65 | 399.5 | 96.78% |

Example 62

This example illustrated the removal of solids from stillage and extraction by desolventizer to recover fatty acids, esters, and triglycerides from the solids. During fermentation, solids are separated from whole stillage and fed to a desolventizer where they are contacted with 1.1 tons/hr of steam. The flow rates for the whole stillage wet cake (extractor feed), solvent, the extractor miscella, and extractor discharge solids are as shown in Table 74. Table values are short tons/hr.

TABLE 74

| | Solids from whole stillage | Solvent | Miscella | Extractor discharge solids |
|---|---|---|---|---|
| Fatty acids | 0.099 | 0 | 0.0982 | 0.001 |
| Undissolved solids | 17.857 | 0 | 0.0009 | 17.856 |
| Fatty acid butyl esters | 2.866 | 0 | 2.837 | 0.0287 |
| Hexane | 0 | 11.02 | 10.467 | 0.555 |
| Triglyceride | 0.992 | 0 | 0.982 | 0.0099 |
| Water | 29.762 | 0 | 29.464 | 0.297 |

Solids exiting the desolventizer are fed to a dryer. The vapor exiting the desolventizer contains 0.55 tons/hr of hexane and 1.102 tons/hr of water. This stream is condensed and fed to a decanter. The water-rich phase exiting the decanter contains about 360 ppm of hexane. This stream is fed to a distillation column where the hexane is removed from the water-rich stream. The hexane enriched stream exiting the top of the distillation column is condensed and fed to the decanter. The organic-rich stream exiting the decanter is fed to a distillation column. Steam (11.02 tons/hr) is fed to the bottom of the distillation column. The composition of the overhead and bottom products for this column are shown in Table 75. Table values are tons/hr.

TABLE 75

| | Bottoms | Overheads |
|---|---|---|
| Fatty acids | 0.0981 | 0 |
| Fatty acid butyl esters | 2.8232 | 0 |
| Hexane | 0.0011 | 11.12 |
| Triglyceride | 0.9812 | 0 |
| Water | 0 | 11.02 |

Example 63

Solids Extraction

Preparation of Hydrous Isobutanol

Into a 100 mL volumetric flask, 65 g of anhydrous reagent grade isobutanol (sourced from Aldrich) was combined with 10 g of distilled water and shaken until a clear colorless homogeneous phase resulted. Another 10 g of distilled water was added to the volumetric flask and shaken again resulting in two persistent clear colorless liquid layers. The top layer is considered to be hydrous isobutanol containing typically 20 wt % moisture and the bottom layer is predominantly water with typically 8 wt % dissolved alcohol.

Extraction Using Screen Filtration and Displacement Wash

A fermentation was completed using recycled fatty acid (Example 19). A 185 g portion representative of the resulting heterogeneous mixture was removed and passed through a 80 MESH screen dish supported and sealed within a Nalgene® plastic filter funnel over 5 minutes using slight vacuum (−20 in H2O) on the underside. The filtrate partitioned into 90.5 g of a reddish brown oil phase and 50.9 g of a hazy aqueous phase containing dispersed fines but no settling particulates. A wet cake remained on the screen dish. A sample of 1.5 g of this unwashed wet cake was removed and air dried. Hydrous isobutanol (23 g) was drawn from the top layer inside the volumetric flask and passed through the wet cake over 5 minutes while mild vacuum on the underside of the screen dish was maintained until no more liquid droplets were collected. The total filtrate mass of 18 g consisted of a small amount of an immiscible bottom hazy aqueous layer and a yellow clear hydrous isobutanol layer. The wet cake was removed from the screen dish and a total mass of 38.4 g was recovered. A sample of 1.5 g of this washed wet cake was removed and air dried. The dried sample of unwashed solids was analyzed and found to contain 53.35 wt % total fat on a triglyceride basis and the dried sample of washed solids was analyzed and found to contain 15.9 wt % total fat on a triglyceride basis.

Extraction Using Centrifugation and Reslurry Wash

A fermentation was completed using recycled fatty acid (Example 19). A 225 g portion representative of the resulting heterogeneous mixture was removed and centrifuged using a Beckman Coulter Allegra 64R machine at 10,000 rpm for 10 minutes. A clear reddish brown oil phase amounting to 67.2 g was decanted off. The remaining material was centrifuged again and 95.1 g of a cloudy aqueous centrate was decanted off. A 1.5 g sample of the wet solids was removed and air dried and 56.5 g were recovered and transferred to a 400 mL beaker. Hydrous isobutanol (20 g) drawn from the top layer inside the volumetric flask was added to the beaker to repulp the wet solids and stirring was carried out for 5 minutes. Another 32 g of hydrous isobutanol along with 32 g of the centrate were added and the solids were agitated in aqueous suspension beneath a quiescent organic layer for 5 minutes. The mixture was then centrifuged at 10,000 rpm for 10 minutes to decant off a clear yellow hydrous isobutanol layer and centrifuged again in order to isolate and dry a 1.5 g sample of washed wet solids. The dried sample of unwashed wet solids were analyzed and found to contain 21.6 wt % total fat on a triglyceride basis and the dried sample of washed wet solids were analyzed and found to contain 4.04 wt % total fat on a triglyceride basis.

Example 64

Removal of Corn Oil by Removing Undissolved Solids

Approximately 1000 g of liquefied corn mash was prepared in a 1 L glass, jacketed resin kettle. The kettle was set up with mechanical agitation, temperature control, and pH control. The following protocol was used: mixed ground corn with tap water (26 wt % corn on a dry basis), heated the slurry to 55° C. while agitating, adjusted pH to 5.8 with either NaOH or $H_2SO_4$, added alpha-amylase (0.02 wt % on a dry corn basis), continued heating to 85° C., adjusted pH to 5.8, held at 85° C. for 2 hrs while maintaining pH at 5.8, cool to 25° C. The corn used was whole kernel yellow corn from Pioneer (3335). It was ground in a hammer-mill using a 1 mm screen. The moisture content of the ground corn was measured to be about 11.7 wt %, and the starch content of the ground corn was measured to be about 71.4 wt % on a dry corn basis. The alpha-amylase enzyme was Liquozyme® SC DS from Novozymes (Franklinton, N.C.). The total amounts of the ingredients used were: 294.5 g of ground corn (11.7% moisture), 705.5 g of tap water, and 0.059 g of Liquozyme® SC DS. $H_2O$ (4.3 g) was added to dilute the enzyme, and a total of 2.3 g of 20% NaOH solution was added to control pH. About 952 g of mash was recovered. Note that there were losses due to mash sticking on walls of kettle and CF bottles.

The liquefied corn mash was centrifuged at 5000 rpm (7260 g's) for 30 minutes at 40° C. to remove the undissolved solids from the aqueous solution of oligosaccharides. Removing the solids by centrifugation also resulted in the removal of free corn oil as a separate organic liquid layer on top of the aqueous phase. Approximately 1.5 g of corn oil was recovered from the organic layer floating on top of the aqueous phase. It was determined by hexane extraction that the ground corn used to produce the liquefied mash contained about 3.5 wt % corn oil on a dry corn basis. This corresponds to about 9 g of corn oil fed to the liquefaction process with the ground corn.

Approximately 1 g of corn oil was recovered from the organic layer floating on top of the aqueous phase. About 617 g of liquefied starch solution was recovered leaving about 334 g of wet cake. The wet cake contained most of the undissolved solids that were in the liquefied mash. The liquefied starch solution contained about 0.2 wt % undissolved solids. The wet cake contained about 21 wt % undissolved solids. The wet cake was washed with 1000 g of tap water to remove the oligosaccharides still in the cake. This was done by mixing the cake with the water to form a slurry. The slurry was then centrifuged under the same conditions used to centrifuge the original mash in order to recover the washed solids. Removing the washed solids by centrifugation also resulted in the removal of some additional free corn oil as a separate organic liquid layer on top of the aqueous phase. Corn oil was recovered from the organic layer floating on top of the aqueous phase.

The wet solids were washed two more times using a 1000 g of tap water each time to remove essentially all of the liquefied starch. The final washed solids were dried in a vacuum oven overnight at 80° C. and about 20 inches Hg vacuum. The amount of corn oil remaining in the dry solids, presumably still in the germ, was determined by hexane extraction. It was measured that a 3.60 g sample of relatively dry solids (about 2 wt % moisture) contained 0.22 g of corn oil. This result corresponds to 0.0624 g corn oil/g dry solids. This was for washed solids which means there are no residual oligosaccharides in the wet solids. After centrifuging the liquefied corn mash to separate the layer of free corn oil and the aqueous solution of oligosaccharides from the wet cake, it was determined that about 334 g of wet cake containing about 21 wt % undissolved solids remained. This corresponds to the wet cake comprising about 70.1 g of undissolved solids. At 0.0624 g corn oil/g dry solids, the solids in the wet cake should contain about 4.4 g of corn oil.

In a separate experiment, a 26 wt % dry corn mash stream was generated using enzyme loads consistent with the liquefaction described above. This liquefied mash stream was processed through a Flottwegg centrifuge where the liquefied mash was separated into an oil stream, a thin mash stream, and a wet cake stream. The rate of oil recovery was roughly 1.1 lbm/bushel of corn to 1.5 lbm/bushel of corn. This recovery percentage is roughly 50% to 67% of the total oil entering the process. This recovery from the front end of the process is a higher percentage than typically recovered from the back end of the process (e.g., typical values of 0.4 lbm/bushel of corn representing 20% of the oil entering the process). Corn oil removed by this process has not gone through fermentation nor distillation and as such represents a cleaner corn oil stream.

Example 65

Lipid Analysis

Lipid analysis was conducted by conversion of the various fatty acid-containing compound classes to fatty acid methyl esters ("FAMEs") by transesterification. Glycerides and phospholipids were transesterified using sodium methoxide in methanol. Glycerides, phospholipids, and free fatty acids were transesterified using acetyl chloride in methanol. The resulting FAMEs were analyzed by gas chromatography using an Agilent 7890 GC fitted with a 30-m×0.25 mm (i.d.) OMEGAWAX™ (Supelco, SigmaAldrich, St. Louis, Mo.) column after dilution in toluene/hexane (2:3). The oven temperature was increased from 160° C. to 200° C. at 5° C./min then 200° C. to 250° C. (hold for 10 min) at 10° C./min. FAME peaks recorded via GC analysis were identified by their retention times, when compared to that of known methyl esters (MEs), and quantitated by comparing the FAME peak areas with that of the internal standard (C15:0 triglyceride, taken through the transesterification procedure with the sample) of known amount. Thus, the approximate amount (mg) of any fatty acid FAME ("mg FAME") is calculated according to the formula: (area of the FAME peak for the specified fatty acid/area of the 15:0 FAME peak)*(mg of the internal standard C15:0 FAME). The FAME result can then be corrected to mg of the corresponding fatty acid by dividing by the appropriate molecular weight conversion factor of 1.052. All internal and reference standards are obtained from Nu-Chek Prep, Inc.

The fatty acid results obtained for samples transesterified using sodium methoxide in methanol are converted to the corresponding triglyceride levels by multiplying the molecular weight conversion factor of 1.045. Triglycerides generally account for approximately 80 to 90% of the glycerides in the samples studies for this example, with the remainder being diglycerides. Monoglyceride and phospholipid contents are generally negligible. The total fatty acid results obtained for a sample transesterified using acetyl chloride in methanol are corrected for glyceride content by subtracting the fatty acids determined for the same sample using the sodium methoxide procedure. The result is the free fatty acid content of the sample.

The distribution of the glyceride content (monoglycerides, diglycerides, triglycerides, and phospholipids) is determined using thin layer chromatography. A solution of the oil dissolved in 6:1 chloroform/methanol is spotted near the bottom of a glass plate precoated with silica gel. The spot is then chromatographed up the plate using a 70:30:1 hexane/diethyl ether/acetic acid solvent system. Separated spots corresponding to monoglycerides, diglycerides, triglycerides, and phospholipids are then detected by staining the plate with iodine vapor. The spots are then scraped off the plate, transesterified using the acetyl chloride in methanol procedure, and analyzed by gas chromatography. The ratios of the totaled peak areas for each spot to the totaled peak areas for all the spots are the distribution of the various glycerides.

Example 66

This example illustrates the recovery of by-products from mash. Corn oil was separated from mash under the conditions described in Example 64 with the exception that a tricanter centrifuge (Flottweg Z23-4, bowl diameter 230 mm, length to diameter ratio 4:1) was used with these conditions:

| | |
|---|---|
| Bowl Speed: | 5000 rpm |
| Differential Speed: | 10 rpm |
| Feed Rate: | 3 gpm |
| Phase Separator Disk: | 138 mm |
| Impeller Setting | 144 mm. |

The corn oil separate had 81% triglycerides, 6% free fatty acids, 4% diglyceride, and 5% total of phospholipids and monoglycerides as determined by the methods described in Example 65 and thin layer chromatography.

The solids separated from mash under the conditions described above had a moisture content of 58% as determined by weight loss upon drying and had 1.2% triglycerides and 0.27% free fatty acids as determined by the method described in Example 65.

The composition of solids separated from whole stillage, oil extracted between evaporator stages, by-product extractant and Condensed Distillers Solubles (CDS) in Table 78 were calculated assuming the composition of whole stillage shown in Table 76 and the assumptions in Table 77 (separation at tricanter centrifuge. The values of Table 75 were obtained from an Aspen Plus® model (Aspen Technology, Inc., Burlington, Mass.). This model assumes that corn oil is not extracted from mash. It is estimated that the protein content on a dry basis of cells, dissolved solids, and suspended solids is approximately 50%, 22%, and 35.5%, respectively. The composition of by-product extractant is estimated to be 70.7% fatty acid and 29.3% fatty acid isobutyl ester on a dry basis.

TABLE 76

| Component | Mass % |
|---|---|
| Water | 57.386% |
| Cells | 0.502% |
| Fatty acids | 6.737% |
| Isobutyl esters of fatty acids | 30.817% |
| Triglyceride | 0.035% |
| Suspended solids | 0.416% |
| Dissolved solids | 4.107% |

TABLE 77

| | Hydrolyzer feed | Thin stillage | Solids |
|---|---|---|---|
| Organics | 99.175% | 0.75% | 0.08% |
| Water and dissolved solids | 1% | 96% | 3% |
| Suspended solids and cells | 1% | 2% | 97% |

TABLE 78

| Stream | C. protein | triglyceride | FFA | FABE |
|---|---|---|---|---|
| Whole stillage wet cake | 40% | trace | 0.5% | 2.2% |
| Oil at evaporator | 0% | 0.08% | 16.1% | 73.8% |
| CDS | 22% | trace % | 0.37% | 1.71% |

Example 67

This example illustrates the recovery of product alcohol from the butyl ester of fatty acid using base hydrolysis. Corn oil fatty acid/butyl ester of fatty acid extracting solvent is isolated from the fermentation broth after fermentation is complete. A dilute sodium hydroxide solution is added to the COFA/FABE mixture. The moles of sodium hydroxide used are roughly 10% in excess of the moles of fatty acid and FABE combined. The reaction mass is maintained at 90° C. for several hours until all of the FABE has reacted with water to make isobutanol and the sodium salt of corn oil fatty acid. After 2 hours, a dilute sulfuric acid solution is added. The moles of sulfuric acid is equal to the moles of sodium hydroxide added in the previous step. The reaction is again held for several hours. The resulting solution is then available for further purification.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing butyl esters comprising:

contacting butanol produced in a fermentation process with at least one exogenous carboxylic acid and at least one extracellular enzyme capable of esterifying the carboxylic acid with the butanol to form butyl esters of the carboxylic acid;

wherein the carboxylic acid in the fermentation process is present at a concentration sufficient to produce a two-phase mixture.

2. A method comprising:

(a) contacting butanol produced in a fermentation process with at least one exogenous carboxylic acid and at least one extracellular enzyme capable of esterifying the carboxylic acid with the butanol to form butyl esters of the carboxylic acid;

wherein the carboxylic acid in the fermentation process is present at a concentration sufficient to produce a two-phase mixture comprising an aqueous phase and a butyl ester-containing organic phase;

(b) separating the butyl ester-containing organic phase from the aqueous phase; and (c) recovering butanol from the butyl esters.

3. A method for producing butanol and butyl esters from a feedstock comprising:

(a) providing a feedstock;

(b) liquefying the feedstock to create a liquefied biomass comprising oligosaccharides;

(c) separating the feedstock slurry to produce a product comprising an aqueous stream, an oil stream, and solids;

(d) adding the aqueous stream to a fermentation vessel containing a fermentation broth (e) saccharifying the aqueous stream;

(f) fermenting the saccharified aqueous stream to produce butanol and concurrently contacting the butanoi with at least one exogenous carboxylic acid and at least one extracellular enzyme capable of esterifying the carboxylic acid with the butanol to form butyl esters of the carboxylic acid wherein the carboxylic acid is present at a concentration sufficient to produce a two-phase mixture;

(g) separating the butyl ester-containing organic phase from the aqueous phase; and (h) recovering butanol from the butyl esters;

and optionally steps (e) and (f) occur concurrently.

4. The method of claim 3, wherein the feedstock in the fermentation process comprises one or more fermentable sugars.

5. The method of claim 3, wherein the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof.

6. The method of claim 3, further comprising obtaining an oil from the oil stream and converting at least a portion of the oil into carboxylic acid.

7. The method of claim 3, wherein the feedstock slurry is separated by decanter bowl centrifugation, tricanter centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof.

8. The method of claim 3, wherein the carboxylic acid comprises fatty acids.

9. The method of claim 3, wherein the carboxylic acid comprises 12 to 22 carbons.

10. The method of claim 3, further comprising:

adding additional carboxylic acid to the fermentation vessel.

11. The method of claim 10, wherein the oil is converted to carboxylic acid after the step of adding the additional carboxylic acid.

12. The method of claim 3, wherein the carboxylic acid is corn oil fatty acid, soya oil fatty acid, or a mixture of corn oil fatty acid and soya oil fatty acid.

13. The method of claim 3, wherein the oil comprises glycerides and the one or more extracellular enzymes hydrolyze the glycerides into fatty acids.

14. The method of claim 3, wherein the extracellular enzyme is an esterase, lipase, phospholipase, or lysophospholipase.

15. The method of claim 3, wherein recovering butanol from the butyl esters comprises hydrolyzing the esters into carboxylic acid and butanol.

16. The method of claim 15, wherein the butyl esters are hydrolyzed in the presence of a hydrolysis catalyst.

17. The method of claim 16, wherein the hydrolysis catalyst comprises an acid catalyst, an organic acid, a water soluble acid, water insoluble acid, or base.

18. The method of claim 16, wherein the hydrolysis catalyst comprises an enzyme capable of hydrolyzing the butyl esters to form a carboxylic acid and butanol.

19. The method of claim 18, wherein the enzyme is an esterase, lipase, phospholipase, or lysophospholipase.

20. The method of claim 3, wherein recovering butanol from the butyl esters comprises transesterifying the butyl esters into butanol and other fatty acid alkyl esters or acyl glycerides.

21. The method of claim 20, wherein the other fatty acid alkyl esters comprise fatty acid methyl esters, fatty acid ethyl esters, or fatty acid propyl esters.

22. The method of claim 3, wherein the solids are processed to form to an animal feed product.

23. The method of claim 1, wherein the carboxylic acid comprises fatty acids.

24. The method of claim 1, wherein the enzyme is an esterase, lipase, phospholipase, lysophospholipase, or mixture thereof.

25. The method of claim 2, wherein the carboxylic acid comprises fatty acids.

26. The method of claim 2, wherein the enzyme is an esterase, lipase, phospholipase, lysophospholipase, or mixture thereof.

* * * * *

SEQUENCE LISTING

```
<160> NUMBER OF SEQ ID NOS: 202

<210> SEQ ID NO 1
<211> LENGTH: 11856
<212> TYPE: DNA
<213> ORGANISM: Artificial sequence
<220> FEATURE:
<223> OTHER INFORMATION: Plasmid

<400> SEQUENCE: 1

tcccattacc gacatttggg cgctatacgt gcatatgttc atgtatgtat ctgtatttaa      60

aacacttttg tattattttt cctcatatat gtgtataggt ttatacggat gatttaatta     120

ttacttcacc accctttatt tcaggctgat atcttagcct tgttactagt tagaaaaaga     180

catttttgct gtcagtcact gtcaagagat tcttttgctg gcatttcttc tagaagcaaa     240

aagagcgatg cgtcttttcc gctgaaccgt tccagcaaaa aagactacca acgcaatatg     300

gattgtcaga atcatataaa agagaagcaa ataactcctt gtcttgtatc aattgcatta     360

taatatcttc ttgttagtgc aatatcatat agaagtcatc gaaatagata ttaagaaaaa     420

caaactgtac aatcaatcaa tcaatcatcg ctgaggatgt tgacaaaagc aacaaaagaa     480

caaaaatccc ttgtgaaaaa cagaggggcg gagcttgttg ttgattgctt agtggagcaa     540

ggtgtcacac atgtatttgg cattccaggt gcaaaaattg atgcggtatt tgacgcttta     600

caagataaag gacctgaaat tatcgttgcc cggcacgaac aaaacgcagc attcatggcc     660

caagcagtcg gccgtttaac tggaaaaccg ggagtcgtgt tagtcacatc aggaccgggt     720

gcctctaact tggcaacagg cctgctgaca gcgaacactg aaggagaccc tgtcgttgcg     780
```

-continued

```
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct ttttatatgt ttttacttct   2580
gtatatcgtg aagtagtaag tgataagcga atttggctaa gaacgttgta agtgaacaag   2640
ggacctcttt tgcctttcaa aaaaggatta aatggagtta atcattgaga tttagttttc   2700
gttagattct gtatccctaa ataactccct tacccgacgg gaaggcacaa aagacttgaa   2760
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg cccctatctg ttcttccgct ctaccgtgag aaataaagca tcgagtacgg   3120
cagttcgctg tcactgaact aaaacaataa ggctagttcg aatgatgaac ttgcttgctg   3180
```

```
tcaaacttct gagttgccgc tgatgtgaca ctgtgacaat aaattcaaac cggttatagc   3240
ggtctcctcc ggtaccggtt ctgccacctc caatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacggaaaat cttttgataa agcaaaagaa gatggctttg aaacatttga agtaggagaa   3840
gcagtagcta aagctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
tccatctcaa atactgctga gtttggcgat tatgtgactg gtccacggat tattactgac   4440
gaagttaaaa agaatatgaa gcttgttttg gctgatattc aatctggaaa atttgctcaa   4500
gatttcgttg atgacttcaa agcggggcgt ccaaaattaa tagcctatcg cgaagctgca   4560
aaaaatcttg aaattgaaaa aattggggca gagctacgtc aagcaatgcc attcacacaa   4620
tctggtgatg acgatgcctt taaaatctat cagtaaggcc ctgcaggcca gaggaaaata   4680
atatcaagtg ctggaaactt tttctcttgg aatttttgca acatcaagtc atagtcaatt   4740
gaattgaccc aatttcacat ttaagatttt tttttttca tccgacatac atctgtacac   4800
taggaagccc tgtttttctg aagcagcttc aaatatatat attttttaca tatttattat   4860
gattcaatga acaatctaat taaatcgaaa acaagaaccg aaacgcgaat aaataattta   4920
tttagatggt gacaagtgta taagtcctca tcgggacagc tacgatttct ctttcggttt   4980
tggctgagct actggttgct gtgacgcagc ggcattagcg cggcgttatg agctaccctc   5040
gtggcctgaa agatggcggg aataaagcgg aactaaaaat tactgactga gccatattga   5100
ggtcaatttg tcaactcgtc aagtcacgtt tggtggacgg cccctttcca acgaatcgta   5160
tatactaaca tgcgcgcgct tcctatatac acatatacat atatatatat atatatatgt   5220
gtgcgtgtat gtgtacacct gtatttaatt tccttactcg cgggtttttc ttttttctca   5280
attcttggct tcctctttct cgagcggacc ggatcctccg cggtgccggc agatctattt   5340
aaatggcgcg ccgacgtcag gtggcacttt tcggggaaat gtgcgcggaa cccctatttg   5400
tttatttttc taaatacatt caaatatgta tccgctcatg agacaataac cctgataaat   5460
gcttcaataa tattgaaaaa ggaagagtat gagtattcaa catttccgtg tcgcccttat   5520
```

-continued

```
tcccttttttt gcggcatttt gccttcctgt ttttgctcac ccagaaacgc tggtgaaagt   5580
aaaagatgct gaagatcagt tgggtgcacg agtgggttac atcgaactgg atctcaacag   5640
cggtaagatc cttgagagtt ttcgccccga agaacgtttt ccaatgatga gcacttttaa   5700
agttctgcta tgtggcgcgg tattatcccg tattgacgcc gggcaagagc aactcggtcg   5760
ccgcatacac tattctcaga atgacttggt tgagtactca ccagtcacag aaaagcatct   5820
tacggatggc atgacagtaa gagaattatg cagtgctgcc ataaccatga gtgataacac   5880
tgcggccaac ttacttctga caacgatcgg aggaccgaag gagctaaccg cttttttgca   5940
caacatgggg gatcatgtaa ctcgccttga tcgttgggaa ccggagctga atgaagccat   6000
accaaacgac gagcgtgaca ccacgatgcc tgtagcaatg gcaacaacgt tgcgcaaact   6060
attaactggc gaactactta ctctagcttc ccggcaacaa ttaatagact ggatggaggc   6120
ggataaagtt gcaggaccac ttctgcgctc ggcccttccg gctggctggt ttattgctga   6180
taaatctgga gccggtgagc gtgggtctcg cggtatcatt gcagcactgg ggccagatgg   6240
taagccctcc cgtatcgtag ttatctacac gacggggagt caggcaacta tggatgaacg   6300
aaatagacag atcgctgaga taggtgcctc actgattaag cattggtaac tgtcagacca   6360
agtttactca tatatacttt agattgattt aaaacttcat ttttaattta aaaggatcta   6420
ggtgaagatc ctttttgata atctcatgac caaaatccct taacgtgagt tttcgttcca   6480
ctgagcgtca gaccccgtag aaaagatcaa aggatcttct tgagatcctt tttttctgcg   6540
cgtaatctgc tgcttgcaaa caaaaaaacc accgctacca gcggtggttt gtttgccgga   6600
tcaagagcta ccaactcttt ttccgaaggt aactggcttc agcagagcgc agataccaaa   6660
tactgttctt ctagtgtagc cgtagttagg ccaccacttc aagaactctg tagcaccgcc   6720
tacatacctc gctctgctaa tcctgttacc agtggctgct gccagtggcg ataagtcgtg   6780
tcttaccggg ttggactcaa gacgatagtt accggataag gcgcagcggt cgggctgaac   6840
ggggggttcg tgcacacagc ccagcttgga gcgaacgacc tacaccgaac tgagatacct   6900
acagcgtgag ctatgagaaa gcgccacgct tcccgaaggg agaaaggcgg acaggtatcc   6960
ggtaagcggc agggtcggaa caggagagcg cacgagggag cttccagggg gaaacgcctg   7020
gtatctttat agtcctgtcg ggtttcgcca cctctgactt gagcgtcgat ttttgtgatg   7080
ctcgtcaggg gggcggagcc tatggaaaaa cgccagcaac gcggcctttt tacggttcct   7140
ggccttttgc tggccttttg ctcacatgtt ctttcctgcg ttatcccctg attctgtgga   7200
taaccgtatt accgcctttg agtgagctga taccgctcgc cgcagccgaa cgaccgagcg   7260
cagcgagtca gtgagcgagg aagcggaaga gcgcccaata cgcaaaccgc ctctccccgc   7320
gcgttggccg attcattaat gcagctggca cgacaggttt cccgactgga aagcgggcag   7380
tgagcgcaac gcaattaatg tgagttagct cactcattag gcaccccagg ctttacactt   7440
tatgcttccg gctcgtatgt tgtgtggaat tgtgagcgga taacaatttc acacaggaaa   7500
cagctatgac catgattacg ccaagctttt tctttccaat ttttttttt tcgtcattat   7560
aaaaatcatt acgaccgaga ttcccgggta ataactgata taattaaatt gaagctctaa   7620
tttgtgagtt tagtatacat gcatttactt ataatacagt tttttagttt tgctggccgc   7680
atcttctcaa atatgcttcc cagcctgctt ttctgtaacg ttcaccctct accttagcat   7740
cccttccctt tgcaaatagt cctcttccaa caataataat gtcagatcct gtagagacca   7800
catcatccac ggttctatac tgttgaccca atgcgtctcc cttgtcatct aaacccacac   7860
cgggtgtcat aatcaaccaa tcgtaacctt catctcttcc acccatgtct ctttgagcaa   7920
```

-continued

```
taaagccgat aacaaaatct ttgtcgctct tcgcaatgtc aacagtaccc ttagtatatt   7980
ctccagtaga tagggagccc ttgcatgaca attctgctaa catcaaaagg cctctaggtt   8040
cctttgttac ttcttctgcc gcctgcttca aaccgctaac aatacctggg cccaccacac   8100
cgtgtgcatt cgtaatgtct gcccattctg ctattctgta tacacccgca gagtactgca   8160
atttgactgt attaccaatg tcagcaaatt ttctgtcttc gaagagtaaa aaattgtact   8220
tggcggataa tgcctttagc ggcttaactg tgccctccat ggaaaaatca gtcaagatat   8280
ccacatgtgt ttttagtaaa caaattttgg gacctaatgc ttcaactaac tccagtaatt   8340
ccttggtggt acgaacatcc aatgaagcac acaagtttgt ttgcttttcg tgcatgatat   8400
taaatagctt ggcagcaaca ggactaggat gagtagcagc acgttcctta tatgtagctt   8460
tcgacatgat ttatcttcgt ttcctgcagg tttttgttct gtgcagttgg gttaagaata   8520
ctgggcaatt tcatgtttct tcaacactac atatgcgtat atataccaat ctaagtctgt   8580
gctccttcct tcgttcttcc ttctgttcgg agattaccga atcaaaaaaa tttcaaggaa   8640
accgaaatca aaaaaaagaa taaaaaaaaa atgatgaatt gaaaagcttg catgcctgca   8700
ggtcgactct agtatactcc gtctactgta cgatacactt ccgctcaggt ccttgtcctt   8760
taacgaggcc ttaccactct tttgttactc tattgatcca gctcagcaaa ggcagtgtga   8820
tctaagattc tatcttcgcg atgtagtaaa actagctaga ccgagaaaga gactagaaat   8880
gcaaaaggca cttctacaat ggctgccatc attattatcc gatgtgacgc tgcatttttt   8940
tttttttttt tttttttttt tttttttttt tttttttttt ttttttgtac aaatatcata   9000
aaaaaagaga atctttttaa gcaaggattt tcttaacttc ttcggcgaca gcatcaccga   9060
cttcggtggt actgttggaa ccacctaaat caccagttct gatacctgca tccaaaacct   9120
ttttaactgc atcttcaatg gctttacctt cttcaggcaa gttcaatgac aatttcaaca   9180
tcattgcagc agacaagata gtggcgatag ggttgacctt attctttggc aaatctggag   9240
cggaaccatg gcatggttcg tacaaaccaa atgcggtgtt cttgtctggc aaagaggcca   9300
aggacgcaga tggcaacaaa cccaaggagc ctgggataac ggaggcttca tcggagatga   9360
tatcaccaaa catgttgctg gtgattataa taccatttag gtgggttggg ttcttaacta   9420
ggatcatggc ggcagaatca atcaattgat gttgaacttt caatgtaggg aattcgttct   9480
tgatggtttc ctccacagtt tttctccata atcttgaaga ggccaaaaca ttagctttat   9540
ccaaggacca aataggcaat ggtggctcat gttgtagggc catgaaagcg gccattcttg   9600
tgattctttg cacttctgga acggtgtatt gttcactatc ccaagcgaca ccatcaccat   9660
cgtcttcctt tctcttacca aagtaaatac ctcccactaa ttctctaaca acaacgaagt   9720
cagtaccttt agcaaattgt ggcttgattg gagataagtc taaaagagag tcggatgcaa   9780
agttacatgg tcttaagttg gcgtacaatt gaagttcttt acggattttt agtaaacctt   9840
gttcaggtct aacactaccg gtaccccatt taggaccacc cacagcacct aacaaaacgg   9900
catcagcctt cttggaggct tccagcgcct catctggaag tggaacacct gtagcatcga   9960
tagcagcacc accaattaaa tgattttcga aatcgaactt gacattggaa cgaacatcag  10020
aaatagcttt aagaacctta atggcttcgg ctgtgatttc ttgaccaacg tggtcacctg  10080
gcaaaacgac gatcttctta ggggcagaca ttacaatggt atatccttga aatatatata  10140
aaaaaaaaaa aaaaaaaaaa aaaaaaaaat gcagcttctc aatgatattc gaatacgctt  10200
tgaggagata cagcctaata tccgacaaac tgttttacag atttacgatc gtacttgtta  10260
```

cccatcattg aattttgaac atccgaacct gggagttttc cctgaaacag atagtatatt 10320
tgaacctgta taataatata tagtctagcg ctttacggaa gacaatgtat gtatttcggt 10380
tcctggagaa actattgcat ctattgcata ggtaatcttg cacgtcgcat ccccggttca 10440
ttttctgcgt ttccatcttg cacttcaata gcatatcttt gttaacgaag catctgtgct 10500
tcattttgta gaacaaaaat gcaacgcgag agcgctaatt tttcaaacaa agaatctgag 10560
ctgcattttt acagaacaga aatgcaacgc gaaagcgcta ttttaccaac gaagaatctg 10620
tgcttcattt ttgtaaaaca aaaatgcaac gcgagagcgc taatttttca aacaaagaat 10680
ctgagctgca tttttacaga acagaaatgc aacgcgagag cgctatttta ccaacaaaga 10740
atctatactt cttttttgtt ctacaaaaat gcatcccgag agcgctattt ttctaacaaa 10800
gcatcttaga ttactttttt tctcctttgt gcgctctata atgcagtctc ttgataactt 10860
tttgcactgt aggtccgtta aggttagaag aaggctactt tggtgtctat tttctcttcc 10920
ataaaaaaag cctgactcca cttcccgcgt ttactgatta ctagcgaagc tgcgggtgca 10980
ttttttcaag ataaaggcat ccccgattat attctatacc gatgtggatt gcgcatactt 11040
tgtgaacaga aagtgatagc gttgatgatt cttcattggt cagaaaatta tgaacggttt 11100
cttctatttt gtctctatat actacgtata ggaaatgttt acattttcgt attgttttcg 11160
attcactcta tgaatagttc ttactacaat ttttttgtct aaagagtaat actagagata 11220
aacataaaaa atgtagaggt cgagtttaga tgcaagttca aggagcgaaa ggtggatggg 11280
taggttatat agggatatag cacagagata tatagcaaag agatactttt gagcaatgtt 11340
tgtggaagcg gtattcgcaa tattttagta gctcgttaca gtccggtgcg tttttggttt 11400
tttgaaagtg cgtcttcaga gcgcttttgg ttttcaaaag cgctctgaag ttcctatact 11460
ttctagagaa taggaacttc ggaataggaa cttcaaagcg tttccgaaaa cgagcgcttc 11520
cgaaaatgca acgcgagctg cgcacataca gctcactgtt cacgtcgcac ctatatctgc 11580
gtgttgcctg tatatatata tacatgagaa gaacggcata gtgcgtgttt atgcttaaat 11640
gcgtacttat atgcgtctat ttatgtagga tgaaaggtag tctagtacct cctgtgatat 11700
tatcccattc catgcggggt atcgtatgct tccttcagca ctacccttta gctgttctat 11760
atgctgccac tcctcaattg gattagtctc atccttcaat gctatcattt cctttgatat 11820
tggatcatat gcatagtacc gagaaactag aggatc 11856

<210> SEQ ID NO 2
<211> LENGTH: 15539
<212> TYPE: DNA
<213> ORGANISM: Artificial sequence
<220> FEATURE:
<223> OTHER INFORMATION: Plasmid

<400> SEQUENCE: 2
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat atttttttat gcctcggtaa tgattttcat 360
tttttttttt ccacctagcg gatgactctt ttttttttctt agcgattggc attatcacat 420
aatgaattat acattatata aagtaatgtg atttcttcga agaatatact aaaaaatgag 480

-continued

```
caggcaagat aaacgaaggc aaagatgaca gagcagaaag ccctagtaaa gcgtattaca     540
aatgaaacca agattcagat tgcgatctct ttaaagggtg gtcccctagc gatagagcac     600
tcgatcttcc cagaaaaaga ggcagaagca gtagcagaac aggccacaca atcgcaagtg     660
attaacgtcc acacaggtat agggtttctg gaccatatga tacatgctct ggccaagcat     720
tccggctggt cgctaatcgt tgagtgcatt ggtgacttac acatagacga ccatcacacc     780
actgaagact gcgggattgc tctcggtcaa gcttttaaag aggccctagg ggccgtgcgt     840
ggagtaaaaa ggtttggatc aggatttgcg cctttggatg aggcactttc cagagcggtg     900
gtagatcttt cgaacaggcc gtacgcagtt gtcgaacttg gtttgcaaag ggagaaagta     960
ggagatctct cttgcgagat gatcccgcat tttcttgaaa gctttgcaga ggctagcaga    1020
attaccctcc acgttgattg tctgcgaggc aagaatgatc atcaccgtag tgagagtgcg    1080
ttcaaggctc ttgcggttgc cataagagaa gccacctcgc ccaatggtac caacgatgtt    1140
ccctccacca aaggtgttct tatgtagtga caccgattat ttaaagctgc agcatacgat    1200
atatatacat gtgtatatat gtatacctat gaatgtcagt aagtatgtat acgaacagta    1260
tgatactgaa gatgacaagg taatgcatca ttctatacgt gtcattctga acgaggcgcg    1320
ctttcctttt ttcttttttgc tttttctttt tttttctctt gaactcgacg gatctatgcg    1380
gtgtgaaata ccgcacagat gcgtaaggag aaaataccgc atcaggaaat tgtaagcgtt    1440
aatattttgt taaaattcgc gttaaatttt tgttaaatca gctcattttt taaccaatag    1500
gccgaaatcg gcaaaatccc ttataaatca aaagaataga ccgagatagg gttgagtgtt    1560
gttccagttt ggaacaagag tccactatta aagaacgtgg actccaacgt caaagggcga    1620
aaaaccgtct atcagggcga tggcccacta cgtgaaccat caccctaatc aagttttttg    1680
gggtcgaggt gccgtaaagc actaaatcgg aaccctaaag ggagcccccg atttagagct    1740
tgacggggaa agccggcgaa cgtggcgaga aaggaaggga agaaagcgaa aggagcgggc    1800
gctagggcgc tggcaagtgt agcggtcacg ctgcgcgtaa ccaccacacc cgccgcgctt    1860
aatgcgccgc tacagggcgc gtccattcgc cattcaggct gcgcaactgt tgggaagggc    1920
gcggtgcggg cctcttcgct attacgccag ctggcgaaag ggggatgtgc tgcaaggcga    1980
ttaagttggg taacgccagg gttttcccag tcacgacgtt gtaaaacgac ggccagtgag    2040
cgcgcgtaat acgactcact atagggcgaa ttgggtaccg ggcccccccct cgaggtcgac    2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tcctttcccc    2400
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttcctttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaaagta ttggatggtt    2820
```

-continued

```
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca aagtttctgg   4320
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gtttttttaat gagtattgaa tctgtttaga aataatggaa   4920
tattattttt atttatttat ttatattatt ggtcggctct tttcttctga aggtcaatga   4980
caaaatgata tgaaggaaat aatgatttct aaaattttac aacgtaagat atttttacaa   5040
aagcctagct catcttttgt catgcactat tttactcacg cttgaaatta acggccagtc   5100
cactgcggag tcatttcaaa gtcatcctaa tcgatctatc gtttttgata gctcattttg   5160
gagttcgcga ttgtcttctg ttattcacaa ctgttttaat tttatttca ttctggaact   5220
```

```
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aactttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc ctttttccct actcctttta   5580
gtacggaaga caatgctaat aaataagagg gtaataataa tattattaat cggcaaaaaa   5640
gattaaacgc caagcgttta attatcagaa agcaaacgtc gtaccaatcc ttgaatgctt   5700
cccaattgta tattaagagt catcacagca acatattctt gttattaaat taattattat   5760
tgatttttga tattgtataa aaaaaccaaa tatgtataaa aaaagtgaat aaaaaaatacc   5820
aagtatggag aaatatatta gaagtctata cgttaaacca cccgggcccc ccctcgaggt   5880
cgacggtatc gataagcttg atatcgaatt cctgcagccc gggggatcca ctagttctag   5940
agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat tttttttata acttatttaa   6240
taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gattttagcg acagatatct cgtccaccac   6960
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
tggcgctact tctacttctt ctatgctaaa cggctttttc tcttcccaca aaactgccgc   7380
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
```

-continued

```
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc cccgggctg caggaattcg atatcaagct    8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct   8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaaagaa aatttattta aatgcaagat ttaaagtaaa ttcacggccc   9240
tgcaggcctc agctcttgtt ttgttctgca aataacttac ccatcttttt caaaacttta   9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
ttcgatttca gaaatataga tgaggcaccg aagaaagaag tgccttgttc agccacgatc   9780
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
```

ttgaaaattt taccttcatc gatattcaag gaaatcattt tattttcatt aagatggtga 10020
gtaaatgcac ccgtactaga atcggtaagc tttacaccca acataagaat aaaatcagca 10080
gattccacaa attccttcaa gtttggctct gacagagtac cgttgtaaat ccccaaaaat 10140
gagggcaatg cttcatcaac agatgattta ccaaagttca aagtagtaat aggtaactta 10200
gtctttgaaa taaactgagt aacagtcttc tctaggccga acgatataat ttcatggcct 10260
gtgattacaa ttggtttctt ggcattcttc agactttcct gtattttgtt cagaatctct 10320
tgatcagatg tattcgacgt ggaattttcc ttcttaagag gcaaggatgg tttttcagcc 10380
ttagcggcag ctacatctac aggtaaattg atgtaaaccg gctttctttc ctttagtaag 10440
gcagacaaca ctctatcaat ttcaacagtt gcattctcgg ctgtcaataa agtcctggca 10500
gcagtaaccg gttcgtgcat cttcataaag tgcttgaaat caccatcagc caacgtatgg 10560
tgaacaaact taccttcgtt ctgcactttc gaggtaggag atcccacgat ctcaacaaca 10620
ggcaggttct cagcatagga gcccgctaag ccattaactg cggataattc gccaacacca 10680
aatgtagtca agaatgccgc agccttttc gttcttgcgt acccgtcggc catataggag 10740
gcatttaact cattagcatt tcccacccat ttcatatctt tgtgtgaaat aatttgatct 10800
agaaattgca aattgtagtc acctggtact ccgaatattt cttctatacc taattcgtgt 10860
aatctgtcca acagatagtc acctactgta tacattttgt ttactagttt atgtgtgttt 10920
attcgaaact aagttcttgg tgttttaaaa ctaaaaaaaa gactaactat aaaagtagaa 10980
tttaagaagt ttaagaaata gatttacaga attacaatca atacctaccg tctttatata 11040
cttattagtc aagtagggga ataatttcag ggaactggtt tcaacctttt ttttcagctt 11100
tttccaaatc agagagagca gaaggtaata gaaggtgtaa gaaaatgaga tagatacatg 11160
cgtgggtcaa ttgccttgtg tcatcattta ctccaggcag gttgcatcac tccattgagg 11220
ttgtgcccgt tttttgcctg tttgtgcccc tgttctctgt agttgcgcta agagaatgga 11280
cctatgaact gatggttggt gaagaaaaca atattttggt gctgggattc ttttttttc 11340
tggatgccag cttaaaaagc gggctccatt atatttagtg gatgccagga ataaactgtt 11400
cacccagaca cctacgatgt tatatattct gtgtaacccg cccccctattt tgggcatgta 11460
cgggttacag cagaattaaa aggctaattt tttgactaaa taaagttagg aaaatcacta 11520
ctattaatta tttacgtatt ctttgaaatg gcagtattga taatgataaa ctcgaactga 11580
aaaagcgtgt tttttattca aaatgattct aactccctta cgtaatcaag gaatcttttt 11640
gccttggcct ccgcgtcatt aaacttcttg ttgttgacgc taacattcaa cgctagtata 11700
tattcgtttt tttcaggtaa gttcttttca acgggtctta ctgatgaggc agtcgcgtct 11760
gaacctgtta agaggtcaaa tatgtcttct tgaccgtacg tgtcttgcat gttattagct 11820
ttgggaattt gcatcaagtc ataggaaaat ttaaatcttg gctctcttgg gctcaaggtg 11880
acaaggtcct cgaaaatagg gcgcgcccca ccgcggtgga gctccagctt ttgttccctt 11940
tagtgagggt taattgcgcg cttggcgtaa tcatggtcat agctgtttcc tgtgtgaaat 12000
tgttatccgc tcacaattcc acacaacata cgagccggaa gcataaagtg taaagcctgg 12060
ggtgcctaat gagtgagcta actcacatta attgcgttgc gctcactgcc cgctttccag 12120
tcgggaaacc tgtcgtgcca gctgcattaa tgaatcggcc aacgcgcggg gagaggcggt 12180
ttgcgtattg ggcgctcttc cgcttcctcg ctcactgact cgctgcgctc ggtcgttcgg 12240
ctgcggcgag cggtatcagc tcactcaaag gcggtaatac ggttatccac agaatcaggg 12300

```
gataacgcag gaaagaacat gtgagcaaaa ggccagcaaa aggccaggaa ccgtaaaaag  12360
gccgcgttgc tggcgttttt ccataggctc cgcccccctg acgagcatca caaaaatcga  12420
cgctcaagtc agaggtggcg aaacccgaca ggactataaa gataccaggc gtttccccct  12480
ggaagctccc tcgtgcgctc tcctgttccg accctgccgc ttaccggata cctgtccgcc  12540
tttctccctt cgggaagcgt ggcgctttct catagctcac gctgtaggta tctcagttcg  12600
gtgtaggtcg ttcgctccaa gctgggctgt gtgcacgaac cccccgttca gcccgaccgc  12660
tgcgccttat ccggtaacta tcgtcttgag tccaacccgg taagacacga cttatcgcca  12720
ctggcagcag ccactggtaa caggattagc agagcgaggt atgtaggcgg tgctacagag  12780
ttcttgaagt ggtggcctaa ctacggctac actagaagaa cagtatttgg tatctgcgct  12840
ctgctgaagc cagttacctt cggaaaaaga gttggtagct cttgatccgg caaacaaacc  12900
accgctggta gcggtggttt ttttgtttgc aagcagcaga ttacgcgcag aaaaaaagga  12960
tctcaagaag atcctttgat cttttctacg gggtctgacg ctcagtggaa cgaaaactca  13020
cgttaaggga ttttggtcat gagattatca aaaaggatct tcacctagat ccttttaaat  13080
taaaaatgaa gttttaaatc aatctaaagt atatatgagt aaacttggtc tgacagttac  13140
caatgcttaa tcagtgaggc acctatctca gcgatctgtc tatttcgttc atccatagtt  13200
gcctgactcc ccgtcgtgta gataactacg atacgggagg gcttaccatc tggccccagt  13260
gctgcaatga taccgcgaga cccacgctca ccggctccag atttatcagc aataaaccag  13320
ccagccggaa gggccgagcg cagaagtggt cctgcaactt tatccgcctc catccagtct  13380
attaattgtt gccgggaagc tagagtaagt agttcgccag ttaatagttt gcgcaacgtt  13440
gttgccattg ctacaggcat cgtggtgtca cgctcgtcgt ttggtatggc ttcattcagc  13500
tccggttccc aacgatcaag gcgagttaca tgatccccca tgttgtgcaa aaaagcggtt  13560
agctccttcg gtcctccgat cgttgtcaga agtaagttgg ccgcagtgtt atcactcatg  13620
gttatggcag cactgcataa ttctcttact gtcatgccat ccgtaagatg cttttctgtg  13680
actggtgagt actcaaccaa gtcattctga gaatagtgta tgcggcgacc gagttgctct  13740
tgcccggcgt caatacggga taataccgcg ccacatagca gaactttaaa agtgctcatc  13800
attggaaaac gttcttcggg gcgaaaactc tcaaggatct taccgctgtt gagatccagt  13860
tcgatgtaac ccactcgtgc acccaactga tcttcagcat cttttacttt caccagcgtt  13920
tctgggtgag caaaaacagg aaggcaaaat gccgcaaaaa agggaataag ggcgacacgg  13980
aaatgttgaa tactcatact cttccttttt caatattatt gaagcattta tcagggttat  14040
tgtctcatga gcggatacat atttgaatgt atttagaaaa ataaacaaat aggggttccg  14100
cgcacatttc cccgaaaagt gccacctgaa cgaagcatct gtgcttcatt ttgtagaaca  14160
aaaatgcaac gcgagagcgc taatttttca aacaaagaat ctgagctgca tttttacaga  14220
acagaaatgc aacgcgaaag cgctatttta ccaacgaaga atctgtgctt catttttgta  14280
aaacaaaaat gcaacgcgag agcgctaatt tttcaaacaa agaatctgag ctgcattttt  14340
acagaacaga aatgcaacgc gagagcgcta ttttaccaac aaagaatcta tacttctttt  14400
ttgttctaca aaaatgcatc ccgagagcgc tatttttcta acaaagcatc ttagattact  14460
tttttctcc tttgtgcgct ctataatgca gtctcttgat aactttttgc actgtaggtc  14520
cgttaaggtt agaagaaggc tactttggtg tctattttct cttccataaa aaaagcctga  14580
ctccacttcc cgcgtttact gattactagc gaagctgcgg gtgcattttt tcaagataaa  14640
ggcatccccg attatattct ataccgatgt ggattgcgca tactttgtga acagaaagtg  14700
```

```
atagcgttga tgattcttca ttggtcagaa aattatgaac ggtttcttct attttgtctc  14760

tatatactac gtataggaaa tgtttacatt ttcgtattgt tttcgattca ctctatgaat  14820

agttcttact acaatttttt tgtctaaaga gtaatactag agataaacat aaaaaatgta  14880

gaggtcgagt ttagatgcaa gttcaaggag cgaaaggtgg atgggtaggt tatataggga  14940

tatagcacag agatatatag caaagagata cttttgagca atgtttgtgg aagcggtatt  15000

cgcaatattt tagtagctcg ttacagtccg gtgcgttttt ggtttttga aagtgcgtct  15060

tcagagcgct tttggttttc aaaagcgctc tgaagttcct atactttcta gagaatagga  15120

acttcggaat aggaacttca aagcgtttcc gaaaacgagc gcttccgaaa atgcaacgcg  15180

agctgcgcac atacagctca ctgttcacgt cgcacctata tctgcgtgtt gcctgtatat  15240

atatatacat gagaagaacg gcatagtgcg tgtttatgct taaatgcgta cttatatgcg  15300

tctatttatg taggatgaaa ggtagtctag tacctcctgt gatattatcc cattccatgc  15360

ggggtatcgt atgcttcctt cagcactacc ctttagctgt tctatatgct gccactcctc  15420

aattggatta gtctcatcct tcaatgctat catttccttt gatattggat catactaaga  15480

aaccattatt atcatgacat taacctataa aaataggcgt atcacgaggc cctttcgtc   15539
```

<210> SEQ ID NO 3
<211> LENGTH: 4586
<212> TYPE: DNA
<213> ORGANISM: Artificial sequence
<220> FEATURE:
<223> OTHER INFORMATION: Template

<400> SEQUENCE: 3

```
gggtaccgag ctcgaattca ctggccgtcg ttttacaacg tcgtgactgg gaaaaccctg     60

gcgttaccca acttaatcgc cttgcagcac atcccccttt cgccagctgg cgtaatagcg    120

aagaggcccg caccgatcgc ccttcccaac agttgcgcag cctgaatggc gaatggcgcc    180

tgatgcggta ttttctcctt acgcatctgt gcggtatttc acaccgcata tggtgcactc    240

tcagtacaat ctgctctgat gccgcatagt taagccagcc ccgacacccg ccaacacccg    300

ctgacgcgcc ctgacgggct tgtctgctcc cggcatccgc ttacagacaa gctgtgaccg    360

tctccgggag ctgcatgtgt cagaggtttt caccgtcatc accgaaacgc gcgagacgaa    420

agggcctcgt gatacgccta tttttatagg ttaatgtcat gataataatg gtttcttaga    480

cgtcaggtgg cacttttcgg ggaaatgtgc gcggaacccc tatttgttta tttttctaaa    540

tacattcaaa tatgtatccg ctcatgagac aataaccctg ataaatgctt caataatatt    600

gaaaaaggaa gagtatgagt attcaacatt tccgtgtcgc ccttattccc ttttttgcgg    660

cattttgcct tcctgttttt gctcacccag aaacgctggt gaaagtaaaa gatgctgaag    720

atcagttggg tgcacgagtg ggttacatcg aactggatct caacagcggt aagatccttg    780

agagttttcg ccccgaagaa cgttttccaa tgatgagcac ttttaaagtt ctgctatgtg    840

gcgcggtatt atcccgtatt gacgccgggc aagagcaact cggtcgccgc atacactatt    900

ctcagaatga cttggttgag tactcaccag tcacagaaaa gcatcttacg gatggcatga    960

cagtaagaga attatgcagt gctgccataa ccatgagtga taacactgcg gccaacttac   1020

ttctgacaac gatcggagga ccgaaggagc taaccgcttt tttgcacaac atgggggatc   1080

atgtaactcg ccttgatcgt tgggaaccgg agctgaatga agccatacca aacgacgagc   1140

gtgacaccac gatgcctgta gcaatggcaa caacgttgcg caaactatta actggcgaac   1200
```

-continued

```
tacttactct agcttcccgg caacaattaa tagactggat ggaggcggat aaagttgcag   1260
gaccacttct gcgctcggcc cttccggctg gctggtttat tgctgataaa tctggagccg   1320
gtgagcgtgg gtctcgcggt atcattgcag cactggggcc agatggtaag ccctcccgta   1380
tcgtagttat ctacacgacg gggagtcagg caactatgga tgaacgaaat agacagatcg   1440
ctgagatagg tgcctcactg attaagcatt ggtaactgtc agaccaagtt tactcatata   1500
tactttagat tgatttaaaa cttcattttt aatttaaaag gatctaggtg aagatccttt   1560
ttgataatct catgaccaaa atcccttaac gtgagttttc gttccactga gcgtcagacc   1620
ccgtagaaaa gatcaaagga tcttcttgag atcctttttt tctgcgcgta atctgctgct   1680
tgcaaacaaa aaaaccaccg ctaccagcgg tggtttgttt gccggatcaa gagctaccaa   1740
ctctttttcc gaaggtaact ggcttcagca gagcgcagat accaaatact gtccttctag   1800
tgtagccgta gttaggccac cacttcaaga actctgtagc accgcctaca tacctcgctc   1860
tgctaatcct gttaccagtg gctgctgcca gtggcgataa gtcgtgtctt accgggttgg   1920
actcaagacg atagttaccg gataaggcgc agcggtcggg ctgaacgggg ggttcgtgca   1980
cacagcccag cttggagcga acgacctaca ccgaactgag atacctacag cgtgagctat   2040
gagaaagcgc cacgcttccc gaagggagaa aggcggacag gtatccggta agcggcaggg   2100
tcggaacagg agagcgcacg agggagcttc caggggggaaa cgcctggtat ctttatagtc   2160
ctgtcgggtt tcgccacctc tgacttgagc gtcgattttt gtgatgctcg tcaggggggc   2220
ggagcctatg gaaaaacgcc agcaacgcgg cctttttacg gttcctggcc ttttgctggc   2280
cttttgctca catgttcttt cctgcgttat cccctgattc tgtggataac cgtattaccg   2340
cctttgagtg agctgatacc gctcgccgca gccgaacgac cgagcgcagc gagtcagtga   2400
gcgaggaagc ggaagagcgc ccaatacgca aaccgcctct ccccgcgcgt tggccgattc   2460
attaatgcag ctggcacgac aggtttcccg actggaaagc gggcagtgag cgcaacgcaa   2520
ttaatgtgag ttagctcact cattaggcac cccaggcttt acactttatg cttccggctc   2580
gtatgttgtg tggaattgtg agcggataac aatttcacac aggaaacagc tatgaccatg   2640
attacgccaa gcttgcatgc ctgcaggtcg actctagagg atccccgcat tgcggattac   2700
gtattctaat gttcagataa cttcgtatag catacattat acgaagttat ctagggattc   2760
ataaccattt tctcaatcga attacacaga acacaccgta caaacctctc tatcataact   2820
acttaatagt cacacacgta ctcgtctaaa tacacatcat cgtcctacaa gttcatcaaa   2880
gtgttggaca gacaactata ccagcatgga tctcttgtat cggttctttt ctcccgctct   2940
ctcgcaataa caatgaacac tgggtcaatc atagcctaca caggtgaaca gagtagcgtt   3000
tatacagggt ttatacggtg attcctacgg caaaaatttt tcatttctaa aaaaaaaaag   3060
aaaaattttt ctttccaacg ctagaaggaa aagaaaaatc taattaaatt gatttggtga   3120
ttttctgaga gttccctttt tcatatatcg aattttgaat ataaaaggag atcgaaaaaa   3180
tttttctatt caatctgttt tctggtttta tttgatagtt tttttgtgta ttattattat   3240
ggattagtac tggtttatat gggtttttct gtataacttc tttttatttt agtttgttta   3300
atcttatttt gagttacatt atagttccct aactgcaaga gaagtaacat taaaactcga   3360
gatgggtaag gaaaagactc acgtttcgag gccgcgatta aattccaaca tggatgctga   3420
tttatatggg tataaatggg ctcgcgataa tgtcgggcaa tcaggtgcga caatctatcg   3480
attgtatggg aagcccgatg cgccagagtt gtttctgaaa catggcaaag gtagcgttgc   3540
caatgatgtt acagatgaga tggtcagact aaactggctg acggaattta tgcctcttcc   3600
```

```
gaccatcaag cattttatcc gtactcctga tgatgcatgg ttactcacca ctgcgatccc   3660

cggcaaaaca gcattccagg tattagaaga atatcctgat tcaggtgaaa atattgttga   3720

tgcgctggca gtgttcctgc gccggttgca ttcgattcct gtttgtaatt gtccttttaa   3780

cagcgatcgc gtatttcgtc tcgctcaggc gcaatcacga atgaataacg gtttggttga   3840

tgcgagtgat tttgatgacg agcgtaatgg ctggcctgtt gaacaagtct ggaaagaaat   3900

gcataagctt ttgccattct caccggattc agtcgtcact catggtgatt tctcacttga   3960

taaccttatt tttgacgagg ggaaattaat aggttgtatt gatgttggac gagtcggaat   4020

cgcagaccga taccaggatc ttgccatcct atggaactgc ctcggtgagt tttctccttc   4080

attacagaaa cggctttttc aaaaatatgg tattgataat cctgatatga ataaattgca   4140

gtttcatttg atgctcgatg agtttttcta agtttaactt gatactacta gatttttctc   4200

cttcatttat aaaatttttg gttataattg aagctttaga agtatgaaaa aatccttttt   4260

tttcattctt tgcaaccaaa ataagaagct tcttttattc attgaaatga tgaatataaa   4320

cctaacaaaa gaaaaagact cgaatatcaa acattaaaaa aaaataaaag aggttatctg   4380

ttttcccatt tagttggagt ttgcattttc taatagatag aactctcaat taatgtggat   4440

ttagtttctc tgttcgtttt tttttgtttt gttctcactg tatttacatt tctatttagt   4500

atttagttat tcatataatc tataacttcg tatagcatac attatacgaa gttatccagt   4560

gatgatacaa cgagttagcc aaggtg                                        4586
```

<210> SEQ ID NO 4
<211> LENGTH: 80
<212> TYPE: DNA
<213> ORGANISM: Artificial sequence
<220> FEATURE:
<223> OTHER INFORMATION: Primer

<400> SEQUENCE: 4

```
ttccggtttc tttgaaattt ttttgattcg gtaatctccg agcagaagga gcattgcgga     60

ttacgtattc taatgttcag                                                 80
```

<210> SEQ ID NO 5
<211> LENGTH: 81
<212> TYPE: DNA
<213> ORGANISM: Artificial sequence
<220> FEATURE:
<223> OTHER INFORMATION: Primer

<400> SEQUENCE: 5

```
gggtaataac tgatataatt aaattgaagc tctaatttgt gagtttagta caccttggct     60

aactcgttgt atcatcactg g                                               81
```

<210> SEQ ID NO 6
<211> LENGTH: 38
<212> TYPE: DNA
<213> ORGANISM: Artificial sequence
<220> FEATURE:
<223> OTHER INFORMATION: Primer

<400> SEQUENCE: 6

```
gcctcgagtt ttaatgttac ttctcttgca gttaggga                             38
```

<210> SEQ ID NO 7
<211> LENGTH: 31
<212> TYPE: DNA

<213> ORGANISM: Artificial sequence
<220> FEATURE:
<223> OTHER INFORMATION: Primer

<400> SEQUENCE: 7
gctaaattcg agtgaaacac aggaagacca g 31

<210> SEQ ID NO 8
<211> LENGTH: 90
<212> TYPE: DNA
<213> ORGANISM: Artificial sequence
<220> FEATURE:
<223> OTHER INFORMATION: Primer

<400> SEQUENCE: 8
gtattttggt agattcaatt ctctttccct ttccttttcc ttcgctcccc ttccttatca 60
gcattgcgga ttacgtattc taatgttcag 90

<210> SEQ ID NO 9
<211> LENGTH: 90
<212> TYPE: DNA
<213> ORGANISM: Artificial sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc 60
accttggcta actcgttgta tcatcactgg 90

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
tcggtgcggg cctcttcgct a 21

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
aatgtgagtt agctcactca t 21

<210> SEQ ID NO 12
<211> LENGTH: 57
<212> TYPE: DNA
<213> ORGANISM: Artificial sequence
<220> FEATURE:
<223> OTHER INFORMATION: Primer

<400> SEQUENCE: 12
aattggatcc ggcgcgccgt ttaaacggcc ggccaatgtg gctgtggttt cagggtc 57

<210> SEQ ID NO 13
<211> LENGTH: 49
<212> TYPE: DNA
<213> ORGANISM: Artificial sequence
<220> FEATURE:
<223> OTHER INFORMATION: Primer

<400> SEQUENCE: 13
aatttctaga ttaattaagc ggccgcaagg ccatgaagct tttctttc 49

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
ttctcgacgt gggccttttt cttg 24

<210> SEQ ID NO 15
<211> LENGTH: 49
<212> TYPE: DNA
<213> ORGANISM: Artificial sequence
<220> FEATURE:
<223> OTHER INFORMATION: Primer

<400> SEQUENCE: 15
tgcagcttta aataatcggt gtcactactt tgccttcgtt tatcttgcc 49

<210> SEQ ID NO 16
<211> LENGTH: 49
<212> TYPE: DNA
<213> ORGANISM: Artificial sequence
<220> FEATURE:
<223> OTHER INFORMATION: Primer

<400> SEQUENCE: 16
gagcaggcaa gataaacgaa ggcaaagtag tgacaccgat tatttaaag 49

<210> SEQ ID NO 17
<211> LENGTH: 49
<212> TYPE: DNA
<213> ORGANISM: Artificial sequence
<220> FEATURE:
<223> OTHER INFORMATION: Primer

<400> SEQUENCE: 17
tatggaccct gaaaccacag ccacattgta accaccacga cggttgttg 49

<210> SEQ ID NO 18
<211> LENGTH: 49
<212> TYPE: DNA
<213> ORGANISM: Artificial sequence
<220> FEATURE:
<223> OTHER INFORMATION: Primer

<400> SEQUENCE: 18
tttagcaaca accgtcgtgg tggttacaat gtggctgtgg tttcagggt 49

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
ccagaaaccc tatacctgtg tggacgtaag gccatgaagc tttttcttt 49

<210> SEQ ID NO 20

<211> LENGTH: 49
<212> TYPE: DNA
<213> ORGANISM: Artificial sequence
<220> FEATURE:
<223> OTHER INFORMATION: Primer

<400> SEQUENCE: 20
attggaaaga aaaagcttca tggccttacg tccacacagg tatagggtt 49

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
cataagaaca cctttggtgg ag 22

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
aggattatca ttcataagtt tc 22

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
ttcttggagc tgggacatgt ttg 23

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
tgatgatatt tcataaataa tg 22

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
atgcgtccat ctttacagtc ctg 23

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
tacgtacgga ccaatcgaag tg 22

<210> SEQ ID NO 27
<211> LENGTH: 49
<212> TYPE: DNA
<213> ORGANISM: Artificial sequence
<220> FEATURE:
<223> OTHER INFORMATION: Primer

<400> SEQUENCE: 27
aattcgtttg agtacactac taatggcttt gttggcaata tgtttttgc 49

<210> SEQ ID NO 28
<211> LENGTH: 49
<212> TYPE: DNA
<213> ORGANISM: Artificial sequence
<220> FEATURE:
<223> OTHER INFORMATION: Primer

<400> SEQUENCE: 28
atatagcaaa aacatattgc caacaaagcc attagtagtg tactcaaac 49

<210> SEQ ID NO 29
<211> LENGTH: 49
<212> TYPE: DNA
<213> ORGANISM: Artificial sequence
<220> FEATURE:
<223> OTHER INFORMATION: Primer

<400> SEQUENCE: 29
tatggaccct gaaaccacag ccacattctt gttatttata aaaagacac 49

<210> SEQ ID NO 30
<211> LENGTH: 49
<212> TYPE: DNA
<213> ORGANISM: Artificial sequence
<220> FEATURE:
<223> OTHER INFORMATION: Primer

<400> SEQUENCE: 30
ctcccgtgtc tttttataaa taacaagaat gtggctgtgg tttcagggt 49

<210> SEQ ID NO 31
<211> LENGTH: 49
<212> TYPE: DNA
<213> ORGANISM: Artificial sequence
<220> FEATURE:
<223> OTHER INFORMATION: Primer

<400> SEQUENCE: 31
taccgtaggc gtccttagga aagatagaag gccatgaagc tttttcttt 49

<210> SEQ ID NO 32
<211> LENGTH: 49
<212> TYPE: DNA
<213> ORGANISM: Artificial sequence
<220> FEATURE:
<223> OTHER INFORMATION: Primer

<400> SEQUENCE: 32
attggaaaga aaaagcttca tggccttcta tctttcctaa ggacgccta 49

<210> SEQ ID NO 33
<211> LENGTH: 21
<212> TYPE: DNA

<213> ORGANISM: Artificial sequence
<220> FEATURE:
<223> OTHER INFORMATION: Primer

<400> SEQUENCE: 33
ttattgtttg gcatttgtag c 21

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
ccaagcatct cataaaccta tg 22

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
tgtgcagatg cagatgtgag ac 22

<210> SEQ ID NO 36
<211> LENGTH: 17
<212> TYPE: DNA
<213> ORGANISM: Artificial sequence
<220> FEATURE:
<223> OTHER INFORMATION: Primer

<400> SEQUENCE: 36
agttattgat accgtac 17

<210> SEQ ID NO 37
<211> LENGTH: 19
<212> TYPE: DNA
<213> ORGANISM: Artificial sequence
<220> FEATURE:
<223> OTHER INFORMATION: Primer

<400> SEQUENCE: 37
cgagataccg taggcgtcc 19

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ttatgtatgc tcttctgact tttc 24

<210> SEQ ID NO 39
<211> LENGTH: 49
<212> TYPE: DNA
<213> ORGANISM: Artificial sequence
<220> FEATURE:
<223> OTHER INFORMATION: Primer

<400> SEQUENCE: 39
aataattaga gattaaatcg ctcatttttt gccagtttct tcaggcttc 49

-continued

<210> SEQ ID NO 40
<211> LENGTH: 49
<212> TYPE: DNA
<213> ORGANISM: Artificial sequence
<220> FEATURE:
<223> OTHER INFORMATION: Primer

<400> SEQUENCE: 40
agcctgaaga aactggcaaa aaatgagcga tttaatctct aattattag 49

<210> SEQ ID NO 41
<211> LENGTH: 49
<212> TYPE: DNA
<213> ORGANISM: Artificial sequence
<220> FEATURE:
<223> OTHER INFORMATION: Primer

<400> SEQUENCE: 41
tatggaccct gaaaccacag ccacattttt caatcattgg agcaatcat 49

<210> SEQ ID NO 42
<211> LENGTH: 49
<212> TYPE: DNA
<213> ORGANISM: Artificial sequence
<220> FEATURE:
<223> OTHER INFORMATION: Primer

<400> SEQUENCE: 42
taaaatgatt gctccaatga ttgaaaaatg tggctgtggt ttcagggtc 49

<210> SEQ ID NO 43
<211> LENGTH: 49
<212> TYPE: DNA
<213> ORGANISM: Artificial sequence
<220> FEATURE:
<223> OTHER INFORMATION: Primer

<400> SEQUENCE: 43
accgtaggtg ttgtttggga aagtggaagg ccatgaagct tttctttc 49

<210> SEQ ID NO 44
<211> LENGTH: 49
<212> TYPE: DNA
<213> ORGANISM: Artificial sequence
<220> FEATURE:
<223> OTHER INFORMATION: Primer

<400> SEQUENCE: 44
ttggaaagaa aaagcttcat ggccttccac tttcccaaac aacacctac 49

<210> SEQ ID NO 45
<211> LENGTH: 23
<212> TYPE: DNA
<213> ORGANISM: Artificial sequence
<220> FEATURE:
<223> OTHER INFORMATION: Primer

<400> SEQUENCE: 45
ttattgctta gcgttggtag cag 23

<210> SEQ ID NO 46
<211> LENGTH: 21
<212> TYPE: DNA
<213> ORGANISM: Artificial sequence
<220> FEATURE:

<223> OTHER INFORMATION: Primer

<400> SEQUENCE: 46
tttttggtgg ttccggcttc c 21

<210> SEQ ID NO 47
<211> LENGTH: 22
<212> TYPE: DNA
<213> ORGANISM: Artificial sequence
<220> FEATURE:
<223> OTHER INFORMATION: Primer

<400> SEQUENCE: 47
aaagttggca tagcggaaac tt 22

<210> SEQ ID NO 48
<211> LENGTH: 16
<212> TYPE: DNA
<213> ORGANISM: Artificial sequence
<220> FEATURE:
<223> OTHER INFORMATION: Primer

<400> SEQUENCE: 48
gtcattgaca ccatct 16

<210> SEQ ID NO 49
<211> LENGTH: 19
<212> TYPE: DNA
<213> ORGANISM: Artificial sequence
<220> FEATURE:
<223> OTHER INFORMATION: Primer

<400> SEQUENCE: 49
agagataccg taggtgttg 19

<210> SEQ ID NO 50
<211> LENGTH: 33
<212> TYPE: DNA
<213> ORGANISM: Artificial sequence
<220> FEATURE:
<223> OTHER INFORMATION: Primer

<400> SEQUENCE: 50
aattggcgcg ccatgaaagc tctggtttat cac 33

<210> SEQ ID NO 51
<211> LENGTH: 49
<212> TYPE: DNA
<213> ORGANISM: Artificial sequence
<220> FEATURE:
<223> OTHER INFORMATION: Primer

<400> SEQUENCE: 51
tgaatcatga gttttatgtt aattagctca ggcagcgcct gcgttcgag 49

<210> SEQ ID NO 52
<211> LENGTH: 49
<212> TYPE: DNA
<213> ORGANISM: Artificial sequence
<220> FEATURE:
<223> OTHER INFORMATION: Primer

<400> SEQUENCE: 52
atcctctcga acgcaggcgc tgcctgagct aattaacata aaactcatg 49

```
<210> SEQ ID NO 53
<211> LENGTH: 34
<212> TYPE: DNA
<213> ORGANISM: Artificial sequence
<220> FEATURE:
<223> OTHER INFORMATION: Primer

<400> SEQUENCE: 53

aattgtttaa acaagtaaat aaattaatca gcat                              34

<210> SEQ ID NO 54
<211> LENGTH: 49
<212> TYPE: DNA
<213> ORGANISM: Artificial sequence
<220> FEATURE:
<223> OTHER INFORMATION: Primer

<400> SEQUENCE: 54

acacaataca ataacaagaa gaacaaaatg aaagctctgg tttatcacg              49

<210> SEQ ID NO 55
<211> LENGTH: 49
<212> TYPE: DNA
<213> ORGANISM: Artificial sequence
<220> FEATURE:
<223> OTHER INFORMATION: Primer

<400> SEQUENCE: 55

agcgtataca tctgttggga aagtagaagg ccatgaagct ttttctttc              49

<210> SEQ ID NO 56
<211> LENGTH: 49
<212> TYPE: DNA
<213> ORGANISM: Artificial sequence
<220> FEATURE:
<223> OTHER INFORMATION: Primer

<400> SEQUENCE: 56

ttggaaagaa aaagcttcat ggccttctac tttcccaaca gatgtatac              49

<210> SEQ ID NO 57
<211> LENGTH: 22
<212> TYPE: DNA
<213> ORGANISM: Artificial sequence
<220> FEATURE:
<223> OTHER INFORMATION: Primer

<400> SEQUENCE: 57

ttattgttta gcgttagtag cg                                           22

<210> SEQ ID NO 58
<211> LENGTH: 72
<212> TYPE: DNA
<213> ORGANISM: Artificial sequence
<220> FEATURE:
<223> OTHER INFORMATION: Primer

<400> SEQUENCE: 58

cataatcaat ctcaaagaga acaacacaat acaataacaa gaagaacaaa atgaaagctc  60

tggtttatca cg                                                     72

<210> SEQ ID NO 59
<211> LENGTH: 21
<212> TYPE: DNA
<213> ORGANISM: Artificial sequence
<220> FEATURE:
```

-continued

<223> OTHER INFORMATION: Primer

<400> SEQUENCE: 59
taggcataat caccgaagaa g 21

<210> SEQ ID NO 60
<211> LENGTH: 21
<212> TYPE: DNA
<213> ORGANISM: Artificial sequence
<220> FEATURE:
<223> OTHER INFORMATION: Primer

<400> SEQUENCE: 60
aaaatggtaa gcagctgaaa g 21

<210> SEQ ID NO 61
<211> LENGTH: 17
<212> TYPE: DNA
<213> ORGANISM: Artificial sequence
<220> FEATURE:
<223> OTHER INFORMATION: Primer

<400> SEQUENCE: 61
agttgttaga actgttg 17

<210> SEQ ID NO 62
<211> LENGTH: 19
<212> TYPE: DNA
<213> ORGANISM: Artificial sequence
<220> FEATURE:
<223> OTHER INFORMATION: Primer

<400> SEQUENCE: 62
gacgatagcg tatacatct 19

<210> SEQ ID NO 63
<211> LENGTH: 22
<212> TYPE: DNA
<213> ORGANISM: Artificial sequence
<220> FEATURE:
<223> OTHER INFORMATION: Primer

<400> SEQUENCE: 63
cttagcctct agccatagcc at 22

<210> SEQ ID NO 64
<211> LENGTH: 23
<212> TYPE: DNA
<213> ORGANISM: Artificial sequence
<220> FEATURE:
<223> OTHER INFORMATION: Primer

<400> SEQUENCE: 64
ttagttttgc tggccgcatc ttc 23

<210> SEQ ID NO 65
<211> LENGTH: 21
<212> TYPE: DNA
<213> ORGANISM: Artificial sequence
<220> FEATURE:
<223> OTHER INFORMATION: Primer

<400> SEQUENCE: 65
cccattaata tactattgag a 21

<210> SEQ ID NO 66
<211> LENGTH: 7523
<212> TYPE: DNA
<213> ORGANISM: Artificial sequence
<220> FEATURE:
<223> OTHER INFORMATION: Plasmid

<400> SEQUENCE: 66

```
ccagcttttg ttccctttag tgagggttaa ttgcgcgctt ggcgtaatca tggtcatagc     60
tgtttcctgt gtgaaattgt tatccgctca caattccaca caacatagga gccggaagca    120
taaagtgtaa agcctggggt gcctaatgag tgaggtaact cacattaatt gcgttgcgct    180
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgtttttcca taggctccgc ccccctgacg    480
agcatcacaa aaatcgacgc tcaagtcaga ggtggcgaaa cccgacagga ctataaagat    540
accaggcgtt tccccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
```

-continued

```
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca atttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tcttttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
```

```
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
ccaacgatgt tccctccacc aaaggtgttc ttatgtagtg acaccgatta tttaaagctg   4800
cagcatacga tatatataca tgtgtatata tgtataccta tgaatgtcag taagtatgta   4860
tacgaacagt atgatactga agatgacaag gtaatgcatc attctatacg tgtcattctg   4920
aacgaggcgc gctttccttt tttctttttg ctttttcttt ttttttctct tgaactcgac   4980
ggatctatgc ggtgtgaaat accgcacaga tgcgtaagga gaaaataccg catcaggaaa   5040
ttgtaaacgt taatattttg ttaaaattcg cgttaaattt ttgttaaatc agctcatttt   5100
ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacagggcg cgtcgcgcca ttcgccattc aggctgcgca   5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
ccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagcttttat ggttatgaag aggaaaaatt   5880
ggcagtaacc tggccccaca aaccttcaaa ttaacgaatc aaattaacaa ccataggatg   5940
ataatgcgat tagtttttta gccttatttc tggggtaatt aatcagcgaa gcgatgattt   6000
ttgatctatt aacagatata taaatggaaa agctgcataa ccactttaac taatactttc   6060
aacattttca gtttgtatta cttcttattc aaatgtcata aaagtatcaa caaaaaattg   6120
ttaatatacc tctatacttt aacgtcaagg agaaaaatgt ccaatttact gcccgtacac   6180
caaaatttgc ctgcattacc ggtcgatgca acgagtgatg aggttcgcaa gaacctgatg   6240
gacatgttca gggatcgcca ggcgttttct gagcatacct ggaaaatgct tctgtccgtt   6300
tgccggtcgt gggcggcatg gtgcaagttg aataaccgga aatggtttcc cgcagaacct   6360
gaagatgttc gcgattatct tctatatctt caggcgcgcg gtctggcagt aaaaactatc   6420
cagcaacatt tgggccagct aaacatgctt catcgtcggt ccgggctgcc acgaccaagt   6480
gacagcaatg ctgtttcact ggttatgcgg cggatccgaa aagaaaacgt tgatgccggt   6540
gaacgtgcaa aacaggctct agcgttcgaa cgcactgatt tcgaccaggt tcgttcactc   6600
atggaaaata gcgatcgctg ccaggatata cgtaatctgg catttctggg gattgcttat   6660
aacaccctgt tacgtatagc cgaaattgcc aggatcaggg ttaaagatat ctcacgtact   6720
gacggtggga gaatgttaat ccatattggc agaacgaaaa cgctggttag caccgcaggt   6780
gtagagaagg cacttagcct gggggtaact aaactggtcg agcgatggat ttccgtctct   6840
```

```
ggtgtagctg atgatccgaa taactacctg ttttgccggg tcagaaaaaa tggtgttgcc   6900
gcgccatctg ccaccagcca gctatcaact cgcgccctgg aagggatttt tgaagcaact   6960
catcgattga tttacggcgc taaggatgac tctggtcaga gatacctggc ctggtctgga   7020
cacagtgccc gtgtcggagc cgcgcgagat atggcccgcg ctggagtttc aataccggag   7080
atcatgcaag ctggtggctg gaccaatgta aatattgtca tgaactatat ccgtaacctg   7140
gatagtgaaa caggggcaat ggtgcgcctg ctggaagatg gcgattagga gtaagcgaat   7200
ttcttatgat ttatgatttt tattattaaa taagttataa aaaaaataag tgtatacaaa   7260
ttttaaagtg actcttaggt tttaaaacga aaattcttat tcttgagtaa ctctttcctg   7320
taggtcaggt tgctttctca ggtatagcat gaggtcgctc ttattgacca cacctctacc   7380
ggcatgccga gcaaatgcct gcaaatcgct ccccatttca cccaattgta gatatgctaa   7440
ctccagcaat gagttgatga atctcggtgt gtattttatg tcctcagagg acaacacctg   7500
tggtccgcca ccgcggtgga gct                                           7523
```

<210> SEQ ID NO 67
<211> LENGTH: 15456
<212> TYPE: DNA
<213> ORGANISM: Artificial sequence
<220> FEATURE:
<223> OTHER INFORMATION: Template

<400> SEQUENCE: 67

```
aaagagtaat actagagata aacataaaaa atgtagaggt cgagtttaga tgcaagttca     60
aggagcgaaa ggtggatggg taggttatat agggatatag cacagagata tatagcaaag    120
agatactttt gagcaatgtt tgtggaagcg gtattcgcaa tattttagta gctcgttaca    180
gtccggtgcg tttttggttt tttgaaagtg cgtcttcaga gcgcttttgg ttttcaaaag    240
cgctctgaag ttcctatact ttctagagaa taggaacttc ggaataggaa cttcaaagcg    300
tttccgaaaa cgagcgcttc cgaaaatgca acgcgagctg cgcacataca gctcactgtt    360
cacgtcgcac ctatatctgc gtgttgcctg tatatatata tacatgagaa gaacggcata    420
gtgcgtgttt atgcttaaat gcgtacttat atgcgtctat ttatgtagga tgaaaggtag    480
tctagtacct cctgtgatat tatcccattc catgcggggt atcgtatgct tccttcagca    540
ctaccottta gctgttctat atgctgccac tcctcaattg gattagtctc atccttcaat    600
gctatcattt cctttgatat tggatcatac taagaaacca ttattatcat gacattaacc    660
tataaaaata ggcgtatcac gaggcccttt cgtctcgcgc gtttcggtga tgacggtgaa    720
aacctctgac acatgcagct cccggagacg gtcacagctt gtctgtaagc ggatgccggg    780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc ctttcccgca attttctttt tctattactc ttggcctcct ctagtacact   1020
ctatattttt ttatgcctcg gtaatgattt tcattttttt ttttccacct agcggatgac   1080
tcttttttt tcttagcgat tggcattatc acataatgaa ttatacatta tataaagtaa   1140
tgtgatttct tcgaagaata tactaaaaaa tgagcaggca agataaacga aggcaaagat   1200
gacagagcag aaagccctag taaagcgtat tacaaatgaa accaagattc agattgcgat   1260
ctctttaaag ggtggtcccc tagcgataga gcactcgatc ttcccagaaa aagaggcaga   1320
agcagtagca gaacaggcca cacaatcgca agtgattaac gtccacacag gtatagggtt   1380
```

-continued

```
tctggaccat atgatacatg ctctggccaa gcattccggc tggtcgctaa tcgttgagtg   1440
cattggtgac ttacacatag acgaccatca caccactgaa gactgcggga ttgctctcgg   1500
tcaagctttt aaagaggccc taggggccgt gcgtggagta aaaaggtttg gatcaggatt   1560
tgcgcctttg gatgaggcac tttccagagc ggtggtagat ctttcgaaca ggccgtacgc   1620
agttgtcgaa cttggtttgc aaagggagaa agtaggagat ctctcttgcg agatgatccc   1680
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
agaagccacc tcgcccaatg gtaccaacga tgttccctcc accaaaggtg ttcttatgta   1860
gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc tttttctttt ttgctttttc   2040
tttttttttc tcttgaactc gacggatcta tgcggtgtga aataccgcac agatgcgtaa   2100
ggagaaaata ccgcatcagg aaattgtaag cgttaatatt ttgttaaaat tcgcgttaaa   2160
tttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt tttggggtcg aggtgccgta aagcactaaa   2400
tcggaaccct aaagggagcc cccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
tcgccattca ggctgcgcaa ctgttgggaa gggcgcggtg cgggcctctt cgctattacg   2640
ccagctggcg aaagggggat gtgctgcaag gcgattaagt tgggtaacgc cagggttttc   2700
ccagtcacga cgttgtaaaa cgacggccag tgagcgcgcg taatacgact cactataggg   2760
cgaattgggt accgggcccc ccctcgaggt cgacggcgcg ccactggtag agagcgactt   2820
tgtatgcccc aattgcgaaa cccgcgatat ccttctcgat tctttagtac ccgaccagga   2880
caaggaaaag gaggtcgaaa cgtttttgaa gaaacaagag gaactacacg gaagctctaa   2940
agatggcaac cagccagaaa ctaagaaaat gaagttgatg gatccaactg gcaccgctgg   3000
cttgaacaac aataccagcc ttccaacttc tgtaaataac ggcggtacgc cagtgccacc   3060
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctatttttcc tttttccatt   3360
ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaacttttt tccttcttct tcgcccacgt taaattttat ccctcatgtt gtctaacgga   3660
tttctgcact tgatttatta taaaaagaca aagacataat acttctctat caatttcagt   3720
```

-continued

```
tattgttctt ccttgcgtta ttcttctgtt cttcttttc ttttgtcata tataaccata   3780
accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
tgggaaccca aggaatgcgt ttctccttga catctcgtga tattattgca gattctattg   4140
aagcagccat gggaggtcat aatgcggatg cttttgtagc cattggcggt tgtgataaaa   4200
acatgcccgg ttctgttatc gctatggcta acatggatat cccagccatt tttgcttacg   4260
gcggaacaat tgcacctggt aatttagacg gcaaagatat cgatttagtc tctgtctttg   4320
aaggtgtcgg ccattggaac cacggcgata tgaccaaaga agaagttaaa gctttggaat   4380
gtaatgcttg tcccggtcct ggaggctgcg gtggtatgta tactgctaac acaatggcga   4440
cagctattga agttttggga cttagccttc cgggttcatc ttctcacccg gctgaatccg   4500
cagaaaagaa agcagatatt gaagaagctg gtcgcgctgt tgtcaaaatg ctcgaaatgg   4560
gcttaaaacc ttctgacatt ttaacgcgtg aagcttttga agatgctatt actgtaacta   4620
tggctctggg aggttcaacc aactcaaccc ttcacctctt agctattgcc catgctgcta   4680
atgtggaatt gacacttgat gatttcaata ctttccaaga aaaagttcct catttggctg   4740
atttgaaacc ttctggtcaa tatgtattcc aagaccttta caaggtcgga ggggtaccag   4800
cagttatgaa atatctcctt aaaaatggct tccttcatgg tgaccgtatc acttgtactg   4860
gcaaaacagt cgctgaaaat ttgaaggctt ttgatgattt aacacctggt caaaaggtta   4920
ttatgccgct tgaaaatcct aaacgtgaag atggtccgct cattattctc catggtaact   4980
tggctccaga cggtgccgtt gccaaagttt ctggtgtaaa agtgcgtcgt catgtcggtc   5040
ctgctaaggt ctttaattct gaagaagaag ccattgaagc tgtcttgaat gatgatattg   5100
ttgatggtga tgttgttgtc gtacgttttg taggaccaaa gggcggtcct ggtatgcctg   5160
aaatgctttc cctttcatca atgattgttg gtaaagggca aggtgaaaaa gttgcccttc   5220
tgacagatgg ccgcttctca ggtggtactt atggtcttgt cgtgggtcat atcgctcctg   5280
aagcacaaga tggcggtcca atcgcctacc tgcaaacagg agacatagtc actattgacc   5340
aagacactaa ggaattacac tttgatatct ccgatgaaga gttaaaacat cgtcaagaga   5400
ccattgaatt gccaccgctc tattcacgcg gtatccttgg taaatatgct cacatcgttt   5460
cgtctgcttc taggggagcc gtaacagact tttggaagcc tgaagaaact ggcaaaaaat   5520
gttgtcctgg ttgctgtggt taagcggccg cgttaattca aattaattga tatagttttt   5580
taatgagtat tgaatctgtt tagaaataat ggaatattat ttttatttat ttatttatat   5640
tattggtcgg ctcttttctt ctgaaggtca atgacaaaat gatatgaagg aaataatgat   5700
ttctaaaatt ttacaacgta agatattttt acaaaagcct agctcatctt ttgtcatgca   5760
ctattttact cacgcttgaa attaacggcc agtccactgc ggagtcattt caaagtcatc   5820
ctaatcgatc tatcgttttt gatagctcat tttggagttc gcgattgtct tctgttattc   5880
acaactgttt taatttttat ttcattctgg aactcttcga gttctttgta aagtctttca   5940
tagtagctta ctttatcctc caacatattt aacttcatgt caatttcggc tcttaaattt   6000
tccacatcat caagttcaac atcatctttt aacttgaatt tattctctag ctcttccaac   6060
caagcctcat tgctccttga tttactggtg aaaagtgata cactttgcgc gcaatccagg   6120
```

-continued

```
tcaaaacttt cctgcaaaga attcaccaat ttctcgacat catagtacaa tttgttttgt   6180
tctcccatca caatttaata tacctgatgg attcttatga agcgctgggt aatggacgtg   6240
tcactctact tcgccttttt ccctactcct tttagtacgg aagacaatgc taataaataa   6300
gagggtaata ataatattat taatcggcaa aaaagattaa acgccaagcg tttaattatc   6360
agaaagcaaa cgtcgtacca atccttgaat gcttcccaat tgtatattaa gagtcatcac   6420
agcaacatat tcttgttatt aaattaatta ttattgattt ttgatattgt ataaaaaaac   6480
caaatatgta taaaaaaagt gaataaaaaa taccaagtat ggagaaatat attagaagtc   6540
tatacgttaa accacccggg ccccccctcg aggtcgacgg tatcgataag cttgatatcg   6600
aattcctgca gcccggggga tccactagtt ctagagcggc cgctctagaa ctagtaccac   6660
aggtgttgtc ctctgaggac ataaaataca caccgagatt catcaactca ttgctggagt   6720
tagcatatct acaattgggt gaaatgggga gcgatttgca ggcatttgct cggcatgccg   6780
gtagaggtgt ggtcaataag agcgacctca tgctatacct gagaaagcaa cctgacctac   6840
aggaaagagt tactcaagaa taagaatttt cgttttaaaa cctaagagtc actttaaaat   6900
ttgtatacac ttattttttt tataacttat ttaataataa aaatcataaa tcataagaaa   6960
ttcgcttact cttaattaat caggcagcgc ctgcgttcga gaggatgatc ttcatcgcct   7020
tctccttggc gccattgagg aatacctgat aggcgtgctc gatctcggcc agctcgaagc   7080
gatgggtaat catcttcttc aacggaagct tgtcggtcga ggcgaccttc atcagcatgg   7140
gcgtcgtgtt cgtgttcacc agtcccgtgg tgatcgtcag gttcttgatc cagagcttct   7200
gaatctcgaa gtcaaccttg acgccatgca cgccgacgtt ggcgatgtgc gcgccgggct   7260
tgacgatctc ctggcagatg tcccaagtcg ccggtatgcc caccgcctcg atcgcaacat   7320
cgactccctc tgccgcaatc ctatgcacgg cttcgacaac gttctccgtg ccggagttga   7380
tggtgtgcgt tgccccgagc tccttggcga gctggaggcg attctcgtcc atgtcgatca   7440
cgatgatggt cgagggggag tagaactggg cggtcaacag tacggacatg ccgacggggc   7500
ccgcgccgac aatagccacc gcatcgcccg gctggacatt cccatactgg acgccgattt   7560
cgtggccggt gggcaggatg tcgctcagca ggacggcgat ttcgtcgtca attgtctggg   7620
ggatcttgta gaggctgttg tcggcatgcg ggatgcggac gtattcggcc tgcacgccat   7680
cgatcatgta acccaggatc cacccgccgt cgcggcaatg ggagtaaagc tgcttcttgc   7740
agtagtcgca cgagccgcaa gaagtgacgc aggaaatcag gaccttgtcg cctttcttga   7800
actgcgtgac actctcgccc acttcctcga tgacgcctac cccttcatgg cccaggatgc   7860
gcccgtcggc gacctctgga ttcttgcctt tgtagatgcc gagatccgtg ccgcagatcg   7920
tggtcttcaa aacccgtact actacatccg tgggcttttg aagggtgggc ttgggcttgt   7980
cttcaagcga gatcttgtgg tcaccgtgat aaaccagagc tttcatcctc agctattgta   8040
atatgtgtgt ttgtttggat tattaagaag aataattaca aaaaaaatta caaaggaagg   8100
taattacaac agaattaaga aaggacaaga aggaggaaga gaatcagttc attatttctt   8160
ctttgttata taacaaaccc aagtagcgat ttggccatac attaaaagtt gagaaccacc   8220
ctccctggca acagccacaa ctcgttacca ttgttcatca cgatcatgaa actcgctgtc   8280
agctgaaatt tcacctcagt ggatctctct ttttattctt catcgttcca ctaacctttt   8340
tccatcagct ggcagggaac ggaaagtgga atcccattta gcgagcttcc tcttttcttc   8400
aagaaaagac gaagcttgtg tgtgggtgcg cgcgctagta tctttccaca ttaagaaata   8460
```

-continued taccataaag gttacttaga catcactatg gctatatata tatatatata tatatatgta 8520
acttagcacc atcgcgcgtg catcactgca tgtgttaacc gaaaagtttg gcgaacactt 8580
caccgacacg gtcatttaga tctgtcgtct gcattgcacg tcccttagcc ttaaatccta 8640
ggcgggagca ttctcgtgta attgtgcagc ctgcgtagca actcaacata gcgtagtcta 8700
cccagttttt caagggttta tcgttagaag attctccctt ttcttcctgc tcacaaatct 8760
taaagtcata cattgcacga ctaaatgcaa gcatgcggat cccccgggct gcaggaattc 8820
gatatcaagc ttatcgatac cgtcgactgg ccattaatct ttcccatatt agatttcgcc 8880
aagccatgaa agttcaagaa aggtctttag acgaattacc cttcatttct caaactggcg 8940
tcaagggatc ctggtatggt tttatcgttt tatttctggt tcttatagca tcgttttgga 9000
cttctctgtt cccattaggc ggttcaggag ccagcgcaga atcattcttt gaaggatact 9060
tatcctttcc aattttgatt gtctgttacg ttggacataa actgtatact agaaattgga 9120
ctttgatggt gaaactagaa gatatggatc ttgataccgg cagaaaacaa gtagatttga 9180
ctcttcgtag ggaagaaatg aggattgagc gagaaacatt agcaaaaaga tccttcgtaa 9240
caagattttt acatttctgg tgttgaaggg aaagatatga gctatacagc ggaatttcca 9300
tatcactcag attttgttat ctaatttttt ccttcccacg tccgcgggaa tctgtgtata 9360
ttactgcatc tagatatatg ttatcttatc ttggcgcgta catttaattt tcaacgtatt 9420
ctataagaaa ttgcgggagt ttttttcatg tagatgatac tgactgcacg caaatatagg 9480
catgatttat aggcatgatt tgatggctgt accgatagga acgctaagag taacttcaga 9540
atcgttatcc tggcggaaaa aattcatttg taaactttaa aaaaaaaagc caatatcccc 9600
aaaattatta agagcgcctc cattattaac taaaatttca ctcagcatcc acaatgtatc 9660
aggtatctac tacagatatt acatgtggcg aaaaagacaa gaacaatgca atagcgcatc 9720
aagaaaaaac acaaagcttt caatcaatga atcgaaaatg tcattaaaat agtatataaa 9780
ttgaaactaa gtcataaagc tataaaaaga aaatttattt aaatgcaaga tttaaagtaa 9840
attcacggcc ctgcaggcct cagctcttgt tttgttctgc aaataactta cccatctttt 9900
tcaaaacttt aggtgcaccc tcctttgcta gaataagttc tatccaatac atcctatttg 9960
gatctgcttg agcttctttc atcacggata cgaattcatt ttctgttctc acaattttgg 10020
acacaactct gtcttccgtt gccccgaaac tttctggcag ttttgagtaa ttccacatag 10080
gaatgtcatt ataactctgg ttcggaccat gaatttccct ctcaaccgtg taaccatcgt 10140
tattaatgat aaagcagatt gggtttatct tctctctaat ggctagtcct aattcttgga 10200
cagtcagttg caatgatcca tctccgataa acaataaatg tctagattct ttatctgcaa 10260
tttggctgcc tagagctgcg gggaaagtgt atcctataga tccccacaag ggttgaccaa 10320
taaaatgtga tttcgatttc agaaatatag atgaggcacc gaagaaagaa gtgccttgtt 10380
cagccacgat cgtctcatta ctttgggtca aattttcgac agcttgccac agtctatctt 10440
gtgacaacag cgcgttagaa ggtacaaaat cttcttgctt tttatctatg tacttgcctt 10500
tatattcaat ttcggacaag tcaagaagag atgatatcag ggattcgaag tcgaaatttt 10560
ggattctttc gttgaaaatt ttaccttcat cgatattcaa ggaaatcatt ttattttcat 10620
taagatggtg agtaaatgca cccgtactag aatcggtaag ctttacaccc aacataagaa 10680
taaaatcagc agattccaca aattccttca agtttggctc tgacagagta ccgttgtaaa 10740
tccccaaaaa tgagggcaat gcttcatcaa cagatgattt accaaagttc aaagtagtaa 10800
taggtaactt agtctttgaa ataaactgag taacagtctt ctctaggccg aacgatataa 10860

-continued

```
tttcatggcc tgtgattaca attggtttct tggcattctt cagactttcc tgtattttgt  10920
tcagaatctc ttgatcagat gtattcgacg tggaattttc cttcttaaga ggcaaggatg  10980
gtttttcagc cttagcggca gctacatcta caggtaaatt gatgtaaacc ggctttcttt  11040
cctttagtaa ggcagacaac actctatcaa tttcaacagt tgcattctcg gctgtcaata  11100
aagtcctggc agcagtaacc ggttcgtgca tcttcataaa gtgcttgaaa tcaccatcag  11160
ccaacgtatg gtgaacaaac ttaccttcgt tctgcacttt cgaggtagga gatcccacga  11220
tctcaacaac aggcaggttc tcagcatagg agcccgctaa gccattaact gcggataatt  11280
cgccaacacc aaatgtagtc aagaatgccg cagccttttt cgttcttgcg tacccgtcgg  11340
ccatatagga ggcatttaac tcattagcat ttcccaccca tttcatatct ttgtgtgaaa  11400
taatttgatc tagaaattgc aaattgtagt cacctggtac tccgaatatt tcttctatac  11460
ctaattcgtg taatctgtcc aacagatagt cacctactgt atacattttg tttactagtt  11520
tatgtgtgtt tattcgaaac taagttcttg gtgttttaaa actaaaaaaa agactaacta  11580
taaaagtaga atttaagaag tttaagaaat agatttacag aattacaatc aatacctacc  11640
gtctttatat acttattagt caagtagggg aataatttca gggaactggt ttcaaccttt  11700
tttttcagct ttttccaaat cagagagagc agaaggtaat agaaggtgta agaaaatgag  11760
atagatacat gcgtgggtca attgccttgt gtcatcattt actccaggca ggttgcatca  11820
ctccattgag gttgtgcccg ttttttgcct gtttgtgccc ctgttctctg tagttgcgct  11880
aagagaatgg acctatgaac tgatggttgg tgaagaaaac aatattttgg tgctgggatt  11940
cttttttttt ctggatgcca gcttaaaaag cgggctccat tatatttagt ggatgccagg  12000
aataaactgt tcacccagac acctacgatg ttatatattc tgtgtaaccc gcccccctatt  12060
ttgggcatgt acgggttaca gcagaattaa aaggctaatt ttttgactaa ataaagttag  12120
gaaaatcact actattaatt atttacgtat tctttgaaat ggcagtattg ataatgataa  12180
actcgaactg aaaaagcgtg ttttttattc aaaatgattc taactccctt acgtaatcaa  12240
ggaatctttt tgccttggcc tccgcgtcat taaacttctt gttgttgacg ctaacattca  12300
acgctagtat atattcgttt ttttcaggta agttcttttc aacgggtctt actgatgagg  12360
cagtcgcgtc tgaacctgtt aagaggtcaa atatgtcttc ttgaccgtac gtgtcttgca  12420
tgttattagc tttgggaatt tgcatcaagt cataggaaaa tttaaatctt ggctctcttg  12480
ggctcaaggt gacaaggtcc tcgaaaatag ggcgcgcccc accgcggtgg agctccagct  12540
tttgttccct ttagtgaggg ttaattgcgc gcttggcgta atcatggtca tagctgtttc  12600
ctgtgtgaaa ttgttatccg ctcacaattc cacacaacat acgagccgga agcataaagt  12660
gtaaagcctg gggtgcctaa tgagtgagct aactcacatt aattgcgttg cgctcactgc  12720
ccgctttcca gtcgggaaac ctgtcgtgcc agctgcatta atgaatcggc caacgcgcgg  12780
ggagaggcgg tttgcgtatt gggcgctctt ccgcttcctc gctcactgac tcgctgcgct  12840
cggtcgttcg gctgcggcga gcggtatcag ctcactcaaa ggcggtaata cggttatcca  12900
cagaatcagg ggataacgca ggaaagaaca tgtgagcaaa aggccagcaa aaggccagga  12960
accgtaaaaa ggccgcgttg ctggcgtttt tccataggct ccgcccccct gacgagcatc  13020
acaaaaatcg acgctcaagt cagaggtggc gaaacccgac aggactataa agataccagg  13080
cgtttccccc tggaagctcc ctcgtgcgct ctcctgttcc gaccctgccg cttaccggat  13140
acctgtccgc ctttctccct tcgggaagcg tggcgctttc tcatagctca cgctgtaggt  13200
```

-continued

```
atctcagttc ggtgtaggtc gttcgctcca agctgggctg tgtgcacgaa ccccccgttc  13260
agcccgaccg ctgcgcctta tccggtaact atcgtcttga gtccaacccg gtaagacacg  13320
acttatcgcc actggcagca gccactggta acaggattag cagagcgagg tatgtaggcg  13380
gtgctacaga gttcttgaag tggtggccta actacggcta cactagaaga acagtatttg  13440
gtatctgcgc tctgctgaag ccagttacct tcggaaaaag agttggtagc tcttgatccg  13500
gcaaacaaac caccgctggt agcggtggtt tttttgtttg caagcagcag attacgcgca  13560
gaaaaaaagg atctcaagaa gatcctttga tcttttctac ggggtctgac gctcagtgga  13620
acgaaaactc acgttaaggg attttggtca tgagattatc aaaaaggatc ttcacctaga  13680
tccttttaaa ttaaaaatga agttttaaat caatctaaag tatatatgag taaacttggt  13740
ctgacagtta ccaatgctta atcagtgagg cacctatctc agcgatctgt ctatttcgtt  13800
catccatagt tgcctgactc cccgtcgtgt agataactac gatacgggag ggcttaccat  13860
ctggccccag tgctgcaatg ataccgcgag acccacgctc accggctcca gatttatcag  13920
caataaacca gccagccgga agggccgagc gcagaagtgg tcctgcaact ttatccgcct  13980
ccatccagtc tattaattgt tgccgggaag ctagagtaag tagttcgcca gttaatagtt  14040
tgcgcaacgt tgttgccatt gctacaggca tcgtggtgtc acgctcgtcg tttggtatgg  14100
cttcattcag ctccggttcc caacgatcaa ggcgagttac atgatccccc atgttgtgca  14160
aaaaagcggt tagctccttc ggtcctccga tcgttgtcag aagtaagttg gccgcagtgt  14220
tatcactcat ggttatggca gcactgcata attctcttac tgtcatgcca tccgtaagat  14280
gcttttctgt gactggtgag tactcaacca agtcattctg agaatagtgt atgcggcgac  14340
cgagttgctc ttgcccggcg tcaatacggg ataataccgc gccacatagc agaactttaa  14400
aagtgctcat cattggaaaa cgttcttcgg ggcgaaaact ctcaaggatc ttaccgctgt  14460
tgagatccag ttcgatgtaa cccactcgtg cacccaactg atcttcagca tcttttactt  14520
tcaccagcgt ttctgggtga gcaaaaacag gaaggcaaaa tgccgcaaaa aagggaataa  14580
gggcgacacg gaaatgttga atactcatac tcttcctttt tcaatattat tgaagcattt  14640
atcagggtta ttgtctcatg agcggataca tatttgaatg tatttagaaa aataaacaaa  14700
taggggttcc gcgcacattt ccccgaaaag tgccacctga acgaagcatc tgtgcttcat  14760
tttgtagaac aaaaatgcaa cgcgagagcg ctaatttttc aaacaaagaa tctgagctgc  14820
atttttacag aacagaaatg caacgcgaaa gcgctatttt accaacgaag aatctgtgct  14880
tcatttttgt aaaacaaaaa tgcaacgcga gagcgctaat ttttcaaaca aagaatctga  14940
gctgcatttt tacagaacag aaatgcaacg cgagagcgct attttaccaa caaagaatct  15000
atacttcttt tttgttctac aaaaatgcat cccgagagcg ctatttttct aacaaagcat  15060
cttagattac ttttttttctc ctttgtgcgc tctataatgc agtctcttga taactttttg  15120
cactgtaggt ccgttaaggt tagaagaagg ctactttggt gtctattttc tcttccataa  15180
aaaaagcctg actccacttc ccgcgtttac tgattactag cgaagctgcg ggtgcatttt  15240
ttcaagataa aggcatcccc gattatattc tataccgatg tggattgcgc atactttgtg  15300
aacagaaagt gatagcgttg atgattcttc attggtcaga aaattatgaa cggtttcttc  15360
tattttgtct ctatatacta cgtataggaa atgtttacat tttcgtattg ttttcgattc  15420
actctatgaa tagttcttac tacaattttt ttgtct                            15456
```

<210> SEQ ID NO 68
<211> LENGTH: 1559

<212> TYPE: DNA
<213> ORGANISM: Artificial sequence
<220> FEATURE:
<223> OTHER INFORMATION: Template

<400> SEQUENCE: 68
gcattgcgga ttacgtattc taatgttcag taccgttcgt ataatgtatg ctatacgaag 60
ttatgcagat tgtactgaga gtgcaccata ccacctttc aattcatcat ttttttttta 120
ttcttttttt tgatttcggt ttccttgaaa tttttttgat tcggtaatct ccgaacagaa 180
ggaagaacga aggaaggagc acagacttag attggtatat atacgcatat gtagtgttga 240
agaaacatga aattgcccag tattcttaac ccaactgcac agaacaaaaa cctgcaggaa 300
acgaagataa atcatgtcga aagctacata taaggaacgt gctgctactc atcctagtcc 360
tgttgctgcc aagctattta atatcatgca cgaaaagcaa acaaacttgt gtgcttcatt 420
ggatgttcgt accaccaagg aattactgga gttagttgaa gcattaggtc ccaaaatttg 480
tttactaaaa acacatgtgg atatcttgac tgatttttcc atggagggca cagttaagcc 540
gctaaaggca ttatccgcca agtacaattt tttactcttc gaagacagaa aatttgctga 600
cattggtaat acagtcaaat tgcagtactc tgcgggtgta tacagaatag cagaatgggc 660
agacattacg aatgcacacg gtgtggtggg cccaggtatt gttagcggtt tgaagcaggc 720
ggcagaagaa gtaacaaagg aacctagagg ccttttgatg ttagcagaat tgtcatgcaa 780
gggctcccta tctactggag aatatactaa gggtactgtt gacattgcga agagcgacaa 840
agattttgtt atcggcttta ttgctcaaag agacatgggt ggaagagatg aaggttacga 900
ttggttgatt atgacacccg gtgtgggttt agatgacaag ggagacgcat tgggtcaaca 960
gtatagaacc gtggatgatg tggtctctac aggatctgac attattattg ttggaagagg 1020
actatttgca aagggaaggg atgctaaggt agagggtgaa cgttacagaa aagcaggctg 1080
ggaagcatat ttgagaagat gcggccagca aaactaaaaa actgtattat aagtaaatgc 1140
atgtatacta aactcacaaa ttagagcttc aatttaatta tatcagttat taccctatgc 1200
ggtgtgaaat accgcacaga tgcgtaagga gaaaataccg catcaggaaa ttgtaaacgt 1260
taatattttg ttaaaattcg cgttaaattt ttgttaaatc agctcatttt ttaaccaata 1320
ggccgaaatc ggcaaaatcc cttataaatc aaaagaatag accgagatag ggttgagtgt 1380
tgttccagtt tggaacaaga gtccactatt aaagaacgtg gactccaacg tcaaagggcg 1440
aaaaaccgtc tatcagggcg atggcccact acgtgaacca tcaccctaat caagataact 1500
tcgtataatg tatgctatac gaacggtacc agtgatgata caacgagtta gccaaggtg 1559

<210> SEQ ID NO 69
<211> LENGTH: 1047
<212> TYPE: DNA
<213> ORGANISM: Achromobacter xylosoxidans

<400> SEQUENCE: 69
atgaaagctc tggtttatca cggtgaccac aagatctcgc ttgaagacaa gcccaagccc 60
acccttcaaa agcccacgga tgtagtagta cgggttttga agaccacgat ctgcggcacg 120
gatctcggca tctacaaagg caagaatcca gaggtcgccg acgggcgcat cctgggccat 180
gaaggggtag gcgtcatcga ggaagtgggc gagagtgtca cgcagttcaa gaaaggcgac 240
aaggtcctga tttcctgcgt cacttcttgc ggctcgtgcg actactgcaa gaagcagctt 300
tactcccatt gccgcgacgg cgggtggatc ctgggttaca tgatcgatgg cgtgcaggcc 360
gaatacgtcc gcatcccgca tgccgacaac agcctctaca agatccccca gacaattgac 420
gacgaaatcg ccgtcctgct gagcgacatc ctgcccaccg gccacgaaat cggcgtccag 480
tatgggaatg tccagccggg cgatgcggtg gctattgtcg gcgcgggccc cgtcggcatg 540
tccgtactgt tgaccgccca gttctactcc ccctcgacca tcatcgtgat cgacatggac 600
gagaatcgcc tccagctcgc caaggagctc ggggcaacgc acaccatcaa ctccggcacg 660
gagaacgttg tcgaagccgt gcataggatt gcggcagagg gagtcgatgt tgcgatcgag 720
gcggtgggca taccggcgac ttgggacatc tgccaggaga tcgtcaagcc cggcgcgcac 780
atcgccaacg tcggcgtgca tggcgtcaag gttgacttcg agattcagaa gctctggatc 840
aagaacctga cgatcaccac gggactggtg aacacgaaca cgacgcccat gctgatgaag 900
gtcgcctcga ccgacaagct tccgttgaag aagatgatta cccatcgctt cgagctggcc 960
gagatcgagc acgcctatca ggtattcctc aatggcgcca aggagaaggc gatgaagatc 1020
atcctctcga acgcaggcgc tgcctga 1047

<210> SEQ ID NO 70
<211> LENGTH: 348
<212> TYPE: PRT
<213> ORGANISM: Achromobacter xylosoxidans

<400> SEQUENCE: 70

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

```
Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 71
<211> LENGTH: 1644
<212> TYPE: DNA
<213> ORGANISM: artificial sequence
<220> FEATURE:
<223> OTHER INFORMATION: codon optimized L. lactis kivD coding region
      for S. cerevisiae expression

<400> SEQUENCE: 71

atgtatacag taggtgacta tctgttggac agattacacg aattaggtat agaagaaata     60

ttcggagtac caggtgacta caatttgcaa tttctagatc aaattatttc acacaaagat    120

atgaaatggg tgggaaatgc taatgagtta aatgcctcct atatggccga cgggtacgca    180

agaacgaaaa aggctgcggc attcttgact acatttggtg ttggcgaatt atccgcagtt    240

aatggcttag cgggctccta tgctgagaac ctgcctgttg ttgagatcgt gggatctcct    300

acctcgaaag tgcagaacga aggtaagttt gttcaccata cgttggctga tggtgatttc    360

aagcacttta tgaagatgca cgaaccggtt actgctgcca ggactttatt gacagccgag    420

aatgcaactg ttgaaattga tagagtgttg tctgccttac taaaggaaag aaagccggtt    480

tacatcaatt tacctgtaga tgtagctgcc gctaaggctg aaaaaccatc cttgcctctt    540

aagaaggaaa attccacgtc gaatacatct gatcaagaga ttctgaacaa aatacaggaa    600

agtctgaaga atgccaagaa accaattgta atcacaggcc atgaaattat atcgttcggc    660

ctagagaaga ctgttactca gtttatttca aagactaagt tacctattac tactttgaac    720

tttggtaaat catctgttga tgaagcattg ccctcatttt tggggattta caacggtact    780

ctgtcagagc caaacttgaa ggaatttgtg gaatctgctg attttattct tatgttgggt    840

gtaaagctta ccgattctag tacgggtgca tttactcacc atcttaatga aaataaaatg    900

atttccttga atatcgatga aggtaaaatt ttcaacgaaa gaatccaaaa tttcgacttc    960

gaatccctga tatcatctct tcttgacttg tccgaaattg aatataaagg caagtacata   1020

gataaaaagc aagaagattt tgtaccttct aacgcgctgt tgtcacaaga tagactgtgg   1080

caagctgtcg aaaatttgac ccaaagtaat gagacgatcg tggctgaaca aggcacttct   1140

ttcttcggtg cctcatctat atttctgaaa tcgaaatcac attttattgg tcaacccttg   1200

tggggatcta taggatacac tttccccgca gctctaggca gccaaattgc agataaagaa   1260

tctagacatt tattgtttat cggagatgga tcattgcaac tgactgtcca agaattagga   1320

ctagccatta gagagaagat aaacccaatc tgctttatca ttaataacga tggttacacg   1380

gttgagaggg aaattcatgg tccgaaccag agttataatg acattcctat gtggaattac   1440

tcaaaactgc cagaaagttt cggggcaacg gaagacagag ttgtgtccaa aattgtgaga   1500
```

acagaaaatg aattcgtatc cgtgatgaaa gaagctcaag cagatccaaa taggatgtat 1560
tggatagaac ttattctagc aaaggagggt gcacctaaag ttttgaaaaa gatgggtaag 1620
ttatttgcag aacaaaacaa gagc 1644

<210> SEQ ID NO 72
<211> LENGTH: 753
<212> TYPE: DNA
<213> ORGANISM: Saccharomyces cerevisiae

<400> SEQUENCE: 72
gcatgcttgc atttagtcgt gcaatgtatg actttaagat ttgtgagcag gaagaaaagg 60
gagaatcttc taacgataaa cccttgaaaa actgggtaga ctacgctatg ttgagttgct 120
acgcaggctg cacaattaca cgagaatgct cccgcctagg atttaaggct aagggacgtg 180
caatgcagac gacagatcta aatgaccgtg tcggtgaagt gttcgccaaa cttttcggtt 240
aacacatgca gtgatgcacg cgcgatggtg ctaagttaca tatatatata tatagccata 300
gtgatgtcta agtaaccttt atggtatatt tcttaatgtg gaaagatact agcgcgcgca 360
cccacacaca agcttcgtct tttcttgaag aaaagaggaa gctcgctaaa tgggattcca 420
ctttccgttc cctgccagct gatggaaaaa ggttagtgga acgatgaaga ataaaaagag 480
agatccactg aggtgaaatt tcagctgaca gcgagtttca tgatcgtgat gaacaatggt 540
aacgagttgt ggctgttgcc agggagggtg gttctcaact tttaatgtat ggccaaatcg 600
ctacttgggt ttgttatata acaaagaaga aataatgaac tgattctctt cctccttctt 660
gtcctttctt aattctgttg taattacctt cctttgtaat ttttttgta attattcttc 720 ttaataatcc aaacaaacac acatattaca ata 753

<210> SEQ ID NO 73
<211> LENGTH: 316
<212> TYPE: DNA
<213> ORGANISM: Saccharomyces cerevisiae

<400> SEQUENCE: 73
gagtaagcga atttcttatg atttatgatt tttattatta aataagttat aaaaaaaata 60
agtgtataca aattttaaag tgactcttag gttttaaaac gaaaattctt attcttgagt 120
aactctttcc tgtaggtcag gttgctttct caggtatagc atgaggtcgc tcttattgac 180
cacacctcta ccggcatgcc gagcaaatgc ctgcaaatcg ctccccattt cacccaattg 240
tagatatgct aactccagca atgagttgat gaatctcggt gtgtatttta tgtcctcaga 300
ggacaacacc tgtggt 316

<210> SEQ ID NO 74
<211> LENGTH: 30
<212> TYPE: DNA
<213> ORGANISM: artificial sequence
<220> FEATURE:
<223> OTHER INFORMATION: primer

<400> SEQUENCE: 74
ggaattcaca catgaaagct ctggtttatc 30

<210> SEQ ID NO 75
<211> LENGTH: 28
<212> TYPE: DNA
<213> ORGANISM: artificial sequence
<220> FEATURE:

-continued

<223> OTHER INFORMATION: primer

<400> SEQUENCE: 75
gcgtccaggg cgtcaaagat caggcagc 28

<210> SEQ ID NO 76
<211> LENGTH: 55
<212> TYPE: DNA
<213> ORGANISM: artificial sequence
<220> FEATURE:
<223> OTHER INFORMATION: primer

<400> SEQUENCE: 76
aaacaaacac acatattaca atagctgagg atgaaagctc tggtttatca cggtg 55

<210> SEQ ID NO 77
<211> LENGTH: 55
<212> TYPE: DNA
<213> ORGANISM: artificial sequence
<220> FEATURE:
<223> OTHER INFORMATION: primer

<400> SEQUENCE: 77
atcataagaa attcgcttac tcttaattaa tcaggcagcg cctgcgttcg agagg 55

<210> SEQ ID NO 78
<211> LENGTH: 8994
<212> TYPE: DNA
<213> ORGANISM: artificial sequence
<220> FEATURE:
<223> OTHER INFORMATION: constructed plasmid

<400> SEQUENCE: 78
ctagttctag agcggccgcc accgcggtgg agctccagct tttgttccct ttagtgaggg 60
ttaattgcgc gcttggcgta atcatggtca tagctgtttc ctgtgtgaaa ttgttatccg 120
ctcacaattc cacacaacat aggagccgga agcataaagt gtaaagcctg gggtgcctaa 180
tgagtgaggt aactcacatt aattgcgttg cgctcactgc ccgctttcca gtcgggaaac 240
ctgtcgtgcc agctgcatta atgaatcggc caacgcgcgg ggagaggcgg tttgcgtatt 300
gggcgctctt ccgcttcctc gctcactgac tcgctgcgct cggtcgttcg gctgcggcga 360
gcggtatcag ctcactcaaa ggcggtaata cggttatcca cagaatcagg ggataacgca 420
ggaaagaaca tgtgagcaaa aggccagcaa aaggccagga accgtaaaaa ggccgcgttg 480
ctggcgtttt tccataggct ccgcccccct gacgagcatc acaaaaatcg acgctcaagt 540
cagaggtggc gaaacccgac aggactataa agataccagg cgtttccccc tggaagctcc 600
ctcgtgcgct ctcctgttcc gaccctgccg cttaccggat acctgtccgc ctttctccct 660
tcgggaagcg tggcgctttc tcatagctca cgctgtaggt atctcagttc ggtgtaggtc 720
gttcgctcca agctgggctg tgtgcacgaa ccccccgttc agcccgaccg ctgcgcctta 780
tccggtaact atcgtcttga gtccaacccg gtaagacacg acttatcgcc actggcagca 840
gccactggta acaggattag cagagcgagg tatgtaggcg gtgctacaga gttcttgaag 900
tggtggccta actacggcta cactagaagg acagtatttg gtatctgcgc tctgctgaag 960
ccagttacct tcggaaaaag agttggtagc tcttgatccg gcaaacaaac caccgctggt 1020
agcggtggtt tttttgtttg caagcagcag attacgcgca gaaaaaaagg atctcaagaa 1080
gatcctttga tcttttctac ggggtctgac gctcagtgga acgaaaactc acgttaaggg 1140
attttggtca tgagattatc aaaaaggatc ttcacctaga tccttttaaa ttaaaaatga 1200

-continued agttttaaat caatctaaag tatatatgag taaacttggt ctgacagtta ccaatgctta 1260
atcagtgagg cacctatctc agcgatctgt ctatttcgtt catccatagt tgcctgactc 1320
cccgtcgtgt agataactac gatacgggag ggcttaccat ctggccccag tgctgcaatg 1380
ataccgcgag acccacgctc accggctcca gatttatcag caataaacca gccagccgga 1440
agggccgagc gcagaagtgg tcctgcaact ttatccgcct ccatccagtc tattaattgt 1500
tgccgggaag ctagagtaag tagttcgcca gttaatagtt tgcgcaacgt tgttgccatt 1560
gctacaggca tcgtggtgtc acgctcgtcg tttggtatgg cttcattcag ctccggttcc 1620
caacgatcaa ggcgagttac atgatccccc atgttgtgca aaaaagcggt tagctccttc 1680
ggtcctccga tcgttgtcag aagtaagttg gccgcagtgt tatcactcat ggttatggca 1740
gcactgcata attctcttac tgtcatgcca tccgtaagat gcttttctgt gactggtgag 1800
tactcaacca agtcattctg agaatagtgt atgcggcgac cgagttgctc ttgcccggcg 1860
tcaatacggg ataataccgc gccacatagc agaactttaa aagtgctcat cattggaaaa 1920
cgttcttcgg ggcgaaaact ctcaaggatc ttaccgctgt tgagatccag ttcgatgtaa 1980
cccactcgtg cacccaactg atcttcagca tcttttactt tcaccagcgt ttctgggtga 2040
gcaaaaacag gaaggcaaaa tgccgcaaaa aagggaataa gggcgacacg gaaatgttga 2100
atactcatac tcttcctttt tcaatattat tgaagcattt atcagggtta ttgtctcatg 2160
agcggataca tatttgaatg tatttagaaa aataaacaaa taggggttcc gcgcacattt 2220
ccccgaaaag tgccacctga acgaagcatc tgtgcttcat tttgtagaac aaaaatgcaa 2280
cgcgagagcg ctaatttttc aaacaaagaa tctgagctgc atttttacag aacagaaatg 2340
caacgcgaaa gcgctatttt accaacgaag aatctgtgct tcatttttgt aaaacaaaaa 2400
tgcaacgcga gagcgctaat ttttcaaaca aagaatctga gctgcatttt tacagaacag 2460
aaatgcaacg cgagagcgct attttaccaa caaagaatct atacttcttt tttgttctac 2520
aaaaatgcat cccgagagcg ctatttttct aacaaagcat cttagattac tttttttctc 2580
ctttgtgcgc tctataatgc agtctcttga taactttttg cactgtaggt ccgttaaggt 2640
tagaagaagg ctactttggt gtctattttc tcttccataa aaaaagcctg actccacttc 2700
ccgcgtttac tgattactag cgaagctgcg ggtgcatttt ttcaagataa aggcatcccc 2760
gattatattc tataccgatg tggattgcgc atactttgtg aacagaaagt gatagcgttg 2820
atgattcttc attggtcaga aaattatgaa cggtttcttc tattttgtct ctatatacta 2880
cgtataggaa atgtttacat tttcgtattg ttttcgattc actctatgaa tagttcttac 2940
tacaattttt ttgtctaaag agtaatacta gagataaaca taaaaaatgt agaggtcgag 3000
tttagatgca agttcaagga gcgaaaggtg gatgggtagg ttatataggg atatagcaca 3060
gagatatata gcaaagagat acttttgagc aatgtttgtg gaagcggtat tcgcaatatt 3120
ttagtagctc gttacagtcc ggtgcgtttt tggttttttg aaagtgcgtc ttcagagcgc 3180
ttttggtttt caaaagcgct ctgaagttcc tatactttct agagaatagg aacttcggaa 3240
taggaacttc aaagcgtttc cgaaaacgag cgcttccgaa aatgcaacgc gagctgcgca 3300
catacagctc actgttcacg tcgcacctat atctgcgtgt tgcctgtata tatatataca 3360
tgagaagaac ggcatagtgc gtgtttatgc ttaaatgcgt acttatatgc gtctatttat 3420
gtaggatgaa aggtagtcta gtacctcctg tgatattatc ccattccatg cggggtatcg 3480
tatgcttcct tcagcactac cctttagctg ttctatatgc tgccactcct caattggatt 3540

```
agtctcatcc ttcaatgcta tcatttcctt tgatattgga tcatactaag aaaccattat   3600
tatcatgaca ttaacctata aaaataggcg tatcacgagg ccctttcgtc tcgcgcgttt   3660
cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt tttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tcctttttct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg atttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
cttcggctgt gatttcttga ccaacgtggt cacctggcaa aacgacgatc ttcttagggg   5400
cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
```

```
atgaacaagg aagtacagga caattgattt tgaagagaat gtggattttg atgtaattgt   6000
tgggattcca tttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaatttttgt taaatcagct   6180
cattttttaa ccaataggcc gaaatcggca aaatccctta taaatcaaaa gaatagaccg   6240
agatagggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
aagggggatg tgctgcaagg cgattaagtt gggtaacgcc agggttttcc cagtcacgac   6720
gttgtaaaac gacggccagt gagcgcgcgt aatacgactc actatagggc gaattgggta   6780
ccgggccccc cctcgaggtc gacggtatcg ataagcttga tatcgaattc ctgcagcccg   6840
ggggatccgc atgcttgcat ttagtcgtgc aatgtatgac tttaagattt gtgagcagga   6900
agaaaaggga gaatcttcta acgataaacc cttgaaaaac tgggtagact acgctatgtt   6960
gagttgctac gcaggctgca caattacacg agaatgctcc cgcctaggat ttaaggctaa   7020
gggacgtgca atgcagacga cagatctaaa tgaccgtgtc ggtgaagtgt tcgccaaact   7080
tttcggttaa cacatgcagt gatgcacgcg cgatggtgct aagttacata tatatatata   7140
tatatatata tagccatagt gatgtctaag taacctttat ggtatatttc ttaatgtgga   7200
aagatactag cgcgcgcacc cacacacaag cttcgtcttt tcttgaagaa aagaggaagc   7260
tcgctaaatg ggattccact ttccgttccc tgccagctga tggaaaaagg ttagtggaac   7320
gatgaagaat aaaaagagag atccactgag gtgaaatttc agctgacagc gagtttcatg   7380
atcgtgatga acaatggtaa cgagttgtgg ctgttgccag ggagggtggt tctcaacttt   7440
taatgtatgg ccaaatcgct acttgggttt gttatataac aaagaagaaa taatgaactg   7500
attctcttcc tccttcttgt cctttcttaa ttctgttgta attaccttcc tttgtaattt   7560
tttttgtaat tattcttctt aataatccaa acaaacacac atattacaat agctagctga   7620
ggatgaaggc attagtttat catggggatc acaaaatttc gttagaagac aaaccaaaac   7680
ccactctgca gaaaccaaca gacgttgtgg ttagggtgtt gaaaacaaca atttgcggta   7740
ctgacttggg aatatacaaa ggtaagaatc ctgaagtggc agatggcaga atcctgggtc   7800
atgagggcgt tggcgtcatt gaagaagtgg gcgaatccgt gacacaattc aaaaaggggg   7860
ataaagtttt aatctcctgc gttactagct gtggatcgtg tgattattgc aagaagcaac   7920
tgtattcaca ctgtagagac ggtggctgga ttttaggtta catgatcgac ggtgtccaag   7980
ccgaatacgt cagaatacca catgctgaca attcattgta taagatcccg caaactatcg   8040
atgatgaaat tgcagtacta ctgtccgata ttttacctac tggacatgaa attggtgttc   8100
aatatggtaa cgttcaacca ggcgatgctg tagcaattgt aggagcaggt cctgttggaa   8160
tgtcagtttt gttaactgct caattttact cgcctagtac cattattgtt atcgacatgg   8220
acgaaaaccg tttacaatta gcgaaggagc ttggggccac acacactatt aactccggta   8280
```

```
ctgaaaatgt tgtcgaagct gtgcatcgta tagcagccga aggagtggat gtagcaatag   8340

aagctgttgg tatacccgca acctgggaca tctgtcagga aattgtaaaa cccggcgctc   8400

atattgccaa cgtgggagtt catggtgtta aggtggactt tgaaattcaa aagttgtgga   8460

ttaagaatct aaccatcacc actggtttgg ttaacactaa tactacccca atgttgatga   8520

aggtagcctc tactgataaa ttgcctttaa agaaaatgat tactcacagg tttgagttag   8580

ctgaaatcga acacgcatat caggttttct tgaatggcgc taaagaaaaa gctatgaaga   8640

ttattctatc taatgcaggt gccgcctaat taattaagag taagcgaatt tcttatgatt   8700

tatgattttt attattaaat aagttataaa aaaaataagt gtatacaaat tttaaagtga   8760

ctcttaggtt ttaaaacgaa aattcttatt cttgagtaac tctttcctgt aggtcaggtt   8820

gctttctcag gtatagcatg aggtcgctct tattgaccac acctctaccg gcatgccgag   8880

caaatgcctg caaatcgctc cccatttcac ccaattgtag atatgctaac tccagcaatg   8940

agttgatgaa tctcggtgtg tattttatgt cctcagagga caacacctgt ggta         8994
```

```
<210> SEQ ID NO 79
<211> LENGTH: 2145
<212> TYPE: DNA
<213> ORGANISM: artificial sequence
<220> FEATURE:
<223> OTHER INFORMATION: constructed chimeric gene

<400> SEQUENCE: 79

gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatatatata    300

tatagccata gtgatgtcta agtaaccttt atggtatatt tcttaatgtg gaaagatact    360

agcgcgcgca cccacacaca agcttcgtct tttcttgaag aaaagaggaa gctcgctaaa    420

tgggattcca ctttccgttc cctgccagct gatggaaaaa ggttagtgga acgatgaaga    480

ataaaaagag agatccactg aggtgaaatt tcagctgaca gcgagtttca tgatcgtgat    540

gaacaatggt aacgagttgt ggctgttgcc agggagggtg gttctcaact tttaatgtat    600

ggccaaatcg ctacttgggt ttgttatata acaaagaaga aataatgaac tgattctctt    660

cctccttctt gtcctttctt aattctgttg taattacctt cctttgtaat ttttttgta    720

attattcttc ttaataatcc aaacaaacac acatattaca atagctagct gaggatgaag    780

gcattagttt atcatgggga tcacaaaatt tcgttagaag acaaaccaaa acccactctg    840

cagaaaccaa cagacgttgt ggttagggtg ttgaaaacaa caatttgcgg tactgacttg    900

ggaatataca aaggtaagaa tcctgaagtg gcagatggca gaatcctggg tcatgagggc    960

gttggcgtca ttgaagaagt gggcgaatcc gtgacacaat tcaaaaaggg ggataaagtt   1020

ttaatctcct gcgttactag ctgtggatcg tgtgattatt gcaagaagca actgtattca   1080

cactgtagag acggtggctg gattttaggt tacatgatcg acggtgtcca agccgaatac   1140

gtcagaatac cacatgctga caattcattg tataagatcc cgcaaactat cgatgatgaa   1200

attgcagtac tactgtccga tattttacct actggacatg aaattggtgt tcaatatggt   1260

aacgttcaac caggcgatgc tgtagcaatt gtaggagcag gtcctgttgg aatgtcagtt   1320

ttgttaactg ctcaatttta ctcgcctagt accattattg ttatcgacat ggacgaaaac   1380
```

cgtttacaat tagcgaagga gcttggggcc acacacacta ttaactccgg tactgaaaat 1440
gttgtcgaag ctgtgcatcg tatagcagcc gaaggagtgg atgtagcaat agaagctgtt 1500 ggtataccog caacctggga catctgtcag gaaattgtaa aacccggcgc tcatattgcc 1560
aacgtgggag ttcatggtgt taaggtggac tttgaaattc aaaagttgtg gattaagaat 1620
ctaaccatca ccactggttt ggttaacact aatactaccc caatgttgat gaaggtagcc 1680
tctactgata aattgccttt aaagaaaatg attactcaca ggtttgagtt agctgaaatc 1740
gaacacgcat atcaggtttt cttgaatggc gctaaagaaa aagctatgaa gattattcta 1800
tctaatgcag gtgccgccta attaattaag agtaagcgaa tttcttatga tttatgattt 1860
ttattattaa ataagttata aaaaaaataa gtgtatacaa attttaaagt gactcttagg 1920
ttttaaaacg aaaattctta ttcttgagta actctttcct gtaggtcagg ttgctttctc 1980
aggtatagca tgaggtcgct cttattgacc acacctctac cggcatgccg agcaaatgcc 2040
tgcaaatcgc tccccatttc acccaattgt agatatgcta actccagcaa tgagttgatg 2100
aatctcggtg tgtattttat gtcctcagag gacaacacct gtggt 2145

<210> SEQ ID NO 80
<211> LENGTH: 4280
<212> TYPE: DNA
<213> ORGANISM: artificial sequence
<220> FEATURE:
<223> OTHER INFORMATION: vector

<400> SEQUENCE: 80
ggggatcctc tagagtcgac ctgcaggcat gcaagcttgg cgtaatcatg gtcatagctg 60
tttcctgtgt gaaattgtta tccgctcaca attccacaca acatacgagc cggaagcata 120
aagtgtaaag cctggggtgc ctaatgagtg agctaactca cattaattgc gttgcgctca 180
ctgcccgctt tccagtcggg aaacctgtcg tgccagctgc attaatgaat cggccaacgc 240
gcggggagag gcggtttgcg tattgggcgc tcttccgctt cctcgctcac tgactcgctg 300
cgctcggtcg ttcggctgcg gcgagcggta tcagctcact caaaggcggt aatacggtta 360
tccacagaat caggggataa cgcaggaaag aacatgtgag caaaaggcca gcaaaaggcc 420
aggaaccgta aaaaggccgc gttgctggcg tttttccata ggctccgccc ccctgacgag 480
catcacaaaa atcgacgctc aagtcagagg tggcgaaacc cgacaggact ataaagatac 540
caggcgtttc cccctggaag ctccctcgtg cgctctcctg ttccgaccct gccgcttacc 600
ggatacctgt ccgcctttct cccttcggga agcgtggcgc tttctcatag ctcacgctgt 660
aggtatctca gttcggtgta ggtcgttcgc tccaagctgg gctgtgtgca cgaacccccc 720
gttcagcccg accgctgcgc cttatccggt aactatcgtc ttgagtccaa cccggtaaga 780
cacgacttat cgccactggc agcagccact ggtaacagga ttagcagagc gaggtatgta 840
ggcggtgcta cagagttctt gaagtggtgg cctaactacg gctacactag aaggacagta 900
tttggtatct gcgctctgct gaagccagtt accttcggaa aaagagttgg tagctcttga 960
tccggcaaac aaaccaccgc tggtagcggt ggtttttttg tttgcaagca gcagattacg 1020
cgcagaaaaa aaggatctca agaagatcct ttgatctttt ctacggggtc tgacgctcag 1080
tggaacgaaa actcacgtta agggattttg gtcatgagat tatcaaaaag gatcttcacc 1140
tagatccttt taaattaaaa atgaagtttt aaatcaatct aaagtatata tgagtaaact 1200
tggtctgaca gttaccaatg cttaatcagt gaggcaccta tctcagcgat ctgtctattt 1260

```
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct tcggggcgaa aactctcaag gatcttaccg   1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040
ataagggcga cacggaaatg ttgaatactc atactcttcc tttttcaata ttattgaagc   2100
atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc cggagacggt cacagcttgt   2340
ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
ttcaggctgc gcaactgttg ggaagggcga tcggtgcggg cctcttcgct attacgccag   2580
ctggcgaaag ggggatgtgc tgcaaggcga ttaagttggg taacgccagg gttttcccag   2640
tcacgacgtt gtaaaacgac ggccagtgaa ttcgagctcg gtacccccgg ctctgagaca   2700
gtagtaggtt agtcatcgct ctaccgacgc gcaggaaaag aaagaagcat tgcggattac   2760
gtattctaat gttcagcccg cggaacgcca gcaaatcacc acccatgcgc atgatactga   2820
gtcttgtaca cgctgggctt ccagtgtact gagagtgcac cataccacag cttttcaatt   2880
caattcatca tttttttttt attctttttt ttgatttcgg tttctttgaa atttttttga   2940
ttcggtaatc tccgaacaga aggaagaacg aaggaaggag cacagactta gattggtata   3000
tatacgcata tgtagtgttg aagaaacatg aaattgccca gtattcttaa cccaactgca   3060
cagaacaaaa acctgcagga aacgaagata aatcatgtcg aaagctacat ataaggaacg   3120
tgctgctact catcctagtc ctgttgctgc caagctattt aatatcatgc acgaaaagca   3180
aacaaacttg tgtgcttcat tggatgttcg taccaccaag gaattactgg agttagttga   3240
agcattaggt cccaaaattt gtttactaaa aacacatgtg gatatcttga ctgatttttc   3300
catggagggc acagttaagc cgctaaaggc attatccgcc aagtacaatt ttttactctt   3360
cgaagacaga aaatttgctg acattggtaa tacagtcaaa ttgcagtact ctgcgggtgt   3420
atacagaata gcagaatggg cagacattac gaatgcacac ggtgtggtgg gcccaggtat   3480
tgttagcggt ttgaagcagg cggcagaaga agtaacaaag gaacctagag gccttttgat   3540
gttagcagaa ttgtcatgca agggctccct atctactgga gaatatacta agggtactgt   3600
tgacattgcg aagagcgaca aagattttgt tatcggcttt attgctcaaa gagacatggg   3660
```

tggaagagat gaaggttacg attggttgat tatgacaccc ggtgtgggtt tagatgacaa 3720
gggagacgca ttgggtcaac agtatagaac cgtggatgat gtggtctcta caggatctga 3780
cattattatt gttggaagag gactatttgc aaagggaagg gatgctaagg tagagggtga 3840
acgttacaga aaagcaggct gggaagcata tttgagaaga tgcggccagc aaaactaaaa 3900
aactgtatta taagtaaatg catgtatact aaactcacaa attagagctt caatttaatt 3960
atatcagtta ttaccctatg cggtgtgaaa taccgcacag atgcgtaagg agaaaatacc 4020
gcatcaggaa attgtaaacg ttaatatttt gttaaaattc gcgttaaatt tttgttaaat 4080
cagctcattt tttaaccaat aggccgaaat cggcaaaatc ttcagcccgc ggaacgccag 4140
caaatcacca cccatgcgca tgatactgag tcttgtacac gctgggcttc cagtgatgat 4200
acaacgagtt agccaaggtg agcacggatg tctaaattag aattacgttt taatatcttt 4260
ttttccatat ctagggctag 4280

<210> SEQ ID NO 81
<211> LENGTH: 30
<212> TYPE: DNA
<213> ORGANISM: artificial sequence
<220> FEATURE:
<223> OTHER INFORMATION: primer

<400> SEQUENCE: 81
gcatgcttgc atttagtcgt gcaatgtatg 30

<210> SEQ ID NO 82
<211> LENGTH: 54
<212> TYPE: DNA
<213> ORGANISM: artificial sequence
<220> FEATURE:
<223> OTHER INFORMATION: primer

<400> SEQUENCE: 82
gaacattaga atacgtaatc cgcaatgcac tagtaccaca ggtgttgtcc tctg 54

<210> SEQ ID NO 83
<211> LENGTH: 54
<212> TYPE: DNA
<213> ORGANISM: artificial sequence
<220> FEATURE:
<223> OTHER INFORMATION: primer

<400> SEQUENCE: 83
cagaggacaa cacctgtggt actagtgcat tgcggattac gtattctaat gttc 54

<210> SEQ ID NO 84
<211> LENGTH: 28
<212> TYPE: DNA
<213> ORGANISM: artificial sequence
<220> FEATURE:
<223> OTHER INFORMATION: primer

<400> SEQUENCE: 84
caccttggct aactcgttgt atcatcac 28

<210> SEQ ID NO 85
<211> LENGTH: 100
<212> TYPE: DNA
<213> ORGANISM: artificial sequence
<220> FEATURE:
<223> OTHER INFORMATION: primer

<400> SEQUENCE: 85
ttttaagccg aatgagtgac agaaaaagcc cacaacttat caagtgatat tgaacaaagg 60
gcgaaacttc gcatgcttgc atttagtcgt gcaatgtatg 100

<210> SEQ ID NO 86
<211> LENGTH: 98
<212> TYPE: DNA
<213> ORGANISM: artificial sequence
<220> FEATURE:
<223> OTHER INFORMATION: primer

<400> SEQUENCE: 86
cccaattggt aaatattcaa caagagacgc gcagtacgta acatgcgaat tgcgtaattc 60
acggcgataa caccttggct aactcgttgt atcatcac 98

<210> SEQ ID NO 87
<211> LENGTH: 29
<212> TYPE: DNA
<213> ORGANISM: artificial sequence
<220> FEATURE:
<223> OTHER INFORMATION: primer

<400> SEQUENCE: 87
caaaagccca tgtcccacac caaaggatg 29

<210> SEQ ID NO 88
<211> LENGTH: 26
<212> TYPE: DNA
<213> ORGANISM: artificial sequence
<220> FEATURE:
<223> OTHER INFORMATION: primer

<400> SEQUENCE: 88
caccatcgcg cgtgcatcac tgcatg 26

<210> SEQ ID NO 89
<211> LENGTH: 28
<212> TYPE: DNA
<213> ORGANISM: artificial sequence
<220> FEATURE:
<223> OTHER INFORMATION: primer

<400> SEQUENCE: 89
tcggtttttg caatatgacc tgtgggcc 28

<210> SEQ ID NO 90
<211> LENGTH: 22
<212> TYPE: DNA
<213> ORGANISM: artificial sequence
<220> FEATURE:
<223> OTHER INFORMATION: primer

<400> SEQUENCE: 90
gagaagatgc ggccagcaaa ac 22

<210> SEQ ID NO 91
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg 60

-continued

```
gttaaatcac ctaatcgtgc tatgttgcgt gcaactggta tgcaagatga agactttgaa    120
aaacctatcg tcggtgtcat ttcaacttgg gctgaaaaca caccttgtaa tatccactta    180
catgactttg gtaaactagc caaagtcggt gttaaggaag ctggtgcttg gccagttcag    240
ttcggaacaa tcacggtttc tgatggaatc gccatgggaa cccaaggaat gcgtttctcc    300
ttgacatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc catttttgct tacggcggaa caattgcacc tggtaattta    480
gacggcaaag atatcgattt agtctctgtc tttgaaggtg tcggccattg gaaccacggc    540
gatatgacca aagaagaagt taaagctttg gaatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga aaccttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttccctttc atcaatgatt   1380
gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gacttttgga agcctgaaga aactggcaaa aaatgttgtc ctggttgctg tggttaagcg   1740
gccgcgttaa ttcaaattaa ttgatatagt tttttaatga gtattgaatc tgtttagaaa   1800
taatggaata ttattttat ttatttattt atattattgg tcggctcttt tcttctgaag   1860
gtcaatgaca aaatgatatg aaggaaataa tgatttctaa aattttacaa cgtaagatat   1920
ttttacaaaa gcctagctca tcttttgtca tgcactattt tactcacgct tgaaattaac   1980
ggccagtcca ctgcggagtc atttcaaagt catcctaatc gatctatcgt tttgatagc   2040
tcattttgga gttcgcgatt gtcttctgtt attcacaact gttttaattt ttatttcatt   2100
ctggaactct tcgagttctt tgtaaagtct ttcatagtag cttactttat cctccaacat   2160
atttaacttc atgtcaattt cggctcttaa attttccaca tcatcaagtt caacatcatc   2220
ttttaacttg aatttattct ctagctcttc caaccaagcc tcattgctcc ttgatttact   2280
ggtgaaaagt gatacacttt gcgcgcaatc caggtcaaaa ctttcctgca aagaattcac   2340
caatttctcg acatcatagt acaatttgtt ttgttctccc atcacaattt aatatacctg   2400
```

atggattctt atgaagcgct gggtaatgga cgtgtcactc tacttcgcct ttttccctac 2460
tccttttagt acggaagaca atgctaataa ataagagggt aataataata ttattaatcg 2520
gcaaaaaaga ttaaacgcca agcgtttaat tatcagaaag caaacgtcgt accaatcctt 2580
gaatgcttcc caattgtata ttaagagtca tcacagcaac atattcttgt tattaaatta 2640
attattattg atttttgata ttgtataaaa aaaccaaata tgtataaaaa aagtgaataa 2700
aaaataccaa gtatggagaa atatattaga agtctatacg ttaaa 2745

<210> SEQ ID NO 92
<211> LENGTH: 27
<212> TYPE: DNA
<213> ORGANISM: artificial sequence
<220> FEATURE:
<223> OTHER INFORMATION: primer

<400> SEQUENCE: 92
gacttttgga agcctgaaga aactggc 27

<210> SEQ ID NO 93
<211> LENGTH: 20
<212> TYPE: DNA
<213> ORGANISM: artificial sequence
<220> FEATURE:
<223> OTHER INFORMATION: primer

<400> SEQUENCE: 93
cttggcagca acaggactag 20

<210> SEQ ID NO 94
<211> LENGTH: 26
<212> TYPE: DNA
<213> ORGANISM: artificial sequence
<220> FEATURE:
<223> OTHER INFORMATION: primer

<400> SEQUENCE: 94
ccaggccaat tcaacagact gtcggc 26

<210> SEQ ID NO 95
<211> LENGTH: 2347
<212> TYPE: DNA
<213> ORGANISM: artificial sequence
<220> FEATURE:
<223> OTHER INFORMATION: constructed URA3 marker with flanking homologous repeat sequences for HIS gene replacement and marker excision

<400> SEQUENCE: 95
gcattgcgga ttacgtattc taatgttcag gtgctggaag aagagctgct taaccgccgc 60
gcccagggtg aagatccacg ctactttacc ctgcgtcgtc tggatttcgg cggctgtcgt 120
ctttcgctgg caacgccggt tgatgaagcc tgggacggtc cgctctcctt aaacggtaaa 180
cgtatcgcca cctcttatcc tcacctgctc aagcgttatc tcgaccagaa aggcatctct 240
tttaaatcct gcttactgaa cggttctgtt gaagtcgccc cgcgtgccgg actggcggat 300
gcgatttgcg atctggtttc caccggtgcc acgctggaag ctaacggcct gcgcgaagtc 360
gaagttatct atcgctcgaa agcctgcctg attcaacgcg atggcgaaat ggaagaatcc 420
aaacagcaac tgatcgacaa actgctgacc cgtattcagg gtgtgatcca ggcgcgcgaa 480
tcaaaataca tcatgatgca cgcaccgacc gaacgtctgg atgaagtcat ggtacctact 540
gagagtgcac cataccacag cttttcaatt caattcatca tttttttttt attctttttt 600
ttgatttcgg tttctttgaa attttttga ttcggtaatc tccgaacaga aggaagaacg 660
aaggaaggag cacagactta gattggtata tatacgcata tgtagtgttg aagaaacatg 720
aaattgccca gtattcttaa cccaactgca cagaacaaaa acctgcagga aacgaagata 780
aatcatgtcg aaagctacat ataaggaacg tgctgctact catcctagtc ctgttgctgc 840
caagctattt aatatcatgc acgaaaagca aacaaacttg tgtgcttcat tggatgttcg 900
taccaccaag gaattactgg agttagttga agcattaggt cccaaaattt gtttactaaa 960
aacacatgtg gatatcttga ctgatttttc catggagggc acagttaagc cgctaaaggc 1020
attatccgcc aagtacaatt ttttactctt cgaagacaga aaatttgctg acattggtaa 1080
tacagtcaaa ttgcagtact ctgcgggtgt atacagaata gcagaatggg cagacattac 1140
gaatgcacac ggtgtggtgg gcccaggtat tgttagcggt ttgaagcagg cggcagaaga 1200
agtaacaaag gaacctagag gccttttgat gttagcagaa ttgtcatgca agggctccct 1260
atctactgga gaatatacta agggtactgt tgacattgcg aagagcgaca aagattttgt 1320
tatcggcttt attgctcaaa gagacatggg tggaagagat gaaggttacg attggttgat 1380
tatgacaccc ggtgtgggtt tagatgacaa gggagacgca ttgggtcaac agtatagaac 1440
cgtggatgat gtggtctcta caggatctga cattattatt gttggaagag gactatttgc 1500
aaagggaagg gatgctaagg tagagggtga acgttacaga aaagcaggct gggaagcata 1560
tttgagaaga tgcggccagc aaaactaaaa aactgtatta taagtaaatg catgtatact 1620
aaactcacaa attagagctt caatttaatt atatcagtta ttaccctatg cggtgtgaaa 1680
taccgcacag atgcgtaagg agaaaatacc gcatcaggaa attgtaaacg ttaatatttt 1740
gttaaaattc gcgttaaatt tttgttaaat cagctcattt tttaaccaat aggccgaaat 1800
cggcaaaatc tctagagtgc tggaagaaga gctgcttaac cgccgcgccc agggtgaaga 1860
tccacgctac tttaccctgc gtcgtctgga tttcggcggc tgtcgtcttt cgctggcaac 1920
gccggttgat gaagcctggg acggtccgct ctccttaaac ggtaaacgta tcgccacctc 1980
ttatcctcac ctgctcaagc gttatctcga ccagaaaggc atctctttta aatcctgctt 2040
actgaacggt tctgttgaag tcgccccgcg tgccggactg gcggatgcga tttgcgatct 2100
ggtttccacc ggtgccacgc tggaagctaa cggcctgcgc gaagtcgaag ttatctatcg 2160
ctcgaaagcc tgcctgattc aacgcgatgg cgaaatggaa gaatccaaac agcaactgat 2220
cgacaaactg ctgacccgta ttcagggtgt gatccaggcg cgcgaatcaa aatacatcat 2280
gatgcacgca ccgaccgaac gtctggatga agtcatccag tgatgataca acgagttagc 2340
caaggtg 2347

<210> SEQ ID NO 96
<211> LENGTH: 80
<212> TYPE: DNA
<213> ORGANISM: artificial sequence
<220> FEATURE:
<223> OTHER INFORMATION: primer

<400> SEQUENCE: 96
cttcgaagaa tatactaaaa aatgagcagg caagataaac gaaggcaaag gcattgcgga 60
ttacgtattc taatgttcag 80

<210> SEQ ID NO 97
<211> LENGTH: 81
<212> TYPE: DNA

<213> ORGANISM: artificial sequence
<220> FEATURE:
<223> OTHER INFORMATION: primer

<400> SEQUENCE: 97
tatacacatg tatatatatc gtatgctgca gctttaaata atcggtgtca caccttggct 60
aactcgttgt atcatcactg g 81

<210> SEQ ID NO 98
<211> LENGTH: 26
<212> TYPE: DNA
<213> ORGANISM: artificial sequence
<220> FEATURE:
<223> OTHER INFORMATION: primer

<400> SEQUENCE: 98
gacttgaata atgcagcggc gcttgc 26

<210> SEQ ID NO 99
<211> LENGTH: 30
<212> TYPE: DNA
<213> ORGANISM: artificial sequence
<220> FEATURE:
<223> OTHER INFORMATION: primer

<400> SEQUENCE: 99
ccaccctctt caattagcta agatcatagc 30

<210> SEQ ID NO 100
<211> LENGTH: 25
<212> TYPE: DNA
<213> ORGANISM: artificial sequence
<220> FEATURE:
<223> OTHER INFORMATION: primer

<400> SEQUENCE: 100
aaaaattgat tctcatcgta aatgc 25

<210> SEQ ID NO 101
<211> LENGTH: 20
<212> TYPE: DNA
<213> ORGANISM: artificial sequence
<220> FEATURE:
<223> OTHER INFORMATION: primer

<400> SEQUENCE: 101
ctgcagcgag gagccgtaat 20

<210> SEQ ID NO 102
<211> LENGTH: 90
<212> TYPE: DNA
<213> ORGANISM: artificial sequence
<220> FEATURE:
<223> OTHER INFORMATION: primer

<400> SEQUENCE: 102
atggttcatt taggtccaaa aaaaccacaa gccagaaagg gttccatggc cgatgtgcca 60
gcattgcgga ttacgtattc taatgttcag 90

<210> SEQ ID NO 103
<211> LENGTH: 91
<212> TYPE: DNA
<213> ORGANISM: artificial sequence
<220> FEATURE:
<223> OTHER INFORMATION: primer

<400> SEQUENCE: 103
ttaagcaccg atgataccaa cggacttacc ttcagcaatt cttttttggg ccaaagcagc    60
caccttggct aactcgttgt atcatcactg g    91

<210> SEQ ID NO 104
<211> LENGTH: 24
<212> TYPE: DNA
<213> ORGANISM: artificial sequence
<220> FEATURE:
<223> OTHER INFORMATION: primer

<400> SEQUENCE: 104
ctaggatgag tagcagcacg ttcc    24

<210> SEQ ID NO 105
<211> LENGTH: 26
<212> TYPE: DNA
<213> ORGANISM: artificial sequence
<220> FEATURE:
<223> OTHER INFORMATION: primer

<400> SEQUENCE: 105
ccaattccgt gatgtctctt tgttgc    26

<210> SEQ ID NO 106
<211> LENGTH: 20
<212> TYPE: DNA
<213> ORGANISM: artificial sequence
<220> FEATURE:
<223> OTHER INFORMATION: primer

<400> SEQUENCE: 106
gtgaacgagt tcacaaccgc    20

<210> SEQ ID NO 107
<211> LENGTH: 22
<212> TYPE: DNA
<213> ORGANISM: artificial sequence
<220> FEATURE:
<223> OTHER INFORMATION: primer

<400> SEQUENCE: 107
gttcgttcca gaattatcac gc    22

<210> SEQ ID NO 108
<211> LENGTH: 28
<212> TYPE: DNA
<213> ORGANISM: artificial sequence
<220> FEATURE:
<223> OTHER INFORMATION: primer

<400> SEQUENCE: 108
ggatccgcat gcttgcattt agtcgtgc    28

<210> SEQ ID NO 109
<211> LENGTH: 20
<212> TYPE: DNA
<213> ORGANISM: artificial sequence
<220> FEATURE:
<223> OTHER INFORMATION: primer

<400> SEQUENCE: 109
gggatgcgga cgtattcggc    20

<210> SEQ ID NO 110
<211> LENGTH: 4506
<212> TYPE: DNA
<213> ORGANISM: Saccharomyces cerevisiae

<400> SEQUENCE: 110
atgtcgaata ccccttataa ttcatctgtg ccttccattg catccatgac ccagtcttcg 60
gtctcaagaa gtcctaacat gcatacagca actacgcccg gtgccaacac cagctctaac 120
tctccaccct tgcacatgtc ttcagattcg tccaagatca agaggaagcg taacagaatt 180
ccgctcagtt gcaccatttg tcggaaaagg aaagtcaaat gtgacaaact cagaccacac 240
tgccagcagt gcactaaaac tggggtagcc catctctgcc actacatgga acagacctgg 300
gcagaagagg cagagaaaga attgctgaag gacaacgaat taaagaagct tagggagcgc 360
gtaaaatctt tagaaaagac tctttctaag gtgcactctt ctccttcgtc taactccttg 420
aaaagttaca acactcccga gagcagcaac ctgtttatgg gtagcgatga acacaccacc 480
cttgttaatg caaatacagg ctctgcttcc tctgcctcgc atatgcatca gcaacaacag 540
caacagcagc aacaggaaca acaacaagac ttttccagaa gtgcgaacgc caacgcgaat 600
tcctcgtccc tttctatctc aaataaatat gacaacgatg agctggactt aactaaggac 660
tttgatcttt tgcatatcaa aagtaacgga accatccact taggtgccac ccactggttg 720
tctatcatga aaggtgaccc gtacctaaaa cttttgtggg gtcatatctt cgctatgagg 780
gaaaagttaa atgaatggta ctaccaaaaa aattcgtact ctaagctgaa gtcaagcaaa 840
tgtcccatca atcacgcgca agcgccgcct tctgccgctg ccgccgctac cagaaaatgt 900
cctgttgatc actccgcgtt ttcgtctggc atggtggccc caaaggagga gactcctctt 960
cctaggaaat gtccagttga ccacaccatg ttctcttcgg gaatgattcc tcccagagag 1020
gacacttcgt cccagaagag gtgtcccgtt gaccacacca tgtattccgc aggaatgatg 1080
ccgcccaagg acgagacacc ttccccattt tccactaaag ctatgataga ccataacaag 1140
catacaatga atccgcctca gtcaaaatgt cctgtggacc atagaaacta tatgaaggat 1200
tatccctctg acatggcaaa ttcttcttcg aacccggcaa gtcgttgccc cattgaccat 1260
tcaagcatga aaaatacagc ggccttacca gcttcaacgc acaataccat cccacaccac 1320
caaccacagt ccggatctca tgctcgttcg catcccgcac aaagcaggaa acatgattcc 1380
tacatgacag aatctgaagt cctcgcaaca ctttgtgaga tgttgccacc aaagcgcgtc 1440
atcgcattat tcatcgagaa attcttcaaa catttatacc ctgccattcc aatcttagat 1500
gaacagaatt tcaaaaatca cgtgaatcaa atgctttcgt tgtcttcgat gaatcccaca 1560
gttaacaact ttggtatgag catgccatct tcatctacac tagagaacca acccataaca 1620
caaatcaatc ttccaaaact ttccgattct tgtaacttag gtattctgat aataatcttg 1680
agattgacat ggctatccat accttctaat tcctgcgaag tcgacctggg agaagaaagt 1740
ggctcatttt tagtgcccaa cgaatctagc aatatgtctg catctgcatt gacctcgatg 1800
gctaaagaag aatcacttct gctaaagcat gagacaccgg tcgaggcact ggagctatgt 1860
caaaaatact tgattaaatt cgatgaactt tctagtattt ccaataacaa cgttaattta 1920
accacggtgc agtttgccat tttttacaac ttctatatga aaagtgcctc taatgatttg 1980
actaccttga caaataccaa caacactggc atggccaatc ctggtcacga ttccgagtct 2040
caccagatcc tattgtccaa tattactcaa atggccttta gttgtgggtt acacagagac 2100
cctgataatt ttcctcaatt aaacgctacc attccagcaa ccagccagga cgtgtctaac 2160

-continued

```
aacgggagca aaaaggcaaa ccctagcacc aatccaactt tgaataacaa catgtctgct   2220
gccactacca acagcagtag cagatctggc agtgctgatt caagaagtgg ttctaaccct   2280
gtgaacaaga aggaaaatca ggttagtatc gaaagattta aacacacttg gaggaaaatt   2340
tggtattaca ttgttagcat ggatgttaac caatctcttt ccctggggag ccctcgacta   2400
ctaagaaatc tgagggattt cagcgataca aagctaccaa gtgcgtcaag gattgattat   2460
gttcgcgata tcaaagagtt aatcattgtg aagaatttta ctcttttttt ccaaattgat   2520
ttgtgtatta ttgctgtatt aaatcacatt ttgaatgttt ctttagcaag aagcgtgaga   2580
aaatttgaac tggattcatt gattaattta ttgaaaaatc tgacctatgg tactgagaat   2640
gtcaatgatg tagtgagctc cttgatcaac aaagggttat taccaacttc ggaaggtggt   2700
tctgtagatt caaataatga tgaaatttac ggtctaccga aactacccga tattctaaac   2760
catggtcaac ataaccaaaa cttgtatgct gatggaagaa atacttctag tagtgatata   2820
gataagaaat tggaccttcc tcacgaatct acaacgagag ctctattctt ttccaagcat   2880
atgacaatta gaatgttgct gtacttattg aactacattt tgtttactca ttatgaacca   2940
atgggcagtg aagatcctgg tactaatatc ctagctaagg agtacgctca agaggcatta   3000
aattttgcca tggatggcta cagaaactgc atgattttct tcaacaatat cagaaacacc   3060
aattcactat tcgattacat gaatgttatc ttgtcttacc cttgtttgga cattggacat   3120
cgttctttac aatttatcgt ttgtttgatc ctgagagcta aatgtggccc attgactggt   3180
atgcgtgaat catcgatcat tactaatggt acatcaagtg gatttaatag ttcggtagaa   3240
gatgaggacg tcaaagttaa acaagaatct tctgatgaat tgaaaaaaga cgatttcatg   3300
aaagatgtaa atttggattc aggcgattca ttagcagaga ttctaatgtc aagaatgctg   3360
ctatttcaaa aactaacaaa acaactatca aagaagtaca actacgctat tcgtatgaac   3420
aaatccactg gattctttgt ctctttacta gatacacctt caaagaaatc agactcgaaa   3480
tcgggtggta gttcattcat gttgggtaat tggaaacatc caaaggtttc aaacatgagc   3540
ggatttcttg ctggtgacaa agaccaatta cagaaatgcc ccgtgtacca agatgcgctg   3600
gggtttgtta gtccaaccgg tgctaatgaa ggttctgctc cgatgcaagg catgtcctta   3660
cagggctcta ctgctaggat gggagggacc cagttgccac caattagatc atacaaacct   3720
atcacgtaca caagtagtaa tctacgtcgt atgaatgaaa cgggtgaggc agaagctaag   3780
agaagaagat ttaatgatgg ctatattgat aataatagta acaacgatat acctagagga   3840
atcagcccaa aaccttcaaa tgggctatca tcggtgcagc cactattatc gtcattttcc   3900
atgaaccagc taaacggggg taccattcca acggttccat cgttaaccaa cattacttca   3960
caaatgggag ctttaccatc tttagatagg atcaccacta atcaaataaa tttgccagac   4020
ccatctagag atgaagcatt tgacaactcc atcaagcaaa tgacgcctat gacaagtgca   4080
ttcatgaatg ctaatactac aattccaagt tcaactttaa acgggaatat gaacatgaat   4140
ggagctggaa ctgcgaatac agatacaagt gccaacggca gtgctttatc gacactgaca   4200
agcccacaag gctcagactt agcatccaat tctgctacac agtataaacc tgacttagaa   4260
gactttttga tgcaaaattc taactttaat gggctaatga taaatccttc cagtctggta   4320
gaagttgttg gtggatacaa cgatcctaat aaccttggaa gaaatgacgc ggttgatttt   4380
ctacccgttg ataatgttga aattgatggt gttggaataa aaatcaacta tcatctacta   4440
actagtattt acgttactag tatattatca tatacggtgt tagaagatga cgcaaatgat   4500
```

-continued gagaaa 4506

<210> SEQ ID NO 111
<211> LENGTH: 99
<212> TYPE: DNA
<213> ORGANISM: artificial sequence
<220> FEATURE:
<223> OTHER INFORMATION: primer

<400> SEQUENCE: 111
tcctttctca attattattt tctactcata acctcacgca aaataacaca gtcaaatcaa 60
tcaaagtatg actgacaaaa aaactcttaa agacttaag 99

<210> SEQ ID NO 112
<211> LENGTH: 77
<212> TYPE: DNA
<213> ORGANISM: artificial sequence
<220> FEATURE:
<223> OTHER INFORMATION: primer

<400> SEQUENCE: 112
gaacattaga atacgtaatc cgcaatgctt ctttcttttc cgtttaacgt atagacttct 60
aatatatttc tccatac 77

<210> SEQ ID NO 113
<211> LENGTH: 45
<212> TYPE: DNA
<213> ORGANISM: artificial sequence
<220> FEATURE:
<223> OTHER INFORMATION: primer

<400> SEQUENCE: 113
aaacggaaaa gaaagaagca ttgcggatta cgtattctaa tgttc 45

<210> SEQ ID NO 114
<211> LENGTH: 88
<212> TYPE: DNA
<213> ORGANISM: artificial sequence
<220> FEATURE:
<223> OTHER INFORMATION: primer

<400> SEQUENCE: 114
tatttttcgt tacataaaaa tgcttataaa actttaacta ataattagag attaaatcgc 60
caccttggct aactcgttgt atcatcac 88

<210> SEQ ID NO 115
<211> LENGTH: 1713
<212> TYPE: DNA
<213> ORGANISM: Streptococcus mutans

<400> SEQUENCE: 115
atgactgaca aaaaaactct taaagactta agaaatcgta gttctgttta cgattcaatg 60
gttaaatcac ctaatcgtgc tatgttgcgt gcaactggta tgcaagatga agactttgaa 120
aaacctatcg tcggtgtcat ttcaacttgg gctgaaaaca caccttgtaa tatccactta 180
catgactttg gtaaactagc caaagtcggt gttaaggaag ctggtgcttg gccagttcag 240
ttcggaacaa tcacggtttc tgatggaatc gccatgggaa cccaaggaat gcgtttctcc 300
ttgacatctc gtgatattat tgcagattct attgaagcag ccatgggagg tcataatgcg 360
gatgcttttg tagccattgg cggttgtgat aaaaacatgc ccggttctgt tatcgctatg 420
gctaacatgg atatcccagc catttttgct tacggcggaa caattgcacc tggtaattta 480

```
gacggcaaag atatcgattt agtctctgtc tttgaaggtg tcggccattg gaaccacggc    540
gatatgacca aagaagaagt taaagctttg gaatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga aaccttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttccctttc atcaatgatt   1380
gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gacttttgga agcctgaaga aactggcaaa aaa                                1713
```

<210> SEQ ID NO 116
<211> LENGTH: 571
<212> TYPE: PRT
<213> ORGANISM: Streptococcus mutans

<400> SEQUENCE: 116

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
```

-continued

```
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570
```

<210> SEQ ID NO 117
<211> LENGTH: 548
<212> TYPE: PRT
<213> ORGANISM: Lactococcus lactis

<400> SEQUENCE: 117

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
```

```
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545


<210> SEQ ID NO 118
<211> LENGTH: 1125
<212> TYPE: DNA
<213> ORGANISM: artificial sequence
<220> FEATURE:
<223> OTHER INFORMATION: horse ADH coding region codon optimized for
      S. cerevisiae expression

<400> SEQUENCE: 118

atgtcaacag ccggtaaagt tattaagtgt aaagcggcag ttttgtggga agagaaaaag      60

ccgtttagca tagaagaagt agaagtagcg ccaccaaaag cacacgaggt tagaatcaag     120

atggttgcca ccggaatctg tagatccgac gaccatgtgg tgagtggcac tctagttact     180

cctttgccag taatcgcggg acacgaggct gccggaatcg ttgaatccat aggtgaaggt     240

gttaccactg ttcgtcctgg tgataaagtg atcccactgt tcactcctca atgtggtaag     300

tgtagagtct gcaaacatcc tgagggtaat ttctgcctta aaaatgattt gtctatgcct     360

agaggtacta tgcaggatgg tacaagcaga tttacatgca gagggaaacc tatacaccat     420

ttccttggta cttctacatt ttcccaatac acagtggtgg acgagatatc tgtcgctaaa     480

atcgatgcag cttcaccact ggaaaaagtt tgcttgatag ggtgcggatt ttccaccggt     540

tacggttccg cagttaaagt tgcaaaggtt acacagggtt cgacttgtgc agtattcggt     600

ttaggaggag taggactaag cgttattatg ggtgtaaaag ctgcaggcgc agcgaggatt     660

ataggtgtag acatcaataa ggacaaattt gcaaaagcta aggaggtcgg ggctactgaa     720

tgtgttaacc ctcaagatta taagaaacca atacaagaag tccttactga aatgtcaaac     780

ggtggagttg atttctcttt tgaagttata ggccgtcttg atactatggt aactgcgttg     840

tcctgctgtc aagaggcata tggagtcagt gtgatcgtag gtgttcctcc tgattcacaa     900

aatttgtcga tgaatcctat gctgttgcta agcggtcgta catggaaggg agctatattt     960

ggcggtttta agagcaagga tagtgttcca aaacttgttg ccgactttat ggcgaagaag    1020
```

```
tttgctcttg atcctttaat tacacatgta ttgccattcg agaaaatcaa tgaagggttt   1080

gatttgttaa gaagtggtga atctattcgt acaattttaa ctttt                   1125


<210> SEQ ID NO 119
<211> LENGTH: 375
<212> TYPE: PRT
<213> ORGANISM: Equus caballus

<400> SEQUENCE: 119

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350
```

```
Phe Glu Lys Ile Asn Glu Gly Phe Asp Leu Leu Arg Ser Gly Glu Ser
        355                 360                 365

Ile Arg Thr Ile Leu Thr Phe
    370                 375


<210> SEQ ID NO 120
<211> LENGTH: 643
<212> TYPE: DNA
<213> ORGANISM: Saccharomyces cerevisiae

<400> SEQUENCE: 120

gaaatgaata acaatactga cagtactaaa taattgccta cttggcttca catacgttgc     60

atacgtcgat atagataata atgataatga cagcaggatt atcgtaatac gtaatagttg    120

aaaatctcaa aatgtgtggg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360

tctgttctct tctgactttg actcctcaaa aaaaaaaaat ctacaatcaa cagatcgctt    420

caattacgcc ctcacaaaaa ctttttttcct tcttcttcgc ccacgttaaa ttttatccct    480

catgttgtct aacggatttc tgcacttgat ttattataaa aagacaaaga cataatactt    540

ctctatcaat ttcagttatt gttcttcctt gcgttattct tctgttcttc tttttctttt    600

gtcatatata accataacca agtaatacat attcaaatct aga                      643


<210> SEQ ID NO 121
<211> LENGTH: 9089
<212> TYPE: DNA
<213> ORGANISM: artificial sequence
<220> FEATURE:
<223> OTHER INFORMATION: constructed plasmid

<400> SEQUENCE: 121

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020
```

```
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggccccccct cgaggtcgac tggccattaa   2040
tctttcccat attagatttc gccaagccat gaaagttcaa gaaaggtctt tagacgaatt   2100
acccttcatt tctcaaactg gcgtcaaggg atcctggtat ggttttatcg ttttatttct   2160
ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttc atgtagatga   2640
tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
caagaacaat gcaatagcgc atcaagaaaa aacacaaagc tttcaatcaa tgaatcgaaa   2940
atgtcattaa aatagtatat aaattgaaac taagtcataa agctataaaa agaaaattta   3000
tttaaatgca agatttaaag taaattcacg gccctgcagg ccctaacctg ctaggacaca   3060
acgtctttgc ctggtaaagt ttctagctga cgtgattcct tcacctgtgg atccggcaat   3120
tgtaaaggtt gtgaaaccct cagcttcata accgacacct gcaaatgact ttgcattctt   3180
aacaaagata gttgtatcaa tttcacgttc gaatctatta aggttatcga tgttcttaga   3240
ataaatgtag gcggaatgtt ttctattctg ctcagctatc ttggcgtatt taatggcttc   3300
atcaatgtcc ttcactctaa ctataggcaa aattggcatc atcaactccg tcataacgaa   3360
```

```
cggatggttt gcgttgactt cacaaataat acactttaca ttacttggtg actctacatc   3420
tatttcatcc aaaaacagtt tagcgtcctt accaacccac ttcttattaa tgaaatattc   3480
ttgagtttca ttgttctttt gaagaacaag gtctatcagc ttggatactt ggtcttcatt   3540
gataatgacg gcgttgtttt tcaacatgtt agagatcaga tcatctgcaa cgttttcaaa   3600
cacgaacact tctttttccg cgatacaagg aagattgttg tcaaacgaac aaccttcaat   3660
aatgcttctg ccggccttct cgatatctgc tgtatcgtct acaataaccg gaggattacc   3720
cgcgccagct ccgatggcct tttaccaga attaagaagg gtttttacca tacccgggcc   3780
acccgtaccg cacaacaatt ttatggatgg atgtttgata atagcgtcta aactttccat   3840
agttgggttc tttatagtag tgacaaggtt ttcaggtcca ccacagctaa ttatggcttt   3900
gtttatcatt tctactgcga aagcgacaca ctttttggcg catgggtgac cattaaatac   3960
aactgcattc cccgcagcta tcatacctat agaattgcag ataacggttt ctgttggatt   4020
cgtgcttgga gttatagcgc cgataactcc gtatggactc atttcaacca ctgttagtcc   4080
attatcgccg gaccatgctg ttgttgtcag atcttcagtg cctggggtat acttggccac   4140
taattcatgt ttcaagattt tatcctcata ccttcccatg tgggtttcct ccaggatcat   4200
tgtggctaag acctctttat tctgtaatgc ggcttttctt atttcggtga ttattttctc   4260
tctttgttcc tttgtgtagt gtagggaaag aatcttttgt gcatgtactg cagaagaaat   4320
ggcattctca acattttcaa atactccaaa acatgaagag ttatctttgt aattctttaa   4380
gttgatgttt tcaccattag tcttcacttt caagtctttg gtggttggga ttaaggtatc   4440
tttatccatg gtgtttgttt atgtgtgttt attcgaaact aagttcttgg tgttttaaaa   4500
ctaaaaaaaa gactaactat aaaagtagaa tttaagaagt ttaagaaata gatttacaga   4560
attacaatca atacctaccg tctttatata cttattagtc aagtagggga ataatttcag   4620
ggaactggtt tcaacctttt ttttcagctt tttccaaatc agagagagca gaaggtaata   4680
gaaggtgtaa gaaaatgaga tagatacatg cgtgggtcaa ttgccttgtg tcatcattta   4740
ctccaggcag gttgcatcac tccattgagg ttgtgcccgt tttttgcctg tttgtgcccc   4800
tgttctctgt agttgcgcta agagaatgga cctatgaact gatggttggt gaagaaaaca   4860
atattttggt gctgggattc tttttttttc tggatgccag cttaaaaagc gggctccatt   4920
atatttagtg gatgccagga ataaactgtt cacccagaca cctacgatgt tatatattct   4980
gtgtaacccg ccccctattt tgggcatgta cgggttacag cagaattaaa aggctaattt   5040
tttgactaaa taaagttagg aaaatcacta ctattaatta tttacgtatt ctttgaaatg   5100
gcagtattga taatgataaa ctcgaactga aaaagcgtgt tttttattca aaatgattct   5160
aactccctta cgtaatcaag gaatcttttt gccttggcct ccgcgtcatt aaacttcttg   5220
ttgttgacgc taacattcaa cgctagtata tattcgtttt tttcaggtaa gttcttttca   5280
acgggtctta ctgatgaggc agtcgcgtct gaacctgtta agaggtcaaa tatgtcttct   5340
tgaccgtacg tgtcttgcat gttattagct ttgggaattt gcatcaagtc ataggaaaat   5400
ttaaatcttg gctctcttgg gctcaaggtg acaaggtcct cgaaaatagg gcgcgcccca   5460
ccgcggtgga gctccagctt ttgttccctt tagtgagggt taattgcgcg cttggcgtaa   5520
tcatggtcat agctgtttcc tgtgtgaaat tgttatccgc tcacaattcc acacaacata   5580
ggagccggaa gcataaagtg taaagcctgg ggtgcctaat gagtgaggta actcacatta   5640
attgcgttgc gctcactgcc cgctttccag tcgggaaacc tgtcgtgcca gctgcattaa   5700
tgaatcggcc aacgcgcggg gagaggcggt ttgcgtattg ggcgctcttc cgcttcctcg   5760
```

ctcactgact cgctgcgctc ggtcgttcgg ctgcggcgag cggtatcagc tcactcaaag 5820
gcggtaatac ggttatccac agaatcaggg gataacgcag gaaagaacat gtgagcaaaa 5880
ggccagcaaa aggccaggaa ccgtaaaaag gccgcgttgc tggcgttttt ccataggctc 5940
cgcccccctg acgagcatca caaaaatcga cgctcaagtc agaggtggcg aaacccgaca 6000
ggactataaa gataccaggc gtttccccct ggaagctccc tcgtgcgctc tcctgttccg 6060
accctgccgc ttaccggata cctgtccgcc tttctccctt cgggaagcgt ggcgctttct 6120
catagctcac gctgtaggta tctcagttcg gtgtaggtcg ttcgctccaa gctgggctgt 6180
gtgcacgaac cccccgttca gcccgaccgc tgcgccttat ccggtaacta tcgtcttgag 6240
tccaacccgg taagacacga cttatcgcca ctggcagcag ccactggtaa caggattagc 6300
agagcgaggt atgtaggcgg tgctacagag ttcttgaagt ggtggcctaa ctacggctac 6360
actagaagga cagtatttgg tatctgcgct ctgctgaagc cagttacctt cggaaaaaga 6420
gttggtagct cttgatccgg caaacaaacc accgctggta gcggtggttt ttttgtttgc 6480
aagcagcaga ttacgcgcag aaaaaaagga tctcaagaag atcctttgat cttttctacg 6540
gggtctgacg ctcagtggaa cgaaaactca cgttaaggga ttttggtcat gagattatca 6600
aaaaggatct tcacctagat ccttttaaat taaaaatgaa gttttaaatc aatctaaagt 6660
atatatgagt aaacttggtc tgacagttac caatgcttaa tcagtgaggc acctatctca 6720
gcgatctgtc tatttcgttc atccatagtt gcctgactcc ccgtcgtgta gataactacg 6780
atacgggagg gcttaccatc tggccccagt gctgcaatga taccgcgaga cccacgctca 6840
ccggctccag atttatcagc aataaaccag ccagccggaa gggccgagcg cagaagtggt 6900
cctgcaactt tatccgcctc catccagtct attaattgtt gccgggaagc tagagtaagt 6960
agttcgccag ttaatagttt gcgcaacgtt gttgccattg ctacaggcat cgtggtgtca 7020
cgctcgtcgt ttggtatggc ttcattcagc tccggttccc aacgatcaag gcgagttaca 7080
tgatccccca tgttgtgcaa aaaagcggtt agctccttcg gtcctccgat cgttgtcaga 7140
agtaagttgg ccgcagtgtt atcactcatg gttatggcag cactgcataa ttctcttact 7200
gtcatgccat ccgtaagatg cttttctgtg actggtgagt actcaaccaa gtcattctga 7260
gaatagtgta tgcggcgacc gagttgctct tgcccggcgt caatacggga taataccgcg 7320
ccacatagca gaactttaaa agtgctcatc attggaaaac gttcttcggg gcgaaaactc 7380
tcaaggatct taccgctgtt gagatccagt tcgatgtaac ccactcgtgc acccaactga 7440
tcttcagcat cttttacttt caccagcgtt tctgggtgag caaaaacagg aaggcaaaat 7500
gccgcaaaaa agggaataag ggcgacacgg aaatgttgaa tactcatact cttccttttt 7560
caatattatt gaagcattta tcagggttat tgtctcatga gcggatacat atttgaatgt 7620
atttagaaaa ataaacaaat aggggttccg cgcacatttc cccgaaaagt gccacctgaa 7680
cgaagcatct gtgcttcatt ttgtagaaca aaaatgcaac gcgagagcgc taatttttca 7740
aacaaagaat ctgagctgca tttttacaga acagaaatgc aacgcgaaag cgctatttta 7800
ccaacgaaga atctgtgctt catttttgta aaacaaaaat gcaacgcgag agcgctaatt 7860
tttcaaacaa agaatctgag ctgcattttt acagaacaga aatgcaacgc gagagcgcta 7920
ttttaccaac aaagaatcta tacttctttt ttgttctaca aaaatgcatc ccgagagcgc 7980
tatttttcta acaaagcatc ttagattact ttttttctcc tttgtgcgct ctataatgca 8040
gtctcttgat aactttttgc actgtaggtc cgttaaggtt agaagaaggc tactttggtg 8100

-continued

```
tctattttct cttccataaa aaaagcctga ctccacttcc cgcgtttact gattactagc   8160

gaagctgcgg gtgcattttt tcaagataaa ggcatccccg attatattct ataccgatgt   8220

ggattgcgca tactttgtga acagaaagtg atagcgttga tgattcttca ttggtcagaa   8280

aattatgaac ggtttcttct attttgtctc tatatactac gtataggaaa tgtttacatt   8340

ttcgtattgt tttcgattca ctctatgaat agttcttact acaatttttt tgtctaaaga   8400

gtaatactag agataaacat aaaaaatgta gaggtcgagt ttagatgcaa gttcaaggag   8460

cgaaaggtgg atgggtaggt tatataggga tatagcacag agatatatag caaagagata   8520

cttttgagca atgtttgtgg aagcggtatt cgcaatattt tagtagctcg ttacagtccg   8580

gtgcgttttt ggttttttga aagtgcgtct tcagagcgct tttggttttc aaaagcgctc   8640

tgaagttcct atactttcta gagaatagga acttcggaat aggaacttca aagcgtttcc   8700

gaaaacgagc gcttccgaaa atgcaacgcg agctgcgcac atacagctca ctgttcacgt   8760

cgcacctata tctgcgtgtt gcctgtatat atatatacat gagaagaacg gcatagtgcg   8820

tgtttatgct taaatgcgta cttatatgcg tctatttatg taggatgaaa ggtagtctag   8880

tacctcctgt gatattatcc cattccatgc ggggtatcgt atgcttcctt cagcactacc   8940

ctttagctgt tctatatgct gccactcctc aattggatta gtctcatcct tcaatgctat   9000

catttccttt gatattggat catactaaga aaccattatt atcatgacat taacctataa   9060

aaataggcgt atcacgaggc cctttcgtc                                     9089
```

<210> SEQ ID NO 122
<211> LENGTH: 1023
<212> TYPE: DNA
<213> ORGANISM: Saccharomyces cerevisiae

<400> SEQUENCE: 122

```
caccgcggtg gggcgcgccc tattttcgag gaccttgtca ccttgagccc aagagagcca     60

agatttaaat tttcctatga cttgatgcaa attcccaaag ctaataacat gcaagacacg    120

tacggtcaag aagacatatt tgacctctta acaggttcag acgcgactgc ctcatcagta    180

agacccgttg aaaagaactt acctgaaaaa aacgaatata tactagcgtt gaatgttagc    240

gtcaacaaca agaagtttaa tgacgcggag gccaaggcaa aaagattcct tgattacgta    300

agggagttag aatcattttg aataaaaaac acgctttttc agttcgagtt tatcattatc    360

aatactgcca tttcaaagaa tacgtaaata attaatagta gtgattttcc taactttatt    420

tagtcaaaaa attagccttt taattctgct gtaacccgta catgcccaaa atagggggcg    480

ggttacacag aatatataac atcgtaggtg tctgggtgaa cagtttattc ctggcatcca    540

ctaaatataa tggagcccgc tttttaagct ggcatccaga aaaaaaaaga atcccagcac    600

caaaatattg ttttcttcac caaccatcag ttcataggtc cattctctta gcgcaactac    660

agagaacagg ggcacaaaca ggcaaaaaac gggcacaacc tcaatggagt gatgcaacct    720

gcctggagta aatgatgaca caaggcaatt gacccacgca tgtatctatc tcattttctt    780

acaccttcta ttaccttctg ctctctctga tttggaaaaa gctgaaaaaa aaggttgaaa    840

ccagttccct gaaattattc ccctacttga ctaataagta tataaagacg gtaggtattg    900

attgtaattc tgtaaatcta tttcttaaac ttcttaaatt ctacttttat agttagtctt    960

ttttttagtt ttaaaacacc aagaacttag tttcgaataa acacacataa actagtaaac   1020

aaa                                                                 1023
```

<210> SEQ ID NO 123
<211> LENGTH: 21
<212> TYPE: DNA
<213> ORGANISM: artificial sequence
<220> FEATURE:
<223> OTHER INFORMATION: primer

<400> SEQUENCE: 123
caaaagctga gctccaccgc g 21

<210> SEQ ID NO 124
<211> LENGTH: 44
<212> TYPE: DNA
<213> ORGANISM: artificial sequence
<220> FEATURE:
<223> OTHER INFORMATION: primer

<400> SEQUENCE: 124
gtttactagt ttatgtgtgt ttattcgaaa ctaagttctt ggtg 44

<210> SEQ ID NO 125

<400> SEQUENCE: 125

000

<210> SEQ ID NO 126
<211> LENGTH: 39
<212> TYPE: DNA
<213> ORGANISM: artificial sequence
<220> FEATURE:
<223> OTHER INFORMATION: primer

<400> SEQUENCE: 126
cacacatatt acaatagcta gctgaggatg aaagctctg 39

<210> SEQ ID NO 127
<211> LENGTH: 39
<212> TYPE: DNA
<213> ORGANISM: artificial sequence
<220> FEATURE:
<223> OTHER INFORMATION: primer

<400> SEQUENCE: 127
cagagctttc atcctcagct agctattgta atatgtgtg 39

<210> SEQ ID NO 128
<211> LENGTH: 9491
<212> TYPE: DNA
<213> ORGANISM: artificial sequence
<220> FEATURE:
<223> OTHER INFORMATION: constructed plasmid

<400> SEQUENCE: 128
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat atttttttat gcctcggtaa tgattttcat 360
tttttttttt cccctagcgg atgactcttt ttttttctta gcgattggca ttatcacata 420
atgaattata cattatataa agtaatgtga tttcttcgaa gaatatacta aaaaatgagc 480

-continued

```
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttttct ttttgctttt tcttttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc atttttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa agggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cgggcccccc ctcgaggtcg   2100
acggcgcgcc actggtagag agcgactttg tatgccccaa ttgcgaaacc cgcgatatcc   2160
ttctcgattc tttagtaccc gaccaggaca aggaaaagga ggtcgaaacg tttttgaaga   2220
aacaagagga actacacgga agctctaaag atggcaacca gccagaaact aagaaaatga   2280
agttgatgga tccaactggc accgctggct tgaacaacaa taccagcctt ccaacttctg   2340
taaataacgg cggtacgcca gtgccaccag taccgttacc tttcggtata cctcctttcc   2400
ccatgtttcc aatgcccttc atgcctccaa cggctactat cacaaatcct catcaagctg   2460
acgcaagccc taagaaatga ataacaatac tgacagtact aaataattgc ctacttggct   2520
tcacatacgt tgcatacgtc gatatagata ataatgataa tgacagcagg attatcgtaa   2580
tacgtaatag ttgaaaatct caaaaatgtg tgggtcatta cgtaaataat gataggaatg   2640
ggattcttct atttttcctt tttccattct agcagccgtc gggaaaacgt ggcatcctct   2700
ctttcgggct caattggagt cacgctgccg tgagcatcct ctctttccat atctaacaac   2760
tgagcacgta accaatggaa aagcatgagc ttagcgttgc tccaaaaaag tattggatgg   2820
```

-continued

```
ttaataccat ttgtctgttc tcttctgact ttgactcctc aaaaaaaaaa aatctacaat   2880
caacagatcg cttcaattac gccctcacaa aaactttttt ccttcttctt cgcccacgtt   2940
aaattttatc cctcatgttg tctaacggat ttctgcactt gatttattat aaaaagacaa   3000
agacataata cttctctatc aatttcagtt attgttcttc cttgcgttat tcttctgttc   3060
ttctttttct tttgtcatat ataaccataa ccaagtaata catattcaaa ctagtatgac   3120
tgacaaaaaa actcttaaag acttaagaaa tcgtagttct gtttacgatt caatggttaa   3180
atcacctaat cgtgctatgt tgcgtgcaac tggtatgcaa gatgaagact ttgaaaaacc   3240
tatcgtcggt gtcatttcaa cttgggctga aaacacacct tgtaatatcc acttacatga   3300
ctttggtaaa ctagccaaag tcggtgttaa ggaagctggt gcttggccag ttcagttcgg   3360
aacaatcacg gtttctgatg gaatcgccat gggaacccaa ggaatgcgtt tctccttgac   3420
atctcgtgat attattgcag attctattga agcagccatg ggaggtcata atgcggatgc   3480
ttttgtagcc attggcggtt gtgataaaaa catgcccggt tctgttatcg ctatggctaa   3540
catggatatc ccagccattt ttgcttacgg cggaacaatt gcacctggta atttagacgg   3600
caaagatatc gatttagtct ctgtctttga aggtgtcggc cattggaacc acggcgatat   3660
gaccaaagaa gaagttaaag ctttggaatg taatgcttgt cccggtcctg gaggctgcgg   3720
tggtatgtat actgctaaca caatggcgac agctattgaa gttttgggac ttagccttcc   3780
gggttcatct tctcacccgg ctgaatccgc agaaaagaaa gcagatattg aagaagctgg   3840
tcgcgctgtt gtcaaaatgc tcgaaatggg cttaaaacct tctgacattt taacgcgtga   3900
agcttttgaa gatgctatta ctgtaactat ggctctggga ggttcaacca actcaaccct   3960
tcacctctta gctattgccc atgctgctaa tgtggaattg acacttgatg atttcaatac   4020
tttccaagaa aaagttcctc atttggctga tttgaaacct tctggtcaat atgtattcca   4080
agacctttac aaggtcggag gggtaccagc agttatgaaa tatctcctta aaaatggctt   4140
ccttcatggt gaccgtatca cttgtactgg caaaacagtc gctgaaaatt tgaaggcttt   4200
tgatgattta acacctggtc aaaaggttat tatgccgctt gaaaatccta aacgtgaaga   4260
tggtccgctc attattctcc atggtaactt ggctccagac ggtgccgttg ccaaagtttc   4320
tggtgtaaaa gtgcgtcgtc atgtcggtcc tgctaaggtc tttaattctg aagaagaagc   4380
cattgaagct gtcttgaatg atgatattgt tgatggtgat gttgttgtcg tacgttttgt   4440
aggaccaaag ggcggtcctg gtatgcctga aatgctttcc ctttcatcaa tgattgttgg   4500
taaagggcaa ggtgaaaaag ttgcccttct gacagatggc cgcttctcag gtggtactta   4560
tggtcttgtc gtgggtcata tcgctcctga agcacaagat ggcggtccaa tcgcctacct   4620
gcaaacagga gacatagtca ctattgacca agacactaag gaattacact ttgatatctc   4680
cgatgaagag ttaaaacatc gtcaagagac cattgaattg ccaccgctct attcacgcgg   4740
tatccttggt aaatatgctc acatcgtttc gtctgcttct aggggagccg taacagactt   4800
ttggaagcct gaagaaactg gcaaaaaatg ttgtcctggt tgctgtggtt aagcggccgc   4860
gttaattcaa attaattgat atagtttttt aatgagtatt gaatctgttt agaaataatg   4920
gaatattatt tttatttatt tatttatatt attggtcggc tcttttcttc tgaaggtcaa   4980
tgacaaaatg atatgaagga aataatgatt tctaaaattt tacaacgtaa gatattttta   5040
caaaagccta gctcatcttt tgtcatgcac tattttactc acgcttgaaa ttaacggcca   5100
gtccactgcg gagtcatttc aaagtcatcc taatcgatct atcgtttttg atagctcatt   5160
ttggagttcg cgattgtctt ctgttattca caactgtttt aatttttatt tcattctgga   5220
```

actcttcgag ttctttgtaa agtctttcat agtagcttac tttatcctcc aacatattta 5280
acttcatgtc aatttcggct cttaaatttt ccacatcatc aagttcaaca tcatctttta 5340
acttgaattt attctctagc tcttccaacc aagcctcatt gctccttgat ttactggtga 5400
aaagtgatac actttgcgcg caatccaggt caaaactttc ctgcaaagaa ttcaccaatt 5460
tctcgacatc atagtacaat ttgttttgtt ctcccatcac aatttaatat acctgatgga 5520
ttcttatgaa gcgctgggta atggacgtgt cactctactt cgcctttttc cctactcctt 5580
ttagtacgga agacaatgct aataaataag agggtaataa taatattatt aatcggcaaa 5640
aaagattaaa cgccaagcgt ttaattatca gaaagcaaac gtcgtaccaa tccttgaatg 5700
cttcccaatt gtatattaag agtcatcaca gcaacatatt cttgttatta aattaattat 5760
tattgatttt tgatattgta taaaaaaacc aaatatgtat aaaaaaagtg aataaaaaat 5820
accaagtatg gagaaatata ttagaagtct atacgttaaa ccaccgcggt ggagctccag 5880
cttttgttcc ctttagtgag ggttaattgc gcgcttggcg taatcatggt catagctgtt 5940
tcctgtgtga aattgttatc cgctcacaat tccacacaac ataggagccg gaagcataaa 6000
gtgtaaagcc tggggtgcct aatgagtgag gtaactcaca ttaattgcgt tgcgctcact 6060
gcccgctttc cagtcgggaa acctgtcgtg ccagctgcat taatgaatcg gccaacgcgc 6120
ggggagaggc ggtttgcgta ttgggcgctc ttccgcttcc tcgctcactg actcgctgcg 6180
ctcggtcgtt cggctgcggc gagcggtatc agctcactca aaggcggtaa tacggttatc 6240
cacagaatca ggggataacg caggaaagaa catgtgagca aaaggccagc aaaaggccag 6300
gaaccgtaaa aaggccgcgt tgctggcgtt tttccatagg ctccgccccc ctgacgagca 6360
tcacaaaaat cgacgctcaa gtcagaggtg gcgaaacccg acaggactat aaagatacca 6420
ggcgtttccc cctggaagct ccctcgtgcg ctctcctgtt ccgaccctgc cgcttaccgg 6480
atacctgtcc gcctttctcc cttcgggaag cgtggcgctt tctcatagct cacgctgtag 6540
gtatctcagt tcggtgtagg tcgttcgctc caagctgggc tgtgtgcacg aaccccccgt 6600
tcagcccgac cgctgcgcct tatccggtaa ctatcgtctt gagtccaacc cggtaagaca 6660
cgacttatcg ccactggcag cagccactgg taacaggatt agcagagcga ggtatgtagg 6720
cggtgctaca gagttcttga agtggtggcc taactacggc tacactagaa ggacagtatt 6780
tggtatctgc gctctgctga agccagttac cttcggaaaa agagttggta gctcttgatc 6840
cggcaaacaa accaccgctg gtagcggtgg tttttttgtt tgcaagcagc agattacgcg 6900
cagaaaaaaa ggatctcaag aagatccttt gatcttttct acggggtctg acgctcagtg 6960
gaacgaaaac tcacgttaag ggattttggt catgagatta tcaaaaagga tcttcaccta 7020
gatcctttta aattaaaaat gaagttttaa atcaatctaa agtatatatg agtaaacttg 7080
gtctgacagt taccaatgct taatcagtga ggcacctatc tcagcgatct gtctatttcg 7140
ttcatccata gttgcctgac tccccgtcgt gtagataact acgatacggg agggcttacc 7200
atctggcccc agtgctgcaa tgataccgcg agacccacgc tcaccggctc cagatttatc 7260
agcaataaac cagccagccg gaagggccga gcgcagaagt ggtcctgcaa ctttatccgc 7320
ctccatccag tctattaatt gttgccggga agctagagta agtagttcgc cagttaatag 7380
tttgcgcaac gttgttgcca ttgctacagg catcgtggtg tcacgctcgt cgtttggtat 7440
ggcttcattc agctccggtt cccaacgatc aaggcgagtt acatgatccc ccatgttgtg 7500
caaaaaagcg gttagctcct tcggtcctcc gatcgttgtc agaagtaagt tggccgcagt 7560

-continued

```
gttatcactc atggttatgg cagcactgca taattctctt actgtcatgc catccgtaag   7620
atgcttttct gtgactggtg agtactcaac caagtcattc tgagaatagt gtatgcggcg   7680
accgagttgc tcttgcccgg cgtcaatacg ggataatacc gcgccacata gcagaacttt   7740
aaaagtgctc atcattggaa aacgttcttc ggggcgaaaa ctctcaagga tcttaccgct   7800
gttgagatcc agttcgatgt aacccactcg tgcacccaac tgatcttcag catcttttac   7860
tttcaccagc gtttctgggt gagcaaaaac aggaaggcaa aatgccgcaa aaaagggaat   7920
aagggcgaca cggaaatgtt gaatactcat actcttcctt tttcaatatt attgaagcat   7980
ttatcagggt tattgtctca tgagcggata catatttgaa tgtatttaga aaaataaaca   8040
aataggggtt ccgcgcacat ttccccgaaa agtgccacct gaacgaagca tctgtgcttc   8100
attttgtaga acaaaaatgc aacgcgagag cgctaatttt tcaaacaaag aatctgagct   8160
gcatttttac agaacagaaa tgcaacgcga aagcgctatt ttaccaacga agaatctgtg   8220
cttcattttt gtaaaacaaa aatgcaacgc gagagcgcta atttttcaaa caaagaatct   8280
gagctgcatt tttacagaac agaaatgcaa cgcgagagcg ctattttacc aacaaagaat   8340
ctatacttct tttttgttct acaaaaatgc atcccgagag cgctattttt ctaacaaagc   8400
atcttagatt actttttttc tcctttgtgc gctctataat gcagtctctt gataactttt   8460
tgcactgtag gtccgttaag gttagaagaa ggctactttg gtgtctattt tctcttccat   8520
aaaaaaagcc tgactccact tcccgcgttt actgattact agcgaagctg cgggtgcatt   8580
ttttcaagat aaaggcatcc ccgattatat tctataccga tgtggattgc gcatactttg   8640
tgaacagaaa gtgatagcgt tgatgattct tcattggtca gaaaattatg aacggtttct   8700
tctattttgt ctctatatac tacgtatagg aaatgtttac attttcgtat tgttttcgat   8760
tcactctatg aatagttctt actacaattt ttttgtctaa agagtaatac tagagataaa   8820
cataaaaaat gtagaggtcg agtttagatg caagttcaag gagcgaaagg tggatgggta   8880
ggttatatag ggatatagca cagagatata tagcaaagag atacttttga gcaatgtttg   8940
tggaagcggt attcgcaata ttttagtagc tcgttacagt ccggtgcgtt tttggttttt   9000
tgaaagtgcg tcttcagagc gcttttggtt ttcaaaagcg ctctgaagtt cctatacttt   9060
ctagagaata ggaacttcgg aataggaact tcaaagcgtt tccgaaaacg agcgcttccg   9120
aaaatgcaac gcgagctgcg cacatacagc tcactgttca cgtcgcacct atatctgcgt   9180
gttgcctgta tatatatata catgagaaga acggcatagt gcgtgtttat gcttaaatgc   9240
gtacttatat gcgtctattt atgtaggatg aaaggtagtc tagtacctcc tgtgatatta   9300
tcccattcca tgcggggtat cgtatgcttc cttcagcact accctttagc tgttctatat   9360
gctgccactc ctcaattgga ttagtctcat ccttcaatgc tatcatttcc tttgatattg   9420
gatcatctaa gaaaccatta ttatcatgac attaacctat aaaaataggc gtatcacgag   9480
gccctttcgt c                                                        9491
```

<210> SEQ ID NO 129
<211> LENGTH: 1000
<212> TYPE: DNA
<213> ORGANISM: Saccharomyces cerevisiae

<400> SEQUENCE: 129

```
gttaattcaa attaattgat atagtttttt aatgagtatt gaatctgttt agaaataatg     60
gaatattatt tttatttatt tatttatatt attggtcggc tcttttcttc tgaaggtcaa    120
tgacaaaatg atatgaagga aataatgatt tctaaaattt tacaacgtaa gatattttta    180
```

-continued caaaagccta gctcatcttt tgtcatgcac tattttactc acgcttgaaa ttaacggcca 240
gtccactgcg gagtcatttc aaagtcatcc taatcgatct atcgtttttg atagctcatt 300
ttggagttcg cgattgtctt ctgttattca caactgtttt aatttttatt tcattctgga 360
actcttcgag ttctttgtaa agtctttcat agtagcttac tttatcctcc aacatattta 420
acttcatgtc aatttcggct cttaaatttt ccacatcatc aagttcaaca tcatctttta 480
acttgaattt attctctagc tcttccaacc aagcctcatt gctccttgat ttactggtga 540
aaagtgatac actttgcgcg caatccaggt caaaactttc ctgcaaagaa ttcaccaatt 600
tctcgacatc atagtacaat ttgttttgtt ctcccatcac aatttaatat acctgatgga 660
ttcttatgaa gcgctgggta atggacgtgt cactctactt cgcctttttc cctactcctt 720
ttagtacgga agacaatgct aataaataag agggtaataa taatattatt aatcggcaaa 780
aaagattaaa cgccaagcgt ttaattatca gaaagcaaac gtcgtaccaa tccttgaatg 840
cttcccaatt gtatattaag agtcatcaca gcaacatatt cttgttatta aattaattat 900
tattgatttt tgatattgta taaaaaaacc aaatatgtat aaaaaaagtg aataaaaaat 960
accaagtatg gagaaatata ttagaagtct atacgttaaa 1000

<210> SEQ ID NO 130
<211> LENGTH: 16387
<212> TYPE: DNA
<213> ORGANISM: Artificial sequence
<220> FEATURE:
<223> OTHER INFORMATION: Plasmid

<400> SEQUENCE: 130
gatcctctag tttctcggta ctatgcatat gatccaatat caaaggaaat gatagcattg 60
aaggatgaga ctaatccaat tgaggagtgg cagcatatag aacagctaaa gggtagtgct 120
gaaggaagca tacgataccc cgcatggaat gggataaatat cacaggaggt actagactac 180
ctttcatcct acataaatag acgcatataa gtacgcattt aagcataaac acgcactatg 240
ccgttcttct catgtatata tatatacagg caacacgcag atataggtgc gacgtgaaca 300
gtgagctgta tgtgcgcagc tcgcgttgca ttttcggaag cgctcgtttt cggaaacgct 360
ttgaagttcc tattccgaag ttcctattct ctagaaagta taggaacttc agagcgcttt 420
tgaaaaccaa aagcgctctg aagacgcact ttcaaaaaac caaaaacgca ccggactgta 480
acgagctact aaaatattgc gaataccgct tccacaaaca ttgctcaaaa gtatctcttt 540
gctatatatc tctgtgctat atccctatat aacctaccca tccacctttc gctccttgaa 600
cttgcatcta aactcgacct ctacattttt tatgtttatc tctagtatta ctctttagac 660
aaaaaaattg tagtaagaac tattcataga gtgaatcgaa aacaatacga aaatgtaaac 720
atttcctata cgtagtatat agagacaaaa tagaagaaac cgttcataat tttctgacca 780
atgaagaatc atcaacgcta tcactttctg ttcacaaagt atgcgcaatc cacatcggta 840
tagaatataa tcggggatgc ctttatcttg aaaaaatgca cccgcagctt cgctagtaat 900
cagtaaacgc gggaagtgga gtcaggcttt ttttatggaa gagaaaatag acaccaaagt 960
agccttcttc taaccttaac ggacctacag tgcaaaaagt tatcaagaga ctgcattata 1020
gagcgcacaa aggagaaaaa aagtaatcta agatgctttg ttagaaaaat agcgctctcg 1080
ggatgcattt ttgtagaaca aaaaagaagt atagattctt tgttggtaaa atagcgctct 1140
cgcgttgcat ttctgttctg taaaaatgca gctcagattc tttgtttgaa aaattagcgc 1200

```
tctcgcgttg catttttgtt ttacaaaaat gaagcacaga ttcttcgttg gtaaaatagc   1260
gctttcgcgt tgcatttctg ttctgtaaaa atgcagctca gattctttgt ttgaaaaatt   1320
agcgctctcg cgttgcattt ttgttctaca aaatgaagca cagatgcttc gttaacaaag   1380
atatgctatt gaagtgcaag atggaaacgc agaaaatgaa ccggggatgc gacgtgcaag   1440
attacctatg caatagatgc aatagtttct ccaggaaccg aaatacatac attgtcttcc   1500
gtaaagcgct agactatata ttattataca ggttcaaata tactatctgt ttcagggaaa   1560
actcccaggt tcggatgttc aaaattcaat gatgggtaac aagtacgatc gtaaatctgt   1620
aaaacagttt gtcggatatt aggctgtatc tcctcaaagc gtattcgaat atcattgaga   1680
agctgcattt tttttttttt tttttttttt tttttttata tatatttcaa ggatatacca   1740
ttgtaatgtc tgcccctaag aagatcgtcg ttttgccagg tgaccacgtt ggtcaagaaa   1800
tcacagccga agccattaag gttcttaaag ctatttctga tgttcgttcc aatgtcaagt   1860
tcgatttcga aaatcattta attggtggtg ctgctatcga tgctacaggt gttccacttc   1920
cagatgaggc gctggaagcc tccaagaagg ctgatgccgt tttgttaggt gctgtgggtg   1980
gtcctaaatg gggtaccggt agtgttagac ctgaacaagg tttactaaaa atccgtaaag   2040
aacttcaatt gtacgccaac ttaagaccat gtaactttgc atccgactct cttttagact   2100
tatctccaat caagccacaa tttgctaaag gtactgactt cgttgttgtt agagaattag   2160
tgggaggtat ttactttggt aagagaaagg aagacgatgg tgatggtgtc gcttgggata   2220
gtgaacaata caccgttcca gaagtgcaaa gaatcacaag aatggccgct ttcatggccc   2280
tacaacatga gccaccattg cctatttggt ccttggataa agctaatgtt ttggcctctt   2340
caagattatg gagaaaaact gtggaggaaa ccatcaagaa cgaattccct acattgaaag   2400
ttcaacatca attgattgat tctgccgcca tgatcctagt taagaaccca acccacctaa   2460
atggtattat aatcaccagc aacatgtttg gtgatatcat ctccgatgaa gcctccgtta   2520
tcccaggctc cttgggtttg ttgccatctg cgtccttggc ctctttgcca gacaagaaca   2580
ccgcatttgg tttgtacgaa ccatgccatg gttccgctcc agatttgcca aagaataagg   2640
tcaaccctat cgccactatc ttgtctgctg caatgatgtt gaaattgtca ttgaacttgc   2700
ctgaagaagg taaagccatt gaagatgcag ttaaaaaggt tttggatgca ggtatcagaa   2760
ctggtgattt aggtggttcc aacagtacca ccgaagtcgg tgatgctgtc gccgaagaag   2820
ttaagaaaat ccttgcttaa aaagattctc tttttttatg atatttgtac aaaaaaaaaa   2880
aaaaaaaaaa aaaaaaaaaa aaaaaaaaaa aaaaaaaaaa aatgcagcgt cacatcggat   2940
aataatgatg gcagccattg tagaagtgcc ttttgcattt ctagtctctt tctcggtcta   3000
gctagtttta ctacatcgcg aagatagaat cttagatcac actgcctttg ctgagctgga   3060
tcaatagagt aacaaaagag tggtaaggcc tcgttaaagg acaaggacct gagcggaagt   3120
gtatcgtaca gtagacggag tatactagag tcgacctgca ggcatgcaag cttttcaatt   3180
catcattttt tttttattct tttttttgat ttcggtttcc ttgaaatttt tttgattcgg   3240
taatctccga acagaaggaa gaacgaagga aggagcacag acttagattg gtatatatac   3300
gcatatgtag tgttgaagaa acatgaaatt gcccagtatt cttaacccaa ctgcacagaa   3360
caaaaacctg caggaaacga agataaatca tgtcgaaagc tacatataag gaacgtgctg   3420
ctactcatcc tagtcctgtt gctgccaagc tatttaatat catgcacgaa aagcaaacaa   3480
acttgtgtgc ttcattggat gttcgtacca ccaaggaatt actggagtta gttgaagcat   3540
taggtcccaa aatttgttta ctaaaaacac atgtggatat cttgactgat ttttccatgg   3600
```

agggcacagt taagccgcta aaggcattat ccgccaagta caatttttta ctcttcgaag 3660
acagaaaatt tgctgacatt ggtaatacag tcaaattgca gtactctgcg ggtgtataca 3720
gaatagcaga atgggcagac attacgaatg cacacggtgt ggtgggccca ggtattgtta 3780
gcggtttgaa gcaggcggca gaagaagtaa caaaggaacc tagaggcctt ttgatgttag 3840
cagaattgtc atgcaagggc tccctatcta ctggagaata tactaagggt actgttgaca 3900
ttgcgaagag cgacaaagat tttgttatcg gctttattgc tcaaagagac atgggtggaa 3960
gagatgaagg ttacgattgg ttgattatga cacccggtgt gggtttagat gacaagggag 4020
acgcattggg tcaacagtat agaaccgtgg atgatgtggt ctctacagga tctgacatta 4080
ttattgttgg aagaggacta tttgcaaagg gaagggatgc taaggtagag ggtgaacgtt 4140
acagaaaagc aggctgggaa gcatatttga gaagatgcgg ccagcaaaac taaaaaactg 4200
tattataagt aaatgcatgt atactaaact cacaaattag agcttcaatt taattatatc 4260
agttattacc cgggaatctc ggtcgtaatg atttttataa tgacgaaaaa aaaaaaattg 4320
gaaagaaaaa gcttggcgta atcatggtca tagctgtttc ctgtgtgaaa ttgttatccg 4380
ctcacaattc cacacaacat acgagccgga agcataaagt gtaaagcctg gggtgcctaa 4440
tgagtgagct aactcacatt aattgcgttg cgctcactgc ccgctttcca gtcgggaaac 4500
ctgtcgtgcc agctgcatta atgaatcggc caacgcgcgg ggagaggcgg tttgcgtatt 4560
gggcgctctt ccgcttcctc gctcactgac tcgctgcgct cggtcgttcg gctgcggcga 4620
gcggtatcag ctcactcaaa ggcggtaata cggttatcca cagaatcagg ggataacgca 4680
ggaaagaaca tgtgagcaaa aggccagcaa aaggccagga accgtaaaaa ggccgcgttg 4740
ctggcgtttt tccataggct ccgcccccct gacgagcatc acaaaaatcg acgctcaagt 4800
cagaggtggc gaaacccgac aggactataa agataccagg cgtttccccc tggaagctcc 4860
ctcgtgcgct ctcctgttcc gaccctgccg cttaccggat acctgtccgc ctttctccct 4920
tcgggaagcg tggcgctttc tcatagctca cgctgtaggt atctcagttc ggtgtaggtc 4980
gttcgctcca agctgggctg tgtgcacgaa ccccccgttc agcccgaccg ctgcgcctta 5040
tccggtaact atcgtcttga gtccaacccg gtaagacacg acttatcgcc actggcagca 5100
gccactggta acaggattag cagagcgagg tatgtaggcg gtgctacaga gttcttgaag 5160
tggtggccta actacggcta cactagaaga acagtatttg gtatctgcgc tctgctgaag 5220
ccagttacct tcggaaaaag agttggtagc tcttgatccg gcaaacaaac caccgctggt 5280
agcggtggtt tttttgtttg caagcagcag attacgcgca gaaaaaaagg atctcaagaa 5340
gatcctttga tcttttctac ggggtctgac gctcagtgga acgaaaactc acgttaaggg 5400
attttggtca tgagattatc aaaaaggatc ttcacctaga tccttttaaa ttaaaaatga 5460
agttttaaat caatctaaag tatatatgag taaacttggt ctgacagtta ccaatgctta 5520
atcagtgagg cacctatctc agcgatctgt ctatttcgtt catccatagt tgcctgactc 5580
cccgtcgtgt agataactac gatacgggag ggcttaccat ctggccccag tgctgcaatg 5640
ataccgcgag acccacgctc accggctcca gatttatcag caataaacca gccagccgga 5700
agggccgagc gcagaagtgg tcctgcaact ttatccgcct ccatccagtc tattaattgt 5760
tgccgggaag ctagagtaag tagttcgcca gttaatagtt tgcgcaacgt tgttgccatt 5820
gctacaggca tcgtggtgtc acgctcgtcg tttggtatgg cttcattcag ctccggttcc 5880
caacgatcaa ggcgagttac atgatccccc atgttgtgca aaaaagcggt tagctccttc 5940
ggtcctccga tcgttgtcag aagtaagttg gccgcagtgt tatcactcat ggttatggca 6000
gcactgcata attctcttac tgtcatgcca tccgtaagat gcttttctgt gactggtgag 6060
tactcaacca agtcattctg agaatagtgt atgcggcgac cgagttgctc ttgcccggcg 6120
tcaatacggg ataataccgc gccacatagc agaactttaa aagtgctcat cattggaaaa 6180
cgttcttcgg ggcgaaaact ctcaaggatc ttaccgctgt tgagatccag ttcgatgtaa 6240
cccactcgtg cacccaactg atcttcagca tcttttactt tcaccagcgt ttctgggtga 6300
gcaaaaacag gaaggcaaaa tgccgcaaaa aagggaataa gggcgacacg gaaatgttga 6360
atactcatac tcttcctttt tcaatattat tgaagcattt atcagggtta ttgtctcatg 6420
agcggataca tatttgaatg tatttagaaa aataaacaaa taggggttcc gcgcacattt 6480
ccccgaaaag tgccacctga cgtctaagaa accattatta tcatgacatt aacctataaa 6540
aataggcgta tcacgaggcc ctttcgtctc gcgcgtttcg gtgatgacgg tgaaaacctc 6600
tgacacatgc agctcccgga gacggtcaca gcttgtctgt aagcggatgc cgggagcaga 6660
caagcccgtc agggcgcgtc agcgggtgtt ggcgggtgtc ggggctggct taactatgcg 6720
gcatcagagc agattgtact gagagtgcac cataaaattg taaacgttaa tattttgtta 6780
aaattcgcgt taaatttttg ttaaatcagc tcatttttta accaatagac cgaaatcggc 6840
aaaatccctt ataaatcaaa agaatagccc gagatagagt tgagtgttgt tccagtttgg 6900
aacaagagtc cactattaaa gaacgtggac tccaacgtca aagggcgaaa aaccgtctat 6960
cagggcgatg gcccactacg tgaaccatca cccaaatcaa gttttttggg gtcgaggtgc 7020
cgtaaagcac taaatcggaa ccctaaaggg agcccccgat ttagagcttg acggggaaag 7080
ccggcgaacg tggcgagaaa ggaagggaag aaagcgaaag gagcgggcgc taaggcgctg 7140
gcaagtgtag cggtcacgct gcgcgtaacc accacacccg ccgcgcttaa tgcgccgcta 7200
cagggcgcgt actatggttg ctttgacgta tgcggtgtga aataccgcac agatgcgtaa 7260
ggagaaaata ccgcatcagg cgccattcgc cattcaggct gcgcaactgt tgggaagggc 7320
gatcggtgcg ggcctcttcg ctattacgcc agctggcgaa agggggatgt gctgcaaggc 7380
gattaagttg ggtaacgcca gggttttccc agtcacgacg ttgtaaaacg acggccagtg 7440
aattcgagct ccaccgcgga tagatctgaa atgaataaca atactgacag tactaaataa 7500
ttgcctactt ggcttcacat acgttgcata cgtcgatata gataataatg ataatgacag 7560
caggattatc gtaatacgta atagttgaaa atctcaaaaa tgtgtgggtc attacgtaaa 7620
taatgatagg aatgggattc ttctattttt cctttttcca ttctagcagc cgtcgggaaa 7680
acgtggcatc ctctctttcg ggctcaattg gagtcacgct gccgtgagca tcctctcttt 7740
ccatatctaa caactgagca cgtaaccaat ggaaaagcat gagcttagcg ttgctccaaa 7800
aaagtattgg atggttaata ccatttgtct gttctcttct gactttgact cctcaaaaaa 7860
aaaaaatcta caatcaacag atcgcttcaa ttacgccctc acaaaaactt ttttccttct 7920
tcttcgccca cgttaaattt tatccctcat gttgtctaac ggatttctgc acttgattta 7980
ttataaaaag acaaagacat aatacttctc tatcaatttc agttattgtt cttccttgcg 8040
ttattcttct gttcttcttt ttcttttgtc atatataacc ataaccaagt aatacatatt 8100
caaatctaga gctgaggatg ttgaagcaaa tcaacttcgg tggtactgtt gaaaccgtct 8160
acgaaagagc tgactggcca agagaaaagt tgttggacta cttcaagaac gacacttttg 8220
ctttgatcgg ttacggttcc caaggttacg gtcaaggttt gaacttgaga gacaacggtt 8280
tgaacgttat cattggtgtc cgtaaagatg gtgcttcttg gaaggctgcc atcgaagacg 8340

-continued

```
gttgggttcc aggcaagaac ttgttcactg ttgaagatgc tatcaagaga ggtagttacg   8400
ttatgaactt gttgtccgat gccgctcaat cagaaacctg gcctgctatc aagccattgt   8460
tgaccaaggg taagactttg tacttctccc acggtttctc cccagtcttc aaggacttga   8520
ctcacgttga accaccaaag gacttagatg ttatcttggt tgctccaaag ggttccggta   8580
gaactgtcag atctttgttc aaggaaggtc gtggtattaa ctcttcttac gccgtctgga   8640
acgatgtcac cggtaaggct cacgaaaagg cccaagcttt ggccgttgcc attggttccg   8700
gttacgttta ccaaaccact ttcgaaagag aagtcaactc tgacttgtac ggtgaaagag   8760
gttgtttaat gggtggtatc cacggtatgt tcttggctca atacgacgtc ttgagagaaa   8820
acggtcactc cccatctgaa gctttcaacg aaaccgtcga agaagctacc caatctctat   8880
acccattgat cggtaagtac ggtatggatt acatgtacga tgcttgttcc accaccgcca   8940
gaagaggtgc tttggactgg tacccaatct tcaagaatgc tttgaagcct gttttccaag   9000
acttgtacga atctaccaag aacggtaccg aaaccaagag atctttggaa ttcaactctc   9060
aacctgacta cagagaaaag ctagaaaagg aattagacac catcagaaac atggaaatct   9120
ggaaggttgg taaggaagtc agaaagttga gaccagaaaa ccaataatta attaatcatg   9180
taattagtta tgtcacgctt acattcacgc cctcccccca catccgctct aaccgaaaag   9240
gaaggagtta gacaacctga agtctaggtc cctatttatt tttttatagt tatgttagta   9300
ttaagaacgt tatttatatt tcaaattttt ctttttttc tgtacagacg cgtgtacgca   9360
tgtaacatta tactgaaaac cttgcttgag aaggttttgg gacgctcgaa ggctttaatt   9420
tgcgggcggc cgctctagag agttgttagc aaccttttgt ttcttttgag ctggttcaga   9480
cattatgtac acgtatatgt gacgagttcg agaagtattt tactatcgta ctaaatttta   9540
cctgaaaaat tatatactcg agaaagagga agccaagaat tgagaaaaaa gaaaaacccg   9600
cgagtaagga aattaaatac aggtgtacac atacacgcac acatatatat atatatatat   9660
atgtatatgt gtatatagga agcgcgcgca tgttagtata tacgattcgt tggaaagggg   9720
ccgtccacca aacgtgactt gacgagttga caaattgacc tcaatatggc tcagtcagta   9780
atttttagtt ccgctttatt cccgccatct ttcaggccac gagggtagct cataacgccg   9840
cgctaatgcc gctgcgtcac agcaaccagt agctcagcca aaaccgaaag agaaatcgta   9900
gctgtcccga tgaggactta tacacttgtc accatctaaa taaattattt attcgcgttt   9960
cggttcttgt tttcgattta attagattgt tcattgaatc ataataaata tgtaaaaaat  10020
atatatattt gaagctgctt cagaaaaaca gggcttccta gtgtacagat gtatgtcgga  10080
tgaaaaaaaa aaaatcttaa atgtgaaatt gggtcaattc aattgactat gacttgatgt  10140
tgcaaaaatt ccaagagaaa aagtttccag cacttgatat tattttcctc tttaattttt  10200
cgccttgtct acgatcttat tagcaccgat ccagggcatc atagacctta actgttcacc  10260
aataatttcg ataccatgtg ctgcattgtt tcttctttta gcagtcatac tcgggtaacc  10320
cgtagcgcct tcacttatga acatcttagc gtattcaccg tcctggatac gtttcaaggc  10380
atttctcatg gcttgtcttg attctgcgtt aatgacttca ggtccggtga catactcacc  10440
atattctgca ttatttgaaa tggaatagtt catattagct ataccacctt catacattaa  10500
gtctactatc aacttcaatt catgtagaca ttcgaagtat gccatttcgg gagcgtaccc  10560
tgcttcgaca agcgtctcaa agcctgcttt aaccaattca acagttcctc cgcacagaac  10620
cgcttgttct ccaaataaat ctgtctcagt ctcgtcttta aaagtggttt ctattatacc  10680
```

cgttctcccg ccaccaactc ctgctgcgta gcttaaagct acattcttag cgtttccgct 10740
tgcgtcttgg tatatagcga tcaaatctgg aataccacca cccttaacaa attcgctcct 10800
aacagtatgc cccggagcct taggtgcaat cataataacg tccaaatctg ccctggggac 10860
tacttgattg taatgaatgg caaatccatg actgaaggcc aaggtagcgc ccttcttaat 10920
gtttggttct atttcatttt tgtacaattg cgattgaaat tcatctggcg ttaaaatcat 10980
gactaaatca gcgccggcaa cagccgctgc aacatctgtg actttcaagc catgtgcttc 11040
agcctttgca acggtagcac taccttttct cagacctact gtcacgtcga ccccagaatc 11100
tttcaagtta caggcttgtg cgtgtccttg ggaaccatat cctataatag caaccttctt 11160
tccctggatg atgctcagat cgcagtcttt atcgtaaaac accttcatgt tttatttttt 11220
acttatattg ctggtagggt aaaaaaatat aactcctagg aataggttgt ctatatgttt 11280
ttgtcttgct tctataattg taacaaacaa ggaaagggaa aatactgggt gtaaaagcca 11340
ttgagtcaag ttaggtcatc ccttttatac aaaatttttc aatttttttt ccaagattct 11400
tgtacgatta attatttttt ttttgcgtcc tacagcgtga tgaaaatttc cgcctgctgc 11460
aagatgagcg ggaacgggcg aaatgtgcac gcgcacaact tacgaaacgc ggatgagtca 11520
ctgacagcca ccgcagaggt tctgactcct actgagctct attggaggtg gcagaaccgg 11580
taccggagga gaccgctata accggtttga atttattgtc acagtgtcac atcagcggca 11640
actcagaagt ttgacagcaa gcaagttcat cattcgaact agccttattg ttttagttca 11700
gtgacagcga actgccgtac tcgatgcttt atttctcacg gtagagcgga agaacagata 11760
ggggcagcgt gagaagagtt agaaagtaaa tttttatcac gtctgaagta ttcttattca 11820
taggaaattt tgcaaggttt tttagctcaa taacgggcta agttatataa ggtgttcacg 11880
cgattttctt gttatgtata cctcttctct gaggaatggt actactgtcc tgatgtaggc 11940
tccttaaatt ggtgggcaag aataacttat cgatattttg tatattggtc ttggagttca 12000
ccacgtaatg cctgtttaag accatcagtt aactctagta ttatttggtc ttggctactg 12060
gccgtttgct attattcaag tcttttgtgc cttcccgtcg ggtaagggag ttatttaggg 12120
atacagaatc taacgaaaac taaatctcaa tgattaactc catttaatcc ttttttgaaa 12180
ggcaaaagag gtcccttgtt cacttacaac gttcttagcc aaattcgctt atcacttact 12240
acttcacgat atacagaagt aaaaacatat aaaaagatgt ctgtttgttt agccatcaca 12300
aaaggtatcg cagtttcttc tataggcctc tactctggtc ttttggcttc cgcttcattg 12360
attacatcta ctactccact agaggtttta acaggatctc taaaaacatc gatatcgtct 12420
ctgcgttcca atcctacggt gaatatattt ccaagcaatt cactgaagaa gaaagagaag 12480
atgttgtgga acatgcatgc ccaggtcctg gttcttgtgg tggtatgtat actgccaaca 12540
caatggcttc tgccgctgaa gtgctaggtt tgaccattcc aaactcctct tccttcccag 12600
ccgtttccaa ggagaagtta gctgagtgtg acaacattgg tgaatacatc aagaagacaa 12660
tggaattggg tattttacct cgtgatatcc tcacaaaaga ggcttttgaa aacgccatta 12720
cttatgtcgt tgcaaccggt gggtccacta atgctgtttt gcatttggtg gctgttgctc 12780
actctgcggg tgtcaagttg tcaccagatg atttccaaag aatcagtgat actacaccat 12840
tgatcggtga cttcaaacct tctggtaaat acgtcatggc cgatttgatt aacgttggtg 12900
gtacccaatc tgtgattaag tatctatatg aaaacaacat gttgcacggt aacacaatga 12960
ctgttaccgg tgacactttg gcagaacgtg caaagaaagc accaagccta cctgaaggac 13020
aagagattat taagccactc tcccacccaa tcaaggccaa cggtcacttg caaattctgt 13080

```
acggttcatt ggcaccaggt ggagctgtgg gtaaaattac cggtaaggaa ggtacttact  13140
tcaagggtag agcacgtgtg ttcgaagagg aaggtgcctt tattgaagcc ttggaaagag  13200
gtgaaatcaa gaagggtgaa aaaaccgttg ttgttatcag atatgaaggt ccaagaggtg  13260
caccaggtat gcctgaaatg ctaaagcctt cctctgctct gatgggttac ggtttgggta  13320
aagatgttgc attgttgact gatggtagat tctctggtgg ttctcacggg ttcttaatcg  13380
gccacattgt tcccgaagcc gctgaaggtg gtcctatcgg gttggtcaga gacggcgatg  13440
agattatcat tgatgctgat aataacaaga ttgacctatt agtctctgat aaggaaatgg  13500
ctcaacgtaa acaaagttgg gttgcacctc cacctcgtta cacaagaggt actctatcca  13560
agtatgctaa gttggtttcc aacgcttcca acggttgtgt tttagatgct tgattaatta  13620
agagtaagcg aatttcttat gatttatgat ttttattatt aaataagtta taaaaaaaat  13680
aagtgtatac aaattttaaa gtgactctta ggttttaaaa cgaaaattct tattcttgag  13740
taactctttc ctgtaggtca ggttgctttc tcaggtatag catgaggtcg ctcttattga  13800
ccacacctct accggcatgc cgagcaaatg cctgcaaatc gctccccatt tcacccaatt  13860
gtagatatgc taactccagc aatgagttga tgaatctcgg tgtgtatttt atgtcctcag  13920
aggacaacac ctgtggtact agttctagag cggccgcccg caaattaaag ccttcgagcg  13980
tcccaaaacc ttctcaagca aggttttcag tataatgtta catgcgtaca cgcgtctgta  14040
cagaaaaaaa agaaaaattt gaaatataaa taacgttctt aatactaaca taactataaa  14100
aaaataaata gggacctaga cttcaggttg tctaactcct tccttttcgg ttagagcgga  14160
tgtgggggga gggcgtgaat gtaagcgtga cataactaat tacatgatta attaactaga  14220
gagctttcgt tttcatgagt tccccgaatt ctttcggaag cttgtcactt gctaaattaa  14280
tgttatcact gtagtcaacc gggacatcga tgatgacagg accttcagcg ttcatgcctt  14340
gacgcagaac atctgccagc tggtctggtg attctacgcg caagccagtt gctccgaagc  14400
tttccgcata tttcacgata tcgatatttc cgaaatcgac cgcagatgta cggttatatt  14460
ttttcaattg ctggaatgca accatgtcat atgtgctgtc gttccataca atgtgtacaa  14520
ttggtgcttt tagtcgaact gctgtctcta attccattgc tgagaataag aaaccgccgt  14580
caccagagac agaaaccact ttttctcccg gtttcaccaa tgaagcgccg attgcccaag  14640
gaagcgcaac gccgagtgtt tgcataccgt tactgatcat taatgttaac ggctcgtagc  14700
tgcggaaata acgtgacatc caaatggcgt gcgaaccgat atcgcaagtt actgtaacat  14760
gatcatcgac tgcattacgc aactctttaa cgatttcaag agggtgcgct ctgtctgatt  14820
tccaatctgc aggcacctgc tcaccttcat gcatatattg ttttaaatca gaaaggattt  14880
tctgctcacg ctctgcaaat tccactttca cagcatcgtg ttcgatatga ttgatcgtgg  14940
acggaatgtc accgatcaat tcaagatcag gctggtaagc atgatcaatg tcagcgataa  15000
tctcgtctaa atggataatt gtccggtctc cattgatatt ccagaatttc ggatcatatt  15060
caatcgggtc atagccgatc gtcagaacaa catctgcctg ctctagcagt aaatcgccag  15120
gctggttgcg gaacaaaccg atacggccaa aatattgatc ctctaaatct ctagaaaggg  15180
taccggcagc ttgatatgtt tcaacaaatg gaagctgaac ctttttcaaa agcttgcgaa  15240
ccgctttaat tgcttccggt cttccgcctt tcatgccgac caaaacgaca ggaagttttg  15300
ctgtttggat ttttgctatg gccgcactga ttgcatcatc tgctgcagga ccgagttttg  15360
gcgctgcaac agcacgcacg tttttcgtat ttgtgacttc attcacaaca tcttgcggaa  15420
```

-continued agctcacaaa agcggcccca gcctgccctg ctgacgctat cctaaatgca tttgtaacag 15480
cttccggtat attttttaca tcttgaactt ctacactgta ttttgtaatc ggctggaata 15540
gcgccgcatt atccaaagat tgatgtgtcc gttttaaacg atctgcacgg atcacgtttc 15600
cagcaagcgc aacgacaggg tctccttcag tgttcgctgt cagcaggcct gttgccaagt 15660
tagaggcacc cggtcctgat gtgactaaca cgactcccgg ttttccagtt aaacggccga 15720
ctgcttgggc catgaatgct gcgttttgtt cgtgccgggc aacgataatt tcaggtcctt 15780
tatcttgtaa agcgtcaaat accgcatcaa tttttgcacc tggaatgcca aatacatgtg 15840
tgacaccttg ctccactaag caatcaacaa caagctccgc ccctctgttt ttcacaaggg 15900
atttttgttc ttttgttgct tttgtcaaca tcctcagcga tgattgattg attgattgta 15960
cagtttgttt ttcttaatat ctatttcgat gacttctata tgatattgca ctaacaagaa 16020
gatattataa tgcaattgat acaagacaag gagttatttg cttctctttt atatgattct 16080
gacaatccat attgcgttgg tagtcttttt tgctggaacg gttcagcgga aaagacgcat 16140
cgctcttttt gcttctagaa gaaatgccag caaaagaatc tcttgacagt gactgacagc 16200
aaaaatgtct ttttctaact agtaacaagg ctaagatatc agcctgaaat aaagggtggt 16260
gaagtaataa ttaaatcatc cgtataaacc tatacacata tatgaggaaa aataatacaa 16320
aagtgtttta aatacagata catacatgaa catatgcacg tatagcgccc aaatgtcggt 16380
aatggga 16387

<210> SEQ ID NO 131
<211> LENGTH: 1188
<212> TYPE: DNA
<213> ORGANISM: Saccharomyces cerevisiae

<400> SEQUENCE: 131
atgttgagaa ctcaagccgc cagattgatc tgcaactccc gtgtcatcac tgctaagaga 60
acctttgctt tggccacccg tgctgctgct tacagcagac cagctgcccg tttcgttaag 120
ccaatgatca ctacccgtgg tttgaagcaa atcaacttcg gtggtactgt tgaaaccgtc 180
tacgaaagag ctgactggcc aagagaaaag ttgttggact acttcaagaa cgacactttt 240
gctttgatcg gttacggttc ccaaggttac ggtcaaggtt tgaacttgag agacaacggt 300
ttgaacgtta tcattggtgt ccgtaaagat ggtgcttctt ggaaggctgc catcgaagac 360
ggttgggttc caggcaagaa cttgttcact gttgaagatg ctatcaagag aggtagttac 420
gttatgaact tgttgtccga tgccgctcaa tcagaaacct ggcctgctat caagccattg 480
ttgaccaagg gtaagacttt gtacttctcc cacggtttct ccccagtctt caaggacttg 540
actcacgttg aaccaccaaa ggacttagat gttatcttgg ttgctccaaa gggttccggt 600
agaactgtca gatctttgtt caaggaaggt cgtggtatta actcttctta cgccgtctgg 660
aacgatgtca ccggtaaggc tcacgaaaag gcccaagctt tggccgttgc cattggttcc 720
ggttacgttt accaaaccac tttcgaaaga gaagtcaact ctgacttgta cggtgaaaga 780
ggttgtttaa tgggtggtat ccacggtatg ttcttggctc aatacgacgt cttgagagaa 840
aacggtcact ccccatctga agctttcaac gaaaccgtcg aagaagctac ccaatctcta 900
tacccattga tcggtaagta cggtatggat tacatgtacg atgcttgttc caccaccgcc 960
agaagaggtg ctttggactg gtacccaatc ttcaagaatg ctttgaagcc tgttttccaa 1020
gacttgtacg aatctaccaa gaacggtacc gaaaccaaga gatctttgga attcaactct 1080
caacctgact acagagaaaa gctagaaaag gaattagaca ccatcagaaa catggaaatc 1140
tggaaggttg gtaaggaagt cagaaagttg agaccagaaa accaataa 1188

<210> SEQ ID NO 132
<211> LENGTH: 1014
<212> TYPE: DNA
<213> ORGANISM: Pseudomonas fluorescens

<400> SEQUENCE: 132
atgaaagttt tctacgataa agactgcgac ctgtcgatca tccaaggtaa gaaagttgcc 60
atcatcggct acggttccca gggccacgct caagcatgca acctgaagga ttccggcgta 120
gacgtgactg ttggcctgcg taaaggctcg gctaccgttg ccaaggctga agcccacggc 180
ttgaaagtga ccgacgttgc tgcagccgtt gccggtgccg acttggtcat gatcctgacc 240
ccggacgagt tccagtccca gctgtacaag aacgaaatcg agccgaacat caagaagggc 300
gccactctgg ccttctccca cggcttcgcg atccactaca accaggttgt gcctcgtgcc 360
gacctcgacg tgatcatgat cgcgccgaag gctccaggcc acaccgtacg ttccgagttc 420
gtcaagggcg gtggtattcc tgacctgatc gcgatctacc aggacgcttc cggcaacgcc 480
aagaacgttg ccctgtccta cgccgcaggc gtgggcggcg gccgtaccgg catcatcgaa 540
accaccttca aggacgagac tgaaaccgac ctgttcggtg agcaggctgt tctgtgtggc 600
ggtaccgtcg agctggtcaa agccggtttc gaaaccctgg ttgaagctgg ctacgctcca 660
gaaatggcct acttcgagtg cctgcacgaa ctgaagctga tcgttgacct catgtacgaa 720
ggcggtatcg ccaacatgaa ctactcgatc tccaacaacg ctgaatacgg cgagtacgtg 780
actggtccag aagtcatcaa cgccgaatcc cgtcaggcca tgcgcaatgc tctgaagcgc 840
atccaggacg gcgaatacgc gaagatgttc atcagcgaag gcgctaccgg ctacccatcg 900
atgaccgcca agcgtcgtaa caacgctgct cacggtatcg aaatcatcgg cgagcaactg 960
cgctcgatga tgccttggat cggtgccaac aaaatcgtcg acaaagccaa gaac 1014

<210> SEQ ID NO 133
<211> LENGTH: 250
<212> TYPE: DNA
<213> ORGANISM: Saccharomyces cerevisiae

<400> SEQUENCE: 133
ccgcaaatta aagccttcga gcgtcccaaa accttctcaa gcaaggtttt cagtataatg 60
ttacatgcgt acacgcgtct gtacagaaaa aaaagaaaaa tttgaaatat aaataacgtt 120
cttaatacta acataactat aaaaaaataa atagggacct agacttcagg ttgtctaact 180
ccttcctttt cggttagagc ggatgtgggg ggagggcgtg aatgtaagcg tgacataact 240
aattacatga 250

<210> SEQ ID NO 134
<211> LENGTH: 1181
<212> TYPE: DNA
<213> ORGANISM: Saccharomyces cerevisiae

<400> SEQUENCE: 134
taaaacctct agtggagtag tagatgtaat caatgaagcg gaagccaaaa gaccagagta 60
gaggcctata gaagaaactg cgataccttt tgtgatggct aaacaaacag acatcttttt 120
atatgttttt acttctgtat atcgtgaagt agtaagtgat aagcgaattt ggctaagaac 180
gttgtaagtg aacaagggac ctcttttgcc tttcaaaaaa ggattaaatg gagttaatca 240

-continued

```
ttgagattta gttttcgtta gattctgtat ccctaaataa ctcccttacc cgacgggaag    300

gcacaaaaga cttgaataat agcaaacggc cagtagccaa gaccaaataa tactagagtt    360

aactgatggt cttaaacagg cattacgtgg tgaactccaa gaccaatata caaaatatcg    420

ataagttatt cttgcccacc aatttaagga gcctacatca ggacagtagt accattcctc    480

agagaagagg tatacataac aagaaaatcg cgtgaacacc ttatataact tagcccgtta    540

ttgagctaaa aaaccttgca aaatttccta tgaataagaa tacttcagac gtgataaaaa    600

tttactttct aactcttctc acgctgcccc tatctgttct tccgctctac cgtgagaaat    660

aaagcatcga gtacggcagt tcgctgtcac tgaactaaaa caataaggct agttcgaatg    720

atgaacttgc ttgctgtcaa acttctgagt tgccgctgat gtgacactgt gacaataaat    780

tcaaaccggt tatagcggtc tcctccggta ccggttctgc cacctccaat agagctcagt    840

aggagtcaga acctctgcgg tggctgtcag tgactcatcc gcgtttcgta agttgtgcgc    900

gtgcacattt cgcccgttcc cgctcatctt gcagcaggcg gaaattttca tcacgctgta    960

ggacgcaaaa aaaaaaataat taatcgtaca agaatcttgg aaaaaaaatt gaaaaatttt   1020

gtataaaagg gatgacctaa cttgactcaa tggcttttac acccagtatt ttccctttcc   1080

ttgtttgtta caattataga agcaagacaa aaacatatag acaacctatt cctaggagtt   1140

atattttttt accctaccag caatataagt aaaaaactag t                        1181
```

<210> SEQ ID NO 135
<211> LENGTH: 759
<212> TYPE: DNA
<213> ORGANISM: Saccharomyces cerevisiae

<400> SEQUENCE: 135

```
ggccctgcag gcctatcaag tgctggaaac tttttctctt ggaatttttg caacatcaag     60

tcatagtcaa ttgaattgac ccaatttcac atttaagatt tttttttttt catccgacat    120

acatctgtac actaggaagc cctgtttttc tgaagcagct tcaaatatat atatttttta    180

catatttatt atgattcaat gaacaatcta attaaatcga aaacaagaac cgaaacgcga    240

ataaataatt tatttagatg gtgacaagtg tataagtcct catcgggaca gctacgattt    300

ctctttcggt tttggctgag ctactggttg ctgtgacgca gcggcattag cgcggcgtta    360

tgagctaccc tcgtggcctg aaagatggcg ggaataaagc ggaactaaaa attactgact    420

gagccatatt gaggtcaatt tgtcaactcg tcaagtcacg tttggtggac ggcccctttc    480

caacgaatcg tatatactaa catgcgcgcg cttcctatat acacatatac atatatatat    540

atatatatat gtgtgcgtgt atgtgtacac ctgtatttaa tttccttact cgcgggtttt    600

tctttttttct caattcttgg cttcctcttt ctcgagtata taatttttca ggtaaaattt    660

agtacgatag taaaatactt ctcgaactcg tcacatatac gtgtacataa tgtctgaacc    720

agctcaaaag aaacaaaagg ttgctaacaa ctctctaga                           759
```

<210> SEQ ID NO 136
<211> LENGTH: 643
<212> TYPE: DNA
<213> ORGANISM: Saccharomyces cerevisiae

<400> SEQUENCE: 136

```
gaaatgaata acaatactga cagtactaaa taattgccta cttggcttca catacgttgc     60

atacgtcgat atagataata atgataatga cagcaggatt atcgtaatac gtaatagttg    120

aaaatctcaa aaatgtgtgg gtcattacgt aaataatgat aggaatggga ttcttctatt    180
```

tttcctttt ccattctagc agccgtcggg aaaacgtggc atcctctctt tcgggctcaa 240
ttggagtcac gctgccgtga gcatcctctc tttccatatc taacaactga gcacgtaacc 300
aatggaaaag catgagctta gcgttgctcc aaaaaagtat tggatggtta ataccatttg 360
tctgttctct tctgactttg actcctcaaa aaaaaaaaat ctacaatcaa cagatcgctt 420
caattacgcc ctcacaaaaa cttttttcct tcttcttcgc ccacgttaaa ttttatccct 480
catgttgtct aacggatttc tgcacttgat ttattataaa aagacaaaga cataatactt 540
ctctatcaat ttcagttatt gttcttcctt gcgttattct tctgttcttc tttttctttt 600
gtcatatata accataacca agtaatacat attcaaatct aga 643

<210> SEQ ID NO 137
<211> LENGTH: 1716
<212> TYPE: DNA
<213> ORGANISM: Bacillus subtilis

<400> SEQUENCE: 137
atgttgacaa aagcaacaaa agaacaaaaa tcccttgtga aaaacagagg ggcggagctt 60
gttgttgatt gcttagtgga gcaaggtgtc acacatgtat ttggcattcc aggtgcaaaa 120
attgatgcgg tatttgacgc tttacaagat aaaggacctg aaattatcgt tgcccggcac 180
gaacaaaacg cagcattcat ggcccaagca gtcggccgtt taactggaaa accgggagtc 240
gtgttagtca catcaggacc gggtgcctct aacttggcaa caggcctgct gacagcgaac 300
actgaaggag accctgtcgt tgcgcttgct ggaaacgtga tccgtgcaga tcgtttaaaa 360
cggacacatc aatctttgga taatgcggcg ctattccagc cgattacaaa atacagtgta 420
gaagttcaag atgtaaaaaa tataccggaa gctgttacaa atgcatttag gatagcgtca 480
gcagggcagg ctggggccgc ttttgtgagc tttccgcaag atgttgtgaa tgaagtcaca 540
aatacgaaaa acgtgcgtgc tgttgcagcg ccaaaactcg gtcctgcagc agatgatgca 600
atcagtgcgg ccatagcaaa aatccaaaca gcaaaacttc ctgtcgtttt ggtcggcatg 660
aaaggcggaa gaccggaagc aattaaagcg gttcgcaagc ttttgaaaaa ggttcagctt 720
ccatttgttg aaacatatca agctgccggt accctttcta gagatttaga ggatcaatat 780
tttggccgta tcggtttgtt ccgcaaccag cctggcgatt tactgctaga gcaggcagat 840
gttgttctga cgatcggcta tgacccgatt gaatatgatc cgaaattctg gaatatcaat 900
ggagaccgga caattatcca tttagacgag attatcgctg acattgatca tgcttaccag 960
cctgatcttg aattgatcgg tgacattccg tccacgatca atcatatcga acacgatgct 1020
gtgaaagtgg aatttgcaga gcgtgagcag aaaatccttt ctgatttaaa acaatatatg 1080
catgaaggtg agcaggtgcc tgcagattgg aaatcagaca gagcgcaccc tcttgaaatc 1140
gttaaagagt tgcgtaatgc agtcgatgat catgttacag taacttgcga tatcggttcg 1200
cacgccattt ggatgtcacg ttatttccgc agctacgagc cgttaacatt aatgatcagt 1260
aacggtatgc aaacactcgg cgttgcgctt ccttgggcaa tcggcgcttc attggtgaaa 1320
ccgggagaaa aagtggtttc tgtctctggt gacggcggtt tcttattctc agcaatggaa 1380
ttagagacag cagttcgact aaaagcacca attgtacaca ttgtatggaa cgacagcaca 1440
tatgacatgg ttgcattcca gcaattgaaa aaatataacc gtacatctgc ggtcgatttc 1500
ggaaatatcg atatcgtgaa atatgcggaa agcttcggag caactggctt gcgcgtagaa 1560
tcaccagacc agctggcaga tgttctgcgt caaggcatga acgctgaagg tcctgtcatc 1620
atcgatgtcc cggttgacta cagtgataac attaatttag caagtgacaa gcttccgaaa 1680
gaattcgggg aactcatgaa aacgaaagct ctctag 1716

<210> SEQ ID NO 138
<211> LENGTH: 571
<212> TYPE: PRT
<213> ORGANISM: Bacillus subtilis

<400> SEQUENCE: 138

Met Leu Thr Lys Ala Thr Lys Glu Gln Lys Ser Leu Val Lys Asn Arg
1 5 10 15

Gly Ala Glu Leu Val Val Asp Cys Leu Val Glu Gln Gly Val Thr His
20 25 30

Val Phe Gly Ile Pro Gly Ala Lys Ile Asp Ala Val Phe Asp Ala Leu
35 40 45

Gln Asp Lys Gly Pro Glu Ile Ile Val Ala Arg His Glu Gln Asn Ala
50 55 60

Ala Phe Met Ala Gln Ala Val Gly Arg Leu Thr Gly Lys Pro Gly Val
65 70 75 80

Val Leu Val Thr Ser Gly Pro Gly Ala Ser Asn Leu Ala Thr Gly Leu
85 90 95

Leu Thr Ala Asn Thr Glu Gly Asp Pro Val Val Ala Leu Ala Gly Asn
100 105 110

Val Ile Arg Ala Asp Arg Leu Lys Arg Thr His Gln Ser Leu Asp Asn
115 120 125

Ala Ala Leu Phe Gln Pro Ile Thr Lys Tyr Ser Val Glu Val Gln Asp
130 135 140

Val Lys Asn Ile Pro Glu Ala Val Thr Asn Ala Phe Arg Ile Ala Ser
145 150 155 160

Ala Gly Gln Ala Gly Ala Ala Phe Val Ser Phe Pro Gln Asp Val Val
165 170 175

Asn Glu Val Thr Asn Thr Lys Asn Val Arg Ala Val Ala Ala Pro Lys
180 185 190

Leu Gly Pro Ala Ala Asp Asp Ala Ile Ser Ala Ala Ile Ala Lys Ile
195 200 205

Gln Thr Ala Lys Leu Pro Val Val Leu Val Gly Met Lys Gly Gly Arg
210 215 220

Pro Glu Ala Ile Lys Ala Val Arg Lys Leu Leu Lys Lys Val Gln Leu
225 230 235 240

Pro Phe Val Glu Thr Tyr Gln Ala Ala Gly Thr Leu Ser Arg Asp Leu
245 250 255

Glu Asp Gln Tyr Phe Gly Arg Ile Gly Leu Phe Arg Asn Gln Pro Gly
260 265 270

Asp Leu Leu Leu Glu Gln Ala Asp Val Val Leu Thr Ile Gly Tyr Asp
275 280 285

Pro Ile Glu Tyr Asp Pro Lys Phe Trp Asn Ile Asn Gly Asp Arg Thr
290 295 300

Ile Ile His Leu Asp Glu Ile Ile Ala Asp Ile Asp His Ala Tyr Gln
305 310 315 320

Pro Asp Leu Glu Leu Ile Gly Asp Ile Pro Ser Thr Ile Asn His Ile
325 330 335

Glu His Asp Ala Val Lys Val Glu Phe Ala Glu Arg Glu Gln Lys Ile
340 345 350

Leu Ser Asp Leu Lys Gln Tyr Met His Glu Gly Glu Gln Val Pro Ala

```
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 139
<211> LENGTH: 448
<212> TYPE: DNA
<213> ORGANISM: Saccharomyces cerevisiae

<400> SEQUENCE: 139

```
cccattaccg acatttgggc gctatacgtg catatgttca tgtatgtatc tgtatttaaa     60

acacttttgt attatttttc ctcatatatg tgtataggtt tatacggatg atttaattat    120

tacttcacca ccctttattt caggctgata tcttagcctt gttactagtt agaaaaagac    180

atttttgctg tcagtcactg tcaagagatt cttttgctgg catttcttct agaagcaaaa    240

agagcgatgc gtcttttccg ctgaaccgtt ccagcaaaaa agactaccaa cgcaatatgg    300

attgtcagaa tcatataaaa gagaagcaaa taactccttg tcttgtatca attgcattat    360

aatatcttct tgttagtgca atatcatata gaagtcatcg aaatagatat taagaaaaac    420

aaactgtaca atcaatcaat caatcatc                                      448
```

<210> SEQ ID NO 140
<211> LENGTH: 16387
<212> TYPE: DNA
<213> ORGANISM: artificial sequence
<220> FEATURE:
<223> OTHER INFORMATION: plasmid construct

<400> SEQUENCE: 140

```
tcccattacc gacatttggg cgctatacgt gcatatgttc atgtatgtat ctgtatttaa     60

aacacttttg tattattttt cctcatatat gtgtataggt ttatacggat gatttaatta    120
```

-continued

```
ttacttcacc accctttatt tcaggctgat atcttagcct tgttactagt tagaaaaaga    180
catttttgct gtcagtcact gtcaagagat tcttttgctg gcatttcttc tagaagcaaa    240
aagagcgatg cgtcttttcc gctgaaccgt tccagcaaaa aagactacca acgcaatatg    300
gattgtcaga atcatataaa agagaagcaa ataactcctt gtcttgtatc aattgcatta    360
taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgctc tagaactagt accacaggtg   2460
ttgtcctctg aggacataaa atacacaccg agattcatca actcattgct ggagttagca   2520
```

-continued

```
tatctacaat tgggtgaaat ggggagcgat ttgcaggcat ttgctcggca tgccggtaga   2580
ggtgtggtca ataagagcga cctcatgcta tacctgagaa agcaacctga cctacaggaa   2640
agagttactc aagaataaga attttcgttt taaaacctaa gagtcacttt aaaatttgta   2700
tacacttatt tttttataa cttatttaat aataaaaatc ataaatcata agaaattcgc   2760
ttactcttaa ttaatcaagc atctaaaaca caaccgttgg aagcgttgga aaccaactta   2820
gcatacttgg atagagtacc tcttgtgtaa cgaggtggag gtgcaaccca actttgttta   2880
cgttgagcca tttccttatc agagactaat aggtcaatct tgttattatc agcatcaatg   2940
ataatctcat cgccgtctct gaccaacccg ataggaccac cttcagcggc ttcgggaaca   3000
atgtggccga ttaagaaccc gtgagaacca ccagagaatc taccatcagt caacaatgca   3060
acatctttac ccaaaccgta acccatcaga gcagaggaag gctttagcat ttcaggcata   3120
cctggtgcac ctcttggacc ttcatatctg ataacaacaa cggtttttttc acccttcttg   3180
atttcacctc tttccaaggc ttcaataaag gcaccttcct cttcgaacac acgtgctcta   3240
cccttgaagt aagtaccttc cttaccggta attttaccca cagctccacc tggtgccaat   3300
gaaccgtaca gaatttgcaa gtgaccgttg gccttgattg ggtgggagag tggcttaata   3360
atctcttgtc cttcaggtag gcttggtgct ttctttgcac gttctgccaa agtgtcaccg   3420
gtaacagtca ttgtgttacc gtgcaacatg ttgttttcat atagatactt aatcacagat   3480
tgggtaccac caacgttaat caaatcggcc atgacgtatt taccagaagg tttgaagtca   3540
ccgatcaatg gtgtagtatc actgattctt tggaaatcat ctggtgacaa cttgacaccc   3600
gcagagtgag caacagccac caaatgcaaa acagcattag tggacccacc ggttgcaacg   3660
acataagtaa tggcgttttc aaaagcctct tttgtgagga tatcacgagg taaaataccc   3720
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gtttttagag atcctgttaa aacctctagt ggagtagtag   4020
atgtaatcaa tgaagcggaa gccaaaagac cagagtagag gcctatagaa gaaactgcga   4080
taccttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaaagactt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
```

ctgtcagtga ctcatccgcg tttcgtaagt tgtgcgcgtg cacatttcgc ccgttcccgc 4920
tcatcttgca gcaggcggaa attttcatca cgctgtagga cgcaaaaaaa aaataattaa 4980
tcgtacaaga atcttggaaa aaaaattgaa aaattttgta taaaagggat gacctaactt 5040
gactcaatgg cttttacacc cagtattttc cctttccttg tttgttacaa ttatagaagc 5100
aagacaaaaa catatagaca acctattcct aggagttata tttttttacc ctaccagcaa 5160
tataagtaaa aaactagtat gaaggtgttt tacgataaag actgcgatct gagcatcatc 5220
cagggaaaga aggttgctat tataggatat ggttcccaag gacacgcaca agccttgaac 5280
ttgaaagatt ctggggtcga cgtgacagta ggtctgtata aaggtgctgc tgatgcagca 5340
aaggctgaag cacatggctt taaagtcaca gatgttgcag cggctgttgc tggcgctgat 5400
ttagtcatga ttttaattcc agatgaattt caatcgcaat tgtacaaaaa tgaaatagaa 5460
ccaaacatta agaagggcgc taccttggcc ttcagtcatg gatttgccat tcattacaat 5520
caagtagtcc ccagggcaga tttggacgtt attatgattg cacctaaggc tccggggcat 5580
actgttagga gcgaatttgt taagggtggt ggtattccag atttgatcgc tatataccaa 5640
gacgttagcg gaaacgctaa gaatgtagct ttaagctacg cagcaggagt tggtggcggg 5700
agaacgggta taatagaaac cacttttaaa gacgagactg agacagattt atttggagaa 5760
caagcggttc tgtgcggagg aactgttgaa ttggttaaag caggctttga gacgcttgtc 5820
gaagcagggt acgctcccga aatggcatac ttcgaatgtc tacatgaatt gaagttgata 5880
gtagacttaa tgtatgaagg tggtatagct aatatgaact attccatttc aaataatgca 5940
gaatatggtg agtatgtcac cggacctgaa gtcattaacg cagaatcaag acaagccatg 6000
agaaatgcct tgaaacgtat ccaggacggt gaatacgcta agatgttcat aagtgaaggc 6060
gctacgggtt acccgagtat gactgctaaa agaagaaaca atgcagcaca tggtatcgaa 6120
attattggtg aacagttaag gtctatgatg ccctggatcg gtgctaataa gatcgtagac 6180
aaggcgaaaa attaaggccc tgcaggccta tcaagtgctg gaaacttttt ctcttggaat 6240
ttttgcaaca tcaagtcata gtcaattgaa ttgacccaat ttcacattta agattttttt 6300
tttttcatcc gacatacatc tgtacactag gaagccctgt ttttctgaag cagcttcaaa 6360
tatatatatt ttttacatat ttattatgat tcaatgaaca atctaattaa atcgaaaaca 6420
agaaccgaaa cgcgaataaa taatttattt agatggtgac aagtgtataa gtcctcatcg 6480
ggacagctac gatttctctt tcggttttgg ctgagctact ggttgctgtg acgcagcggc 6540
attagcgcgg cgttatgagc taccctcgtg gcctgaaaga tggcgggaat aaagcggaac 6600
taaaaattac tgactgagcc atattgaggt caatttgtca actcgtcaag tcacgtttgg 6660
tggacggccc ctttccaacg aatcgtatat actaacatgc gcgcgcttcc tatatacaca 6720
tatacatata tatatatata tatatgtgtg cgtgtatgtg tacacctgta tttaatttcc 6780
ttactcgcgg gtttttcttt tttctcaatt cttggcttcc tctttctcga gtatataatt 6840
tttcaggtaa aatttagtac gatagtaaaa tacttctcga actcgtcaca tatacgtgta 6900
cataatgtct gaaccagctc aaaagaaaca aaaggttgct aacaactctc tagagcggcc 6960
gcccgcaaat taaagccttc gagcgtccca aaaccttctc aagcaaggtt ttcagtataa 7020
tgttacatgc gtacacgcgt ctgtacagaa aaaaaagaaa aatttgaaat ataaataacg 7080
ttcttaatac taacataact ataaaaaaat aaatagggac ctagacttca ggttgtctaa 7140
ctccttcctt ttcggttaga gcggatgtgg ggggagggcg tgaatgtaag cgtgacataa 7200
ctaattacat gattaattaa ttattggttt tctggtctca actttctgac ttccttacca 7260
accttccaga tttccatgtt tctgatggtg tctaattcct tttctagctt ttctctgtag 7320
tcaggttgag agttgaattc caaagatctc ttggtttcgg taccgttctt ggtagattcg 7380
tacaagtctt ggaaaacagg cttcaaagca ttcttgaaga ttgggtacca gtccaaagca 7440
cctcttctgg cggtggtgga acaagcatcg tacatgtaat ccataccgta cttaccgatc 7500
aatgggtata gagattgggt agcttcttcg acggtttcgt tgaaagcttc agatggggag 7560
tgaccgtttt ctctcaagac gtcgtattga gccaagaaca taccgtggat accacccatt 7620
aaacaacctc tttcaccgta caagtcagag ttgacttctc tttcgaaagt ggtttggtaa 7680
acgtaaccgg aaccaatggc aacggccaaa gcttgggcct tttcgtgagc cttaccggtg 7740
acatcgttcc agacggcgta agaagagtta ataccacgac cttccttgaa caaagatctg 7800
acagttctac cggaaccctt tggagcaacc aagataacat ctaagtcctt tggtggttca 7860
acgtgagtca agtccttgaa gactggggag aaaccgtggg agaagtacaa agtcttaccc 7920
ttggtcaaca atggcttgat agcaggccag gtttctgatt gagcggcatc ggacaacaag 7980
ttcataacgt aactacctct cttgatagca tcttcaacag tgaacaagtt cttgcctgga 8040
acccaaccgt cttcgatggc agccttccaa gaagcaccat ctttacggac accaatgata 8100
acgttcaaac cgttgtctct caagttcaaa ccttgaccgt aaccttggga accgtaaccg 8160
atcaaagcaa aagtgtcgtt cttgaagtag tccaacaact tttctcttgg ccagtcagct 8220
ctttcgtaga cggtttcaac agtaccaccg aagttgattt gcttcaacat cctcagctct 8280
agatttgaat atgtattact tggttatggt tatatatgac aaaagaaaaa gaagaacaga 8340
agaataacgc aaggaagaac aataactgaa attgatagag aagtattatg tctttgtctt 8400
tttataataa atcaagtgca gaaatccgtt agacaacatg agggataaaa tttaacgtgg 8460
gcgaagaaga aggaaaaaag tttttgtgag ggcgtaattg aagcgatctg ttgattgtag 8520
attttttttt tttgaggagt caaagtcaga agagaacaga caaatggtat taaccatcca 8580
atactttttt ggagcaacgc taagctcatg cttttccatt ggttacgtgc tcagttgtta 8640
gatatggaaa gagaggatgc tcacggcagc gtgactccaa ttgagcccga aagagaggat 8700
gccacgtttt cccgacggct gctagaatgg aaaaaggaaa aatagaagaa tcccattcct 8760
atcattattt acgtaatgac ccacacattt ttgagatttt caactattac gtattacgat 8820
aatcctgctg tcattatcat tattatctat atcgacgtat gcaacgtatg tgaagccaag 8880
taggcaatta tttagtactg tcagtattgt tattcatttc agatctatcc gcggtggagc 8940
tcgaattcac tggccgtcgt tttacaacgt cgtgactggg aaaaccctgg cgttacccaa 9000
cttaatcgcc ttgcagcaca tccccctttc gccagctggc gtaatagcga agaggcccgc 9060
accgatcgcc cttcccaaca gttgcgcagc ctgaatggcg aatggcgcct gatgcggtat 9120
tttctcctta cgcatctgtg cggtatttca caccgcatac gtcaaagcaa ccatagtacg 9180
cgccctgtag cggcgcatta agcgcggcgg gtgtggtggt tacgcgcagc gtgaccgcta 9240
cacttgccag cgccttagcg cccgctcctt tcgctttctt cccttccttt ctcgccacgt 9300
tcgccggctt tccccgtcaa gctctaaatc gggggctccc tttagggttc cgatttagtg 9360
ctttacggca cctcgacccc aaaaaacttg atttgggtga tggttcacgt agtgggccat 9420
cgccctgata gacggttttt cgccctttga cgttggagtc cacgttcttt aatagtggac 9480
tcttgttcca aactggaaca acactcaact ctatctcggg ctattctttt gatttataag 9540
ggattttgcc gatttcggtc tattggttaa aaaatgagct gatttaacaa aaatttaacg 9600

```
cgaattttaa caaaatatta acgtttacaa ttttatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag acgaaagggc ctcgtgatac   9840
gcctattttt ataggttaat gtcatgataa taatggtttc ttagacgtca ggtggcactt   9900
ttcggggaaa tgtgcgcgga acccctattt gtttattttt ctaaatacat tcaaatatgt   9960
atccgctcat gagacaataa ccctgataaa tgcttcaata atattgaaaa aggaagagta  10020
tgagtattca acatttccgt gtcgccctta ttcccttttt tgcggcattt tgccttcctg  10080
tttttgctca cccagaaacg ctggtgaaag taaaagatgc tgaagatcag ttgggtgcac  10140
gagtgggtta catcgaactg gatctcaaca gcggtaagat ccttgagagt tttcgccccg  10200
aagaacgttt tccaatgatg agcactttta aagttctgct atgtggcgcg gtattatccc  10260
gtattgacgc cgggcaagag caactcggtc gccgcataca ctattctcag aatgacttgg  10320
ttgagtactc accagtcaca gaaaagcatc ttacggatgg catgacagta agagaattat  10380
gcagtgctgc cataaccatg agtgataaca ctgcggccaa cttacttctg acaacgatcg  10440
gaggaccgaa ggagctaacc gcttttttgc acaacatggg ggatcatgta actcgccttg  10500
atcgttggga accggagctg aatgaagcca taccaaacga cgagcgtgac accacgatgc  10560
ctgtagcaat ggcaacaacg ttgcgcaaac tattaactgg cgaactactt actctagctt  10620
cccggcaaca attaatagac tggatggagg cggataaagt tgcaggacca cttctgcgct  10680
cggcccttcc ggctggctgg tttattgctg ataaatctgg agccggtgag cgtgggtctc  10740
gcggtatcat tgcagcactg gggccagatg gtaagccctc ccgtatcgta gttatctaca  10800
cgacggggag tcaggcaact atggatgaac gaaatagaca gatcgctgag ataggtgcct  10860
cactgattaa gcattggtaa ctgtcagacc aagtttactc atatatactt tagattgatt  10920
taaaacttca tttttaattt aaaaggatct aggtgaagat cctttttgat aatctcatga  10980
ccaaaatccc ttaacgtgag ttttcgttcc actgagcgtc agaccccgta gaaaagatca  11040
aaggatcttc ttgagatcct ttttttctgc gcgtaatctg ctgcttgcaa acaaaaaaac  11100
caccgctacc agcggtggtt tgtttgccgg atcaagagct accaactctt tttccgaagg  11160
taactggctt cagcagagcg cagataccaa atactgttct tctagtgtag ccgtagttag  11220
gccaccactt caagaactct gtagcaccgc ctacatacct cgctctgcta atcctgttac  11280
cagtggctgc tgccagtggc gataagtcgt gtcttaccgg gttggactca agacgatagt  11340
taccggataa ggcgcagcgg tcgggctgaa cggggggttc gtgcacacag cccagcttgg  11400
agcgaacgac ctacaccgaa ctgagatacc tacagcgtga gctatgagaa agcgccacgc  11460
ttcccgaagg gagaaaggcg gacaggtatc cggtaagcgg cagggtcgga acaggagagc  11520
gcacgaggga gcttccaggg ggaaacgcct ggtatcttta tagtcctgtc gggtttcgcc  11580
acctctgact tgagcgtcga tttttgtgat gctcgtcagg ggggcggagc ctatggaaaa  11640
acgccagcaa cgcggccttt ttacggttcc tggccttttg ctggcctttt gctcacatgt  11700
tctttcctgc gttatcccct gattctgtgg ataaccgtat taccgccttt gagtgagctg  11760
ataccgctcg ccgcagccga acgaccgagc gcagcgagtc agtgagcgag gaagcggaag  11820
agcgcccaat acgcaaaccg cctctccccg cgcgttggcc gattcattaa tgcagctggc  11880
acgacaggtt tcccgactgg aaagcgggca gtgagcgcaa cgcaattaat gtgagttagc  11940
tcactcatta ggcaccccag gctttacact ttatgcttcc ggctcgtatg ttgtgtggaa  12000
```

```
ttgtgagcgg ataacaattt cacacaggaa acagctatga ccatgattac gccaagcttt   12060

ttctttccaa ttttttttt ttcgtcatta taaaaatcat tacgaccgag attcccgggt   12120

aataactgat ataattaaat tgaagctcta atttgtgagt ttagtataca tgcatttact   12180

tataatacag tttttagtt ttgctggccg catcttctca aatatgcttc ccagcctgct   12240

tttctgtaac gttcaccctc taccttagca tcccttccct ttgcaaatag tcctcttcca   12300

acaataataa tgtcagatcc tgtagagacc acatcatcca cggttctata ctgttgaccc   12360

aatgcgtctc ccttgtcatc taaacccaca ccgggtgtca taatcaacca atcgtaacct   12420

tcatctcttc cacccatgtc tctttgagca ataaagccga taacaaaatc tttgtcgctc   12480

ttcgcaatgt caacagtacc cttagtatat tctccagtag atagggagcc cttgcatgac   12540

aattctgcta acatcaaaag gcctctaggt tcctttgtta cttcttctgc cgcctgcttc   12600

aaaccgctaa caatacctgg gcccaccaca ccgtgtgcat tcgtaatgtc tgcccattct   12660

gctattctgt atacacccgc agagtactgc aatttgactg tattaccaat gtcagcaaat   12720

tttctgtctt cgaagagtaa aaaattgtac ttggcggata atgcctttag cggcttaact   12780

gtgccctcca tggaaaaatc agtcaagata tccacatgtg tttttagtaa acaaatttg    12840

ggacctaatg cttcaactaa ctccagtaat tccttggtgg tacgaacatc caatgaagca   12900

cacaagtttg tttgcttttc gtgcatgata ttaaatagct tggcagcaac aggactagga   12960

tgagtagcag cacgttcctt atatgtagct ttcgacatga tttatcttcg tttcctgcag   13020

gtttttgttc tgtgcagttg ggttaagaat actgggcaat ttcatgtttc ttcaacacta   13080

catatgcgta tatataccaa tctaagtctg tgctccttcc ttcgttcttc cttctgttcg   13140

gagattaccg aatcaaaaaa atttcaagga aaccgaaatc aaaaaaaaga ataaaaaaaa   13200

aatgatgaat tgaaaagctt gcatgcctgc aggtcgactc tagtatactc cgtctactgt   13260

acgatacact tccgctcagg tccttgtcct ttaacgaggc cttaccactc ttttgttact   13320

ctattgatcc agctcagcaa aggcagtgtg atctaagatt ctatcttcgc gatgtagtaa   13380

aactagctag accgagaaag agactagaaa tgcaaaaggc acttctacaa tggctgccat   13440

cattattatc cgatgtgacg ctgcattttt tttttttttt tttttttttt tttttttttt   13500

tttttttttt tttttttgta caaatatcat aaaaaaagag aatctttta agcaaggatt   13560

ttcttaactt cttcggcgac agcatcaccg acttcggtgg tactgttgga accacctaaa   13620

tcaccagttc tgatacctgc atccaaaacc ttttaactg catcttcaat ggctttacct    13680

tcttcaggca agttcaatga caatttcaac atcattgcag cagacaagat agtggcgata   13740

gggttgacct tattctttgg caaatctgga gcggaaccat ggcatggttc gtacaaacca   13800

aatgcggtgt tcttgtctgg caaagaggcc aaggacgcag atggcaacaa acccaaggag   13860

cctgggataa cggaggcttc atcggagatg atatcaccaa acatgttgct ggtgattata   13920

ataccattta ggtgggttgg gttcttaact aggatcatgg cggcagaatc aatcaattga   13980

tgttgaactt tcaatgtagg gaattcgttc ttgatggttt cctccacagt ttttctccat   14040

aatcttgaag aggccaaaac attagcttta tccaaggacc aaataggcaa tggtggctca   14100

tgttgtaggg ccatgaaagc ggccattctt gtgattcttt gcacttctgg aacggtgtat   14160

tgttcactat cccaagcgac accatcacca tcgtcttcct ttctcttacc aaagtaaata   14220

cctcccacta attctctaac aacaacgaag tcagtacctt tagcaaattg tggcttgatt   14280

ggagataagt ctaaaagaga gtcggatgca aagttacatg gtcttaagtt ggcgtacaat   14340
```

```
tgaagttctt tacggatttt tagtaaacct tgttcaggtc taacactacc ggtaccccat  14400
ttaggaccac ccacagcacc taacaaaacg gcatcagcct tcttggaggc ttccagcgcc  14460
tcatctggaa gtggaacacc tgtagcatcg atagcagcac caccaattaa atgattttcg  14520
aaatcgaact tgacattgga acgaacatca gaaatagctt taagaacctt aatggcttcg  14580
gctgtgattt cttgaccaac gtggtcacct ggcaaaacga cgatcttctt aggggcagac  14640
attacaatgg tatatccttg aaatatatat aaaaaaaaaa aaaaaaaaaa aaaaaaaaaa  14700
tgcagcttct caatgatatt cgaatacgct ttgaggagat acagcctaat atccgacaaa  14760
ctgttttaca gatttacgat cgtacttgtt acccatcatt gaattttgaa catccgaacc  14820
tgggagtttt ccctgaaaca gatagtatat ttgaacctgt ataataatat atagtctagc  14880
gctttacgga agacaatgta tgtatttcgg ttcctggaga aactattgca tctattgcat  14940
aggtaatctt gcacgtcgca tccccggttc attttctgcg tttccatctt gcacttcaat  15000
agcatatctt tgttaacgaa gcatctgtgc ttcattttgt agaacaaaaa tgcaacgcga  15060
gagcgctaat tttcaaaca aagaatctga gctgcatttt tacagaacag aaatgcaacg  15120
cgaaagcgct attttaccaa cgaagaatct gtgcttcatt tttgtaaaac aaaaatgcaa  15180
cgcgagagcg ctaatttttc aaacaaagaa tctgagctgc atttttacag aacagaaatg  15240
caacgcgaga gcgctatttt accaacaaag aatctatact tctttttgt tctacaaaaa  15300
tgcatcccga gagcgctatt tttctaacaa agcatcttag attacttttt ttctcctttg  15360
tgcgctctat aatgcagtct cttgataact ttttgcactg taggtccgtt aaggttagaa  15420
gaaggctact ttggtgtcta ttttctcttc cataaaaaaa gcctgactcc acttcccgcg  15480
tttactgatt actagcgaag ctgcgggtgc attttttcaa gataaaggca tccccgatta  15540
tattctatac cgatgtggat tgcgcatact ttgtgaacag aaagtgatag cgttgatgat  15600
tcttcattgg tcagaaaatt atgaacggtt tcttctattt tgtctctata tactacgtat  15660
aggaaatgtt tacattttcg tattgttttc gattcactct atgaatagtt cttactacaa  15720
ttttttgtc taaagagtaa tactagagat aaacataaaa aatgtagagg tcgagtttag  15780
atgcaagttc aaggagcgaa aggtggatgg gtaggttata tagggatata gcacagagat  15840
atatagcaaa gagatacttt tgagcaatgt ttgtggaagc ggtattcgca atattttagt  15900
agctcgttac agtccggtgc gtttttggtt ttttgaaagt gcgtcttcag agcgcttttg  15960
gttttcaaaa gcgctctgaa gttcctatac tttctagaga ataggaactt cggaatagga  16020
acttcaaagc gtttccgaaa acgagcgctt ccgaaaatgc aacgcgagct gcgcacatac  16080
agctcactgt tcacgtcgca cctatatctg cgtgttgcct gtatatatat atacatgaga  16140
agaacggcat agtgcgtgtt tatgcttaaa tgcgtactta tatgcgtcta tttatgtagg  16200
atgaaaggta gtctagtacc tcctgtgata ttatcccatt ccatgcgggg tatcgtatgc  16260
ttccttcagc actacccttt agctgttcta tatgctgcca ctcctcaatt ggattagtct  16320
catccttcaa tgctatcatt tcctttgata ttggatcata tgcatagtac cgagaaacta  16380
gaggatc                                                            16387
```

<210> SEQ ID NO 141
<211> LENGTH: 2237
<212> TYPE: DNA
<213> ORGANISM: Artificial sequence
<220> FEATURE:
<223> OTHER INFORMATION: Fragment

<400> SEQUENCE: 141

-continued

```
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt ttcttcataa    180
ttgcataata ttgtccgctg ccccttttc tgttagacgg tgtcttgatc tacttgctat     240
cgttcaacac caccttattt tctaactatt ttttttttag ctcatttgaa tcagcttatg    300
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
tcggccattg gaaccacggc gatatgacca aagaagaagt taaagctttg gaatgtaatg   1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttccctttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattatt                                                  2237
```

<210> SEQ ID NO 142

<211> LENGTH: 4420
<212> TYPE: DNA
<213> ORGANISM: Artificial sequence
<220> FEATURE:
<223> OTHER INFORMATION: Cassette

<400> SEQUENCE: 142

```
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt ttcttcataa    180
ttgcataata ttgtccgctg cccctttttc tgttagacgg tgtcttgatc tacttgctat    240
cgttcaacac caccttattt tctaactatt ttttttttag ctcatttgaa tcagcttatg    300
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatggaatc gccatgggaa    780
cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
tcggccattg gaaccacggc gatatgacca aagaagaagt taaagctttg gaatgtaatg   1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttccctttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
```

-continued

```
cttctagggg agccgtaaca gacttttgga agcctgaaga aactggcaaa aaatgagcga   2220
tttaatctct aattattagt taaagtttta taagcatttt tatgtaacga aaaataaatt   2280
ggttcatatt attactgcac tgtcacttac catggaaaga ccagacaaga agttgccgac   2340
agtctgttga attggcctgg ttaggcttaa gtctgggtcc gcttctttac aaatttggag   2400
aatttctctt aaacgatatg tatattcttt tcgttggaaa agatgtcttc caaaaaaaaa   2460
accgatgaat tagtggaacc aaggaaaaaa aaagaggtat ccttgattaa ggaacactgt   2520
ttaaacagtg tggtttccaa aaccctgaaa ctgcattagt gtaatagaag actagacacc   2580
tcgatacaaa taatggttac tcaattcaaa actgccagcg aattcgactc tgcaattgct   2640
caagacaagc tagttgtcgt agatttctac gccacttggt gcggtccatg taaaatgatt   2700
gctccaatga ttgaaaaatg tggctgtggt ttcagggtcc ataaagcttt tcaattcatc   2760
ttttttttt ttgttctttt ttttgattcc ggtttctttg aaattttttt gattcggtaa   2820
tctccgagca gaaggaagaa cgaaggaagg agcacagact tagattggta tatatacgca   2880
tatgtggtgt tgaagaaaca tgaaattgcc cagtattctt aacccaactg cacagaacaa   2940
aaacctgcag gaaacgaaga taaatcatgt cgaaagctac atataaggaa cgtgctgcta   3000
ctcatcctag tcctgttgct gccaagctat ttaatatcat gcacgaaaag caaacaaact   3060
tgtgtgcttc attggatgtt cgtaccacca aggaattact ggagttagtt gaagcattag   3120
gtcccaaaat ttgtttacta aaaacacatg tggatatctt gactgatttt tccatggagg   3180
gcacagttaa gccgctaaag gcattatccg ccaagtacaa tttttactc ttcgaagaca   3240
gaaaatttgc tgacattggt aatacagtca aattgcagta ctctgcgggt gtatacagaa   3300
tagcagaatg ggcagacatt acgaatgcac acggtgtggt gggcccaggt attgttagcg   3360
gtttgaagca ggcggcggaa gaagtaacaa aggaacctag aggccttttg atgttagcag   3420
aattgtcatg caagggctcc ctagctactg gagaatatac taagggtact gttgacattg   3480
cgaagagcga caaagatttt gttatcggct ttattgctca aagagacatg ggtggaagag   3540
atgaaggtta cgattggttg attatgacac ccggtgtggg tttagatgac aagggagacg   3600
cattgggtca acagtataga accgtggatg atgtggtctc tacaggatct gacattatta   3660
ttgttggaag aggactattt gcaaagggaa gggatgctaa ggtagagggt gaacgttaca   3720
gaaaagcagg ctgggaagca tatttgagaa gatgcggcca gcaaaactaa aaaactgtat   3780
tataagtaaa tgcatgtata ctaaactcac aaattagagc ttcaatttaa ttatatcagt   3840
tattacccgg gaatctcggt cgtaatgatt tctataatga cgaaaaaaaa aaaattggaa   3900
agaaaaagct tcatggcctt ccactttccc aaacaacacc tacggtatct ctcaagtctt   3960
atggggttcc attggtttca ccactggtgc taccttgggt gctgctttcg ctgctgaaga   4020
aattgatcca aagaagagag ttatcttatt cattggtgac ggttctttgc aattgactgt   4080
tcaagaaatc tccaccatga tcagatgggg cttgaagcca tacttgttcg tcttgaacaa   4140
cgatggttac accattgaaa agttgattca cggtccaaag gctcaataca acgaaattca   4200
aggttgggac cacctatcct tgttgccaac tttcggtgct aaggactatg aaacccacag   4260
agtcgctacc accggtgaat gggacaagtt gacccaagac aagtctttca acgacaactc   4320
taagatcaga atgattgaaa tcatgttgcc agtcttcgat gctccacaaa acttggttga   4380
acaagctaag ttgactgctg ctaccaacgc taagcaataa                          4420
```

<210> SEQ ID NO 143

<211> LENGTH: 3521
<212> TYPE: DNA
<213> ORGANISM: Artificial sequence
<220> FEATURE:
<223> OTHER INFORMATION: Cassette

<400> SEQUENCE: 143
aaggaaataa agcaaataac aataacacca ttattttaat tttttttcta ttactgtcgc 60
taacacctgt atggttgcaa ccaggtgaga atccttctga tgcatacttt atgcgtttat 120
gcgttttgcg ccccttggaa aaaaattgat tctcatcgta aatgcatact acatgcgttt 180
atgggaaaag cctccatatc caaaggtcgc gtttctttta gaaaaactaa tacgtaaacc 240
tgcattaagg taagattata tcagaaaatg tgttgcaaga aatgcattat gcaatttttt 300
gattatgaca atctctcgaa agaaatttca tatgatgaga cttgaataat gcagcggcgc 360
ttgctaaaag aacttgtata taagagctgc cattctcgat caatatactg tagtaagtcc 420
tttcctctct ttcttattac acttatttca cataatcaat ctcaaagaga acaacacaat 480
acaataacaa gaagaacaaa atgaaagctc tggtttatca cggtgaccac aagatctcgc 540
ttgaagacaa gcccaagccc acccttcaaa agcccacgga tgtagtagta cgggttttga 600
agaccacgat ctgcggcacg gatctcggca tctacaaagg caagaatcca gaggtcgccg 660
acgggcgcat cctgggccat gaaggggtag gcgtcatcga ggaagtgggc gagagtgtca 720
cgcagttcaa gaaaggcgac aaggtcctga tttcctgcgt cacttcttgc ggctcgtgcg 780
actactgcaa gaagcagctt tactcccatt gccgcgacgg cgggtggatc ctgggttaca 840
tgatcgatgg cgtgcaggcc gaatacgtcc gcatcccgca tgccgacaac agcctctaca 900
agatccccca gacaattgac gacgaaatcg ccgtcctgct gagcgacatc ctgcccaccg 960
gccacgaaat cggcgtccag tatgggaatg tccagccggg cgatgcggtg gctattgtcg 1020
gcgcgggccc cgtcggcatg tccgtactgt tgaccgccca gttctactcc ccctcgacca 1080
tcatcgtgat cgacatggac gagaatcgcc tccagctcgc caaggagctc ggggcaacgc 1140
acaccatcaa ctccggcacg gagaacgttg tcgaagccgt gcataggatt gcggcagagg 1200
gagtcgatgt tgcgatcgag gcggtgggca taccggcgac ttgggacatc tgccaggaga 1260
tcgtcaagcc cggcgcgcac atcgccaacg tcggcgtgca tggcgtcaag gttgacttcg 1320
agattcagaa gctctggatc aagaacctga cgatcaccac gggactggtg aacacgaaca 1380
cgacgcccat gctgatgaag gtcgcctcga ccgacaagct tccgttgaag aagatgatta 1440
cccatcgctt cgagctggcc gagatcgagc acgcctatca ggtattcctc aatggcgcca 1500
aggagaaggc gatgaagatc atcctctcga acgcaggcgc tgcctgagct aattaacata 1560
aaactcatga ttcaacgttt gtgtattttt ttacttttga aggttataga tgtttaggta 1620
aataattggc atagatatag ttttagtata ataaatttct gatttggttt aaaatatcaa 1680
ctattttttt tcacatatgt tcttgtaatt acttttctgt cctgtcttcc aggttaaaga 1740
ttagcttcta atattttagg tggtttatta tttaatttta tgctgattaa tttatttact 1800
tgtttaaacg gccggccaat gtggctgtgg tttcagggtc cataaagctt ttcaattcat 1860
cttttttttt tttgttcttt tttttgattc cggtttcttt gaaatttttt tgattcggta 1920
atctccgagc agaaggaaga acgaaggaag gagcacagac ttagattggt atatatacgc 1980
atatgtggtg ttgaagaaac atgaaattgc ccagtattct taacccaact gcacagaaca 2040
aaaacctgca ggaaacgaag ataaatcatg tcgaaagcta catataagga acgtgctgct 2100
actcatccta gtcctgttgc tgccaagcta tttaatatca tgcacgaaaa gcaaacaaac 2160

```
ttgtgtgctt cattggatgt tcgtaccacc aaggaattac tggagttagt tgaagcatta   2220

ggtcccaaaa tttgtttact aaaaacacat gtggatatct tgactgattt ttccatggag   2280

ggcacagtta agccgctaaa ggcattatcc gccaagtaca attttttact cttcgaagac   2340

agaaaatttg ctgacattgg taatacagtc aaattgcagt actctgcggg tgtatacaga   2400

atagcagaat gggcagacat tacgaatgca cacggtgtgg tgggcccagg tattgttagc   2460

ggtttgaagc aggcggcgga agaagtaaca aaggaaccta gaggcctttt gatgttagca   2520

gaattgtcat gcaagggctc cctagctact ggagaatata ctaagggtac tgttgacatt   2580

gcgaagagcg acaaagattt tgttatcggc tttattgctc aaagagacat gggtggaaga   2640

gatgaaggtt acgattggtt gattatgaca cccggtgtgg gtttagatga caagggagac   2700

gcattgggtc aacagtatag aaccgtggat gatgtggtct ctacaggatc tgacattatt   2760

attgttggaa gaggactatt tgcaaaggga agggatgcta aggtagaggg tgaacgttac   2820

agaaaagcag gctgggaagc atatttgaga agatgcggcc agcaaaacta aaaaactgta   2880

ttataagtaa atgcatgtat actaaactca caaattagag cttcaattta attatatcag   2940

ttattacccg ggaatctcgg tcgtaatgat ttctataatg acgaaaaaaa aaaaattgga   3000

aagaaaaagc ttcatggcct tctactttcc caacagatgt atacgctatc gtccaagtct   3060

tgtggggttc cattggtttc acagtcggcg ctctattggg tgctactatg gccgctgaag   3120

aacttgatcc aaagaagaga gttattttat tcattggtga cggttctcta caattgactg   3180

ttcaagaaat ctctaccatg attagatggg gtttgaagcc atacattttt gtcttgaata   3240

acaacggtta caccattgaa aaattgattc acggtcctca tgccgaatat aatgaaattc   3300

aaggttggga ccacttggcc ttattgccaa cttttggtgc tagaaactac gaaacccaca   3360

gagttgctac cactggtgaa tggaaaaagt tgactcaaga caaggacttc caagacaact   3420

ctaagattag aatgattgaa gttatgttgc cagtctttga tgctccacaa aacttggtta   3480

aacaagctca attgactgcc gctactaacg ctaaacaata a                       3521
```

<210> SEQ ID NO 144
<211> LENGTH: 571
<212> TYPE: PRT
<213> ORGANISM: Bacillus subtilis

<400> SEQUENCE: 144

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125
```

```
Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
```

```
545                 550                 555                 560

Glu Phe Gly Glu Leu Met Lys Thr Lys Ala Leu
                565                 570


<210> SEQ ID NO 145
<211> LENGTH: 340
<212> TYPE: PRT
<213> ORGANISM: Lactococcus lactis

<400> SEQUENCE: 145

Met Ala Val Thr Met Tyr Tyr Glu Asp Asp Val Glu Val Ser Ala Leu
1               5                   10                  15

Ala Gly Lys Gln Ile Ala Val Ile Gly Tyr Gly Ser Gln Gly His Ala
            20                  25                  30

His Ala Gln Asn Leu Arg Asp Ser Gly His Asn Val Ile Ile Gly Val
        35                  40                  45

Arg His Gly Lys Ser Phe Asp Lys Ala Lys Glu Asp Gly Phe Glu Thr
    50                  55                  60

Phe Glu Val Gly Glu Ala Val Ala Lys Ala Asp Val Ile Met Val Leu
65                  70                  75                  80

Ala Pro Asp Glu Leu Gln Gln Ser Ile Tyr Glu Glu Asp Ile Lys Pro
                85                  90                  95

Asn Leu Lys Ala Gly Ser Ala Leu Gly Phe Ala His Gly Phe Asn Ile
            100                 105                 110

His Phe Gly Tyr Ile Lys Val Pro Glu Asp Val Asp Val Phe Met Val
        115                 120                 125

Ala Pro Lys Ala Pro Gly His Leu Val Arg Arg Thr Tyr Thr Glu Gly
    130                 135                 140

Phe Gly Thr Pro Ala Leu Phe Val Ser His Gln Asn Ala Ser Gly His
145                 150                 155                 160

Ala Arg Glu Ile Ala Met Asp Trp Ala Lys Gly Ile Gly Cys Ala Arg
                165                 170                 175

Val Gly Ile Ile Glu Thr Thr Phe Lys Glu Glu Thr Glu Glu Asp Leu
            180                 185                 190

Phe Gly Glu Gln Ala Val Leu Cys Gly Gly Leu Thr Ala Leu Val Glu
        195                 200                 205

Ala Gly Phe Glu Thr Leu Thr Glu Ala Gly Tyr Ala Gly Glu Leu Ala
    210                 215                 220

Tyr Phe Glu Val Leu His Glu Met Lys Leu Ile Val Asp Leu Met Tyr
225                 230                 235                 240

Glu Gly Gly Phe Thr Lys Met Arg Gln Ser Ile Ser Asn Thr Ala Glu
                245                 250                 255

Phe Gly Asp Tyr Val Thr Gly Pro Arg Ile Ile Thr Asp Glu Val Lys
            260                 265                 270

Lys Asn Met Lys Leu Val Leu Ala Asp Ile Gln Ser Gly Lys Phe Ala
        275                 280                 285

Gln Asp Phe Val Asp Asp Phe Lys Ala Gly Arg Pro Lys Leu Ile Ala
    290                 295                 300

Tyr Arg Glu Ala Ala Lys Asn Leu Glu Ile Glu Lys Ile Gly Ala Glu
305                 310                 315                 320

Leu Arg Gln Ala Met Pro Phe Thr Gln Ser Gly Asp Asp Asp Ala Phe
                325                 330                 335

Lys Ile Tyr Gln
            340
```

<210> SEQ ID NO 146
<211> LENGTH: 571
<212> TYPE: PRT
<213> ORGANISM: Streptococcus mutans

<400> SEQUENCE: 146

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
    130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
    370                 375                 380
```

```
Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Val Arg Phe Val Gly Pro Lys Gly Gly Pro
        435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570


<210> SEQ ID NO 147
<211> LENGTH: 548
<212> TYPE: PRT
<213> ORGANISM: Lactococcus lactis

<400> SEQUENCE: 147

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
```

-continued

```
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545


<210> SEQ ID NO 148
<211> LENGTH: 375
<212> TYPE: PRT
<213> ORGANISM: Equus caballus

<400> SEQUENCE: 148
```

```
Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375
```

<210> SEQ ID NO 149
<211> LENGTH: 348
<212> TYPE: PRT
<213> ORGANISM: Achromobacter xylosoxidans

<400> SEQUENCE: 149

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345


<210> SEQ ID NO 150
<211> LENGTH: 2686
<212> TYPE: DNA
<213> ORGANISM: Artificial sequence
<220> FEATURE:
<223> OTHER INFORMATION: Plasmid

<400> SEQUENCE: 150

tcgcgcgttt cggtgatgac ggtgaaaacc tctgacacat gcagctcccg gagacggtca      60
```

-continued

```
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg gttatccaca    780
gaatcagggg ataacgcagg aaagaacatg tgagcaaaag gccagcaaaa ggccaggaac    840
cgtaaaaagg ccgcgttgct ggcgtttttc cataggctcc gcccccctga cgagcatcac    900
aaaaatcgac gctcaagtca gaggtggcga aacccgacag gactataaag ataccaggcg    960
tttccccctg gaagctccct cgtgcgctct cctgttccga ccctgccgct taccggatac   1020
ctgtccgcct ttctcccttc gggaagcgtg gcgctttctc atagctcacg ctgtaggtat   1080
ctcagttcgg tgtaggtcgt tcgctccaag ctgggctgtg tgcacgaacc ccccgttcag   1140
cccgaccgct gcgccttatc cggtaactat cgtcttgagt ccaacccggt aagacacgac   1200
ttatcgccac tggcagcagc cactggtaac aggattagca gagcgaggta tgtaggcggt   1260
gctacagagt tcttgaagtg gtggcctaac tacggctaca ctagaaggac agtatttggt   1320
atctgcgctc tgctgaagcc agttaccttc ggaaaaagag ttggtagctc ttgatccggc   1380
aaacaaacca ccgctggtag cggtggtttt tttgtttgca agcagcagat tacgcgcaga   1440
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatcccccat gttgtgcaaa   2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
```

gcgacacgga aatgttgaat actcatactc ttcctttttc aatattattg aagcatttat 2520
cagggttatt gtctcatgag cggatacata tttgaatgta tttagaaaaa taaacaaata 2580
ggggttccgc gcacatttcc ccgaaaagtg ccacctgacg tctaagaaac cattattatc 2640
atgacattaa cctataaaaa taggcgtatc acgaggccct ttcgtc 2686

<210> SEQ ID NO 151
<211> LENGTH: 1685
<212> TYPE: DNA
<213> ORGANISM: Artificial sequence
<220> FEATURE:
<223> OTHER INFORMATION: Cassette

<400> SEQUENCE: 151
gtattttggt agattcaatt ctctttccct ttccttttcc ttcgctcccc ttccttatca 60
gcattgcgga ttacgtattc taatgttcag ataacttcgt atagcataca ttatacgaag 120
ttatgcagat tgtactgaga gtgcaccata ccacagcttt tcaattcaat tcatcatttt 180 tttttattc ttttttttga tttcggtttc tttgaaattt ttttgattcg gtaatctccg 240
aacagaagga agaacgaagg aaggagcaca gacttagatt ggtatatata cgcatatgta 300
gtgttgaaga aacatgaaat tgcccagtat tcttaaccca actgcacaga acaaaaacct 360
gcaggaaacg aagataaatc atgtcgaaag ctacatataa ggaacgtgct gctactcatc 420
ctagtcctgt tgctgccaag ctatttaata tcatgcacga aaagcaaaca aacttgtgtg 480
cttcattgga tgttcgtacc accaaggaat tactggagtt agttgaagca ttaggtccca 540
aaatttgttt actaaaaaca catgtggata tcttgactga tttttccatg gagggcacag 600
ttaagccgct aaaggcatta tccgccaagt acaatttttt actcttcgaa gacagaaaat 660
ttgctgacat tggtaataca gtcaaattgc agtactctgc gggtgtatac agaatagcag 720
aatgggcaga cattacgaat gcacacggtg tggtgggccc aggtattgtt agcggtttga 780
agcaggcggc agaagaagta acaaaggaac ctagaggcct tttgatgtta gcagaattgt 840
catgcaaggg ctccctatct actggagaat atactaaggg tactgttgac attgcgaaga 900
gcgacaaaga ttttgttatc ggctttattg ctcaaagaga catgggtgga agagatgaag 960
gttacgattg gttgattatg acacccggtg tgggtttaga tgacaaggga gacgcattgg 1020
gtcaacagta tagaaccgtg gatgatgtgg tctctacagg atctgacatt attattgttg 1080
gaagaggact atttgcaaag ggaagggatg ctaaggtaga gggtgaacgt tacagaaaag 1140
caggctggga agcatatttg agaagatgcg gccagcaaaa ctaaaaaact gtattataag 1200
taaatgcatg tatactaaac tcacaaatta gagcttcaat ttaattatat cagttattac 1260
cctatgcggt gtgaaatacc gcacagatgc gtaaggagaa aataccgcat caggaaattg 1320
taaacgttaa tattttgtta aaattcgcgt taaatttttg ttaaatcagc tcatttttta 1380
accaataggc cgaaatcggc aaaatccctt ataaatcaaa agaatagacc gagatagggt 1440
tgagtgttgt tccagtttgg aacaagagtc cactattaaa gaacgtggac tccaacgtca 1500
aagggcgaaa aaccgtctat cagggcgatg gcccactacg tgaaccatca ccctaatcaa 1560
gataacttcg tatagcatac attatacgaa gttatccagt gatgatacaa cgagttagcc 1620
aaggtgacac tctccccccc cctccccctc tgatctttcc tgttgcctct tttcccccca 1680
accaa 1685

<210> SEQ ID NO 152

<211> LENGTH: 22
<212> TYPE: DNA
<213> ORGANISM: Artificial Sequence
<220> FEATURE:
<223> OTHER INFORMATION: Primer oBP594

<400> SEQUENCE: 152
agctgtctcg tgttgtgggt tt 22

<210> SEQ ID NO 153
<211> LENGTH: 49
<212> TYPE: DNA
<213> ORGANISM: Artificial Sequence
<220> FEATURE:
<223> OTHER INFORMATION: Primer oBP595

<400> SEQUENCE: 153
cttaataata gaacaatatc atcctttacg ggcatcttat agtgtcgtt 49

<210> SEQ ID NO 154
<211> LENGTH: 49
<212> TYPE: DNA
<213> ORGANISM: Artificial Sequence
<220> FEATURE:
<223> OTHER INFORMATION: Primer oBP596

<400> SEQUENCE: 154
gcgccaacga cactataaga tgcccgtaaa ggatgatatt gttctatta 49

<210> SEQ ID NO 155
<211> LENGTH: 49
<212> TYPE: DNA
<213> ORGANISM: Artificial Sequence
<220> FEATURE:
<223> OTHER INFORMATION: Primer oBP597

<400> SEQUENCE: 155
tatggaccct gaaaccacag ccacattgca acgacgacaa tgccaaacc 49

<210> SEQ ID NO 156
<211> LENGTH: 49
<212> TYPE: DNA
<213> ORGANISM: Artificial Sequence
<220> FEATURE:
<223> OTHER INFORMATION: Primer oBP598

<400> SEQUENCE: 156
tccttggttt ggcattgtcg tcgttgcaat gtggctgtgg tttcagggt 49

<210> SEQ ID NO 157
<211> LENGTH: 49
<212> TYPE: DNA
<213> ORGANISM: Artificial Sequence
<220> FEATURE:
<223> OTHER INFORMATION: Primer oBP599

<400> SEQUENCE: 157
atcctctcgc ggagtccctg ttcagtaaag gccatgaagc tttttcttt 49

<210> SEQ ID NO 158
<211> LENGTH: 49
<212> TYPE: DNA
<213> ORGANISM: Artificial Sequence
<220> FEATURE:
<223> OTHER INFORMATION: Primer oBP600

<400> SEQUENCE: 158

-continued attggaaaga aaaagcttca tggcctttac tgaacaggga ctccgcgag 49

<210> SEQ ID NO 159
<211> LENGTH: 22
<212> TYPE: DNA
<213> ORGANISM: Artificial Sequence
<220> FEATURE:
<223> OTHER INFORMATION: Primer oBP601

<400> SEQUENCE: 159
tcataccaca atcttagacc at 22

<210> SEQ ID NO 160
<211> LENGTH: 21
<212> TYPE: DNA
<213> ORGANISM: Artificial Sequence
<220> FEATURE:
<223> OTHER INFORMATION: Primer oBP602

<400> SEQUENCE: 160
tgttcaaacc cctaaccaac c 21

<210> SEQ ID NO 161
<211> LENGTH: 22
<212> TYPE: DNA
<213> ORGANISM: Artificial Sequence
<220> FEATURE:
<223> OTHER INFORMATION: Primer oBP603

<400> SEQUENCE: 161
tgttcccaca atctattacc ta 22

<210> SEQ ID NO 162
<211> LENGTH: 21
<212> TYPE: DNA
<213> ORGANISM: Artificial Sequence
<220> FEATURE:
<223> OTHER INFORMATION: Primer oBP605

<400> SEQUENCE: 162
tactgaacag ggactccgcg a 21

<210> SEQ ID NO 163
<211> LENGTH: 21
<212> TYPE: DNA
<213> ORGANISM: Artificial Sequence
<220> FEATURE:
<223> OTHER INFORMATION: Primer oBP606

<400> SEQUENCE: 163
tcataccaca atcttagacc a 21

<210> SEQ ID NO 164
<211> LENGTH: 34
<212> TYPE: DNA
<213> ORGANISM: Artificial Sequence
<220> FEATURE:
<223> OTHER INFORMATION: Primer oBP562

<400> SEQUENCE: 164
aattgtttaa acatgtatac agtaggtgac tatc 34

<210> SEQ ID NO 165
<211> LENGTH: 49
<212> TYPE: DNA

<213> ORGANISM: Artificial Sequence
<220> FEATURE:
<223> OTHER INFORMATION: Primer oBP563

<400> SEQUENCE: 165
aatcataaat cataagaaat tcgcttatca gctcttgttt tgttctgca 49

<210> SEQ ID NO 166
<211> LENGTH: 49
<212> TYPE: DNA
<213> ORGANISM: Artificial Sequence
<220> FEATURE:
<223> OTHER INFORMATION: Primer oBP564

<400> SEQUENCE: 166
ttatttgcag aacaaaacaa gagctgataa gcgaatttct tatgattta 49

<210> SEQ ID NO 167
<211> LENGTH: 34
<212> TYPE: DNA
<213> ORGANISM: Artificial Sequence
<220> FEATURE:
<223> OTHER INFORMATION: Primer oBP565

<400> SEQUENCE: 167
aattggccgg ccaaaaaaag catgcacgta taca 34

<210> SEQ ID NO 168
<211> LENGTH: 32
<212> TYPE: DNA
<213> ORGANISM: Artificial Sequence
<220> FEATURE:
<223> OTHER INFORMATION: Primer oBP505

<400> SEQUENCE: 168
aattgagctc actgtagccc tagacttgat ag 32

<210> SEQ ID NO 169
<211> LENGTH: 35
<212> TYPE: DNA
<213> ORGANISM: Artificial Sequence
<220> FEATURE:
<223> OTHER INFORMATION: Primer oBP506

<400> SEQUENCE: 169
aattggcgcg cctgtatatg agatagttga ttgta 35

<210> SEQ ID NO 170
<211> LENGTH: 35
<212> TYPE: DNA
<213> ORGANISM: Artificial Sequence
<220> FEATURE:
<223> OTHER INFORMATION: Primer oBP507

<400> SEQUENCE: 170
aattttaatt aagtctaggt tctttggctg ttcaa 35

<210> SEQ ID NO 171
<211> LENGTH: 33
<212> TYPE: DNA
<213> ORGANISM: Artificial Sequence
<220> FEATURE:
<223> OTHER INFORMATION: Primer oBP508

<400> SEQUENCE: 171
aattgtcgac tttagaagtg tcaacaacgt atc 33

<210> SEQ ID NO 172
<211> LENGTH: 8366
<212> TYPE: DNA
<213> ORGANISM: Artificial Sequence
<220> FEATURE:
<223> OTHER INFORMATION: pRS316-UAS(PGK1)-PFBA1-GUS

<400> SEQUENCE: 172
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc atttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa ggggggatgt gctgcaaggc gattaagttg ggtaacgcca 1920
gggttttccc agtcacgacg ttgtaaaacg acggccagtg aattgtaata cgactcacta 1980
tagggcgaat tggagctcca ccgcggtggt ttaacgtata gacttctaat atatttctcc 2040

-continued

```
atacttggta tttttattc acttttttta tacatatttg gttttttat acaatatcaa   2100
aaatcaataa taattaattt aataacaaga atatgttgct gtgatgactc ttaatataca   2160
attgggaagc attcaaggat tggtacgacg tttgctttct gataattaaa cgcttggcgt   2220
ttaatctttt ttgccgatta ataatattat tattaccctc ttatttatta gcattgtctt   2280
ccgtactaaa aggagtaggg aaaaaggcga agtagagtga cacgtccatt acccagcgct   2340
tcataagaat ccatcaggta tattaaattg tgatgggaga acaaaacaaa ttgtactatg   2400
atgtcgagaa attggtgaat tctttgcagg aaagttttga cctggattgc gcgcaaagtg   2460
tatcactttt caccagtaaa tcaaggagca atgaggcttg gttggaagag ctagagaata   2520
aattcaagtt aaaagatgat gttgaacttg atgatgtgga aaatttaaga gccgaaattg   2580
acatgaagtt aaatatgttg gaggataaag taagctacta tgaaagactt tacaaagaac   2640
tcgaagagtt ccagaatgaa ataaaaatta aaacagttgt gaataacaga agacaatcgc   2700
gaactccaaa atgagctatc aaaaacgata gatcgattag gatgactttg aaatgactcc   2760
gcagtggact ggccgttaat ttcaagcgtg agtaaaatag tgcatgacaa aagatgagct   2820
aggcttttgt aaaaatatct tacgttgtaa aattttagaa atcattattt ccttcatatc   2880
attttgtcat tgaccttcag aagaaaagag ccgaccaata atataaataa ataaataaaa   2940
ataatattcc attatttcta aacagattca atactcatta aaaaactata tcaattaatt   3000
tgaattaacg cggccgctct agttaattaa tcattgtttg cctccctgct gcggtttttc   3060
accgaagttc atgccagtcc agcgtttttg cagcagaaaa gccgccgact tcggtttgcg   3120
gtcgcgagtg aagatccctt tcttgttacc gccaacgcgc aatatgcctt gcgaggtcgc   3180
aaaatcggcg aaattccata cctgttcacc gacgacggcg ctgacgcgat caaagacgcg   3240
gtgatacata tccagccatg cacactgata ctcttcactc cacatgtcgg tgtacattga   3300
gtgcagcccg gctaacgtat ccacgccgta ttcggtgatg ataatcggct gatgcagttt   3360
ctcctgccag gccagaagtt ctttttccag taccttctct gccgtttcca aatcgccgct   3420
ttggacatac catccgtaat aacggttcag gcacagcaca tcaaagagat cgctgatggt   3480
atcggtgtga gcgtcgcaga acattacatt gacgcaggtg atcggacgcg tcgggtcgag   3540
tttacgcgtt gcttccgcca gtggcgcgaa atattcccgt gcaccttgcg gacgggtatc   3600
cggttcgttg gcaatactcc acatcaccac gcttgggtgg tttttgtcac gcgctatcag   3660
ctctttaatc gcctgtaagt gcgcttgctg agtttccccg ttgactgcct cttcgctgta   3720
cagttctttc ggcttgttgc ccgcttcgaa accaatgcct aaagagaggt taaagccgac   3780
agcagcagtt tcatcaatca ccacgatgcc atgttcatct gcccagtcga gcatctcttc   3840
agcgtaaggg taatgcgagg tacggtagga gttggcccca atccagtcca ttaatgcgtg   3900
gtcgtgcacc atcagcacgt tatcgaatcc tttgccacgc aagtccgcat cttcatgacg   3960
accaaagcca gtaaagtaga acggtttgtg gttaatcagg aactgttcgc ccttcactgc   4020
cactgaccgg atgccgacgc gaagcgggta gatatcacac tctgtctggc ttttggctgt   4080
gacgcacagt tcatagagat aaccttcacc cggttgccag aggtgcggat tcaccacttg   4140
caaagtcccg ctagtgcctt gtccagttgc aaccacctgt tgatccgcat cacgcagttc   4200
aacgctgaca tcaccattgg ccaccacctg ccagtcaaca gacgcgtggt tacagtcttg   4260
cgcgacatgc gtcaccacgg tgatatcgtc cacccaggtg ttcggcgtgg tgtagagcat   4320
tacgctgcga tggattccgg catagttaaa gaaatcatgg aagtaagact gctttttctt   4380
gccgttttcg tcggtaatca ccattcccgg cgggatagtc tgccagttca gttcgttgtt   4440
```

```
cacacaaacg gtgatacgta cacttttccc ggcaataaca tacggcgtga catcggcttc   4500
aaatggagta tagccgccct gatgctccat cacttcctga ttattgaccc acactttgcc   4560
gtaatgagtg accgcatcga aacgcagcac gatacgctgg cctgcccaac ctttcggtat   4620
aaagacttcg cgctgatacc agacgttgcc cgcataatta cgaatatctg catcggcgaa   4680
ctgatcgtta aaactgcctg gcacagcaat tgcccggctt tcttgtaacg cgctttccca   4740
ccaacgctga tcaattccac agttttcgcg atccagactg aatgcccaca ggccgtcgag   4800
tttttgatt tcacgggttg gggtttctac aggacgtacc atactagttt gaatatgtat   4860
tacttggtta tggttatata tgacaaaaga aaaagaagaa cagaagaata acgcaaggaa   4920
gaacaataac tgaaattgat agagaagtat tatgtctttg tctttttata ataaatcaag   4980
tgcagaaatc cgttagacaa catgagggat aaaatttaac gtgggcgaag aagaaggaaa   5040
aaagtttttg tgagggcgta attgaagcga tctgttgatt gtagattttt tttttttgag   5100
gagtcaaagt cagaagagaa cagacaaatg gtattaacca tccaatactt ttttggagca   5160
acgctaagct catgcttttc cattggttac gtgctcagtt gttagatatg gaaagagagg   5220
atgctcacgg cagcgtgact ccaattgagc ccgaaagaga ggatgccacg ttttcccgac   5280
ggctgctaga atggaaaaag gaaaaataga agaatcccat tcctatcatt atttacgtaa   5340
tgacccacac atttttgaga ttttcaacta ttacgtatta cgataatcct gctgtcatta   5400
tcattattat ctatatcgac gtatgcaacg tatgtgaagc caagtaggcg tcgacaggac   5460
cttgttgtgt gacgaaattg gaagctgcaa tcaataggaa gacaggaagt cgagcgtgtc   5520
tgggtttttt cagttttgtt ctttttgcaa acaaatcacg agcgacggta attggtaccc   5580
agcttttgtt ccctttagtg agggttaatt ccgagcttgg cgtaatcatg gtcatagctg   5640
tttcctgtgt gaaattgtta tccgctcaca attccacaca acataggagc cggaagcata   5700
aagtgtaaag cctggggtgc ctaatgagtg aggtaactca cattaattgc gttgcgctca   5760
ctgcccgctt tccagtcggg aaacctgtcg tgccagctgc attaatgaat cggccaacgc   5820
gcggggagag gcggtttgcg tattgggcgc tcttccgctt cctcgctcac tgactcgctg   5880
cgctcggtcg ttcggctgcg gcgagcggta tcagctcact caaaggcggt aatacggtta   5940
tccacagaat caggggataa cgcaggaaag aacatgtgag caaaaggcca gcaaaaggcc   6000
aggaaccgta aaaaggccgc gttgctggcg tttttccata ggctcggccc ccctgacgag   6060
catcacaaaa atcgacgctc aagtcagagg tggcgaaacc cgacaggact ataaagatac   6120
caggcgttcc ccctggaag ctccctcgtg cgctctcctg ttccgaccct gccgcttacc   6180
ggatacctgt ccgcctttct cccttcggga agcgtggcgc tttctcaatg ctcacgctgt   6240
aggtatctca gttcggtgta ggtcgttcgc tccaagctgg gctgtgtgca cgaacccccc   6300
gttcagcccg accgctgcgc cttatccggt aactatcgtc ttgagtccaa cccggtaaga   6360
cacgacttat cgccactggc agcagccact ggtaacagga ttagcagagc gaggtatgta   6420
ggcggtgcta cagagttctt gaagtggtgg cctaactacg gctacactag aaggacagta   6480
tttggtatct gcgctctgct gaagccagtt accttcggaa aaagagttgg tagctcttga   6540
tccggcaaac aaaccaccgc tggtagcggt ggtttttttg tttgcaagca gcagattacg   6600
cgcagaaaaa aaggatctca agaagatcct ttgatctttt ctacggggtc tgacgctcag   6660
tggaacgaaa actcacgtta agggattttg gtcatgagat tatcaaaaag gatcttcacc   6720
tagatccttt taaattaaaa atgaagtttt aaatcaatct aaagtatata tgagtaaact   6780
```

-continued

```
tggtctgaca gttaccaatg cttaatcagt gaggcaccta tctcagcgat ctgtctattt   6840

cgttcatcca tagttgcctg actgcccgtc gtgtagataa ctacgatacg ggagggctta   6900

ccatctggcc ccagtgctgc aatgataccg cgagacccac gctcaccggc tccagattta   6960

tcagcaataa accagccagc cggaagggcc gagcgcagaa gtggtcctgc aactttatcc   7020

gcctccatcc agtctattaa ttgttgccgg gaagctagag taagtagttc gccagttaat   7080

agtttgcgca acgttgttgc cattgctaca ggcatcgtgg tgtcacgctc gtcgtttggt   7140

atggcttcat tcagctccgg ttcccaacga tcaaggcgag ttacatgatc ccccatgttg   7200

tgaaaaaaag cggttagctc cttcggtcct ccgatcgttg tcagaagtaa gttggccgca   7260

gtgttatcac tcatggttat ggcagcactg cataattctc ttactgtcat gccatccgta   7320

agatgctttt ctgtgactgg tgagtactca accaagtcat tctgagaata gtgtatgcgg   7380

cgaccgagtt gctcttgccc ggcgtcaata cgggataata ccgcgccaca tagcagaact   7440

ttaaaagtgc tcatcattgg aaaacgttct tcggggcgaa aactctcaag gatcttaccg   7500

ctgttgagat ccagttcgat gtaacccact cgtgcaccca actgatcttc agcatctttt   7560

actttcacca gcgtttctgg gtgagcaaaa acaggaaggc aaaatgccgc aaaaaaggga   7620

ataagggcga cacggaaatg ttgaatactc atactcttcc tttttcaata ttattgaagc   7680

atttatcagg gttattgtct catgagcgga tacatatttg aatgtattta gaaaaataaa   7740

caaatagggg ttccgcgcac atttccccga aaagtgccac ctgggtcctt ttcatcacgt   7800

gctataaaaa taattataat ttaaattttt taatataaat atataaatta aaaatagaaa   7860

gtaaaaaaag aaattaaaga aaaaatagtt tttgttttcc gaagatgtaa aagactctag   7920

ggggatcgcc aacaaatact accttttatc ttgctcttcc tgctctcagg tattaatgcc   7980

gaattgtttc atcttgtctg tgtagaagac cacacacgaa aatcctgtga ttttacattt   8040

tacttatcgt taatcgaatg tatatctatt taatctgctt ttcttgtcta ataaatatat   8100

atgtaaagta cgctttttgt tgaaattttt taaacctttg tttatttttt tttcttcatt   8160

ccgtaactct tctaccttct ttatttactt tctaaaatcc aaatacaaaa cataaaaata   8220

aataaacaca gagtaaattc ccaaattatt ccatcattaa aagatacgag gcgcgtgtaa   8280

gttacaggca agcgatccgt cctaagaaac cattattatc atgacattaa cctataaaaa   8340

taggcgtatc acgaggccct ttcgtc                                        8366
```

<210> SEQ ID NO 173
<211> LENGTH: 34
<212> TYPE: DNA
<213> ORGANISM: Artificial Sequence
<220> FEATURE:
<223> OTHER INFORMATION: Primer oBP674

<400> SEQUENCE: 173

```
aattggcgcg ccaattaccg tcgctcgtga tttg                                 34
```

<210> SEQ ID NO 174
<211> LENGTH: 34
<212> TYPE: DNA
<213> ORGANISM: Artificial Sequence
<220> FEATURE:
<223> OTHER INFORMATION: Primer oBP675

<400> SEQUENCE: 174

```
aattgtttaa acttgaatat gtattacttg gtta                                 34
```

<210> SEQ ID NO 175
<211> LENGTH: 22
<212> TYPE: DNA
<213> ORGANISM: Artificial Sequence
<220> FEATURE:
<223> OTHER INFORMATION: Primer oBP495

<400> SEQUENCE: 175
ggagatatac aatagaacag at 22

<210> SEQ ID NO 176
<211> LENGTH: 22
<212> TYPE: DNA
<213> ORGANISM: Artificial Sequence
<220> FEATURE:
<223> OTHER INFORMATION: Primer oBP496

<400> SEQUENCE: 176
tagcaatggg gtttttttca gt 22

<210> SEQ ID NO 177
<211> LENGTH: 725
<212> TYPE: DNA
<213> ORGANISM: Artificial Sequence
<220> FEATURE:
<223> OTHER INFORMATION: UAS(PGK1)-FBA1p

<400> SEQUENCE: 177
aattaccgtc gctcgtgatt tgtttgcaaa aagaacaaaa ctgaaaaaac ccagacacgc 60
tcgacttcct gtcttcctat tgattgcagc ttccaatttc gtcacacaac aaggtcctgt 120
cgacgcctac ttggcttcac atacgttgca tacgtcgata tagataataa tgataatgac 180
agcaggatta tcgtaatacg taatagttga aaatctcaaa aatgtgtggg tcattacgta 240
aataatgata ggaatgggat tcttctattt ttcctttttc cattctagca gccgtcggga 300
aaacgtggca tcctctcttt cgggctcaat tggagtcacg ctgccgtgag catcctctct 360
ttccatatct aacaactgag cacgtaacca atggaaaagc atgagcttag cgttgctcca 420
aaaaagtatt ggatggttaa taccatttgt ctgttctctt ctgactttga ctcctcaaaa 480
aaaaaaaatc tacaatcaac agatcgcttc aattacgccc tcacaaaaac tttttttcctt 540 cttcttcgcc cacgttaaat tttatccctc atgttgtcta acggatttct gcacttgatt 600
tattataaaa agacaaagac ataatacttc tctatcaatt tcagttattg ttcttccttg 660
cgttattctt ctgttcttct ttttcttttg tcatatataa ccataaccaa gtaatacata 720
ttcaa 725

<210> SEQ ID NO 178
<211> LENGTH: 47
<212> TYPE: DNA
<213> ORGANISM: Artificial Sequence
<220> FEATURE:
<223> OTHER INFORMATION: Primer T-FBA1(SalI)

<400> SEQUENCE: 178
attctacgta cgtcgacgcc tacttggctt cacatacgtt gcatacg 47

<210> SEQ ID NO 179
<211> LENGTH: 49
<212> TYPE: DNA
<213> ORGANISM: Artificial Sequence
<220> FEATURE:
<223> OTHER INFORMATION: Primer B-FBA1(SpeI)

<400> SEQUENCE: 179
gtatcaaata ctagtttgaa tatgtattac ttggttatgg ttatatatg 49

<210> SEQ ID NO 180
<211> LENGTH: 10494
<212> TYPE: DNA
<213> ORGANISM: Artificial Sequence
<220> FEATURE:
<223> OTHER INFORMATION: pWS358-PGK1p-GUS

<400> SEQUENCE: 180
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctctag tacactctat atttttttat gcctcggtaa tgattttcat 360
tttttttttt cccctagcgg atgactcttt tttttctta gcgattggca ttatcacata 420
atgaattata cattatataa agtaatgtga tttcttcgaa gaatatacta aaaaatgagc 480
aggcaagata aacgaaggca aagatgacag agcagaaagc cctagtaaag cgtattacaa 540
atgaaaccaa gattcagatt gcgatctctt taaagggtgg tcccctagcg atagagcact 600
cgatcttccc agaaaaagag gcagaagcag tagcagaaca ggccacacaa tcgcaagtga 660
ttaacgtcca cacaggtata gggtttctgg accatatgct agggattcat aaccattttc 720
tcaatcgaat tacacagaac acaccgtaca aacctctcta tcataactac ttaatagtca 780
cacacgtact cgtctaaata cacatcatcg tcctacaagt tcatcaaagt gttggacaga 840
caactatacc agcatggatc tcttgtatcg gttcttttct cccgctctct cgcaataaca 900
atgaacactg ggtcaatcat agcctacaca ggtgaacaga gtagcgttta tacagggttt 960
atacggtgat tcctacggca aaaatttttc atttctaaaa aaaaaaagaa aaatttttct 1020
ttccaacgct agaaggaaaa gaaaaatcta attaaattga tttggtgatt ttctgagagt 1080
tccctttttc atatatcgaa ttttgaatat aaaaggagat cgaaaaaatt tttctattca 1140
atctgttttc tggttttatt tgatagtttt tttgtgtatt attattatgg attagtactg 1200
gtttatatgg gtttttctgt ataacttctt tttattttag tttgtttaat cttattttga 1260
gttacattat agttccctaa ctgcaagaga agtaacatta aaactcgaga tgggtaagga 1320
aaagactcac gtttcgaggc cgcgattaaa ttccaacatg gatgctgatt tatatgggta 1380
taaatgggct cgcgataatg tcgggcaatc aggtgcgaca atctatcgat tgtatgggaa 1440
gcccgatgcg ccagagttgt ttctgaaaca tggcaaaggt agcgttgcca atgatgttac 1500
agatgagatg gtcagactaa actggctgac ggaatttatg cctcttccga ccatcaagca 1560
ttttatccgt actcctgatg atgcatggtt actcaccact gcgatccccg gcaaaacagc 1620
attccaggta ttagaagaat atcctgattc aggtgaaaat attgttgatg cgctggcagt 1680
gttcctgcgc cggttgcatt cgattcctgt ttgtaattgt ccttttaaca gcgatcgcgt 1740
atttcgtctc gctcaggcgc aatcacgaat gaataacggt ttggttgatg cgagtgattt 1800
tgatgacgag cgtaatggct ggcctgttga acaagtctgg aaagaaatgc ataagctttt 1860
gccattctca ccggattcag tcgtcactca tggtgatttc tcacttgata accttatttt 1920
tgacgagggg aaattaatag gttgtattga tgttggacga gtcggaatcg cagaccgata 1980

-continued

```
ccaggatctt gccatcctat ggaactgcct cggtgagttt tctccttcat tacagaaacg   2040
gctttttcaa aaatatggta ttgataatcc tgatatgaat aaattgcagt ttcatttgat   2100
gctcgatgag tttttctaag tttaacttga tactactaga tttttttctct tcatttataa   2160
aatttttggt tataattgaa gctttagaag tatgaaaaaa tccttttttt tcattctttg   2220
caaccaaaat aagaagcttc ttttattcat tgaaatgatg aatataaacc taacaaaaga   2280
aaaagactcg aatatcaaac attaaaaaaa aataaaagag gttatctgtt ttcccattta   2340
gttggagttt gcattttcta atagatagaa ctctcaatta atgtggattt agtttctctg   2400
ttcgctgcag catacgatat atatacatgt gtatatatgt atacctatga atgtcagtaa   2460
gtatgtatac gaacagtatg atactgaaga tgacaaggta atgcatcatt ctatacgtgt   2520
cattctgaac gaggcgcgct ttcctttttt ctttttgctt tttctttttt tttctcttga   2580
actcgacgga tctatgcggt gtgaaatacc gcacagatgc gtaaggagaa aataccgcat   2640
caggaaattg taaacgttaa tattttgtta aaattcgcgt taaatttttg ttaaatcagc   2700
tcatttttta accaataggc cgaaatcggc aaaatccctt ataaatcaaa agaatagacc   2760
gagatagggt tgagtgttgt tccagtttgg aacaagagtc cactattaaa gaacgtggac   2820
tccaacgtca aagggcgaaa aaccgtctat cagggcgatg gcccactacg tgaaccatca   2880
ccctaatcaa gttttttggg gtcgaggtgc cgtaaagcac taaatcggaa ccctaaaggg   2940
agcccccgat ttagagcttg acggggaaag ccggcgaacg tggcgagaaa ggaagggaag   3000
aaagcgaaag gagcgggcgc tagggcgctg gcaagtgtag cggtcacgct gcgcgtaacc   3060
accacacccg ccgcgcttaa tgcgccgcta cagggcgcgt cgcgccattc gccattcagg   3120
ctgcgcaact gttgggaagg gcgatcggtg cgggcctctt cgctattacg ccagctggcg   3180
aaagggggat gtgctgcaag gcgattaagt tgggtaacgc cagggttttc ccagtcacga   3240
cgttgtaaaa cgacggccag tgagcgcgcg taatacgact cactataggg cgaattgggt   3300
accgggcccc ccctcgaggt cgacgtgagt aaggaaagag tgaggaacta tcgcatacct   3360
gcatttaaag atgccgattt gggcgcgaat cctttatttt ggcttcaccc tcatactatt   3420
atcagggcca gaaaaaggaa gtgtttccct ccttcttgaa ttgatgttac cctcataaag   3480
cacgtggcct cttatcgaga aagaaattac cgtcgctcgt gatttgtttg caaaaagaac   3540
aaaactgaaa aaacccagac acgctcgact tcctgtcttc ctattgattg cagcttccaa   3600
tttcgtcaca caacaaggtc ctagcgacgg ctcacaggtt ttgtaacaag caatcgaagg   3660
ttctggaatg gcgggaaagg gtttagtacc acatgctatg atgcccactg tgatctccag   3720
agcaaagttc gttcgatcgt actgttactc tctctctttc aaacagaatt gtccgaatcg   3780
tgtgacaaca acagcctgtt ctcacacact cttttcttct aaccaagggg gtggtttagt   3840
ttagtagaac ctcgtgaaac ttacatttac atatatataa acttgcataa attggtcaat   3900
gcaagaaata catatttggt cttttctaat tcgtagtttt tcaagttctt agatgctttc   3960
tttttctctt ttttacagat catcaaggaa gtaattatct actttttaca acaaatataa   4020
aacaactagt atggtacgtc ctgtagaaac cccaacccgt gaaatcaaaa aactcgacgg   4080
cctgtgggca ttcagtctgg atcgcgaaaa ctgtggaatt gatcagcgtt ggtgggaaag   4140
cgcgttacaa gaaagccggg caattgctgt gccaggcagt tttaacgatc agttcgccga   4200
tgcagatatt cgtaattatg cgggcaacgt ctggtatcag cgcgaagtct ttataccgaa   4260
aggttgggca ggccagcgta tcgtgctgcg tttcgatgcg gtcactcatt acggcaaagt   4320
```

-continued

```
gtgggtcaat aatcaggaag tgatggagca tcagggcggc tatactccat ttgaagccga   4380
tgtcacgccg tatgttattg ccgggaaaag tgtacgtatc accgtttgtg tgaacaacga   4440
actgaactgg cagactatcc cgccgggaat ggtgattacc gacgaaaacg gcaagaaaaa   4500
gcagtcttac ttccatgatt tctttaacta tgccggaatc catcgcagcg taatgctcta   4560
caccacgccg aacacctggg tggacgatat caccgtggtg acgcatgtcg cgcaagactg   4620
taaccacgcg tctgttgact ggcaggtggt ggccaatggt gatgtcagcg ttgaactgcg   4680
tgatgcggat caacaggtgg ttgcaactgg acaaggcact agcgggactt tgcaagtggt   4740
gaatccgcac ctctggcaac cgggtgaagg ttatctctat gaactgtgcg tcacagccaa   4800
aagccagaca gagtgtgata tctacccgct tcgcgtcggc atccggtcag tggcagtgaa   4860
gggcgaacag ttcctgatta accacaaacc gttctacttt actggctttg gtcgtcatga   4920
agatgcggac ttgcgtggca aaggattcga taacgtgctg atggtgcacg accacgcatt   4980
aatggactgg attggggcca actcctaccg tacctcgcat tacccttacg ctgaagagat   5040
gctcgactgg gcagatgaac atggcatcgt ggtgattgat gaaactgctg ctgtcggctt   5100
taacctctct ttaggcattg gtttcgaagc gggcaacaag ccgaaagaac tgtacagcga   5160
agaggcagtc aacggggaaa ctcagcaagc gcacttacag gcgattaaag agctgatagc   5220
gcgtgacaaa aaccacccaa gcgtggtgat gtggagtatt gccaacgaac cggatacccg   5280
tccgcaaggt gcacgggaat atttcgcgcc actggcggaa gcaacgcgta aactcgaccc   5340
gacgcgtccg atcacctgcg tcaatgtaat gttctgcgac gctcacaccg ataccatcag   5400
cgatctcttt gatgtgctgt gcctgaaccg ttattacgga tggtatgtcc aaagcggcga   5460
tttggaaacg gcagagaagg tactggaaaa agaacttctg gcctggcagg agaaactgca   5520
tcagccgatt atcatcaccg aatacggcgt ggatacgtta gccgggctgc actcaatgta   5580
caccgacatg tggagtgaag agtatcagtg tgcatggctg gatatgtatc accgcgtctt   5640
tgatcgcgtc agcgccgtcg tcggtgaaca ggtatggaat ttcgccgatt ttgcgacctc   5700
gcaaggcata ttgcgcgttg gcggtaacaa gaaagggatc ttcactcgcg accgcaaacc   5760
gaagtcggcg gcttttctgc tgcaaaaacg ctggactggc atgaacttcg gtgaaaaacc   5820
gcagcaggga ggcaaacaat gattaattaa ctagagcggc cgcgttaatt caaattaatt   5880
gatatagttt tttaatgagt attgaatctg tttagaaata atggaatatt atttttattt   5940
atttatttat attattggtc ggctcttttc ttctgaaggt caatgacaaa atgatatgaa   6000
ggaaataatg atttctaaaa ttttacaacg taagatattt ttacaaaagc ctagctcatc   6060
ttttgtcatg cactatttta ctcacgcttg aaattaacgg ccagtccact gcggagtcat   6120
ttcaaagtca tcctaatcga tctatcgttt ttgatagctc attttggagt tcgcgattgt   6180
cttctgttat tcacaactgt tttaattttt atttcattct ggaactcttc gagttctttg   6240
taaagtcttt catagtagct tactttatcc tccaacatat ttaacttcat gtcaatttcg   6300
gctcttaaat tttccacatc atcaagttca acatcatctt ttaacttgaa tttattctct   6360
agctcttcca accaagcctc attgctcctt gatttactgg tgaaaagtga tacactttgc   6420
gcgcaatcca ggtcaaaact ttcctgcaaa gaattcacca atttctcgac atcatagtac   6480
aatttgtttt gttctcccat cacaatttaa tatacctgat ggattcttat gaagcgctgg   6540
gtaatggacg tgtcactcta cttcgccttt ttccctactc cttttagtac ggaagacaat   6600
gctaataaat aagagggtaa taataatatt attaatcggc aaaaaagatt aaacgccaag   6660
cgtttaatta tcagaaagca aacgtcgtac caatccttga atgcttccca attgtatatt   6720
```

aagagtcatc acagcaacat attcttgtta ttaaattaat tattattgat ttttgatatt 6780
gtataaaaaa accaaatatg tataaaaaaa gtgaataaaa aataccaagt atggagaaat 6840
atattagaag tctatacgtt aaaccaccgc ggtggagctc cagcttttgt tccctttagt 6900
gagggttaat tgcgcgcttg gcgtaatcat ggtcatagct gtttcctgtg tgaaattgtt 6960
atccgctcac aattccacac aacataggag ccggaagcat aaagtgtaaa gcctggggtg 7020
cctaatgagt gaggtaactc acattaattg cgttgcgctc actgcccgct ttccagtcgg 7080
gaaacctgtc gtgccagctg cattaatgaa tcggccaacg cgcggggaga ggcggtttgc 7140
gtattgggcg ctcttccgct tcctcgctca ctgactcgct gcgctcggtc gttcggctgc 7200
ggcgagcggt atcagctcac tcaaaggcgg taatacggtt atccacagaa tcaggggata 7260
acgcaggaaa gaacatgtga gcaaaaggcc agcaaaaggc caggaaccgt aaaaaggccg 7320
cgttgctggc gtttttccat aggctccgcc cccctgacga gcatcacaaa aatcgacgct 7380
caagtcagag gtggcgaaac ccgacaggac tataaagata ccaggcgttt ccccctggaa 7440
gctccctcgt gcgctctcct gttccgaccc tgccgcttac cggatacctg tccgcctttc 7500
tcccttcggg aagcgtggcg ctttctcata gctcacgctg taggtatctc agttcggtgt 7560
aggtcgttcg ctccaagctg ggctgtgtgc acgaaccccc cgttcagccc gaccgctgcg 7620
ccttatccgg taactatcgt cttgagtcca acccggtaag acacgactta tcgccactgg 7680
cagcagccac tggtaacagg attagcagag cgaggtatgt aggcggtgct acagagttct 7740
tgaagtggtg gcctaactac ggctacacta gaaggacagt atttggtatc tgcgctctgc 7800
tgaagccagt taccttcgga aaaagagttg gtagctcttg atccggcaaa caaaccaccg 7860
ctggtagcgg tggttttttt gtttgcaagc agcagattac gcgcagaaaa aaaggatctc 7920
aagaagatcc tttgatcttt tctacggggt ctgacgctca gtggaacgaa aactcacgtt 7980
aagggatttt ggtcatgaga ttatcaaaaa ggatcttcac ctagatcctt ttaaattaaa 8040
aatgaagttt taaatcaatc taaagtatat atgagtaaac ttggtctgac agttaccaat 8100
gcttaatcag tgaggcacct atctcagcga tctgtctatt tcgttcatcc atagttgcct 8160
gactccccgt cgtgtagata actacgatac gggagggctt accatctggc cccagtgctg 8220
caatgatacc gcgagaccca cgctcaccgg ctccagattt atcagcaata aaccagccag 8280
ccggaagggc cgagcgcaga agtggtcctg caactttatc cgcctccatc cagtctatta 8340
attgttgccg ggaagctaga gtaagtagtt cgccagttaa tagtttgcgc aacgttgttg 8400
ccattgctac aggcatcgtg gtgtcacgct cgtcgtttgg tatggcttca ttcagctccg 8460
gttcccaacg atcaaggcga gttacatgat cccccatgtt gtgcaaaaaa gcggttagct 8520
ccttcggtcc tccgatcgtt gtcagaagta agttggccgc agtgttatca ctcatggtta 8580
tggcagcact gcataattct cttactgtca tgccatccgt aagatgcttt tctgtgactg 8640
gtgagtactc aaccaagtca ttctgagaat agtgtatgcg gcgaccgagt tgctcttgcc 8700
cggcgtcaat acgggataat accgcgccac atagcagaac tttaaaagtg ctcatcattg 8760
gaaaacgttc ttcggggcga aaactctcaa ggatcttacc gctgttgaga tccagttcga 8820
tgtaacccac tcgtgcaccc aactgatctt cagcatcttt tactttcacc agcgtttctg 8880
ggtgagcaaa aacaggaagg caaaatgccg caaaaaaggg aataagggcg acacggaaat 8940
gttgaatact catactcttc ctttttcaat attattgaag catttatcag ggttattgtc 9000
tcatgagcgg atacatattt gaatgtattt agaaaaataa acaaataggg gttccgcgca 9060

```
catttccccg aaaagtgcca cctgaacgaa gcatctgtgc ttcattttgt agaacaaaaa   9120

tgcaacgcga gagcgctaat ttttcaaaca aagaatctga gctgcatttt tacagaacag   9180

aaatgcaacg cgaaagcgct attttaccaa cgaagaatct gtgcttcatt tttgtaaaac   9240

aaaaatgcaa cgcgagagcg ctaatttttc aaacaaagaa tctgagctgc atttttacag   9300

aacagaaatg caacgcgaga gcgctatttt accaacaaag aatctatact tcttttttgt   9360

tctacaaaaa tgcatcccga gagcgctatt tttctaacaa agcatcttag attacttttt   9420

ttctcctttg tgcgctctat aatgcagtct cttgataact ttttgcactg taggtccgtt   9480

aaggttagaa gaaggctact ttggtgtcta ttttctcttc cataaaaaaa gcctgactcc   9540

acttcccgcg tttactgatt actagcgaag ctgcgggtgc atttttcaa gataaaggca   9600

tccccgatta tattctatac cgatgtggat tgcgcatact ttgtgaacag aaagtgatag   9660

cgttgatgat tcttcattgg tcagaaaatt atgaacggtt tcttctattt tgtctctata   9720

tactacgtat aggaaatgtt tacattttcg tattgtttc gattcactct atgaatagtt   9780

cttactacaa tttttttgtc taaagagtaa tactagagat aaacataaaa aatgtagagg   9840

tcgagtttag atgcaagttc aaggagcgaa aggtggatgg gtaggttata tagggatata   9900

gcacagagat atatagcaaa gagatacttt tgagcaatgt ttgtggaagc ggtattcgca   9960

atattttagt agctcgttac agtccggtgc gtttttggtt ttttgaaagt gcgtcttcag  10020

agcgcttttg gttttcaaaa gcgctctgaa gttcctatac tttctagaga ataggaactt  10080

cggaatagga acttcaaagc gtttccgaaa acgagcgctt ccgaaaatgc aacgcgagct  10140

gcgcacatac agctcactgt tcacgtcgca cctatatctg cgtgttgcct gtatatatat  10200

atacatgaga agaacggcat agtgcgtgtt tatgcttaaa tgcgtactta tatgcgtcta  10260

tttatgtagg atgaaaggta gtctagtacc tcctgtgata ttatcccatt ccatgcgggg  10320

tatcgtatgc ttccttcagc actacccttt agctgttcta tatgctgcca ctcctcaatt  10380

ggattagtct catccttcaa tgctatcatt tcctttgata ttggatcatc taagaaacca  10440

ttattatcat gacattaacc tataaaaata ggcgtatcac gaggcccttt cgtc        10494
```

<210> SEQ ID NO 181
<211> LENGTH: 43
<212> TYPE: DNA
<213> ORGANISM: Artificial Sequence
<220> FEATURE:
<223> OTHER INFORMATION: Primer T-U/PGK1(KpnI)

<400> SEQUENCE: 181

```
actacagatg gtaccaatta ccgtcgctcg tgatttgttt gca                        43
```

<210> SEQ ID NO 182
<211> LENGTH: 45
<212> TYPE: DNA
<213> ORGANISM: Artificial Sequence
<220> FEATURE:
<223> OTHER INFORMATION: Primer B-U/PGK1(SalI)

<400> SEQUENCE: 182

```
agcatccttg tcgacaggac cttgttgtgt gacgaaattg gaagc                      45
```

<210> SEQ ID NO 183
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 183
cgtgttagtc acatcaggac 20

<210> SEQ ID NO 184
<211> LENGTH: 22
<212> TYPE: DNA
<213> ORGANISM: Artificial Sequence
<220> FEATURE:
<223> OTHER INFORMATION: Primer N99SeqR2

<400> SEQUENCE: 184
catcgactgc attacgcaac tc 22

<210> SEQ ID NO 185
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 185
ggtttctgtc tctggtgacg 20

<210> SEQ ID NO 186
<211> LENGTH: 30
<212> TYPE: DNA
<213> ORGANISM: Artificial Sequence
<220> FEATURE:
<223> OTHER INFORMATION: Primer N1111

<400> SEQUENCE: 186
tatttgtatc gaggtgtcta gtcttctatt 30

<210> SEQ ID NO 187
<211> LENGTH: 30
<212> TYPE: DNA
<213> ORGANISM: Artificial Sequence
<220> FEATURE:
<223> OTHER INFORMATION: Primer N1110

<400> SEQUENCE: 187
gcgatttaat ctctaattat tagttaaagt 30

<210> SEQ ID NO 188
<211> LENGTH: 38
<212> TYPE: DNA
<213> ORGANISM: Artificial Sequence
<220> FEATURE:
<223> OTHER INFORMATION: Primer BK468

<400> SEQUENCE: 188
gcctcgagtt ttaatgttac ttctcttgca gttaggga 38

<210> SEQ ID NO 189
<211> LENGTH: 22
<212> TYPE: DNA
<213> ORGANISM: Artificial Sequence
<220> FEATURE:
<223> OTHER INFORMATION: Primer N160SeqF5

<400> SEQUENCE: 189
cctgaagtct aggtccctat tt 22

<210> SEQ ID NO 190

<211> LENGTH: 7589
<212> TYPE: DNA
<213> ORGANISM: Artificial Sequence
<220> FEATURE:
<223> OTHER INFORMATION: pUC19-kan::pdc1::FBA-alsS::TRX1 (clone A)

<400> SEQUENCE: 190
tatttgtatc gaggtgtcta gtcttctatt acactaatgc agtttcaggg ttttggaaac 60
cacactgttt aaacagtgtt ccttaatcaa ggatacctct tttttttcc ttggttccac 120 taattcatcg gttttttttt tggaagacat cttttccaac gaaaagaata tacatatcgt 180
ttaagagaaa ttctccaaat ttgtaaagaa gcggacccag acttaaggcc gcccgcaaat 240
taaagccttc gagcgtccca aaaccttctc aagcaaggtt ttcagtataa tgttacatgc 300
gtacacgcgt ctgtacagaa aaaaaagaaa aatttgaaat ataaataacg ttcttaatac 360
taacataact ataaaaaaat aaatagggac ctagacttca ggttgtctaa ctccttcctt 420
ttcggttaga gcggatgtgg ggggagggcg tgaatgtaag cgtgacataa ctaattacat 480
gattaattaa ctagagagct ttcgttttca tgagttcccc gaattctttc ggaagcttgt 540
cacttgctaa attaatgtta tcactgtagt caaccgggac atcgatgatg acaggacctt 600
cagcgttcat gccttgacgc agaacatctg ccagctggtc tggtgattct acgcgcaagc 660
cagttgctcc gaagctttcc gcatatttca cgatatcgat atttccgaaa tcgaccgcag 720
atgtacggtt atatttttc aattgctgga atgcaaccat gtcatatgtg ctgtcgttcc 780
atacaatgtg tacaattggt gcttttagtc gaactgctgt ctctaattcc attgctgaga 840
ataagaaacc gccgtcacca gagacagaaa ccactttttc tcccggtttc accaatgaag 900
cgccgattgc ccaaggaagc gcaacgccga gtgtttgcat accgttactg atcattaatg 960
ttaacggctc gtagctgcgg aaataacgtg acatccaaat ggcgtgcgaa ccgatatcgc 1020
aagttactgt aacatgatca tcgactgcat tacgcaactc tttaacgatt tcaagagggt 1080
gcgctctgtc tgatttccaa tctgcaggca cctgctcacc ttcatgcata tattgtttta 1140
aatcagaaag gattttctgc tcacgctctg caaattccac tttcacagca tcgtgttcga 1200
tatgattgat cgtggacgga atgtcaccga tcaattcaag atcaggctgg taagcatgat 1260
caatgtcagc gataatctcg tctaaatgga taattgtccg gtctccattg atattccaga 1320
atttcggatc atattcaatc gggtcatagc cgatcgtcag aacaacatct gcctgctcta 1380
gcagtaaatc gccaggctgg ttgcggaaca aaccgatacg gccaaaatat tgatcctcta 1440
aatctctaga aagggtaccg gcagcttgat atgtttcaac aaatggaagc tgaacctttt 1500
tcaaaagctt gcgaaccgct ttaattgctt ccggtcttcc gcctttcatg ccgaccaaaa 1560
cgacaggaag ttttgctgtt tggatttttg ctatggccgc actgattgca tcatctgctg 1620
caggaccgag ttttggcgct gcaacagcac gcacgttttt cgtatttgtg acttcattca 1680
caacatcttg cggaaagctc acaaaagcgg ccccagcctg ccctgctgac gctatcctaa 1740
atgcatttgt aacagcttcc ggtatatttt ttacatcttg aacttctaca ctgtattttg 1800
taatcggctg gaatagcgcc gcattatcca aagattgatg tgtccgtttt aaacgatctg 1860
cacggatcac gtttccagca agcgcaacga cagggtctcc ttcagtgttc gctgtcagca 1920
ggcctgttgc caagttagag gcacccggtc ctgatgtgac taacacgact cccggttttc 1980
cagttaaacg gccgactgct tgggccatga atgctgcgtt ttgttcgtgc cgggcaacga 2040
taatttcagg tcctttatct tgtaaagcgt caaataccgc atcaattttt gcacctggaa 2100
tgccaaatac atgtgtgaca ccttgctcca ctaagcaatc aacaacaagc tccgcccctc 2160

```
tgtttttcac aagggatttt tgttcttttg ttgcttttgt caacatcctc agctctagat   2220
ttgaatatgt attacttggt tatggttata tatgacaaaa gaaaaagaag aacagaagaa   2280
taacgcaagg aagaacaata actgaaattg atagagaagt attatgtctt tgtcttttta   2340
taataaatca agtgcagaaa tccgttagac aacatgaggg ataaaattta acgtgggcga   2400
agaagaagga aaaaagtttt tgtgagggcg taattgaagc gatctgttga ttgtagattt   2460
tttttttttg aggagtcaaa gtcagaagag aacagacaaa tggtattaac catccaatac   2520
ttttttggag caacgctaag ctcatgcttt tccattggtt acgtgctcag ttgttagata   2580
tggaaagaga ggatgctcac ggcagcgtga ctccaattga gcccgaaaga gaggatgcca   2640
cgttttcccg acggctgcta gaatggaaaa aggaaaaata gaagaatccc attcctatca   2700
ttatttacgt aatgacccac acatttttga gattttcaac tattacgtat tacgataatc   2760
ctgctgtcat tatcattatt atctatatcg acgtatgcaa cgtatgtgaa gccaagtagg   2820
caattattta gtactgtcag tattgttatt catttcagat cttaagccta accaggccaa   2880
ttcaacagac tgtcggcaac ttcttgtctg gtctttccat ggtaagtgac agtgcagtaa   2940
taatatgaac caatttattt ttcgttacat aaaaatgctt ataaaacttt aactaataat   3000
tagagattaa atcgcaaacg gccgactcta gaggatcccc caccttggct aactcgttgt   3060
atcatcactg gataacttcg tatagcatac attatacgaa gttatctagg gattcataac   3120
cattttctca atcgaattac acagaacaca ccgtacaaac ctctctatca taactactta   3180
atagtcacac acgtactcgt ctaaatacac atcatcgtcc tacaagttca tcaaagtgtt   3240
ggacagacaa ctataccagc atggatctct tgtatcggtt cttttctccc gctctctcgc   3300
aataacaatg aacactgggt caatcatagc ctacacaggt gaacagagta gcgtttatac   3360
agggtttata cggtgattcc tacggcaaaa atttttcatt tctaaaaaaa aaaagaaaaa   3420
tttttctttc caacgctaga aggaaaagaa aaatctaatt aaattgattt ggtgattttc   3480
tgagagttcc ctttttcata tatcgaattt tgaatataaa aggagatcga aaaaattttt   3540
ctattcaatc tgttttctgg ttttatttga tagttttttt gtgtattatt attatggatt   3600
agtactggtt tatatgggtt tttctgtata acttcttttt attttagttt gtttaatctt   3660
attttgagtt acattatagt tccctaactg caagagaagt aacattaaaa ctcgagatgg   3720
gtaaggaaaa gactcacgtt tcgaggccgc gattaaattc caacatggat gctgatttat   3780
atgggtataa atgggctcgc gataatgtcg ggcaatcagg tgcgacaatc tatcgattgt   3840
atgggaagcc cgatgcgcca gagttgtttc tgaaacatgg caaaggtagc gttgccaatg   3900
atgttacaga tgagatggtc agactaaact ggctgacgga atttatgcct cttccgacca   3960
tcaagcattt tatccgtact cctgatgatg catggttact caccactgcg atccccggca   4020
aaacagcatt ccaggtatta gaagaatatc ctgattcagg tgaaaatatt gttgatgcgc   4080
tggcagtgtt cctgcgccgg ttgcattcga ttcctgtttg taattgtcct tttaacagcg   4140
atcgcgtatt tcgtctcgct caggcgcaat cacgaatgaa taacggtttg gttgatgcga   4200
gtgattttga tgacgagcgt aatggctggc ctgttgaaca agtctggaaa gaaatgcata   4260
agcttttgcc attctcaccg gattcagtcg tcactcatgg tgatttctca cttgataacc   4320
ttatttttga cgaggggaaa ttaataggtt gtattgatgt tggacgagtc ggaatcgcag   4380
accgatacca ggatcttgcc atcctatgga actgcctcgg tgagttttct ccttcattac   4440
agaaacggct tttcaaaaa tatggtattg ataatcctga tatgaataaa ttgcagtttc   4500
```

```
atttgatgct cgatgagttt ttctaagttt aacttgatac tactagattt tttctcttca    4560
tttataaaat ttttggttat aattgaagct ttagaagtat gaaaaaatcc ttttttttca    4620
ttctttgcaa ccaaaataag aagcttcttt tattcattga aatgatgaat ataaacctaa    4680
caaaagaaaa agactcgaat atcaaacatt aaaaaaaaat aaaagaggtt atctgttttc    4740
ccatttagtt ggagtttgca ttttctaata gatagaactc tcaattaatg tggatttagt    4800
ttctctgttc gataacttcg tatagcatac attatacgaa gttatctgaa cattagaata    4860
cgtaatccgc aatgcggggc cgcttaatta atctagagtc gacctgcagg catgcaagct    4920
tggcgtaatc atggtcatag ctgtttcctg tgtgaaattg ttatccgctc acaattccac    4980
acaacatacg agccggaagc ataaagtgta aagcctgggg tgcctaatga gtgagctaac    5040
tcacattaat tgcgttgcgc tcactgcccg ctttccagtc gggaaacctg tcgtgccagc    5100
tgcattaatg aatcggccaa cgcgcgggga gaggcggttt gcgtattggg cgctcttccg    5160
cttcctcgct cactgactcg ctgcgctcgg tcgttcggct gcggcgagcg gtatcagctc    5220
actcaaaggc ggtaatacgg ttatccacag aatcagggga taacgcagga aagaacatgt    5280
gagcaaaagg ccagcaaaag gccaggaacc gtaaaaaggc cgcgttgctg gcgtttttcc    5340
ataggctccg cccccctgac gagcatcaca aaaatcgacg ctcaagtcag aggtggcgaa    5400
acccgacagg actataaaga taccaggcgt ttccccctgg aagctccctc gtgcgctctc    5460
ctgttccgac cctgccgctt accggatacc tgtccgcctt tctcccttcg ggaagcgtgg    5520
cgctttctca tagctcacgc tgtaggtatc tcagttcggt gtaggtcgtt cgctccaagc    5580
tgggctgtgt gcacgaaccc cccgttcagc ccgaccgctg cgccttatcc ggtaactatc    5640
gtcttgagtc caacccggta agacacgact tatcgccact ggcagcagcc actggtaaca    5700
ggattagcag agcgaggtat gtaggcggtg ctacagagtt cttgaagtgg tggcctaact    5760
acggctacac tagaaggaca gtatttggta tctgcgctct gctgaagcca gttaccttcg    5820
gaaaaagagt tggtagctct tgatccggca aacaaaccac cgctggtagc ggtggttttt    5880
ttgtttgcaa gcagcagatt acgcgcagaa aaaaaggatc tcaagaagat cctttgatct    5940
tttctacggg gtctgacgct cagtggaacg aaaactcacg ttaagggatt ttggtcatga    6000
gattatcaaa aaggatcttc acctagatcc ttttaaatta aaaatgaagt tttaaatcaa    6060
tctaaagtat atatgagtaa acttggtctg acagttacca atgcttaatc agtgaggcac    6120
ctatctcagc gatctgtcta tttcgttcat ccatagttgc ctgactcccc gtcgtgtaga    6180
taactacgat acgggagggc ttaccatctg gccccagtgc tgcaatgata ccgcgagacc    6240
cacgctcacc ggctccagat ttatcagcaa taaaccagcc agccggaagg gccgagcgca    6300
gaagtggtcc tgcaacttta tccgcctcca tccagtctat taattgttgc cgggaagcta    6360
gagtaagtag ttcgccagtt aatagtttgc gcaacgttgt tgccattgct acaggcatcg    6420
tggtgtcacg ctcgtcgttt ggtatggctt cattcagctc cggttcccaa cgatcaaggc    6480
gagttacatg atcccccatg ttgtgcaaaa aagcggttag ctccttcggt cctccgatcg    6540
ttgtcagaag taagttggcc gcagtgttat cactcatggt tatggcagca ctgcataatt    6600
ctcttactgt catgccatcc gtaagatgct tttctgtgac tggtgagtac tcaaccaagt    6660
cattctgaga atagtgtatg cggcgaccga gttgctcttg cccggcgtca atacgggata    6720
ataccgcgcc acatagcaga actttaaaag tgctcatcat tggaaaacgt tcttcggggc    6780
gaaaactctc aaggatctta ccgctgttga gatccagttc gatgtaaccc actcgtgcac    6840
ccaactgatc ttcagcatct tttactttca ccagcgtttc tgggtgagca aaaacaggaa    6900
```

ggcaaaatgc cgcaaaaaag ggaataaggg cgacacggaa atgttgaata ctcatactct 6960
tcctttttca atattattga agcatttatc agggttattg tctcatgagc ggatacatat 7020
ttgaatgtat ttagaaaaat aaacaaatag gggttccgcg cacatttccc cgaaaagtgc 7080
cacctgacgt ctaagaaacc attattatca tgacattaac ctataaaaat aggcgtatca 7140
cgaggccctt tcgtctcgcg cgtttcggtg atgacggtga aaacctctga cacatgcagc 7200
tcccggagac ggtcacagct tgtctgtaag cggatgccgg gagcagacaa gcccgtcagg 7260
gcgcgtcagc gggtgttggc gggtgtcggg gctggcttaa ctatgcggca tcagagcaga 7320
ttgtactgag agtgcaccat atgcggtgtg aaataccgca cagatgcgta aggagaaaat 7380
accgcatcag gcgccattcg ccattcaggc tgcgcaactg ttgggaaggg cgatcggtgc 7440
gggcctcttc gctattacgc cagctggcga aagggggatg tgctgcaagg cgattaagtt 7500
gggtaacgcc agggttttcc cagtcacgac gttgtaaaac gacggccagt gaattcgagc 7560
tcggtacccg gggatccggc gcgccgttt 7589

<210> SEQ ID NO 191
<211> LENGTH: 38
<212> TYPE: DNA
<213> ORGANISM: Artificial Sequence
<220> FEATURE:
<223> OTHER INFORMATION: Primer N191

<400> SEQUENCE: 191
atccgcggat agatctccca ttaccgacat ttgggcgc 38

<210> SEQ ID NO 192
<211> LENGTH: 9593
<212> TYPE: DNA
<213> ORGANISM: Artificial Sequence
<220> FEATURE:
<223> OTHER INFORMATION: pYZ090 alsS

<400> SEQUENCE: 192
ggccgcacct ggtaaaacct ctagtggagt agtagatgta atcaatgaag cggaagccaa 60
aagaccagag tagaggccta tagaagaaac tgcgatacct tttgtgatgg ctaaacaaac 120
agacatcttt ttatatgttt ttacttctgt atatcgtgaa gtagtaagtg ataagcgaat 180
ttggctaaga acgttgtaag tgaacaaggg acctcttttg cctttcaaaa aaggattaaa 240
tggagttaat cattgagatt tagttttcgt tagattctgt atccctaaat aactccctta 300
cccgacggga aggcacaaaa gacttgaata atagcaaacg gccagtagcc aagaccaaat 360
aatactagag ttaactgatg gtcttaaaca ggcattacgt ggtgaactcc aagaccaata 420
tacaaaatat cgataagtta ttcttgccca ccaatttaag gagcctacat caggacagta 480
gtaccattcc tcagagaaga ggtatacata acaagaaaat cgcgtgaaca ccttatataa 540
cttagcccgt tattgagcta aaaaaccttg caaaatttcc tatgaataag aatacttcag 600
acgtgataaa aatttacttt ctaactcttc tcacgctgcc cctatctgtt cttccgctct 660
accgtgagaa ataaagcatc gagtacggca gttcgctgtc actgaactaa aacaataagg 720
ctagttcgaa tgatgaactt gcttgctgtc aaacttctga gttgccgctg atgtgacact 780
gtgacaataa attcaaaccg gttatagcgg tctcctccgg taccggttct gccacctcca 840
atagagctca gtaggagtca gaacctctgc ggtggctgtc agtgactcat ccgcgtttcg 900
taagttgtgc gcgtgcacat ttcgcccgtt cccgctcatc ttgcagcagg cggaaatttt 960

```
catcacgctg taggacgcaa aaaaaaaata attaatcgta caagaatctt ggaaaaaaaa   1020
ttgaaaaatt ttgtataaaa gggatgacct aacttgactc aatggctttt acacccagta   1080
ttttcccttt ccttgtttgt tacaattata gaagcaagac aaaaacatat agacaaccta   1140
ttcctaggag ttatattttt ttaccctacc agcaatataa gtaaaaaact gtttaaacag   1200
tatggcagtt acaatgtatt atgaagatga tgtagaagta tcagcacttg ctggaaagca   1260
aattgcagta atcggttatg gttcacaagg acatgctcac gcacagaatt tgcgtgattc   1320
tggtcacaac gttatcattg gtgtgcgcca cggaaaatct tttgataaag caaaagaaga   1380
tggctttgaa acatttgaag taggagaagc agtagctaaa gctgatgtta ttatggtttt   1440
ggcaccagat gaacttcaac aatccattta tgaagaggac atcaaaccaa acttgaaagc   1500
aggttcagca cttggttttg ctcacggatt taatatccat tttggctata ttaaagtacc   1560
agaagacgtt gacgtcttta tggttgcgcc taaggctcca ggtcaccttg tccgtcggac   1620
ttatactgaa ggttttggta caccagcttt gtttgtttca caccaaaatg caagtggtca   1680
tgcgcgtgaa atcgcaatgg attgggccaa aggaattggt tgtgctcgag tgggaattat   1740
tgaaacaact tttaaagaag aaacagaaga agatttgttt ggagaacaag ctgttctatg   1800
tggaggtttg acagcacttg ttgaagccgg ttttgaaaca ctgacagaag ctggatacgc   1860
tggcgaattg gcttactttg aagttttgca cgaaatgaaa ttgattgttg acctcatgta   1920
tgaaggtggt tttactaaaa tgcgtcaatc catctcaaat actgctgagt ttggcgatta   1980
tgtgactggt ccacggatta ttactgacga agttaaaaag aatatgaagc ttgttttggc   2040
tgatattcaa tctggaaaat ttgctcaaga tttcgttgat gacttcaaag cggggcgtcc   2100
aaaattaata gcctatcgcg aagctgcaaa aaatcttgaa attgaaaaaa ttggggcaga   2160
gctacgtcaa gcaatgccat tcacacaatc tggtgatgac gatgccttta aaatctatca   2220
gtaaggccct gcaggccaga ggaaaataat atcaagtgct ggaaactttt tctcttggaa   2280
tttttgcaac atcaagtcat agtcaattga attgacccaa tttcacattt aagatttttt   2340
ttttttcatc cgacatacat ctgtacacta ggaagccctg tttttctgaa gcagcttcaa   2400
atatatatat tttttacata tttattatga ttcaatgaac aatctaatta aatcgaaaac   2460
aagaaccgaa acgcgaataa ataatttatt tagatggtga caagtgtata agtcctcatc   2520
gggacagcta cgatttctct ttcggttttg gctgagctac tggttgctgt gacgcagcgg   2580
cattagcgcg gcgttatgag ctaccctcgt ggcctgaaag atggcgggaa taaagcggaa   2640
ctaaaaatta ctgactgagc catattgagg tcaatttgtc aactcgtcaa gtcacgtttg   2700
gtggacggcc cctttccaac gaatcgtata tactaacatg cgcgcgcttc ctatatacac   2760
atatacatat atatatatat atatatgtgt gcgtgtatgt gtacacctgt atttaatttc   2820
cttactcgcg ggtttttctt ttttctcaat tcttggcttc ctctttctcg agcggaccgg   2880
atcctccgcg gtgccggcag atctatttaa atggcgcgcc gacgtcaggt ggcacttttc   2940
ggggaaatgt gcgcggaacc cctatttgtt tatttttcta aatacattca aatatgtatc   3000
cgctcatgag acaataaccc tgataaatgc ttcaataata ttgaaaaagg aagagtatga   3060
gtattcaaca tttccgtgtc gcccttattc cctttttgc ggcattttgc cttcctgttt   3120
ttgctcaccc agaaacgctg gtgaaagtaa aagatgctga agatcagttg ggtgcacgag   3180
tgggttacat cgaactggat ctcaacagcg gtaagatcct tgagagtttt cgccccgaag   3240
aacgttttcc aatgatgagc acttttaaag ttctgctatg tggcgcggta ttatcccgta   3300
ttgacgccgg gcaagagcaa ctcggtcgcc gcatacacta ttctcagaat gacttggttg   3360
```

-continued

```
agtactcacc agtcacagaa aagcatctta cggatggcat gacagtaaga gaattatgca   3420
gtgctgccat aaccatgagt gataacactg cggccaactt acttctgaca acgatcggag   3480
gaccgaagga gctaaccgct tttttgcaca acatgggga tcatgtaact cgccttgatc    3540
gttgggaacc ggagctgaat gaagccatac caaacgacga gcgtgacacc acgatgcctg   3600
tagcaatggc aacaacgttg cgcaaactat taactggcga actacttact ctagcttccc   3660
ggcaacaatt aatagactgg atggaggcgg ataaagttgc aggaccactt ctgcgctcgg   3720
cccttccggc tggctggttt attgctgata aatctggagc cggtgagcgt gggtctcgcg   3780
gtatcattgc agcactgggg ccagatggta agccctcccg tatcgtagtt atctacacga   3840
cggggagtca ggcaactatg gatgaacgaa atagacagat cgctgagata ggtgcctcac   3900
tgattaagca ttggtaactg tcagaccaag tttactcata tatactttag attgatttaa   3960
aacttcattt ttaatttaaa aggatctagg tgaagatcct ttttgataat ctcatgacca   4020
aaatccctta acgtgagttt tcgttccact gagcgtcaga ccccgtagaa aagatcaaag   4080
gatcttcttg agatcctttt tttctgcgcg taatctgctg cttgcaaaca aaaaaaccac   4140
cgctaccagc ggtggtttgt ttgccggatc aagagctacc aactcttttt ccgaaggtaa   4200
ctggcttcag cagagcgcag ataccaaata ctgttcttct agtgtagccg tagttaggcc   4260
accacttcaa gaactctgta gcaccgccta catacctcgc tctgctaatc ctgttaccag   4320
tggctgctgc cagtggcgat aagtcgtgtc ttaccgggtt ggactcaaga cgatagttac   4380
cggataaggc gcagcggtcg ggctgaacgg ggggttcgtg cacacagccc agcttggagc   4440
gaacgaccta caccgaactg agatacctac agcgtgagct atgagaaagc gccacgcttc   4500
ccgaagggag aaaggcggac aggtatccgg taagcggcag ggtcggaaca ggagagcgca   4560
cgagggagct tccaggggga aacgcctggt atctttatag tcctgtcggg tttcgccacc   4620
tctgacttga gcgtcgattt ttgtgatgct cgtcaggggg gcggagccta tggaaaaacg   4680
ccagcaacgc ggccttttta cggttcctgg ccttttgctg gccttttgct cacatgttct   4740
ttcctgcgtt atcccctgat tctgtggata accgtattac cgcctttgag tgagctgata   4800
ccgctcgccg cagccgaacg accgagcgca gcgagtcagt gagcgaggaa gcggaagagc   4860
gcccaatacg caaaccgcct ctccccgcgc gttggccgat tcattaatgc agctggcacg   4920
acaggtttcc cgactggaaa gcgggcagtg agcgcaacgc aattaatgtg agttagctca   4980
ctcattaggc accccaggct ttacacttta tgcttccggc tcgtatgttg tgtggaattg   5040
tgagcggata acaatttcac acaggaaaca gctatgacca tgattacgcc aagctttttc   5100
tttccaattt ttttttttc gtcattataa aaatcattac gaccgagatt cccgggtaat    5160
aactgatata attaaattga agctctaatt tgtgagttta gtatacatgc atttacttat   5220
aatacagttt tttagttttg ctggccgcat cttctcaaat atgcttccca gcctgctttt   5280
ctgtaacgtt caccctctac cttagcatcc cttccctttg caaatagtcc tcttccaaca   5340
ataataatgt cagatcctgt agagaccaca tcatccacgg ttctatactg ttgacccaat   5400
gcgtctccct tgtcatctaa acccacaccg ggtgtcataa tcaaccaatc gtaaccttca   5460
tctcttccac ccatgtctct ttgagcaata aagccgataa caaaatcttt gtcgctcttc   5520
gcaatgtcaa cagtaccctt agtatattct ccagtagata gggagccctt gcatgacaat   5580
tctgctaaca tcaaaaggcc tctaggttcc tttgttactt cttctgccgc ctgcttcaaa   5640
ccgctaacaa tacctgggcc caccacaccg tgtgcattcg taatgtctgc ccattctgct   5700
```

attctgtata cacccgcaga gtactgcaat ttgactgtat taccaatgtc agcaaatttt 5760
ctgtcttcga agagtaaaaa attgtacttg gcggataatg cctttagcgg cttaactgtg 5820
ccctccatgg aaaaatcagt caagatatcc acatgtgttt ttagtaaaca aattttggga 5880
cctaatgctt caactaactc cagtaattcc ttggtggtac gaacatccaa tgaagcacac 5940
aagtttgttt gcttttcgtg catgatatta aatagcttgg cagcaacagg actaggatga 6000
gtagcagcac gttccttata tgtagctttc gacatgattt atcttcgttt cctgcaggtt 6060
tttgttctgt gcagttgggt taagaatact gggcaatttc atgtttcttc aacactacat 6120
atgcgtatat ataccaatct aagtctgtgc tccttccttc gttcttcctt ctgttcggag 6180
attaccgaat caaaaaaatt tcaaggaaac cgaaatcaaa aaaaagaata aaaaaaaaat 6240
gatgaattga aaagcttgca tgcctgcagg tcgactctag tatactccgt ctactgtacg 6300
atacacttcc gctcaggtcc ttgtccttta acgaggcctt accactcttt tgttactcta 6360
ttgatccagc tcagcaaagg cagtgtgatc taagattcta tcttcgcgat gtagtaaaac 6420
tagctagacc gagaaagaga ctagaaatgc aaaaggcact tctacaatgg ctgccatcat 6480
tattatccga tgtgacgctg cattttttt ttttttttt ttttttttt ttttttttt 6540
ttttttttt ttttgtacaa atatcataaa aaaagagaat ctttttaagc aaggattttc 6600
ttaacttctt cggcgacagc atcaccgact tcggtggtac tgttggaacc acctaaatca 6660
ccagttctga tacctgcatc caaaaccttt ttaactgcat cttcaatggc tttaccttct 6720
tcaggcaagt tcaatgacaa tttcaacatc attgcagcag acaagatagt ggcgataggg 6780
ttgaccttat tctttggcaa atctggagcg gaaccatggc atggttcgta caaaccaaat 6840
gcggtgttct tgtctggcaa agaggccaag gacgcagatg gcaacaaacc caaggagcct 6900
gggataacgg aggcttcatc ggagatgata tcaccaaaca tgttgctggt gattataata 6960
ccatttaggt gggttgggtt cttaactagg atcatggcgg cagaatcaat caattgatgt 7020
tgaactttca atgtagggaa ttcgttcttg atggtttcct ccacagtttt tctccataat 7080
cttgaagagg ccaaaacatt agctttatcc aaggaccaaa taggcaatgg tggctcatgt 7140
tgtagggcca tgaaagcggc cattcttgtg attctttgca cttctggaac ggtgtattgt 7200
tcactatccc aagcgacacc atcaccatcg tcttcctttc tcttaccaaa gtaaatacct 7260
cccactaatt ctctaacaac aacgaagtca gtacctttag caaattgtgg cttgattgga 7320
gataagtcta aaagagagtc ggatgcaaag ttacatggtc ttaagttggc gtacaattga 7380
agttctttac ggatttttag taaaccttgt tcaggtctaa cactaccggt accccattta 7440
ggaccaccca cagcacctaa caaaacggca tcagccttct tggaggcttc cagcgcctca 7500
tctggaagtg gaacacctgt agcatcgata gcagcaccac caattaaatg attttcgaaa 7560
tcgaacttga cattggaacg aacatcagaa atagctttaa gaaccttaat ggcttcggct 7620
gtgatttctt gaccaacgtg gtcacctggc aaaacgacga tcttcttagg ggcagacatt 7680
acaatggtat atccttgaaa tatatataaa aaaaaaaaaa aaaaaaaaaa aaaaaaatgc 7740
agcttctcaa tgatattcga atacgctttg aggagataca gcctaatatc cgacaaactg 7800
ttttacagat ttacgatcgt acttgttacc catcattgaa ttttgaacat ccgaacctgg 7860
gagttttccc tgaaacagat agtatatttg aacctgtata ataatatata gtctagcgct 7920
ttacggaaga caatgtatgt atttcggttc ctggagaaac tattgcatct attgcatagg 7980
taatcttgca cgtcgcatcc ccggttcatt ttctgcgttt ccatcttgca cttcaatagc 8040
atatctttgt taacgaagca tctgtgcttc attttgtaga acaaaaatgc aacgcgagag 8100
cgctaatttt tcaaacaaag aatctgagct gcatttttac agaacagaaa tgcaacgcga 8160
aagcgctatt ttaccaacga agaatctgtg cttcattttt gtaaaacaaa aatgcaacgc 8220
gagagcgcta atttttcaaa caaagaatct gagctgcatt tttacagaac agaaatgcaa 8280
cgcgagagcg ctattttacc aacaaagaat ctatacttct tttttgttct acaaaaatgc 8340
atcccgagag cgctattttt ctaacaaagc atcttagatt actttttttc tcctttgtgc 8400
gctctataat gcagtctctt gataactttt tgcactgtag gtccgttaag gttagaagaa 8460
ggctactttg gtgtctattt tctcttccat aaaaaaagcc tgactccact tcccgcgttt 8520
actgattact agcgaagctg cgggtgcatt ttttcaagat aaaggcatcc ccgattatat 8580
tctataccga tgtggattgc gcatactttg tgaacagaaa gtgatagcgt tgatgattct 8640
tcattggtca gaaaattatg aacggtttct tctattttgt ctctatatac tacgtatagg 8700
aaatgtttac attttcgtat tgttttcgat tcactctatg aatagttctt actacaattt 8760
ttttgtctaa agagtaatac tagagataaa cataaaaaat gtagaggtcg agtttagatg 8820
caagttcaag gagcgaaagg tggatgggta ggttatatag ggatatagca cagagatata 8880
tagcaaagag atacttttga gcaatgtttg tggaagcggt attcgcaata ttttagtagc 8940
tcgttacagt ccggtgcgtt tttggttttt tgaaagtgcg tcttcagagc gcttttggtt 9000
ttcaaaagcg ctctgaagtt cctatacttt ctagagaata ggaacttcgg aataggaact 9060
tcaaagcgtt tccgaaaacg agcgcttccg aaaatgcaac gcgagctgcg cacatacagc 9120
tcactgttca cgtcgcacct atatctgcgt gttgcctgta tatatatata catgagaaga 9180
acggcatagt gcgtgtttat gcttaaatgc gtacttatat gcgtctattt atgtaggatg 9240
aaaggtagtc tagtacctcc tgtgatatta tcccattcca tgcggggtat cgtatgcttc 9300
cttcagcact accctttagc tgttctatat gctgccactc ctcaattgga ttagtctcat 9360
ccttcaatgc tatcatttcc tttgatattg gatcatatgc atagtaccga gaaactagag 9420
gatctcccat taccgacatt tgggcgctat acgtgcatat gttcatgtat gtatctgtat 9480
ttaaaacact tttgtattat ttttcctcat atatgtgtat aggtttatac ggatgattta 9540
attattactt caccaccctt tatttcaggc tgatatctta gccttgttac tag 9593

<210> SEQ ID NO 193
<211> LENGTH: 22
<212> TYPE: DNA
<213> ORGANISM: Artificial Sequence
<220> FEATURE:
<223> OTHER INFORMATION: Primer oBP556

<400> SEQUENCE: 193
tattttcgag gaccttgtca cc 22

<210> SEQ ID NO 194
<211> LENGTH: 25
<212> TYPE: DNA
<213> ORGANISM: Artificial Sequence
<220> FEATURE:
<223> OTHER INFORMATION: Primer oBP561

<400> SEQUENCE: 194
tggccattaa tctttcccat attag 25

<210> SEQ ID NO 195
<211> LENGTH: 12896
<212> TYPE: DNA

<213> ORGANISM: Artificial Sequence
<220> FEATURE:
<223> OTHER INFORMATION: pBP915

<400> SEQUENCE: 195

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt ccacctagcg gatgactctt tttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat ttttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttcttttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtgaaccat caccctaatc aagttttttg   1680
gggtcgaggt gccgtaaagc actaaatcgg aaccctaaag ggagcccccg atttagagct   1740
tgacggggaa agccggcgaa cgtggcgaga aaggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg ggcccccccct cgaggtcgac   2100
ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
```

```
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
acatacgttg catacgtcga tatagataat aatgataatg acagcaggat tatcgtaata   2580
cgtaatagct gaaaatctca aaaatgtgtg ggtcattacg taaataatga taggaatggg   2640
attcttctat ttttcctttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca aagtttctgg   4320
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
```

-continued

```
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gtttttttaat gagtattgaa tctgtttaga aataatggaa   4920
tattattttt atttatttat ttatattatt ggtcggctct tttcttctga aggtcaatga   4980
caaaatgata tgaaggaaat aatgatttct aaaattttac aacgtaagat atttttacaa   5040
aagcctagct catcttttgt catgcactat tttactcacg cttgaaatta acggccagtc   5100
cactgcggag tcatttcaaa gtcatcctaa tcgatctatc gtttttgata gctcattttg   5160
gagttcgcga ttgtcttctg ttattcacaa ctgttttaat ttttatttca ttctggaact   5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aactttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc ctttttccct actcctttta   5580
gtacggaaga caatgctaat aaataagagg gtaataataa tattattaat cggcaaaaaa   5640
gattaaacgc caagcgttta attatcagaa agcaaacgtc gtaccaatcc ttgaatgctt   5700
cccaattgta tattaagagt catcacagca acatattctt gttattaaat taattattat   5760
tgatttttga tattgtataa aaaaaccaaa tatgtataaa aaaagtgaat aaaaaatacc   5820
aagtatggag aaatatatta gaagtctata cgttaaacca cccgggcccc ccctcgaggt   5880
cgacggtatc gataagcttg atatcgaatt cctgcagccc gggggatcca ctagttctag   5940
agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat ttttttttata acttatttaa   6240
taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gattttagcg acagatatct cgtccaccac   6960
```

-continued

```
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
tggcgctact tctacttctt ctatgctaaa cggctttttc tcttcccaca aaactgccgc   7380
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc ccccgggctg caggaattcg atatcaagct   8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct   8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaaagaa aatttattta aatcttggct ctcttgggct caaggtgaca   9240
aggtcctcga aaatagggcg cgccccaccg cggtggagct ccagcttttg ttccctttag   9300
```

```
tgagggttaa ttgcgcgctt ggcgtaatca tggtcatagc tgtttcctgt gtgaaattgt   9360
tatccgctca caattccaca caacatacga gccggaagca taaagtgtaa agcctggggt   9420
gcctaatgag tgagctaact cacattaatt gcgttgcgct cactgcccgc tttccagtcg   9480
ggaaacctgt cgtgccagct gcattaatga atcggccaac gcgcggggag aggcggtttg   9540
cgtattgggc gctcttccgc ttcctcgctc actgactcgc tgcgctcggt cgttcggctg   9600
cggcgagcgg tatcagctca ctcaaaggcg gtaatacggt tatccacaga atcaggggat   9660
aacgcaggaa agaacatgtg agcaaaaggc cagcaaaagg ccaggaaccg taaaaaggcc   9720
gcgttgctgg cgtttttcca taggctccgc ccccctgacg agcatcacaa aaatcgacgc   9780
tcaagtcaga ggtggcgaaa cccgacagga ctataaagat accaggcgtt tccccctgga   9840
agctccctcg tgcgctctcc tgttccgacc ctgccgctta ccggatacct gtccgccttt   9900
ctcccttcgg gaagcgtggc gctttctcat agctcacgct gtaggtatct cagttcggtg   9960
taggtcgttc gctccaagct gggctgtgtg cacgaacccc ccgttcagcc cgaccgctgc  10020
gccttatccg gtaactatcg tcttgagtcc aacccggtaa gacacgactt atcgccactg  10080
gcagcagcca ctggtaacag gattagcaga gcgaggtatg taggcggtgc tacagagttc  10140
ttgaagtggt ggcctaacta cggctacact agaagaacag tatttggtat ctgcgctctg  10200
ctgaagccag ttaccttcgg aaaaagagtt ggtagctctt gatccggcaa acaaaccacc  10260
gctggtagcg gtggtttttt tgtttgcaag cagcagatta cgcgcagaaa aaaaggatct  10320
caagaagatc ctttgatctt ttctacgggg tctgacgctc agtggaacga aaactcacgt  10380
taagggattt tggtcatgag attatcaaaa aggatcttca cctagatcct tttaaattaa  10440
aaatgaagtt ttaaatcaat ctaaagtata tatgagtaaa cttggtctga cagttaccaa  10500
tgcttaatca gtgaggcacc tatctcagcg atctgtctat ttcgttcatc catagttgcc  10560
tgactccccg tcgtgtagat aactacgata cgggagggct taccatctgg ccccagtgct  10620
gcaatgatac cgcgagaccc acgctcaccg gctccagatt tatcagcaat aaaccagcca  10680
gccggaaggg ccgagcgcag aagtggtcct gcaactttat ccgcctccat ccagtctatt  10740
aattgttgcc gggaagctag agtaagtagt tcgccagtta atagtttgcg caacgttgtt  10800
gccattgcta caggcatcgt ggtgtcacgc tcgtcgtttg gtatggcttc attcagctcc  10860
ggttcccaac gatcaaggcg agttacatga tcccccatgt tgtgcaaaaa agcggttagc  10920
tccttcggtc ctccgatcgt tgtcagaagt aagttggccg cagtgttatc actcatggtt  10980
atggcagcac tgcataattc tcttactgtc atgccatccg taagatgctt ttctgtgact  11040
ggtgagtact caaccaagtc attctgagaa tagtgtatgc ggcgaccgag ttgctcttgc  11100
ccggcgtcaa tacgggataa taccgcgcca catagcagaa ctttaaaagt gctcatcatt  11160
ggaaaacgtt cttcggggcg aaaactctca aggatcttac cgctgttgag atccagttcg  11220
atgtaaccca ctcgtgcacc caactgatct tcagcatctt ttactttcac cagcgtttct  11280
gggtgagcaa aaacaggaag gcaaaatgcc gcaaaaaagg gaataagggc gacacggaaa  11340
tgttgaatac tcatactctt cctttttcaa tattattgaa gcatttatca gggttattgt  11400
ctcatgagcg gatacatatt tgaatgtatt tagaaaaata aacaaatagg ggttccgcgc  11460
acatttcccc gaaaagtgcc acctgaacga agcatctgtg cttcattttg tagaacaaaa  11520
atgcaacgcg agagcgctaa tttttcaaac aaagaatctg agctgcattt ttacagaaca  11580
gaaatgcaac gcgaaagcgc tattttacca acgaagaatc tgtgcttcat tttgtaaaa  11640
caaaaatgca acgcgagagc gctaattttt caaacaaaga atctgagctg catttttaca  11700
```

```
gaacagaaat gcaacgcgag agcgctattt taccaacaaa gaatctatac ttcttttttg  11760

ttctacaaaa atgcatcccg agagcgctat ttttctaaca aagcatctta gattactttt  11820

tttctccttt gtgcgctcta taatgcagtc tcttgataac tttttgcact gtaggtccgt  11880

taaggttaga agaaggctac tttggtgtct attttctctt ccataaaaaa agcctgactc  11940

cacttcccgc gtttactgat tactagcgaa gctgcgggtg cattttttca agataaaggc  12000

atccccgatt atattctata ccgatgtgga ttgcgcatac tttgtgaaca gaaagtgata  12060

gcgttgatga ttcttcattg gtcagaaaat tatgaacggt ttcttctatt ttgtctctat  12120

atactacgta taggaaatgt ttacattttc gtattgtttt cgattcactc tatgaatagt  12180

tcttactaca attttttgt ctaaagagta atactagaga taaacataaa aaatgtagag  12240

gtcgagttta gatgcaagtt caaggagcga aaggtggatg ggtaggttat atagggatat  12300

agcacagaga tatatagcaa agagatactt ttgagcaatg tttgtggaag cggtattcgc  12360

aatattttag tagctcgtta cagtccggtg cgtttttggt tttttgaaag tgcgtcttca  12420

gagcgctttt ggttttcaaa agcgctctga agttcctata ctttctagag aataggaact  12480

tcggaatagg aacttcaaag cgtttccgaa aacgagcgct tccgaaaatg caacgcgagc  12540

tgcgcacata cagctcactg ttcacgtcgc acctatatct gcgtgttgcc tgtatatata  12600

tatacatgag aagaacggca tagtgcgtgt ttatgcttaa atgcgtactt atatgcgtct  12660

atttatgtag gatgaaaggt agtctagtac ctcctgtgat attatcccat tccatgcggg  12720

gtatcgtatg cttccttcag cactaccctt tagctgttct atatgctgcc actcctcaat  12780

tggattagtc tcatccttca atgctatcat ttcctttgat attggatcat actaagaaac  12840

cattattatc atgacattaa cctataaaaa taggcgtatc acgaggccct ttcgtc      12896
```

```
<210> SEQ ID NO 196
<211> LENGTH: 3015
<212> TYPE: DNA
<213> ORGANISM: Artificial Sequence
<220> FEATURE:
<223> OTHER INFORMATION: FBA1-alsS- CYCt in Chr. XII; Upstream region =
      nt 1-154; FBA1 promoter = nt 155-802; alsS CDS = nt; CYC1
      terminator = nt 2534-2788; Downstream region = nt 2790-3015

<400> SEQUENCE: 196

gcgatttaat ctctaattat tagttaaagt tttataagca tttttatgta acgaaaaata     60

aattggttca tattattact gcactgtcac ttaccatgga aagaccagac aagaagttgc    120

cgacagtctg ttgaattggc ctggttaggc ttaagatctg aaatgaataa caatactgac    180

agtactaaat aattgcctac ttggcttcac atacgttgca tacgtcgata tagataataa    240

tgataatgac agcaggatta tcgtaatacg taatagttga aaatctcaaa aatgtgtggg    300

tcattacgta aataatgata ggaatgggat tcttctattt ttcctttttc cattctagca    360

gccgtcggga aaacgtggca tcctctcttt cgggctcaat tggagtcacg ctgccgtgag    420

catcctctct ttccatatct aacaactgag cacgtaacca atggaaaagc atgagcttag    480

cgttgctcca aaaaagtatt ggatggttaa taccatttgt ctgttctctt ctgactttga    540

ctcctcaaaa aaaaaaaatc tacaatcaac agatcgcttc aattacgccc tcacaaaaac    600

ttttttcctt cttcttcgcc cacgttaaat tttatccctc atgttgtcta acggatttct    660

gcacttgatt tattataaaa agacaaagac ataatacttc tctatcaatt tcagttattg    720

ttcttccttg cgttattctt ctgttcttct ttttcttttg tcatatataa ccataaccaa    780
```

-continued

```
gtaatacata ttcaaatcta gagctgagga tgttgacaaa agcaacaaaa gaacaaaaat    840
cccttgtgaa aaacagaggg gcggagcttg ttgttgattg cttagtggag caaggtgtca    900
cacatgtatt tggcattcca ggtgcaaaaa ttgatgcggt atttgacgct ttacaagata    960
aaggacctga aattatcgtt gcccggcacg aacaaaacgc agcattcatg gcccaagcag   1020
tcggccgttt aactggaaaa ccgggagtcg tgttagtcac atcaggaccg ggtgcctcta   1080
acttggcaac aggcctgctg acagcgaaca ctgaaggaga ccctgtcgtt gcgcttgctg   1140
gaaacgtgat ccgtgcagat cgtttaaaac ggacacatca atctttggat aatgcggcgc   1200
tattccagcc gattacaaaa tacagtgtag aagttcaaga tgtaaaaaat ataccggaag   1260
ctgttacaaa tgcatttagg atagcgtcag cagggcaggc tggggccgct tttgtgagct   1320
ttccgcaaga tgttgtgaat gaagtcacaa atacgaaaaa cgtgcgtgct gttgcagcgc   1380
caaaactcgg tcctgcagca gatgatgcaa tcagtgcggc catagcaaaa atccaaacag   1440
caaaacttcc tgtcgttttg gtcggcatga aaggcggaag accggaagca attaaagcgg   1500
ttcgcaagct tttgaaaaag gttcagcttc catttgttga aacatatcaa gctgccggta   1560
ccctttctag agatttagag gatcaatatt ttggccgtat cggtttgttc cgcaaccagc   1620
ctggcgattt actgctagag caggcagatg ttgttctgac gatcggctat gacccgattg   1680
aatatgatcc gaaattctgg aatatcaatg gagaccggac aattatccat ttagacgaga   1740
ttatcgctga cattgatcat gcttaccagc ctgatcttga attgatcggt gacattccgt   1800
ccacgatcaa tcatatcgaa cacgatgctg tgaaagtgga atttgcagag cgtgagcaga   1860
aaatcctttc tgatttaaaa caatatatgc atgaaggtga gcaggtgcct gcagattgga   1920
aatcagacag agcgcaccct cttgaaatcg ttaaagagtt gcgtaatgca gtcgatgatc   1980
atgttacagt aacttgcgat atcggttcgc acgccatttg gatgtcacgt tatttccgca   2040
gctacgagcc gttaacatta atgatcagta acggtatgca aacactcggc gttgcgcttc   2100
cttgggcaat cggcgcttca ttggtgaaac cgggagaaaa agtggtttct gtctctggtg   2160
acggcggttt cttattctca gcaatggaat tagagacagc agttcgacta aaagcaccaa   2220
ttgtacacat tgtatggaac gacagcacat atgacatggt tgcattccag caattgaaaa   2280
aatataaccg tacatctgcg gtcgatttcg gaaatatcga tatcgtgaaa tatgcggaaa   2340
gcttcggagc aactggcttg cgcgtagaat caccagacca gctggcagat gttctgcgtc   2400
aaggcatgaa cgctgaaggt cctgtcatca tcgatgtccc ggttgactac agtgataaca   2460
ttaatttagc aagtgacaag cttccgaaag aattcgggga actcatgaaa acgaaagctc   2520
tctagttaat taatcatgta attagttatg tcacgcttac attcacgccc tccccccaca   2580
tccgctctaa ccgaaaagga aggagttaga caacctgaag tctaggtccc tatttatttt   2640
tttatagtta tgttagtatt aagaacgtta tttatatttc aaatttttct tttttttctg   2700
tacagacgcg tgtacgcatg taacattata ctgaaaacct tgcttgagaa ggttttggga   2760
cgctcgaagg ctttaatttg cgggcggcct taagtctggg tccgcttctt tacaaatttg   2820
gagaatttct cttaaacgat atgtatattc ttttcgttgg aaaagatgtc ttccaaaaaa   2880
aaaaccgatg aattagtgga accaaggaaa aaaaaagagg tatccttgat taaggaacac   2940
tgtttaaaca gtgtggtttc caaaaccctg aaactgcatt agtgtaatag aagactagac   3000
acctcgatac aaata                                                    3015
```

<210> SEQ ID NO 197
<211> LENGTH: 2900

<212> TYPE: DNA
<213> ORGANISM: Artificial Sequence
<220> FEATURE:
<223> OTHER INFORMATION: fra2delta::PDC1-hADH-ADHt; Upstream region = nt 1-300; PDC1 promoter = nt 309-1178; hADH coding region = nt 1179-2306; ADH1 terminator = nt 2315-2630;Downstream region = nt 2639-2900

<400> SEQUENCE: 197
gttagcatcc acagcttctt gagcaactga cttcgtgagg tctacagtca aaaggacctt 60
tgttttagcg tttgcatcgg cagtggtgac ttgtgcagtg gaacaatcga tgagaagacc 120
cgtattgtcc cagctcttgt ctgcgtactt ttgagggtag aacttggtaa tgctacgcac 180
aagtttgtcc aattgtgctc tagtaatagc tctgctcatt gcgtttcggt ggactcttgt 240
tctgtttcct tccgactgtg tattggaata agtttttcgg tgttatatat atacatatat 300
ggcgcgcccc gcacgccgaa atgcatgcaa gtaacctatt caaagtaata tctcatacat 360
gtttcatgag ggtaacaaca tgcgactggg tgagcatatg ttccgctgat gtgatgtgca 420
agataaacaa gcaaggcaga aactaacttc ttcttcatgt aataaacaca ccccgcgttt 480
atttacctat ctctaaactt caacacctta tatcataact aatatttctt gagataagca 540
cactgcaccc ataccttcct taaaaacgta gcttccagtt tttggtggtt ccggcttcct 600
tcccgattcc gcccgctaaa cgcatatttt tgttgcctgg tggcatttgc aaaatgcata 660
acctatgcat ttaaaagatt atgtatgctc ttctgacttt tcgtgtgatg aggctcgtgg 720
aaaaaatgaa taatttatga atttgagaac aattttgtgt tgttacggta ttttactatg 780
gaataatcaa tcaattgagg attttatgca aatatcgttt gaatattttt ccgacccttt 840
gagtactttt cttcataatt gcataatatt gtccgctgcc ccttttctg ttagacggtg 900 tcttgatcta cttgctatcg ttcaacacca ccttattttc taactatttt ttttttagct 960
catttgaatc agcttatggt gatggcacat ttttgcataa acctagctgt cctcgttgaa 1020
cataggaaaa aaaaatatat aaacaaggct ctttcactct ccttgcaatc agatttgggt 1080
ttgttccctt tattttcata tttcttgtca tattcctttc tcaattatta ttttctactc 1140
ataacctcac gcaaaataac acagtcaaat caatcaaaat gtcaacagcc ggtaaagtta 1200
ttaagtgtaa agcggcagtt ttgtgggaag agaaaaagcc gtttagcata gaagaagtag 1260
aagtagcgcc accaaaagca cacgaggtta gaatcaagat ggttgccacc ggaatctgta 1320
gatccgacga ccatgtggtg agtggcactc tagttactcc tttgccagta atcgcgggac 1380
acgaggctgc cggaatcgtt gaatccatag gtgaaggtgt taccactgtt cgtcctggtg 1440
ataaagtgat cccactgttc actcctcaat gtggtaagtg tagagtctgc aaacatcctg 1500
agggtaattt ctgccttaaa aatgatttgt ctatgcctag aggtactatg caggatggta 1560
caagcagatt tacatgcaga gggaaaccta tacaccattt ccttggtact tctacatttt 1620
cccaatacac agtggtggac gagatatctg tcgctaaaat cgatgcagct tcaccactgg 1680
aaaaagtttg cttgataggg tgcggatttt ccaccggtta cggttccgca gttaaagttg 1740
caaaggttac acagggttcg acttgtgcag tattcggttt aggaggagta ggactaagcg 1800
ttattatggg gtgtaaagct gcaggcgcag cgaggattat aggtgtagac atcaataagg 1860
acaaatttgc aaaagctaag gaggtcgggg ctactgaatg tgttaaccct caagattata 1920
agaaaccaat acaagaagtc cttactgaaa tgtcaaacgg tggagttgat ttctcttttg 1980
aagttatagg ccgtcttgat actatggtaa ctgcgttgtc ctgctgtcaa gaggcatatg 2040
gagtcagtgt gatcgtaggt gttcctcctg attcacaaaa tttgtcgatg aatcctatgc 2100

```
tgttgctaag cggtcgtaca tggaagggag ctatatttgg cggttttaag agcaaggata   2160
gtgttccaaa acttgttgcc gactttatgg cgaagaagtt tgctcttgat cctttaatta   2220
cacatgtatt gccattcgag aaaatcaatg aagggtttga tttgttaaga agtggtgaat   2280
ctattcgtac aattttaact ttttgattaa ttaagagtaa gcgaatttct tatgatttat   2340
gatttttatt attaaataag ttataaaaaa aataagtgta tacaaatttt aaagtgactc   2400
ttaggtttta aaacgaaaat tcttattctt gagtaactct ttcctgtagg tcaggttgct   2460
ttctcaggta tagcatgagg tcgctcttat tgaccacacc tctaccggca tgccgagcaa   2520
atgcctgcaa atcgctcccc atttcaccca attgtagata tgctaactcc agcaatgagt   2580
tgatgaatct cggtgtgtat tttatgtcct cagaggacaa cacctgtggt gtttaaacaa   2640
aggatgatat tgttctatta ttaagtttcg aaaggagacg gcattgaatc tttttggcat   2700
agacgatttt gctttcttac gttatttaca tcggagagta tgtatttgtg tagttatgta   2760
cttagatatg taacttaatt taatgatatg gtggggggct atcctccatg ccccatttcc   2820
agttatttga aggttcttgc gagttcaaac ctatgaagta aaacggtttc tttttagatg   2880
tatctttctt ggagtccaaa                                                2900
```

<210> SEQ ID NO 198
<211> LENGTH: 2656
<212> TYPE: DNA
<213> ORGANISM: Artificial Sequence
<220> FEATURE:
<223> OTHER INFORMATION: yprcdelta15delta ::PDC5-hADH-ADHt; Upstream region = nt 1-150; PDC5 promoter = nt 159-696; hADH coding region = nt 697-1824; ADH1 terminator = nt 1833-2148; Downstream region = nt 2157-2656

<400> SEQUENCE: 198

```
ccaaaaggaa tattgggtca gatgaatgga cgcgaatgca agacagaagt ccaaatcacg     60
tcaagacaaa gaaagaaaga aagaaaaact aacacattaa tgtagtttta aaatttcaaa    120
tccgaacaac agagcatagg gtttcgcaaa ggcgcgccta tttgtaatac gtatacgaat    180
tccttcaaca aaggccaagg aaataaagca aataacaata acaccattat tttaattttt    240
tttctattac tgtcgctaac acctgtatgg ttgcaaccag gtgagaatcc ttctgatgca    300
tactttatgc gtttatgcgt tttgcgcccc ttggaaaaaa attgattctc atcgtaaatg    360
catactacat gcgtttatgg gaaaagcctc catatccaaa ggtcgcgttt cttttagaaa    420
aactaatacg taaacctgca ttaaggtaag attatatcag aaaatgtgtt gcaagaaatg    480
cattatgcaa ttttttgatt atgacaatct ctcgaaagaa atttcatatg atgagacttg    540
aataatgcag cggcgcttgc taaaagaact tgtatataag agctgccatt ctcgatcaat    600
atactgtagt aagtcctttc ctctctttct tattacactt atttcacata atcaatctca    660
aagagaacaa cacaatacaa taacaagaag aacaaaatgt caacagccgg taaagttatt    720
aagtgtaaag cggcagtttt gtgggaagag aaaaagccgt ttagcataga agaagtagaa    780
gtagcgccac caaaagcaca cgaggttaga atcaagatgg ttgccaccgg aatctgtaga    840
tccgacgacc atgtggtgag tggcactcta gttactcctt tgccagtaat cgcgggacac    900
gaggctgccg gaatcgttga atccataggt gaaggtgtta ccactgttcg tcctggtgat    960
aaagtgatcc cactgttcac tcctcaatgt ggtaagtgta gagtctgcaa acatcctgag   1020
ggtaatttct gccttaaaaa tgatttgtct atgcctagag gtactatgca ggatggtaca   1080
agcagattta catgcagagg gaaacctata caccatttcc ttggtacttc tacattttcc   1140
```

caatacacag tggtggacga gatatctgtc gctaaaatcg atgcagcttc accactggaa 1200
aaagtttgct tgatagggtg cggattttcc accggttacg gttccgcagt taaagttgca 1260
aaggttacac agggttcgac ttgtgcagta ttcggtttag gaggagtagg actaagcgtt 1320
attatggggt gtaaagctgc aggcgcagcg aggattatag gtgtagacat caataaggac 1380
aaatttgcaa aagctaagga ggtcggggct actgaatgtg ttaaccctca agattataag 1440
aaaccaatac aagaagtcct tactgaaatg tcaaacggtg gagttgattt ctcttttgaa 1500
gttataggcc gtcttgatac tatggtaact gcgttgtcct gctgtcaaga ggcatatgga 1560
gtcagtgtga tcgtaggtgt tcctcctgat tcacaaaatt tgtcgatgaa tcctatgctg 1620
ttgctaagcg gtcgtacatg gaagggagct atatttggcg gttttaagag caaggatagt 1680
gttccaaaac ttgttgccga ctttatggcg aagaagtttg ctcttgatcc tttaattaca 1740
catgtattgc cattcgagaa aatcaatgaa gggtttgatt tgttaagaag tggtgaatct 1800
attcgtacaa ttttaacttt ttgattaatt aagagtaagc gaatttctta tgatttatga 1860
tttttattat taaataagtt ataaaaaaaa taagtgtata caaattttaa agtgactctt 1920
aggttttaaa acgaaaattc ttattcttga gtaactcttt cctgtaggtc aggttgcttt 1980
ctcaggtata gcatgaggtc gctcttattg accacacctc taccggcatg ccgagcaaat 2040
gcctgcaaat cgctccccat ttcacccaat tgtagatatg ctaactccag caatgagttg 2100
atgaatctcg gtgtgtattt tatgtcctca gaggacaaca cctgtggtgt ttaaacaatg 2160
gaaggtcggg atgagcatat acaagcacta agaagaacaa tacagaactc tacacggtat 2220
tattgtgcta caagctcgag taaaaccgag tgttttgacg atactaacgt tgttaagaaa 2280
gtaacttgtt atcaaactca ttaccaactt gtgattaatt ggtgaataat atgataattg 2340
tcgaaattcc attgttggta aagcctataa tattatgtat acagattata ctagaaattc 2400
tctcgagaat ataagaatcc ccaaaattga atcggtattt ctacatacta atattaccat 2460
tacttctcct ttcgttttat atgtttcatt cctattacat tatcgatctt tgcatttcag 2520
cttccattat atttgatgtc tgttttatgt ccccacgtta caccgcatgt gacagtatac 2580
tagtaacatg agtgctaccg aatagatgac attttagact ttcattccaa caacttggtt 2640
gacagaatgt tacgta 2656

<210> SEQ ID NO 199
<211> LENGTH: 451
<212> TYPE: DNA
<213> ORGANISM: Artificial Sequence
<220> FEATURE:
<223> OTHER INFORMATION: ymr226c delta; Upstream region = nt 1-250;
Downstream region = nt 251-451

<400> SEQUENCE: 199
gatgatgcta tttggtgcag agggtgatga gtaagttctc tttatcatct atatattact 60
cttatacact atacgactct actctatgac gtatagcatt gatatatatt aaggcacgac 120
accgattttt cttatcggag cgatataaaa agctgaagaa aggaggatag atgaaacagc 180
atggcgcata gaaagtgttc aagctcacta gtaaaggcgg gaaatagaac attgagaacg 240
tattttgata acctagctaa actaagtaaa tctgtatact ttttatacat gtaagacttt 300
ttagctattt cattcttccc tgaaccgttt tgcgcgattc tacggaatat accggcgaaa 360
taaaagagat aaacttatgg atcctcaaat agaggatgaa cagatgtgaa gaagaaacga 420
gcttaattat atcttcgcca tgataactaa a 451

<210> SEQ ID NO 200
<211> LENGTH: 1128
<212> TYPE: DNA
<213> ORGANISM: Artificial Sequence
<220> FEATURE:
<223> OTHER INFORMATION: ald6 delta::loxP; Upstream region = nt 1-500;
loxP site = nt 551-584; Downstream region = nt 678-1128

<400> SEQUENCE: 200
tgatctgatg cgctttgcat atctcatatt ccttcactag cataaaaatc caaaaaaaaa 60
gaatatttag gccgaatgga attattcgta acgtcatacg aaaaaagttt caattcgtac 120
aatgcctggc atgttcattc gaatataagg ccgccgcctt ccagtcaggg tagccaaaag 180
tataatcccg ggtggaaact aaactaaaaa ccgtactcac aactttccgc ggacgctaac 240
agacaaatag acacactatc aggtcaggaa ctgccgtcac atacgacact gcccctcacg 300
taagggcatg atagaattgg attatgtaaa aggtgaagat accattgtag aagcaaccag 360
cacgtcgccg tggctgatga ggtctcctct tgcccgggcc gcagaaaaga ggggcagtgg 420
cctgtttttc gacataaatg aggggcatgg ccagcaccga gacgtcattg ttgcatatgg 480
cgtatccaag ccgaaacggc ggtaccgcaa gggcgaattc accttggcta actcgttgta 540
tcatcactgg ataacttcgt ataatgtatg ctatacgaag ttatctgaac attagaatac 600
gtaatccgca atgcggatcc tctagagtcg acctgcaggc atgctcgagc ggccgccagt 660
gtgatggata tctgcagaat tcgcccttgc cgatcgtgta ccaacctgca tttctttccg 720
tcatatacac aaaatacttt catataaact tacttggtct tacgtcataa ataaatatgt 780
atacatataa attaaaaaat ttggttttat atttttacaa aaagaatcgt ttacttcatt 840
tctccctttt aagcgataca atccatgaaa aaagagaaaa agagagaaca ggcttgtgcc 900
ttctttaaaa catcccacac aaaatcatat tgaattgaat tttacatctt aagctagtgt 960
acaacaactg ctatatccaa agaaaactaa cgtggaccgc ttttagagtt gagaaaaagg 1020
tttgaaaaaa atagcaatac aaagacttgt ttcatatata aaatacaggg agcacattga 1080
gctaatataa cataaacact gcgaaccaat tccaatcaaa aggtacac 1128

<210> SEQ ID NO 201
<211> LENGTH: 9612
<212> TYPE: DNA
<213> ORGANISM: Artificial Sequence
<220> FEATURE:
<223> OTHER INFORMATION: pLH702

<400> SEQUENCE: 201
aaacagtatg gaagaatgta agatggctaa gatttactac caagaagact gtaacttgtc 60
cttgttggat ggtaagacta tcgccgttat cggttacggt tctcaaggtc acgctcatgc 120
cctgaatgct aaggaatccg gttgtaacgt tatcattggt ttatacgaag gtgctaagga 180
ttggaaaaga gctgaagaac aaggtttcga agtctacacc gctgctgaag ctgctaagaa 240
ggctgacatc attatgatct tgatcaacga tgaaaagcag gctaccatgt acaaaaacga 300
catcgaacca aacttggaag ccggtaacat gttgatgttc gctcacggtt tcaacatcca 360
tttcggttgt attgttccac caaaggacgt tgatgtcact atgatcgctc caaagggtcc 420
aggtcacacc gttagatccg aatacgaaga aggtaaaggt gtcccatgct tggttgctgt 480
cgaacaagac gctactggca aggctttgga tatggctttg gcctacgctt tagccatcgg 540
tggtgctaga gccggtgtct tggaaactac cttcagaacc gaaactgaaa ccgacttgtt 600

```
cggtgaacaa gctgttttat gtggtggtgt ctgcgctttg atgcaggccg gttttgaaac    660
cttggttgaa gccggttacg acccaagaaa cgcttacttc gaatgtatcc acgaaatgaa    720
gttgatcgtt gacttgatct accaatctgg tttctccggt atgcgttact ctatctccaa    780
cactgctgaa tacggtgact acattaccgg tccaaagatc attactgaag ataccaagaa    840
ggctatgaag aagattttgt ctgacattca agatggtacc tttgccaagg acttcttggt    900
tgacatgtct gatgctggtt cccaggtcca cttcaaggct atgagaaagt tggcctccga    960
acacccagct gaagttgtcg gtgaagaaat tagatccttg tactcctggt ccgacgaaga   1020
caagttgatt aacaactgat attttcctct ggccctgcag gcctatcaag tgctggaaac   1080
tttttctctt ggaattttg caacatcaag tcatagtcaa ttgaattgac ccaatttcac   1140
atttaagatt ttttttttt catccgacat acatctgtac actaggaagc cctgtttttc   1200
tgaagcagct tcaaatatat atatttttta catatttatt atgattcaat gaacaatcta   1260
attaaatcga aaacaagaac cgaaacgcga ataaataatt tatttagatg gtgacaagtg   1320
tataagtcct catcgggaca gctacgattt ctctttcggt tttggctgag ctactggttg   1380
ctgtgacgca gcggcattag cgcggcgtta tgagctaccc tcgtggcctg aaagatggcg   1440
ggaataaagc ggaactaaaa attactgact gagccatatt gaggtcaatt tgtcaactcg   1500
tcaagtcacg tttggtggac ggcccctttc caacgaatcg tatatactaa catgcgcgcg   1560
cttcctatat acacatatac atatatatat atatatatat gtgtgcgtgt atgtgtacac   1620
ctgtatttaa tttccttact cgcgggtttt tcttttttct caattcttgg cttcctcttt   1680
ctcgagcgga ccggatcctc cgcggtgccg gcagatctat ttaaatggcg cgccgacgtc   1740
aggtggcact tttcggggaa atgtgcgcgg aacccctatt tgtttatttt tctaaataca   1800
ttcaaatatg tatccgctca tgagacaata accctgataa atgcttcaat aatattgaaa   1860
aaggaagagt atgagtattc aacatttccg tgtcgccctt attccctttt ttgcggcatt   1920
ttgccttcct gtttttgctc acccagaaac gctggtgaaa gtaaaagatg ctgaagatca   1980
gttgggtgca cgagtgggtt acatcgaact ggatctcaac agcggtaaga tccttgagag   2040
ttttcgcccc gaagaacgtt ttccaatgat gagcactttt aaagttctgc tatgtggcgc   2100
ggtattatcc cgtattgacg ccgggcaaga gcaactcggt cgccgcatac actattctca   2160
gaatgacttg gttgagtact caccagtcac agaaaagcat cttacggatg gcatgacagt   2220
aagagaatta tgcagtgctg ccataaccat gagtgataac actgcggcca acttacttct   2280
gacaacgatc ggaggaccga aggagctaac cgcttttttg cacaacatgg gggatcatgt   2340
aactcgcctt gatcgttggg aaccggagct gaatgaagcc ataccaaacg acgagcgtga   2400
caccacgatg cctgtagcaa tggcaacaac gttgcgcaaa ctattaactg gcgaactact   2460
tactctagct tcccggcaac aattaataga ctggatggag gcggataaag ttgcaggacc   2520
acttctgcgc tcggcccttc cggctggctg gtttattgct gataaatctg gagccggtga   2580
gcgtgggtct cgcggtatca ttgcagcact ggggccagat ggtaagccct cccgtatcgt   2640
agttatctac acgacgggga gtcaggcaac tatggatgaa cgaaatagac agatcgctga   2700
gataggtgcc tcactgatta agcattggta actgtcagac caagtttact catatatact   2760
ttagattgat ttaaaacttc atttttaatt taaaaggatc taggtgaaga tcctttttga   2820
taatctcatg accaaaatcc cttaacgtga gttttcgttc cactgagcgt cagaccccgt   2880
agaaaagatc aaaggatctt cttgagatcc tttttttctg cgcgtaatct gctgcttgca   2940
```

-continued

```
aacaaaaaaa ccaccgctac cagcggtggt ttgtttgccg gatcaagagc taccaactct   3000
ttttccgaag gtaactggct tcagcagagc gcagatacca aatactgttc ttctagtgta   3060
gccgtagtta ggccaccact tcaagaactc tgtagcaccg cctacatacc tcgctctgct   3120
aatcctgtta ccagtggctg ctgccagtgg cgataagtcg tgtcttaccg ggttggactc   3180
aagacgatag ttaccggata aggcgcagcg gtcgggctga acggggggtt cgtgcacaca   3240
gcccagcttg gagcgaacga cctacaccga actgagatac ctacagcgtg agctatgaga   3300
aagcgccacg cttcccgaag ggagaaaggc ggacaggtat ccggtaagcg gcagggtcgg   3360
aacaggagag cgcacgaggg agcttccagg gggaaacgcc tggtatcttt atagtcctgt   3420
cgggtttcgc cacctctgac ttgagcgtcg atttttgtga tgctcgtcag gggggcggag   3480
cctatggaaa aacgccagca acgcggcctt tttacggttc ctggcctttt gctggccttt   3540
tgctcacatg ttctttcctg cgttatcccc tgattctgtg gataaccgta ttaccgcctt   3600
tgagtgagct gataccgctc gccgcagccg aacgaccgag cgcagcgagt cagtgagcga   3660
ggaagcggaa gagcgcccaa tacgcaaacc gcctctcccc gcgcgttggc cgattcatta   3720
atgcagctgg cacgacaggt ttcccgactg gaaagcgggc agtgagcgca acgcaattaa   3780
tgtgagttag ctcactcatt aggcacccca ggctttacac tttatgcttc cggctcgtat   3840
gttgtgtgga attgtgagcg gataacaatt tcacacagga aacagctatg accatgatta   3900
cgccaagctt tttctttcca attttttttt tttcgtcatt ataaaaatca ttacgaccga   3960
gattcccggg taataactga tataattaaa ttgaagctct aatttgtgag tttagtatac   4020
atgcatttac ttataataca gtttttttagt tttgctggcc gcatcttctc aaatatgctt   4080
cccagcctgc ttttctgtaa cgttcaccct ctaccttagc atcccttccc tttgcaaata   4140
gtcctcttcc aacaataata atgtcagatc ctgtagagac cacatcatcc acggttctat   4200
actgttgacc caatgcgtct cccttgtcat ctaaacccac accgggtgtc ataatcaacc   4260
aatcgtaacc ttcatctctt ccacccatgt ctctttgagc aataaagccg ataacaaaat   4320
ctttgtcgct cttcgcaatg tcaacagtac ccttagtata ttctccagta gatagggagc   4380
ccttgcatga caattctgct aacatcaaaa ggcctctagg ttcctttgtt acttcttctg   4440
ccgcctgctt caaaccgcta acaatacctg ggcccaccac accgtgtgca ttcgtaatgt   4500
ctgcccattc tgctattctg tatacacccg cagagtactg caatttgact gtattaccaa   4560
tgtcagcaaa ttttctgtct tcgaagagta aaaaattgta cttggcggat aatgccttta   4620
gcggcttaac tgtgccctcc atggaaaaat cagtcaagat atccacatgt gtttttagta   4680
aacaaatttt gggacctaat gcttcaacta actccagtaa ttccttggtg gtacgaacat   4740
ccaatgaagc acacaagttt gtttgctttt cgtgcatgat attaaatagc ttggcagcaa   4800
caggactagg atgagtagca gcacgttcct tatatgtagc tttcgacatg atttatcttc   4860
gtttcctgca ggtttttgtt ctgtgcagtt gggttaagaa tactgggcaa tttcatgttt   4920
cttcaacact acatatgcgt atatatacca atctaagtct gtgctccttc cttcgttctt   4980
ccttctgttc ggagattacc gaatcaaaaa aatttcaagg aaaccgaaat caaaaaaaag   5040
aataaaaaaa aaatgatgaa ttgaaaagct tgcatgcctg caggtcgact ctagtatact   5100
ccgtctactg tacgatacac ttccgctcag gtccttgtcc tttaacgagg ccttaccact   5160
cttttgttac tctattgatc cagctcagca aaggcagtgt gatctaagat tctatcttcg   5220
cgatgtagta aaactagcta gaccgagaaa gagactagaa atgcaaaagg cacttctaca   5280
atggctgcca tcattattat ccgatgtgac gctgcatttt tttttttttt tttttttttt   5340
```

```
tttttttttt tttttttttt tttttttgt acaaatatca taaaaaaaga gaatcttttt   5400
aagcaaggat tttcttaact tcttcggcga cagcatcacc gacttcggtg gtactgttgg   5460
aaccacctaa atcaccagtt ctgatacctg catccaaaac ctttttaact gcatcttcaa   5520
tggctttacc ttcttcaggc aagttcaatg acaatttcaa catcattgca gcagacaaga   5580
tagtggcgat agggttgacc ttattctttg gcaaatctgg agcggaacca tggcatggtt   5640
cgtacaaacc aaatgcggtg ttcttgtctg gcaaagaggc caaggacgca gatggcaaca   5700
aacccaagga gcctgggata acggaggctt catcggagat gatatcacca aacatgttgc   5760
tggtgattat aataccattt aggtgggttg ggttcttaac taggatcatg gcggcagaat   5820
caatcaattg atgttgaact ttcaatgtag ggaattcgtt cttgatggtt tcctccacag   5880
tttttctcca taatcttgaa gaggccaaaa cattagcttt atccaaggac caaataggca   5940
atggtggctc atgttgtagg gccatgaaag cggccattct tgtgattctt tgcacttctg   6000
gaacggtgta ttgttcacta tcccaagcga caccatcacc atcgtcttcc tttctcttac   6060
caaagtaaat acctcccact aattctctaa caacaacgaa gtcagtacct ttagcaaatt   6120
gtggcttgat tggagataag tctaaaagag agtcggatgc aaagttacat ggtcttaagt   6180
tggcgtacaa ttgaagttct ttacggattt ttagtaaacc ttgttcaggt ctaacactac   6240
cggtacccca tttaggacca cccacagcac ctaacaaaac ggcatcagcc ttcttggagg   6300
cttccagcgc ctcatctgga agtggaacac ctgtagcatc gatagcagca ccaccaatta   6360
aatgattttc gaaatcgaac ttgacattgg aacgaacatc agaaatagct ttaagaacct   6420
taatggcttc ggctgtgatt tcttgaccaa cgtggtcacc tggcaaaacg acgatcttct   6480
taggggcaga cattacaatg gtatatcctt gaaatatata taaaaaaaaa aaaaaaaaaa   6540
aaaaaaaaaa atgcagcttc tcaatgatat tcgaatacgc tttgaggaga tacagcctaa   6600
tatccgacaa actgttttac agatttacga tcgtacttgt tacccatcat tgaattttga   6660
acatccgaac ctgggagttt tccctgaaac agatagtata tttgaacctg tataataata   6720
tatagtctag cgctttacgg aagacaatgt atgtatttcg gttcctggag aaactattgc   6780
atctattgca taggtaatct tgcacgtcgc atccccggtt cattttctgc gtttccatct   6840
tgcacttcaa tagcatatct ttgttaacga agcatctgtg cttcattttg tagaacaaaa   6900
atgcaacgcg agagcgctaa tttttcaaac aaagaatctg agctgcattt ttacagaaca   6960
gaaatgcaac gcgaaagcgc tattttacca acgaagaatc tgtgcttcat ttttgtaaaa   7020
caaaaatgca acgcgagagc gctaattttt caaacaaaga atctgagctg catttttaca   7080
gaacagaaat gcaacgcgag agcgctattt taccaacaaa gaatctatac ttcttttttg   7140
ttctacaaaa atgcatcccg agagcgctat ttttctaaca aagcatctta gattactttt   7200
tttctccttt gtgcgctcta taatgcagtc tcttgataac tttttgcact gtaggtccgt   7260
taaggttaga agaaggctac tttggtgtct attttctctt ccataaaaaa agcctgactc   7320
cacttcccgc gtttactgat tactagcgaa gctgcgggtg cattttttca agataaaggc   7380
atccccgatt atattctata ccgatgtgga ttgcgcatac tttgtgaaca gaaagtgata   7440
gcgttgatga ttcttcattg gtcagaaaat tatgaacggt ttcttctatt ttgtctctat   7500
atactacgta taggaaatgt ttacattttc gtattgtttt cgattcactc tatgaatagt   7560
tcttactaca attttttgt ctaaagagta atactagaga taaacataaa aaatgtagag   7620
gtcgagttta gatgcaagtt caaggagcga aaggtggatg ggtaggttat atagggatat   7680
```

agcacagaga tatatagcaa agagatactt ttgagcaatg tttgtggaag cggtattcgc 7740
aatattttag tagctcgtta cagtccggtg cgtttttggt tttttgaaag tgcgtcttca 7800
gagcgctttt ggttttcaaa agcgctctga agttcctata ctttctagag aataggaact 7860
tcggaatagg aacttcaaag cgtttccgaa aacgagcgct tccgaaaatg caacgcgagc 7920
tgcgcacata cagctcactg ttcacgtcgc acctatatct gcgtgttgcc tgtatatata 7980
tatacatgag aagaacggca tagtgcgtgt ttatgcttaa atgcgtactt atatgcgtct 8040
atttatgtag gatgaaaggt agtctagtac ctcctgtgat attatcccat tccatgcggg 8100
gtatcgtatg cttccttcag cactaccctt tagctgttct atatgctgcc actcctcaat 8160
tggattagtc tcatccttca atgctatcat ttcctttgat attggatcat atgcatagta 8220
ccgagaaact agaggatctc ccattaccga catttgggcg ctatacgtgc atatgttcat 8280
gtatgtatct gtatttaaaa cacttttgta ttatttttcc tcatatatgt gtataggttt 8340
atacggatga tttaattatt acttcaccac cctttatttc aggctgatat cttagccttg 8400
ttactagtca ccggtggcgg ccgcacctgg taaaacctct agtggagtag tagatgtaat 8460
caatgaagcg gaagccaaaa gaccagagta gaggcctata gaagaaactg cgataccttt 8520
tgtgatggct aaacaaacag acatcttttt atatgttttt acttctgtat atcgtgaagt 8580
agtaagtgat aagcgaattt ggctaagaac gttgtaagtg aacaagggac ctcttttgcc 8640
tttcaaaaaa ggattaaatg gagttaatca ttgagattta gttttcgtta gattctgtat 8700
ccctaaataa ctcccttacc cgacgggaag gcacaaaaga cttgaataat agcaaacggc 8760
cagtagccaa gaccaaataa tactagagtt aactgatggt cttaaacagg cattacgtgg 8820
tgaactccaa gaccaatata caaaatatcg ataagttatt cttgcccacc aatttaagga 8880
gcctacatca ggacagtagt accattcctc agagaagagg tatacataac aagaaaatcg 8940
cgtgaacacc ttatataact tagcccgtta ttgagctaaa aaaccttgca aaatttccta 9000
tgaataagaa tacttcagac gtgataaaaa tttactttct aactcttctc acgctgcccc 9060
tatctgttct tccgctctac cgtgagaaat aaagcatcga gtacggcagt tcgctgtcac 9120
tgaactaaaa caataaggct agttcgaatg atgaacttgc ttgctgtcaa acttctgagt 9180
tgccgctgat gtgacactgt gacaataaat tcaaaccggt tatagcggtc tcctccggta 9240
ccggttctgc cacctccaat agagctcagt aggagtcaga acctctgcgg tggctgtcag 9300
tgactcatcc gcgtttcgta agttgtgcgc gtgcacattt cgcccgttcc cgctcatctt 9360
gcagcaggcg gaaattttca tcacgctgta ggacgcaaaa aaaaaataat taatcgtaca 9420
agaatcttgg aaaaaaaatt gaaaaatttt gtataaaagg gatgacctaa cttgactcaa 9480
tggcttttac acccagtatt ttccctttcc ttgtttgtta caattataga agcaagacaa 9540
aaacatatag acaacctatt cctaggagtt atattttttt accctaccag caatataagt 9600
aaaaaactgt tt 9612

<210> SEQ ID NO 202
<211> LENGTH: 7938
<212> TYPE: DNA
<213> ORGANISM: Artificial Sequence
<220> FEATURE:
<223> OTHER INFORMATION: pYZ067DkivDDhADH

<400> SEQUENCE: 202
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120

-continued

```
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt ccacctagcg gatgactctt ttttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat tttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttcttttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtggccggc ttcacatacg ttgcatacgt   1680
cgatatagat aataatgata atgacagcag gattatcgta atacgtaata gctgaaaatc   1740
tcaaaaatgt gtgggtcatt acgtaaataa tgataggaat gggattcttc tatttttcct   1800
ttttccattc tagcagccgt cgggaaaacg tggcatcctc tctttcgggc tcaattggag   1860
tcacgctgcc gtgagcatcc tctctttcca tatctaacaa ctgagcacgt aaccaatgga   1920
aaagcatgag cttagcgttg ctccaaaaaa gtattggatg gttaatacca tttgtctgtt   1980
ctcttctgac tttgactcct caaaaaaaaa aatctacaat caacagatcg cttcaattac   2040
gccctcacaa aaactttttt ccttcttctt cgcccacgtt aaattttatc cctcatgttg   2100
tctaacggat ttctgcactt gatttattat aaaaagacaa agacataata cttctctatc   2160
aatttcagtt attgttcttc cttgcgttat tcttctgttc ttcttttttct tttgtcatat   2220
ataaccataa ccaagtaata catattcaaa cacgtgagta tgactgacaa aaaaactctt   2280
aaagacttaa gaaatcgtag ttctgtttac gattcaatgg ttaaatcacc taatcgtgct   2340
atgttgcgtg caactggtat gcaagatgaa gactttgaaa aacctatcgt cggtgtcatt   2400
tcaacttggg ctgaaaacac accttgtaat atccacttac atgactttgg taaactagcc   2460
```

-continued

```
aaagtcggtg ttaaggaagc tggtgcttgg ccagttcagt tcggaacaat cacggtttct   2520

gatggaatcg ccatgggaac ccaaggaatg cgtttctcct tgacatctcg tgatattatt   2580

gcagattcta ttgaagcagc catgggaggt cataatgcgg atgcttttgt agccattggc   2640

ggttgtgata aaaacatgcc cggttctgtt atcgctatgg ctaacatgga tatcccagcc   2700

atttttgctt acggcggaac aattgcacct ggtaatttag acggcaaaga tatcgattta   2760

gtctctgtct ttgaaggtgt cggccattgg aaccacggcg atatgaccaa agaagaagtt   2820

aaagctttgg aatgtaatgc ttgtcccggt cctggaggct gcggtggtat gtatactgct   2880

aacacaatgg cgacagctat tgaagttttg ggacttagcc ttccgggttc atcttctcac   2940

ccggctgaat ccgcagaaaa gaaagcagat attgaagaag ctggtcgcgc tgttgtcaaa   3000

atgctcgaaa tgggcttaaa accttctgac attttaacgc gtgaagcttt tgaagatgct   3060

attactgtaa ctatggctct gggaggttca accaactcaa cccttcacct cttagctatt   3120

gcccatgctg ctaatgtgga attgacactt gatgatttca atactttcca agaaaaagtt   3180

cctcatttgg ctgatttgaa accttctggt caatatgtat tccaagacct ttacaaggtc   3240

ggaggggtac cagcagttat gaaatatctc cttaaaaatg gcttccttca tggtgaccgt   3300

atcacttgta ctggcaaaac agtcgctgaa aatttgaagg cttttgatga tttaacacct   3360

ggtcaaaagg ttattatgcc gcttgaaaat cctaaacgtg aagatggtcc gctcattatt   3420

ctccatggta acttggctcc agacggtgcc gttgccaaag tttctggtgt aaaagtgcgt   3480

cgtcatgtcg gtcctgctaa ggtctttaat tctgaagaag aagccattga agctgtcttg   3540

aatgatgata ttgttgatgg tgatgttgtt gtcgtacgtt ttgtaggacc aaagggcggt   3600

cctggtatgc ctgaaatgct ttccctttca tcaatgattg ttggtaaagg gcaaggtgaa   3660

aaagttgccc ttctgacaga tggccgcttc tcaggtggta cttatggtct tgtcgtgggt   3720

catatcgctc ctgaagcaca agatggcggt ccaatcgcct acctgcaaac aggagacata   3780

gtcactattg accaagacac taaggaatta cactttgata tctccgatga agagttaaaa   3840

catcgtcaag agaccattga attgccaccg ctctattcac gcggtatcct tggtaaatat   3900

gctcacatcg tttcgtctgc ttctagggga gccgtaacag acttttggaa gcctgaagaa   3960

actggcaaaa aatgttgtcc tggttgctgt ggttaagcgg ccgcgttaat tcaaattaat   4020

tgatatagtt ttttaatgag tattgaatct gtttagaaat aatggaatat tattttttatt   4080

tatttattta tattattggt cggctctttt cttctgaagg tcaatgacaa aatgatatga   4140

aggaaataat gatttctaaa attttacaac gtaagatatt tttacaaaag cctagctcat   4200

cttttgtcat gcactatttt actcacgctt gaaattaacg gccagtccac tgcggagtca   4260

tttcaaagtc atcctaatcg atctatcgtt tttgatagct cattttggag ttcgcgagga   4320

tcccagcttt tgttcccttt agtgagggtt aattgcgcgc ttggcgtaat catggtcata   4380

gctgtttcct gtgtgaaatt gttatccgct cacaattcca cacaacatac gagccggaag   4440

cataaagtgt aaagcctggg gtgcctaatg agtgagctaa ctcacattaa ttgcgttgcg   4500

ctcactgccc gctttccagt cgggaaacct gtcgtgccag ctgcattaat gaatcggcca   4560

acgcgcgggg agaggcggtt tgcgtattgg gcgctcttcc gcttcctcgc tcactgactc   4620

gctgcgctcg gtcgttcggc tgcggcgagc ggtatcagct cactcaaagg cggtaatacg   4680

gttatccaca gaatcagggg ataacgcagg aaagaacatg tgagcaaaag gccagcaaaa   4740

ggccaggaac cgtaaaaagg ccgcgttgct ggcgtttttc cataggctcc gcccccctga   4800

cgagcatcac aaaaatcgac gctcaagtca gaggtggcga aacccgacag gactataaag   4860
```

```
ataccaggcg tttccccctg gaagctccct cgtgcgctct cctgttccga ccctgccgct   4920

taccggatac ctgtccgcct ttctcccttc gggaagcgtg gcgctttctc atagctcacg   4980

ctgtaggtat ctcagttcgg tgtaggtcgt tcgctccaag ctgggctgtg tgcacgaacc   5040

ccccgttcag cccgaccgct gcgccttatc cggtaactat cgtcttgagt ccaacccggt   5100

aagacacgac ttatcgccac tggcagcagc cactggtaac aggattagca gagcgaggta   5160

tgtaggcggt gctacagagt tcttgaagtg gtggcctaac tacggctaca ctagaagaac   5220

agtatttggt atctgcgctc tgctgaagcc agttaccttc ggaaaaagag ttggtagctc   5280

ttgatccggc aaacaaacca ccgctggtag cggtggtttt tttgtttgca agcagcagat   5340

tacgcgcaga aaaaaaggat ctcaagaaga tcctttgatc ttttctacgg ggtctgacgc   5400

tcagtggaac gaaaactcac gttaagggat tttggtcatg agattatcaa aaaggatctt   5460

cacctagatc cttttaaatt aaaaatgaag ttttaaatca atctaaagta tatatgagta   5520

aacttggtct gacagttacc aatgcttaat cagtgaggca cctatctcag cgatctgtct   5580

atttcgttca tccatagttg cctgactccc cgtcgtgtag ataactacga tacgggaggg   5640

cttaccatct ggccccagtg ctgcaatgat accgcgagac ccacgctcac cggctccaga   5700

tttatcagca ataaaccagc cagccggaag ggccgagcgc agaagtggtc ctgcaacttt   5760

atccgcctcc atccagtcta ttaattgttg ccgggaagct agagtaagta gttcgccagt   5820

taatagtttg cgcaacgttg ttgccattgc tacaggcatc gtggtgtcac gctcgtcgtt   5880

tggtatggct tcattcagct ccggttccca acgatcaagg cgagttacat gatcccccat   5940

gttgtgcaaa aaagcggtta gctccttcgg tcctccgatc gttgtcagaa gtaagttggc   6000

cgcagtgtta tcactcatgg ttatggcagc actgcataat tctcttactg tcatgccatc   6060

cgtaagatgc ttttctgtga ctggtgagta ctcaaccaag tcattctgag aatagtgtat   6120

gcggcgaccg agttgctctt gcccggcgtc aatacgggat aataccgcgc cacatagcag   6180

aactttaaaa gtgctcatca ttggaaaacg ttcttcgggg cgaaaactct caaggatctt   6240

accgctgttg agatccagtt cgatgtaacc cactcgtgca cccaactgat cttcagcatc   6300

ttttactttc accagcgttt ctgggtgagc aaaaacagga aggcaaaatg ccgcaaaaaa   6360

gggaataagg gcgacacgga aatgttgaat actcatactc ttcctttttc aatattattg   6420

aagcatttat cagggttatt gtctcatgag cggatacata tttgaatgta tttagaaaaa   6480

taaacaaata ggggttccgc gcacatttcc ccgaaaagtg ccacctgaac gaagcatctg   6540

tgcttcattt tgtagaacaa aaatgcaacg cgagagcgct aatttttcaa acaaagaatc   6600

tgagctgcat ttttacagaa cagaaatgca acgcgaaagc gctattttac caacgaagaa   6660

tctgtgcttc atttttgtaa aacaaaaatg caacgcgaga gcgctaattt ttcaaacaaa   6720

gaatctgagc tgcattttta cagaacagaa atgcaacgcg agagcgctat tttaccaaca   6780

aagaatctat acttcttttt tgttctacaa aaatgcatcc cgagagcgct atttttctaa   6840

caaagcatct tagattactt tttttctcct ttgtgcgctc tataatgcag tctcttgata   6900

actttttgca ctgtaggtcc gttaaggtta gaagaaggct actttggtgt ctattttctc   6960

ttccataaaa aaagcctgac tccacttccc gcgtttactg attactagcg aagctgcggg   7020

tgcatttttt caagataaag gcatccccga ttatattcta taccgatgtg gattgcgcat   7080

actttgtgaa cagaaagtga tagcgttgat gattcttcat tggtcagaaa attatgaacg   7140

gtttcttcta ttttgtctct atatactacg tataggaaat gtttacattt tcgtattgtt   7200
```

-continued

```
ttcgattcac tctatgaata gttcttacta caatttttt gtctaaagag taatactaga   7260

gataaacata aaaaatgtag aggtcgagtt tagatgcaag ttcaaggagc gaaaggtgga   7320

tgggtaggtt atatagggat atagcacaga gatatatagc aaagagatac ttttgagcaa   7380

tgtttgtgga agcggtattc gcaatatttt agtagctcgt tacagtccgg tgcgtttttg   7440

gtttttgaa agtgcgtctt cagagcgctt ttggttttca aaagcgctct gaagttccta   7500

tactttctag agaataggaa cttcggaata ggaacttcaa agcgtttccg aaaacgagcg   7560

cttccgaaaa tgcaacgcga gctgcgcaca tacagctcac tgttcacgtc gcacctatat   7620

ctgcgtgttg cctgtatata tatatacatg agaagaacgg catagtgcgt gtttatgctt   7680

aaatgcgtac ttatatgcgt ctatttatgt aggatgaaag gtagtctagt acctcctgtg   7740

atattatccc attccatgcg gggtatcgta tgcttccttc agcactaccc tttagctgtt   7800

ctatatgctg ccactcctca attggattag tctcatcctt caatgctatc atttcctttg   7860

atattggatc atactaagaa accattatta tcatgacatt aacctataaa aataggcgta   7920

tcacgaggcc ctttcgtc                                                  7938
```